United States Patent
Sasada et al.

(10) Patent No.: US 10,497,885 B2
(45) Date of Patent: Dec. 3, 2019

(54) LIGHT EMITTING DEVICE AND COMPOSITION USED FOR THIS LIGHT EMITTING DEVICE

(71) Applicant: Sumitomo Chemical Company, Limited, Tokyo (JP)

(72) Inventors: Toshiaki Sasada, Tsukuba (JP); Makoto Anryu, Tokyo (JP); Takakazu Saito, Tsukuba (JP); Rei Okamura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/565,755

(22) PCT Filed: Apr. 24, 2015

(86) PCT No.: PCT/JP2015/062487
§ 371 (c)(1),
(2) Date: Oct. 11, 2017

(87) PCT Pub. No.: WO2016/170671
PCT Pub. Date: Oct. 27, 2016

(65) Prior Publication Data
US 2018/0123056 A1 May 3, 2018

(51) Int. Cl.
| H01L 51/54 | (2006.01) |
| C09K 11/06 | (2006.01) |
| H01L 51/00 | (2006.01) |
| C08G 61/12 | (2006.01) |
| H01L 51/50 | (2006.01) |
| C08G 61/10 | (2006.01) |
| C07D 251/24 | (2006.01) |
| C07F 15/00 | (2006.01) |

(52) U.S. Cl.
CPC ........ *H01L 51/0085* (2013.01); *C07D 251/24* (2013.01); *C07F 15/0033* (2013.01); *C08G 61/10* (2013.01); *C08G 61/12* (2013.01); *C09K 11/06* (2013.01); *H01L 51/0039* (2013.01); *H01L 51/0043* (2013.01); *H01L 51/0059* (2013.01); *H01L 51/0067* (2013.01); *H01L 51/0072* (2013.01); *H01L 51/50* (2013.01); *C08G 2261/124* (2013.01); *C08G 2261/148* (2013.01); *C08G 2261/1414* (2013.01); *C08G 2261/18* (2013.01); *C08G 2261/228* (2013.01); *C08G 2261/312* (2013.01); *C08G 2261/314* (2013.01); *C08G 2261/3142* (2013.01); *C08G 2261/3162* (2013.01); *C08G 2261/512* (2013.01); *C08G 2261/95* (2013.01); *C09K 2211/1029* (2013.01); *C09K 2211/1044* (2013.01); *C09K 2211/1059* (2013.01); *C09K 2211/1074* (2013.01); *C09K 2211/185* (2013.01); *H01L 51/5016* (2013.01); *H01L 51/5056* (2013.01)

(58) Field of Classification Search
None
See application file for complete search history.

(56) References Cited

U.S. PATENT DOCUMENTS

| 2011/0108814 A1 | 5/2011 | Iida et al. |
| 2012/0068170 A1 | 3/2012 | Pflumm et al. |
| 2014/0034938 A1* | 2/2014 | Ishibashi et al. .... C07D 239/26 257/40 |
| 2014/0319505 A1 | 10/2014 | Nagayama et al. |
| 2016/0233444 A1 | 8/2016 | Hayer et al. |
| 2017/0250353 A1 | 8/2017 | Koenen et al. |

FOREIGN PATENT DOCUMENTS

| EP | 2665342 A1 | 11/2013 |
| JP | 2006114844 A | 4/2006 |
| JP | 2009114369 A | 5/2009 |
| JP | 2009263665 A | 11/2009 |
| JP | 2010503193 A | 1/2010 |
| JP | 2010155985 A | 7/2010 |
| JP | 2010165768 A | 7/2010 |
| JP | 2010209320 A | 9/2010 |
| JP | 2011253722 A | 12/2011 |
| JP | 201333915 A | 2/2013 |
| JP | 2013527989 A | 7/2013 |
| JP | 2014131973 A | 7/2014 |

(Continued)

OTHER PUBLICATIONS

Machine translation of WO 2009/060742 (May 2009).*
Office Action dated Feb. 28, 2017 in JP Application No. 2016-564640.
Office Action dated Jul. 4, 2017 in JP Application No. 2016-564640.
Office Action dated Mar. 21, 2018 in KR Application No. 10-2017-7033343 (English Translation).
Office Action dated Jun. 20, 2018 in KR Application No. 10-2017-7033343.
Office Action dated Jun. 13, 2018 in CN Application No. 201580079094.9.
Notice of Opposition filed Aug. 2, 2018 in JP Patent No. 6256630.
Office Action dated Sep. 19, 2018 in EP Application No. 15889910.4.

(Continued)

*Primary Examiner* — Jennifer A Chriss
*Assistant Examiner* — Dylan C Kershner
(74) *Attorney, Agent, or Firm* — Panitch Schwarze Belisario & Nadel LLP

(57) ABSTRACT

A light emitting device including an anode, a cathode, a light emitting layer disposed between the anode and the cathode, and a hole transporting layer disposed between the anode and the light emitting layer is described. The light emitting layer is a layer containing an iridium complex (A) and a heterocyclic compound constituted of typical elements (B), the hole transporting layer is a layer containing a crosslinked body of a crosslinkable material. The molecular weight (MA) of the iridium complex (A) and the molecular weight (MB) of the heterocyclic compound (B) satisfy the formula $2700 \leq MA+MB \leq 10000$ (M1-1) and the formula $0.35 \leq MA/MB \leq 3.00$ (M2-1).

12 Claims, No Drawings

(56) References Cited

FOREIGN PATENT DOCUMENTS

| JP | 2015110751 A | 6/2015 |
| JP | 2016538323 A | 12/2016 |
| WO | 02066552 A1 | 8/2002 |
| WO | 2008025997 A1 | 3/2008 |
| WO | 2009060742 A1 | 5/2009 |
| WO | 2010004877 A1 | 1/2010 |
| WO | 2011141714 A1 | 11/2011 |
| WO | 2012096263 A1 | 7/2012 |
| WO | 2013064814 A1 | 5/2013 |
| WO | 2013105615 A1 | 7/2013 |
| WO | 2013180036 A1 | 12/2013 |
| WO | 2015039723 A1 | 3/2015 |
| WO | 2016015815 A1 | 2/2016 |

OTHER PUBLICATIONS

Office Action dated Feb. 2, 2019 in CN Application No. 201580079094.9 (English Translation).
Office Action dated Jan. 22, 2019 in JP Application No. 2017-223368 (English Translation).
Third Party Observations filed in JP Application No. 2017223368 communicated to applicant by the JP on Jan. 29, 2019 (English Translation).
Office Action dated Oct. 8, 2019 in JP Application No. 2017-223368 (with English Translation).
Third party observations submitted to Japanese Patent Office on Jul. 25, 2019 in Japanese Patent Application No. 2017-223368. (With English Translation).
Examination Report issued by European Patent Office on Jul. 26, 2019 in European Patent Application No. 15889910.4.

* cited by examiner

LIGHT EMITTING DEVICE AND COMPOSITION USED FOR THIS LIGHT EMITTING DEVICE

CROSS-REFERENCE TO RELATED APPLICATION

This application is a Section 371 of International Application No. PCT/JP2015/062487, filed Apr. 24, 2015, which was published in the Japanese language on Oct. 27, 2016 under International Publication No. WO 2016/170671 A1, and the disclosure of which is incorporated herein by reference.

TECHNICAL FIELD

The present invention relates to a light emitting device and a composition used for the light emitting device.

BACKGROUND ART

An organic electroluminescent device (hereinafter, referred to also as "light emitting device") can be suitably used in applications of display and illumination, and is under active research and development. This light emitting device has organic layers such as a light emitting layer and a charge transporting layer.

Patent document 1 discloses a light emitting device comprising a light emitting layer comprising an iridium complex (Ir-A1) and a heterocyclic compound (H-B1) and a hole transporting layer comprising a crosslinked body of a crosslinkable material. The sum of the molecular weight of the iridium complex (Ir-A1) and the molecular weight of the heterocyclic compound (H-B1) is 1139. The ratio of the molecular weight of the iridium complex (Ir-A1) to the molecular weight of the heterocyclic compound (H-B1) is 1.35.

[Chemical Formula 1]

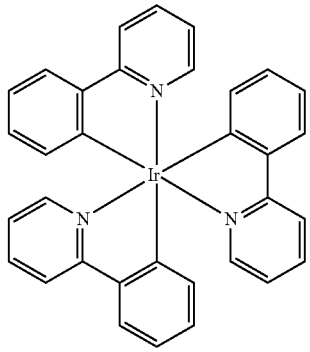

Iridium complex (Ir-A1)

Molecular Weight: 654.8

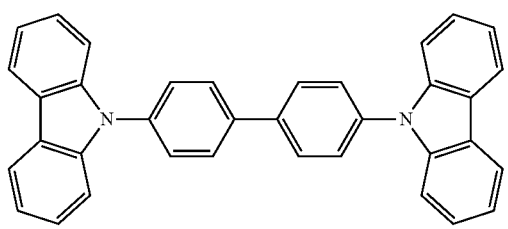

Heterocyclic compound (H-B1)

Molecular Weight: 484.6

Patent document 2 discloses a light emitting device comprising a light emitting layer comprising an iridium complex (Ir-A2) and an aromatic amine compound (H-B2) and a hole transporting layer comprising a crosslinked body of a crosslinkable material. The sum of the molecular weight of the iridium complex (Ir-A2) and the molecular weight of the aromatic amine compound (H-B2) is 2689. The ratio of the molecular weight of the iridium complex (Ir-A2) to the molecular weight of the aromatic amine compound (H-B2) is 1.66.

[Chemical Formula 2]

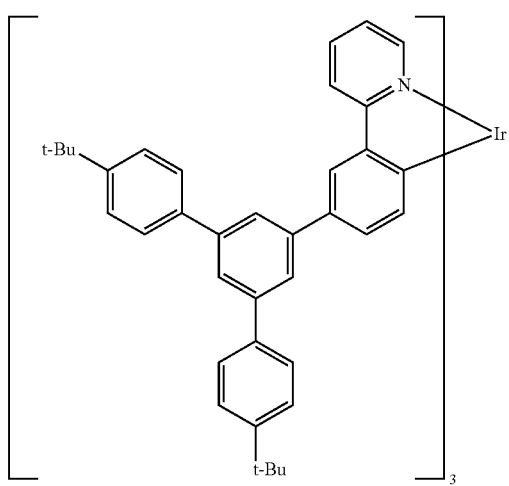

Iridium complex (Ir-A2)

Molecular Weight: 1676.3

-continued aromatic amine compound (H-B2)

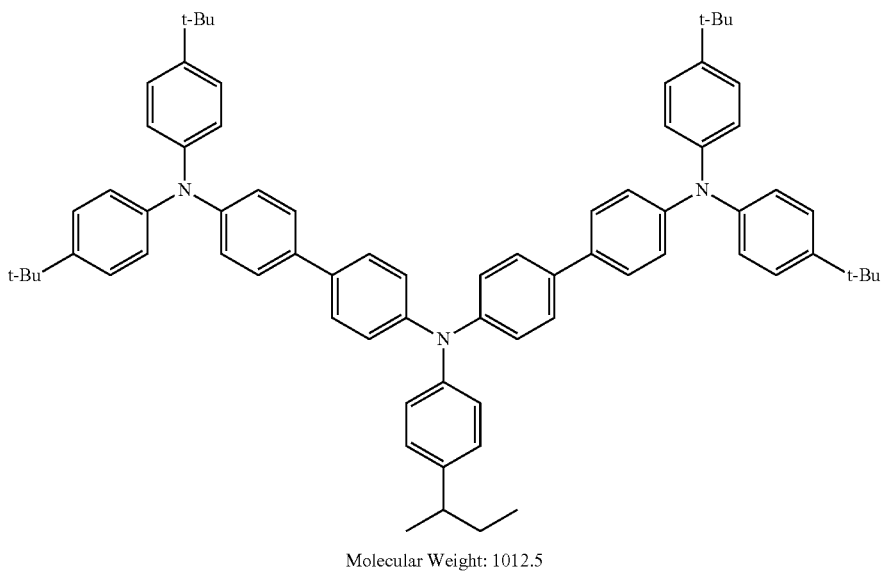

Molecular Weight: 1012.5

PRIOR ART DOCUMENT

Patent Document

[Patent document 1] JP-A No. 2009-263665
[Patent document 2] International Publication WO2013/064814

SUMMARY OF THE INVENTION

Problem to be Solved by the Invention

However, the above-described light emitting devices disclosed in Patent documents 1 and 2 are not always sufficient in external quantum efficiency.

Accordingly, the present invention has an object of providing a light emitting device excellent in external quantum efficiency. Further, the present invention has an object of providing a composition which is useful for production of a light emitting device excellent in external quantum efficiency.

Means for Solving the Problem

The present invention provides the following [1] to [11].

[1] A light emitting device comprising an anode, a cathode, a light emitting layer disposed between the anode and the cathode, and a hole transporting layer disposed between the anode and the light emitting layer, wherein
the light emitting layer is a layer comprising an iridium complex (A) and a heterocyclic compound constituted of typical elements (B),
the hole transporting layer is a layer comprising a crosslinked body of a crosslinkable material, and
the molecular weight (MA) of the iridium complex (A) and the molecular weight (MB) of the heterocyclic compound (B) satisfy the formula (M1-1) and the formula (M2-1):

$2700 \leq MA+MB \leq 10000$ (M1-1)

$0.35 \leq MA/MB \leq 3.00$ (M2-1).

[2] The light emitting device according to [1], wherein the molecular weight (MA) and the molecular weight (MB) satisfy the formula (M1-2) and the formula (M2-2):

$3400 \leq MA+MB \leq 7000$ (M1-2)

$0.35 \leq MA/MB \leq 2.00$ (M2-2).

[3] The light emitting device according to [2], wherein the molecular weight (MA) and the molecular weight (MB) satisfy the formula (M1-3) and the formula (M2-3):

$4000 \leq MA+MB \leq 6000$ (M1-3)

$0.65 \leq MA/MB \leq 1.30$ (M2-3).

[4] The light emitting device according to any one of [1] to [3], wherein the light emitting layer and the hole transporting layer are adjacent to each other.

[5] The light emitting device according to any one of [1] to [4], wherein the iridium complex (A) is an iridium complex represented by the formula (A):

[Chemical Formula 3]

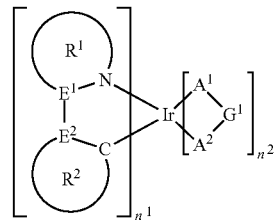

(A)

[wherein,
$n^1$ represents an integer of 1 or more, $n^2$ represents an integer of 0 or more, and $n^1+n^2$ is 3.
$E^1$ and $E^2$ each independently represent a carbon atom or a nitrogen atom. At least one of $E^1$ and $E^2$ is a carbon atom.
The ring $R^1$ represents an aromatic heterocyclic ring, and this ring optionally has a substituent. When a plurality of the substituents are present, they may be the same or different and may be combined together to form a ring together with the atoms to which they are attached. When a plurality of the rings $R^1$ are present, they may be the same or different.

The ring $R^2$ represents an aromatic hydrocarbon ring or an aromatic heterocyclic ring, and these rings each optionally have a substituent. When a plurality of the substituents are present, they may be the same or different and may be combined together to form a ring together with the atoms to which they are attached. When a plurality of the rings $R^2$ are present, they may be the same or different.

The substituent which the ring $R^1$ optionally has and the substituent which the ring $R^1$ optionally has may be combined together to form a ring together with the atoms to which they are attached.

$A^1$-$G^1$-$A^2$ represents an anionic bidentate ligand. $A^1$ and $A^2$ each independently represent a carbon atom, an oxygen atom or a nitrogen atom, and these atoms may be an atom constituting a ring. $G^1$ represents a single bond or an atomic group constituting the bidentate ligand together with $A^1$ and $A^2$. When a plurality of $A^1$-$G^1$-$A^2$ are present, they may be the same or different.].

[6] The light emitting device according to [5], wherein the iridium complex represented by the formula (A) is an iridium complex represented by the formula (A-A) or an iridium complex represented by the formula (A-B):

[Chemical Formula 4]

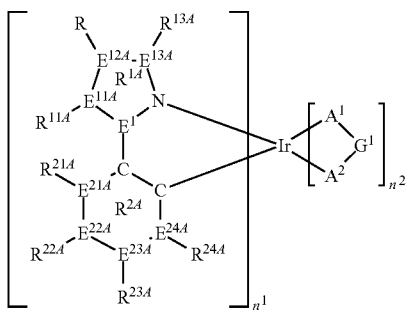

(A-A)

[wherein, $n^1$, $n^2$, $E^1$ and $A^1$-$G^1$-$A^2$ represent the same meaning as described above.

$E^{11A}$, $E^{12A}$, $E^{13A}$, $E^{21A}$, $E^{22A}$, $E^{23A}$ and $E^{24A}$ each independently represent a nitrogen atom or a carbon atom. When a plurality of $E^{11A}$, $E^{12A}$, $E^{13A}$, $E^{21A}$, $E^{22A}$, $E^{23A}$ and $E^{24A}$ are present, they may be the same or different at each occurrence. $R^{11A}$ may be present or may not be present when $E^{11A}$ is a nitrogen atom. $R^{12A}$ may be present or may not be present when $E^{12A}$ is a nitrogen atom. $R^{13A}$ may be present or may not be present when $E^{13A}$ is a nitrogen atom. $R^{21A}$ is not present when $E^{21A}$ is a nitrogen atom. $R^{22A}$ is not present when $E^{22A}$ is a nitrogen atom. $R^{23A}$ is not present when $E^{23A}$ is a nitrogen atom. $R^{24A}$ is not present when $E^{24A}$ is a nitrogen atom.

$R^{11A}$, $R^{12A}$, $R^{13A}$, $R^{21A}$, $R^{22A}$, $R^{23A}$ and $R^{24A}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{11A}$, $R^{12A}$, $R^{13A}$, $R^{21A}$, $R^{22A}$, $R^{23A}$ and $R^{24A}$ are present, they may be the same or different at each occurrence. $R^{11A}$ and $R^{12A}$, $R^{12A}$ and $R^{13A}$, $R^{11A}$ and $R^{21A}$, $R^{21A}$ and $R^{22A}$, $R^{22A}$ and $R^{23A}$, and $R^{23A}$ and $R^{24A}$ each may be combined together to form a ring together with the atoms to which they are attached.

The ring $R^{1A}$ represents a triazole ring or a diazole ring constituted of a nitrogen atom, $E^1$, $E^{11A}$, $E^{12A}$ and $E^{13A}$.

The Ring $R^{2A}$ represents a benzene ring, a pyridine ring or a pyrimidine ring constituted of two carbon atoms, $E^{21A}$, $E^{22A}$, $E^{23A}$ and $E^{24A}$.]

[Chemical Formula 5]

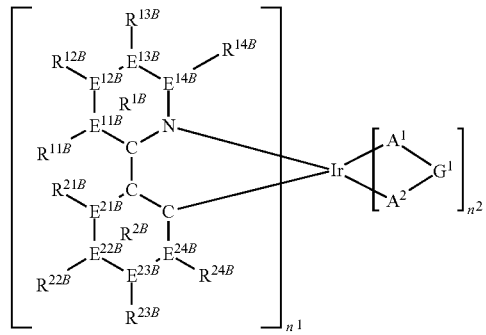

(A-B)

[wherein, $n^1$, $n^2$ and $A^1$-$G^1$-$A^2$ represent the same meaning as described above.

$E^{11B}$, $E^{12B}$, $E^{13B}$, $E^{14B}$, $E^{21B}$, $E^{22B}$, $E^{23B}$ and $E^{24B}$ each independently represent a nitrogen atom or a carbon atom. When a plurality of $E^{11B}$, $E^{12B}$, $E^{13B}$, $E^{14B}$, $E^{21B}$, $E^{22B}$, $E^{23B}$ and $E^{24B}$ are present, they may be the same or different at each occurrence. $R^{11B}$ is not present when $E^{11B}$ is a nitrogen atom. $R^{12B}$ is not present when $E^{12B}$ is a nitrogen atom. $R^{13B}$ is not present when $E^{13B}$ is a nitrogen atom. $R^{14B}$ is not present when $E^{14B}$ is a nitrogen atom. $R^{21B}$ is not present when $E^{21B}$ is a nitrogen atom. $R^{22B}$ is not present when $E^{22B}$ is a nitrogen atom. $R^{23B}$ is not present when $E^{23B}$ is a nitrogen atom. $R^{24B}$ is not present when $E^{24B}$ is a nitrogen atom.

$R^{11B}$, $R^{12B}$, $R^{13B}$, $R^{14B}$, $R^{21B}$, $R^{22B}$, $R^{23B}$ and $R^{24B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{11B}$, $R^{12B}$, $R^{13B}$, $R^{14B}$, $R^{21B}$, $R^{22B}$, $R^{23B}$ and $R^{24B}$ are present, they may be the same or different at each occurrence. $R^{11B}$ and $R^{12B}$, $R^{12B}$ and $R^{13B}$, $R^{13B}$ and $R^{14B}$, $R^{11B}$ and $R^{21B}$, $R^{21B}$ and $R^{22B}$, $R^{22B}$ and $R^{23B}$, and $R^{23B}$ and $R^{24B}$ each may be combined together to form a ring together with the atoms to which they are attached.

The ring $R^{1B}$ represents a pyridine ring or a pyrimidine ring constituted of a nitrogen atom, a carbon atom, $E^{11B}$, $E^{12B}$, $E^{13B}$ and $E^{14B}$.

The ring $R^{2B}$ represents a benzene ring, a pyridine ring or a pyrimidine ring constituted of two carbon atoms, $E^{21B}$, $E^{22B}$, $E^{23B}$ and $E^{24B}$.]

[7] The light emitting device according to any one of [1] to [6], wherein the heterocyclic compound (B) is a heterocyclic compound represented by the formula (B):

[Chemical Formula 6]

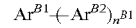

(B)

[wherein, $n^{B1}$ represents an integer of 1 or more.

$Ar^{B1}$ represents a heterocyclic group, and this group optionally has a substituent.

$Ar^{B2}$ represents a group represented by the formula (D-A), (D-B) or (D-C). When a plurality of $Ar^{B2}$ are present, they may be the same or different.]

[Chemical Formula 7]

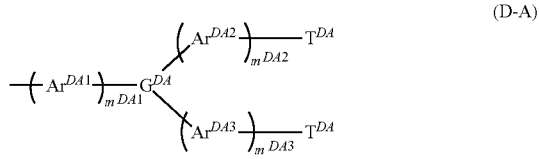

(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and these groups each optionally have a substituent.

$Ar^{DA1}$, $Ar^{DA2}$ and $Ar^{DA3}$ each independently represent an arylene group or a divalent heterocyclic group, and these groups each optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and these groups each optionally have a substituent. The plurality of $T^{DA}$ may be the same or different.]

[Chemical Formula 8]

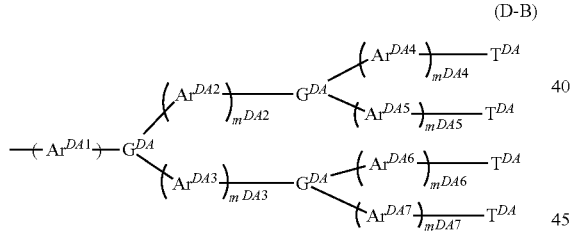

(D-B)

[wherein, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, and these groups each optionally have a substituent. The plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and these groups each optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.

$T^{DA}$ represents an aryl group or a monovalent heterocyclic group, and these groups each optionally have a substituent. The plurality of $T^{DA}$ may be the same or different.]

[Chemical Formula 9]

(D-C)

[wherein, $m^{DA1}$ represents an integer of 0 or more.

$Ar^{DA1}$ represents an arylene group or a divalent heterocyclic group, and these groups each optionally have a substituent. When a plurality of $Ar^{DA1}$ are present, they may be the same or different.

$T^{DA}$ represents an aryl group or a monovalent heterocyclic group, and these groups each optionally have a substituent.].

[8] The light emitting device according to any one of [1] to [7], wherein the crosslinkable material is a low molecular weight compound having at least one crosslinkable group selected from Group A of crosslinkable group or a polymer compound comprising a crosslinkable constitutional unit having at least one crosslinkable group selected from Group A of crosslinkable group:

(Group A of Crosslinkable Group)

[Chemical Formula 10]

(XL-1)

(XL-2)

(XL-3)

(XL-4)

(XL-5)

(XL-6)

(XL-7)

(XL-8)

-continued (XL-9) 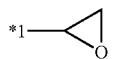

(XL-10) 

(XL-11) 

(XL-12) 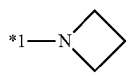

(XL-13) 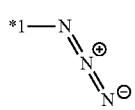

(XL-14) 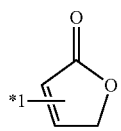

(XL-15) 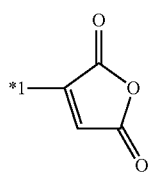

(XL-16) 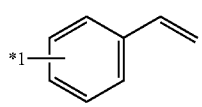

(XL-17) 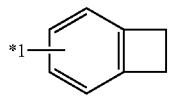

[wherein, $R^{XL}$ represents a methylene group, an oxygen atom or a sulfur atom, and $n^{XL}$ represents an integer of 0 to 5. When a plurality of $R^{XL}$ are present, they may be the same or different, and when a plurality of $n^{XL}$ are present, they may be the same or different. *1 represents a binding site. These crosslink groups each optionally have a substituent.].

[9] The light emitting device according to [8], wherein the crosslinkable material is a polymer compound comprising a crosslinkable constitutional unit having at least one crosslinkable group selected from Group A of crosslinkable group.

[10] The light emitting device according to [9], wherein the crosslinkable constitutional unit is a constitutional unit represented by the formula (2) or a constitutional unit represented by the formula (2'):

[Chemical Formula 11]

(2) 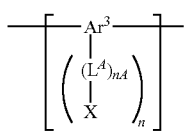

[wherein,
nA represents an integer of 0 to 5, and n represents 1 or 2.

$Ar^3$ represents an aromatic hydrocarbon group or a heterocyclic group, and these groups each optionally have a substituent.

$L^A$ represents an alkylene group, a cycloalkylene group, an arylene group, a divalent heterocyclic group, -a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $L^A$ are present, they may be the same or different.

X represents a crosslinkable group selected from Group A of crosslinkable group. When a plurality of X are present, they may be the same or different.]

[Chemical Formula 12]

(2') 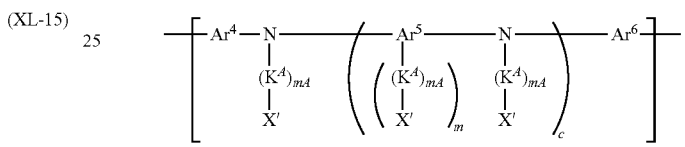

[wherein,
mA represents an integer of 0 to 5, m represents an integer of 1 to 4, and c represents an integer of 0 or 1. When a plurality of mA are present, they may be the same or different.

$Ar^5$ represents an aromatic hydrocarbon group, a heterocyclic group or a group in which at least one aromatic hydrocarbon ring and at least one heterocyclic ring are bonded directly to each other, and these groups each optionally have a substituent.

$Ar^4$ and $Ar^6$ each independently represent an arylene group or a divalent heterocyclic group, and these groups each optionally have a substituent.

$Ar^4$, $Ar^5$ and $Ar^6$ each may be bonded directly or via an oxygen atom or a sulfur atom to a group other than these groups bonding to the nitrogen atom to which these groups are attached, thereby forming a ring.

$K^A$ represents an alkylene group, a cycloalkylene group, an arylene group, a divalent heterocyclic group, a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $K^A$ are present, they may be the same or different.

X' represents a crosslinkable group selected from Group A of crosslinkable group, a hydrogen atom, an alkyl group, a cycloalkyl group, an aryl group or a monovalent heterocyclic group, and these groups each optionally have a substituent. At least one X' is a crosslinkable group selected from Group A of crosslinkable group.].

[11] A composition comprising an iridium complex (A) and a heterocyclic compound constituted of typical elements (B), wherein
the iridium complex (A) is an iridium complex represented by the above-described formula (A), and the molecular weight (MA) of the iridium complex (A) and the molecular weight (MB) of the heterocyclic compound (B) satisfy the formula (M1-3) and the formula (M2-3):

$$4000 \leq MA+MB \leq 6000 \quad (M1\text{-}3)$$

$$0.65 \leq MA/MB \leq 1.30 \quad (M2\text{-}3).$$

Effect of the Invention

According to the present invention, a light emitting device excellent in external quantum efficiency can be provided. Further, according to the present invention, a composition which is useful for production of a light emitting device excellent in external quantum efficiency can be provided.

MODES FOR CARRYING OUT THE INVENTION

Suitable embodiments of the present invention will be illustrated in detail below.

Explanation of Common Term

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

A solid line representing a bond to a central metal in a formula representing a metal complex denotes a covalent bond or a coordinate bond.

"Polymer compound" denotes a polymer having molecular weight distribution and having a polystyrene-equivalent number average molecular weight of $1 \times 10^3$ to $1 \times 10^8$.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes, for example, groups bonding to an aryl group or a monovalent heterocyclic group via a carbon-carbon bond.

"Low molecular weight compound" denotes a compound having no molecular weight distribution and having a molecular weight of $1 \times 10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group, and groups obtained by substituting a hydrogen atom in these groups with a cycloalkyl group, an alkoxy group, a cycloalkoxy group, an aryl group, a fluorine atom or the like, and the alkyl group having a substituent includes a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauryloxy group, and groups obtained by substituting a hydrogen atom in these groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 6 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidinyl group, a quinolinyl group, an isoquinolinyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl)amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

[Chemical Formula 13]

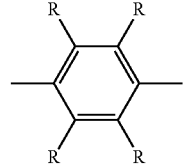

(A-1)

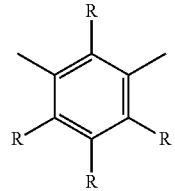

(A-2)

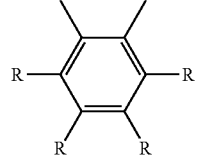

(A-3)

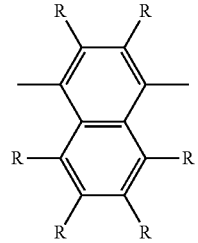

(A-4)

(A-5)
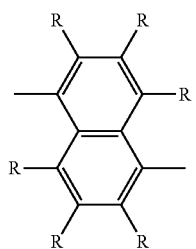
(A-6)
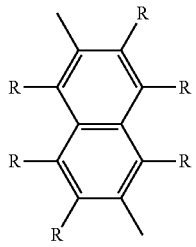
[Chemical Formula 14]
(A-7)
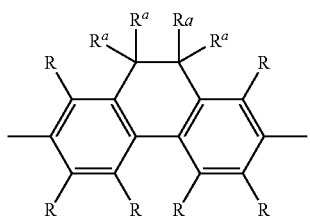
(A-8)
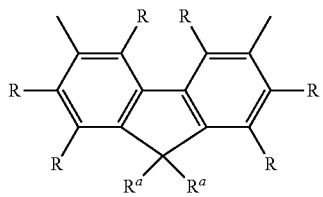
(A-9)
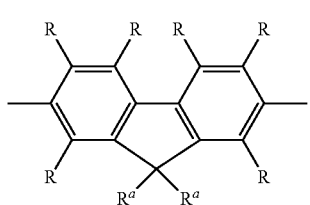
(A-10)
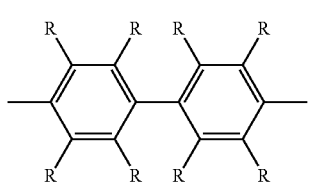
[Chemical Formula 15]
(A-11)
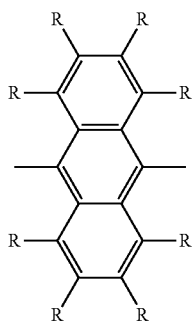
(A-12)
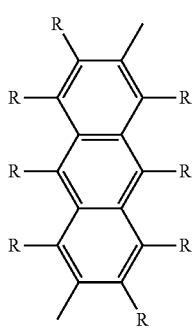
(A-13)
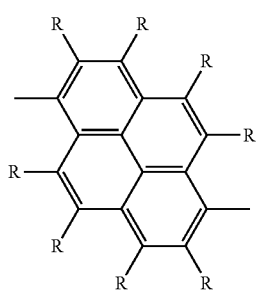
(A-14)
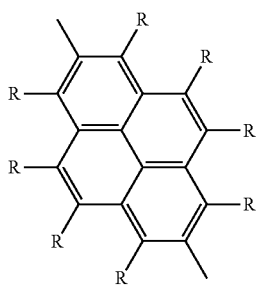
(A-15)
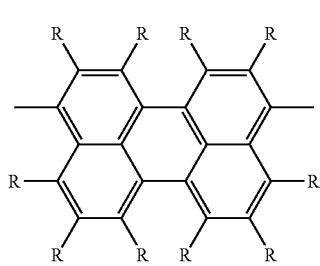

-continued

[Chemical Formula 16]

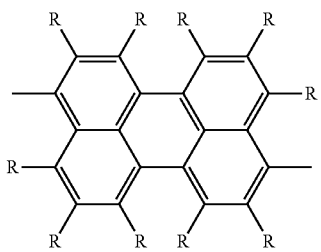
(A-16)

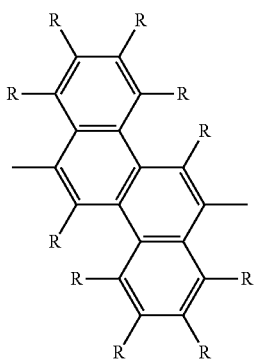
(A-17)

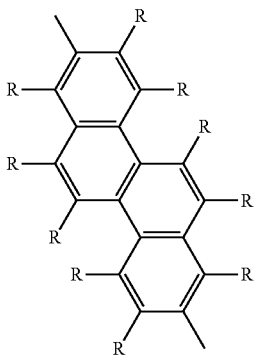
(A-18)

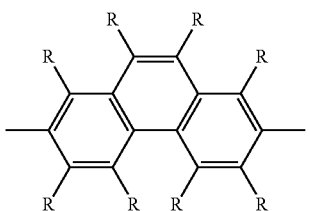
(A-19)

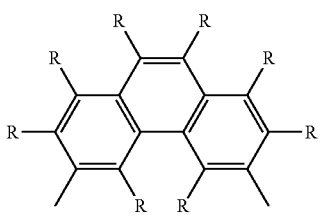
(A-20)

[wherein, R and $R^a$ each independently represent a hydrogen atom, an alkyl group, a cycloalkyl group, an aryl group or a monovalent heterocyclic group. The plurality of R and $R^a$ each may be the same or different, and groups $R^a$ may be combined together to form a ring together with the atoms to which they are attached.]

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

[Chemical Formula 17]

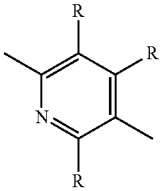
(AA-1)

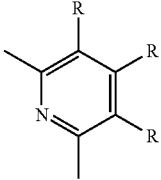
(AA-2)

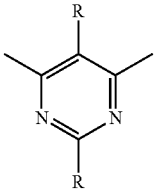
(AA-3)

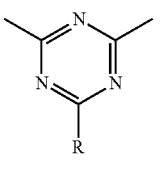
(AA-4)

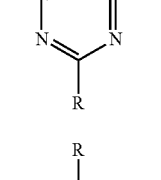
(AA-5)

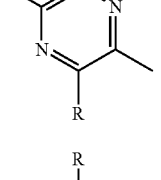
(AA-6)

[Chemical Formula 18]
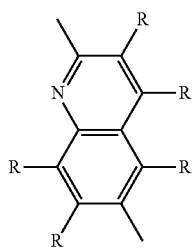
(AA-7)
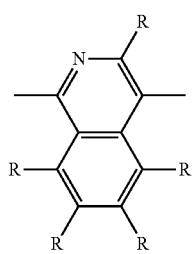
(AA-8)
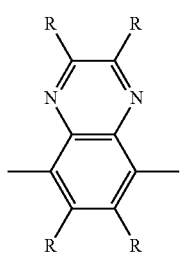
(AA-9)
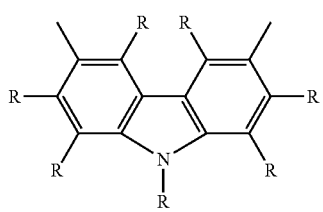
(AA-10)
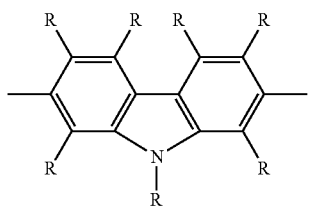
(AA-11)
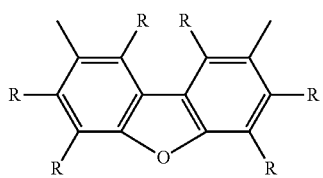
(AA-12)
[Chemical Formula 19]
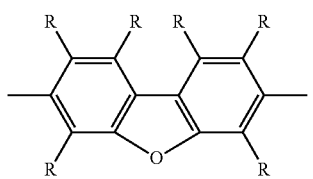
(AA-13)
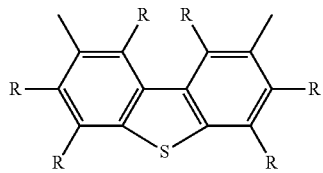
(AA-14)
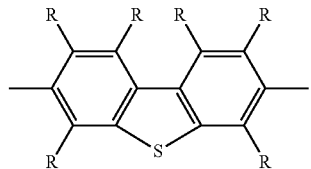
(AA-15)
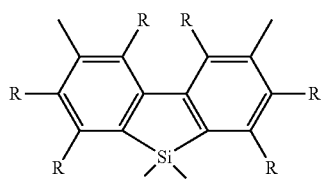
(AA-16)
[Chemical Formula 20]
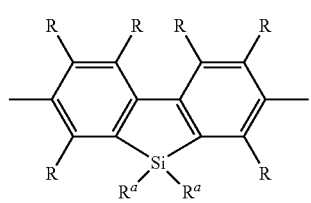
(AA-17)
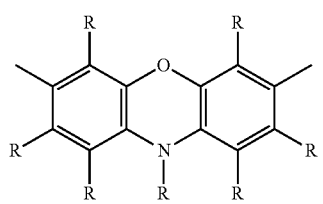
(AA-18)
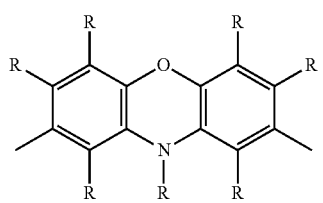
(AA-19)
(AA-20)
[Chemical Formula 21]
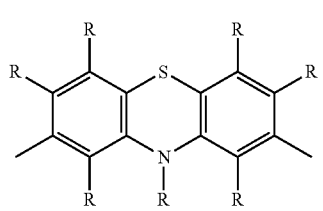
(AA-21)

-continued (AA-22)
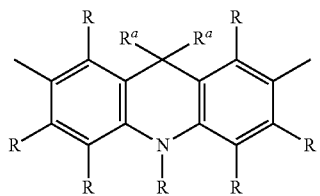

(AA-23)
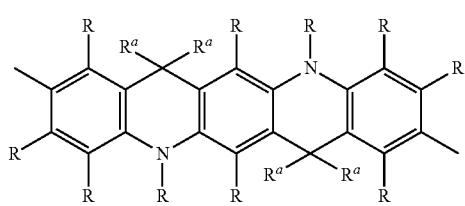

[Chemical Formula 22]

(AA-24)
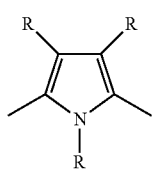

(AA-25)
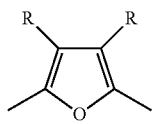

(AA-26)
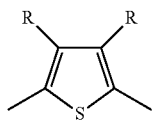

(AA-27)
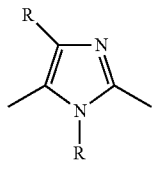

(AA-28)
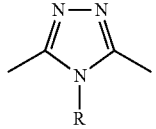

(AA-29)
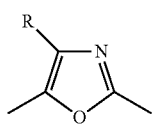

(AA-30)
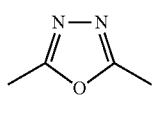

(AA-31)
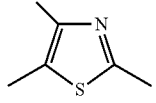

(AA-32)
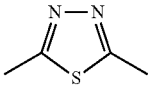

[Chemical Formula 23]

(AA-33)
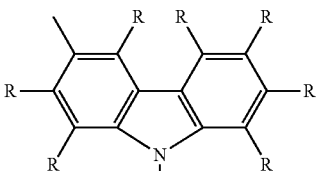

(AA-34)
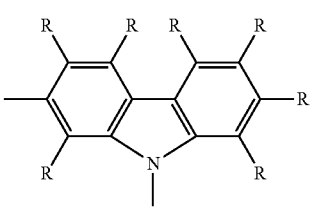

[wherein, R and $R^a$ represent the same meaning as described above.]

"Crosslinkable group" is a group capable of forming a new bond by being subjected to heating, ultraviolet irradiation, near ultraviolet irradiation, visible light irradiation, infrared irradiation, a radical reaction and the like, and the crosslinkable groups are preferably groups represented by the formulae (XL-1) to (XL-17) in Group A of crosslinkable group.

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substutuent may be a crosslinkable group.

<Light Emitting Device>

Next, the light emitting device of the present invention will be illustrated.

The light emitting device of the present invention is a light emitting device comprising an anode, a cathode, a light emitting layer disposed between the anode and the cathode, and a hole transporting layer disposed between the anode and the light emitting layer, wherein the light emitting layer is a layer comprising an iridium complex (A) and a heterocyclic compound constituted of typical elements (B), the hole transporting layer is a layer comprising a crosslinked body of a crosslinkable material, and the molecular weight (MA) of the iridium complex (A) and the molecular weight (MB) of the heterocyclic compound (B) satisfy the above-described formula (1-1) and the above-described formula (2-1).

The method of forming a light emitting layer and a hole transporting layer includes, for example, a vacuum vapor deposition method, and application methods typified by a spin coat method and an inkjet printing method, and preferable are application methods.

When a light emitting layer is formed by an application method, it is preferable to use an ink of a light emitting layer described later.

When a hole transporting layer is formed by an application method, it is preferable to use an ink of a hole transporting layer described later. After forming a hole transporting layer, a crosslinkable material contained in the hole transporting layer can be cross-linked by heating or light irradiation. When a crosslinkable material in cross-linked state (a crosslinked body of a crosslinkable material) is contained in a hole transporting layer, the hole transporting layer is substantially insolubilized in a solvent. For this reason, the hole transporting layer can be suitably used for lamination of a light emitting device.

The temperature of heating for crosslinking is usually 25 to 300° C., preferably 50 to 250° C., more preferably 150 to 200° C.

The light used for light irradiation for crosslinking is, for example, ultraviolet light, near-ultraviolet light and visible light.

The method of analyzing the condition of a light emitting layer (whether an iridium complex and a low molecular weight compound are contained) and the condition of a hole transporting layer (whether a crosslinked body of a crosslinkable material is contained) includes, for example, chemical separation analysis methods typified by extraction and the like, instrumental analysis methods typified by IR spectroscopy (IR), nuclear magnetic resonance spectroscopy (NMR), mass spectroscopy (MS) and the like, and analysis methods combining chemical separation analysis methods and instrumental analysis methods.

A light emitting layer or a hole transporting layer can be subjected to solid-liquid extraction using an organic solvent typified by toluene, xylene, chloroform, tetrahydrofuran and the like, to be separated into components substantially insoluble in an organic solvent (insoluble component) and components soluble in an organic solvent (soluble component). The resultant insoluble component can be analyzed by IR spectroscopy (IR) or nuclear magnetic resonance spectroscopy (NMR), and the resultant soluble component can be analyzed by nuclear magnetic resonance spectroscopy (NMR) or mass spectroscopy (MS).

<Light Emitting Layer>

The light emitting layer is a layer comprising an iridium complex (A) and a heterocyclic compound (B).

[Iridium Complex (A)]

First, the iridium complex (A) will be illustrated.

The iridium complex (A) is usually an iridium complex showing phosphorescence at room temperature (25° C.), preferably an iridium complex showing light emission from triplet excited state at room temperature (25° C.). This iridium complex has an iridium atom (central metal) and a ligand.

The ligand includes, for example, a neutral or anionic monodentate ligand or a neutral or anionic polydentate ligand which forms at least one bond selected from the group consisting of a coordinate bond and a covalent bond between an iridium atom and the ligand. The bond between an iridium atom and a ligand includes, for example, a metal-nitrogen bond, a metal-carbon bond, a metal-oxygen bond, a metal-phosphorus bond, a metal-sulfur bond and a metal-halogen bond. The polydentate ligand usually denotes a 2 or more-dentate and 6 or less-dentate ligand.

The iridium complex (A) is available from Aldrich, Luminescence Technology Corp., American Dye Source, and the like.

The iridium complex (A) can be synthesized according to methods disclosed in, for example, "Journal of American Chemical Society, Vol. 107, 1431-1432 (1985)", "Journal of American Chemical Society, Vol. 106, 6647-6653 (1984)", Japanese Patent Application National Publication No. 2004-530254, JP-A No. 2008-179617, JP-A No. 2011-105701, Japanese Patent Application National Publication No. 2007-504272, International Publication WO2006/121811 and JP-A No. 2013-147450, as the other acquisition means.

The iridium complex (A) is preferably an iridium complex represented by the formula (A), because the light emitting device of the present invention is more excellent in external quantum efficiency.

<Iridium Complex Represented by the Formula (A)>

The iridium complex represented by the formula (A) is an iridium complex constituted of an iridium atom as the central metal, a ligand the number of which is prescribed by a subscript $n^1$ and a ligand the number of which is prescribed by a subscript $n^2$.

$n^1$ is preferably 2 or 3, more preferably 3.

It is preferable that $E^1$ and $E^2$ represent a carbon atom.

The ring $R^1$ is preferably a 5-membered aromatic heterocyclic ring or a 6-membered aromatic heterocyclic ring, preferably a 5-membered aromatic heterocyclic ring having 2 to 4 nitrogen atoms as a constituent atom or a 6-membered aromatic heterocyclic ring having 1 to 4 nitrogen atoms as a constituent atom, more preferably a diazole ring, a triazole ring, a pyridine ring, a azobenzene ring, a quinoline ring or an isoquinoline ring, and these rings each optionally have a substituent.

The ring $R^2$ is preferably a 5-membered or 6-membered aromatic hydrocarbon ring or a 5-membered or 6-membered aromatic heterocyclic ring, more preferably a 6-membered aromatic hydrocarbon ring or a 6-membered aromatic heterocyclic ring, further preferably a 6-membered aromatic hydrocarbon ring, and these rings each optionally have a substituent. When the ring $R^2$ is a 6-membered aromatic heterocyclic ring, $E^2$ is a carbon atom.

The ring $R^2$ includes, for example, a benzene ring, a naphthalene ring, a fluorene ring, a phenanthrene ring, a pyridine ring, a diazabenzene ring and a triazine ring, preferably a benzene ring, a pyridine ring or a pyrimidine ring, more preferably a benzene ring, and these rings each optionally have a substituent.

The substituent which the ring $R^1$ and the ring $R^2$ optionally have is preferably a halogen atom, an alkyl group, a cycloalkyl group, an alkoxy group, a cycloalkoxy group, an aryloxy group, an aryl group, a monovalent heterocyclic group or a substituted amino group, more preferably an alkyl group, a cycloalkyl group, an alkoxy group, an aryl group, a monovalent heterocyclic group or a substituted amino group.

The aryl group as the substituent which the ring $R^1$ and the ring $R^2$ optionally have is preferably a phenyl group, a naphthyl group, an anthracenyl group, a phenanthrenyl group, a dihydrophenanthrenyl group, a fluorenyl group or a pyrenyl group, more preferably a phenyl group, a naphthyl group or a fluorenyl group, further preferably a phenyl group, and these groups each optionally have a substituent.

The monovalent heterocyclic group as the substituent which the ring $R^1$ and the ring $R^2$ optionally have is preferably a pyridyl group, a pyrimidinyl group, a triazinyl group, a quinolinyl group, an isoquinolinyl group, a dibenzofuranyl group, a dibenzothienyl group, a carbazolyl group, an azacarbazolyl group, a diazacarbazolyl group, a phenoxadinyl group or a phenothiadinyl group, more preferably a pyridyl group, a pyrimidinyl group, a triazinyl group, a carbazolyl group, an azacarbazolyl group or a diazacarbazolyl group, further preferably a pyridyl group, a pyrimidinyl group or a triazinyl group, and these groups each optionally have a substituent.

The substituent which the amino group has in the substituted amino group as the substituent which the ring $R^1$ and the ring $R^2$ optionally have is preferably an aryl group or a monovalent heterocyclic group, and these groups each optionally further have a substituent. The examples and the preferable range of the aryl group as the substituent which the amino group has are the same as the examples and the preferable range of the aryl group as the substituent which the ring $R^1$ and the ring $R^2$ optionally have. The examples and the preferable range of the monovalent heterocyclic group as the substituent which the amino group has are the same as the examples and the preferable range of the monovalent heterocyclic group as the substituent which the ring $R^1$ and the ring $R^2$ optionally have.

The substituent which the substituent which the ring $R^1$ and the ring $R^2$ optionally have optionally further has is preferably an alkyl group, a cycloalkyl group, an aryl group, a monovalent heterocyclic group, an alkoxy group, a cycloalkoxy group, an aryloxy group or a substituted amino group, more preferably an alkyl group, a cycloalkyl group, an aryl group, a monovalent heterocyclic group or a substituted amino group, further preferably an alkyl group, a cycloalkyl group, an aryl group or a monovalent heterocyclic group, particularly preferably an alkyl group, a cycloalkyl group or an aryl group, and these groups each optionally further have a substituent.

The aryl group, the monovalent heterocyclic group or the substituted amino group as the substituent which the ring $R^1$ and the ring $R^2$ optionally have is preferably a group represented by the formula (D-A), (D-B) or (D-C), because the light emitting device of the present invention is more excellent in external quantum efficiency.

In the group represented by the formulae (D-A), (D-B) and (D-C), $m^{DA1}$, $m^{DA2}$, $m^{DA3}$, $m^{DA4}$, $m^{DA5}$, $m^{DA6}$ and $m^{DA7}$ represent usually an integer of 10 or less, preferably an integer of 5 or less, more preferably an integer of 2 or less, further preferably 0 or 1. It is preferable that $m^{DA2}$, $m^{DA3}$, $m^{DA4}$, $m^{DA5}$, $m^{DA6}$ and $m^{DA7}$ are the same integer.

In the group represented by the formulae (D-A), (D-B) and (D-C), $G^{DA}$ is preferably a group represented by the formulae (GDA-11) to (GDA-15), more preferably a group represented by the formula (GDA-11), (GDA-14) or (GDA-15).

[Chemical Formula 24]

(GDA-11)

(GDA-12)

(GDA-13)

(GDA-14)

(GDA-15)

[wherein,
\* represents a bond to $Ar^{DA1}$ in the formula (D-A), $Ar^{DA1}$ in the formula (D-B), $Ar^{DA2}$ in the formula (D-B) or $Ar^{DA3}$ in the formula (D-B).
\*\* represents a bond to $Ar^{DA2}$ in the formula (D-A), $Ar^{DA2}$ in the formula (D-B), $Ar^{DA4}$ in the formula (D-B) or $Ar^{DA6}$ in the formula (D-B).
\*\*\* represents a bond to $Ar^{DA3}$ in the formula (D-A), $Ar^{DA3}$ in the formula (D-B), $Ar^{DA5}$ in the formula (D-B) or $Ar^{DA7}$ in the formula (D-B).
$R^{DA}$ represents a hydrogen atom, an alkyl group, a cycloalkyl group, an alkoxy group, a cycloalkoxy group, an aryl group or a monovalent heterocyclic group, and these groups each optionally further have a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or a cycloalkyl group, and these groups each optionally have a substituent.

In the group represented by the formulae (D-A), (D-B) and (D-C), $Ar^{DA1}$, $Ar^{DA2}$, $Ar^{DA3}$, $Ar^{DA4}$, $Ar^{DA5}$, $Ar^{DA6}$ and $Ar^{DA7}$ represent preferably a phenylene group, a fluorenediyl group or a carbazolediyl group, more preferably a group represented by the formula (A-1) to (A-3), (A-8), (A-9), (AA-10), (AA-11), (AA-33) or (AA-34), further preferably a group represented by the formulae (ArDA-1) to (ArDA-5), particularly preferably a group represented by the formula (ArDA-1) to the formula (ArDA-3), especially preferably a group represented by the formula (ArDA-1).

[Chemical Formula 25]

(ArDA-1)

(ArDA-2)

(ArDA-3)

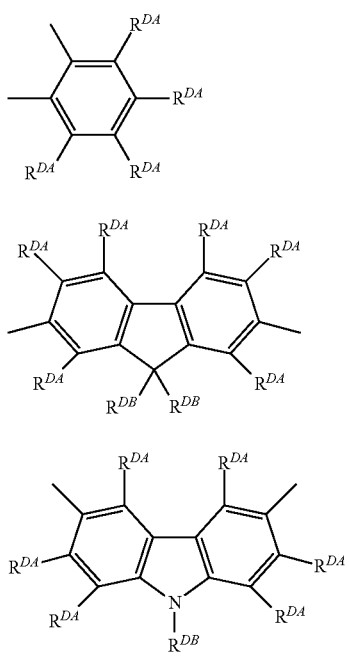

(ArDA-4)

(ArDA-5)

[wherein, $R^{DA}$ represents the same meaning as described above.

$R^{DB}$ represents a hydrogen atom, an alkyl group, a cycloalkyl group, an alkyl group or a monovalent heterocyclic group, and these groups each optionally have a substituent. When a plurality of $R^{DB}$ are present, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group, and these groups each optionally have a substituent.

In the group represented by the formulae (D-A), (D-B) and (D-C), $T^{DA}$ is preferably a group represented by the formulae (TDA-1) to (TDA-3), more preferably a group represented by the formula (TDA-1) or (TDA-3).

[Chemical Formula 26]

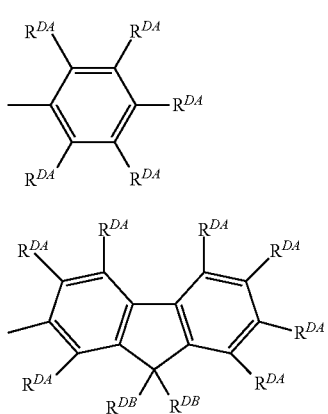

(TDA-1)

(TDA-2)

(TDA-3)

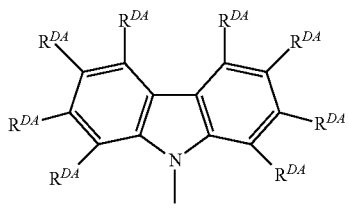

[wherein, $R^{DA}$ and $R^{DB}$ represent the same meaning as described above.]

The group represented by the formula (D-A) is preferably a group represented by the formulae (D-A1) to (D-A7), more preferably a group represented by the formulae (D-A1) or (D-A3) to (D-A7).

[Chemical Formula 27]

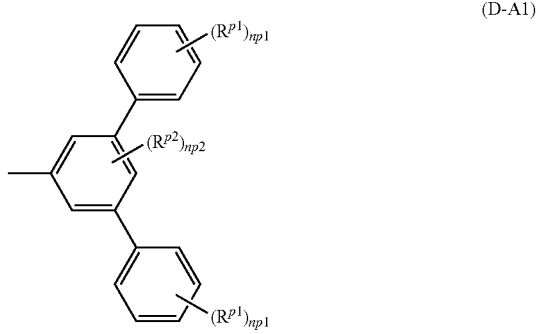

(D-A1)

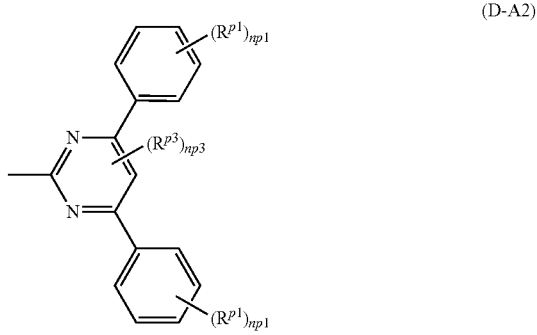

(D-A2)

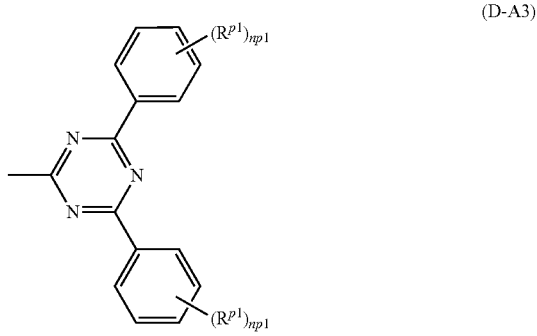

(D-A3)

(D-A4)
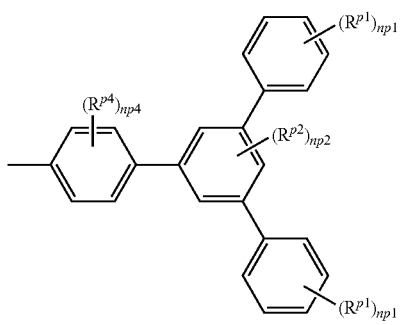

[Chemical Formula 28]

(D-A5)
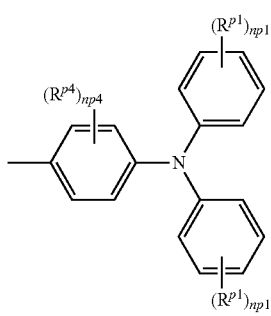

(D-A6)
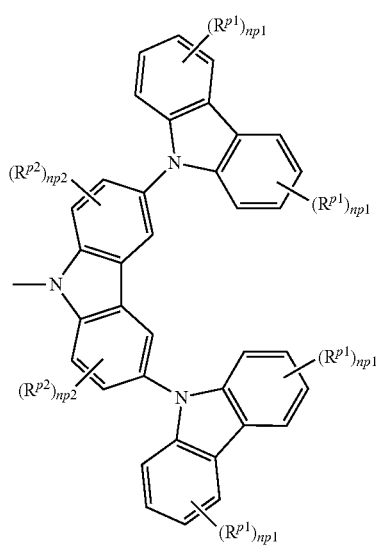

(D-A7)
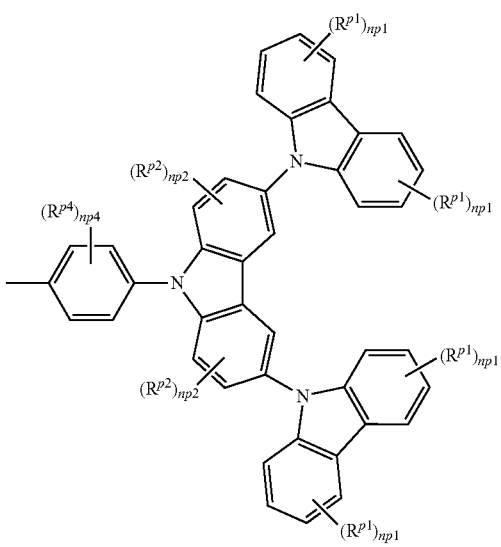

[wherein, $R^{p1}$, $R^{p2}$, $R^{p3}$ and $R^{p4}$ each independently represent an alkyl group, a cycloalkyl group, an alkoxy group, a cycloalkoxy group or a halogen atom. When a plurality of $R^{p1}$, $R^{p2}$ and $R^{p4}$ are present, they may be the same or different at each occurrence.

np1 represents an integer of 0 to 5, np2 represents an integer of 0 to 3, np3 represents 0 or 1, and np4 represents an integer of 0 to 4. The plurality of np1 may be the same or different. When a plurality of np2 are present, they may be the same or different.]

The group represented by the formula (D-B) is preferably a group represented by the formulae (D-B1) to (D-B4), more preferably a group represented by the formula (D-B1), (D-B2) or (D-B4), further preferably a group represented by the formula (D-B1) or (D-B2).

[Chemical Formula 29]

(D-B1)
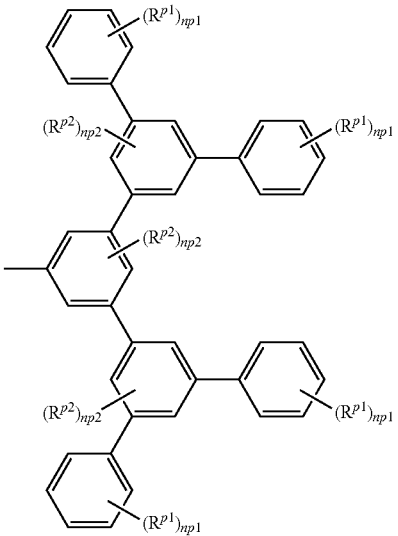

-continued (D-B2)

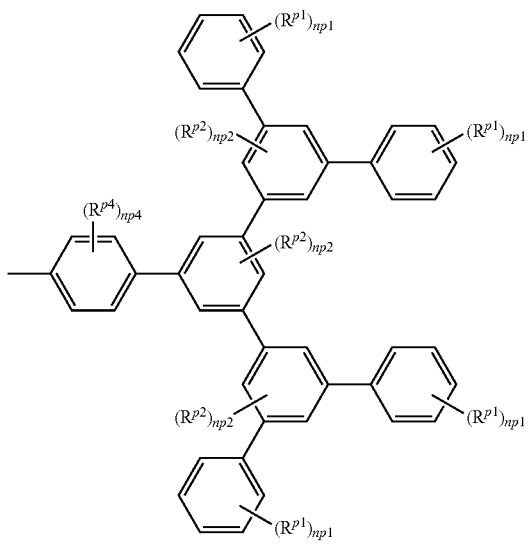

[Chemical Formula 30]

(D-B3)

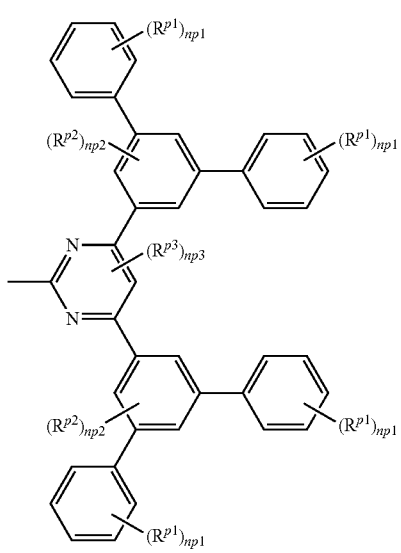

-continued (D-B4)

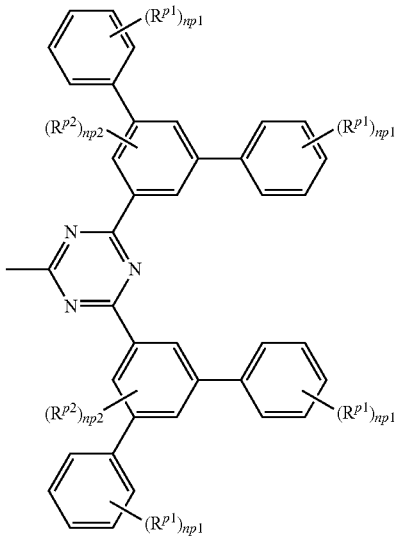

[wherein, $R^{p1}$, $R^{p2}$, $R^{p3}$ and $R^{p4}$ each independently represent an alkyl group, a cycloalkyl group, an alkoxy group, a cycloalkoxy group or a halogen atom. When a plurality of $R^{p1}$, $R^{p2}$ and $R^{p4}$ are present, they may be the same or different at each occurrence.

np1 represents an integer of 0 to 5, np2 represents an integer of 0 to 3, and np3 represents 0 or 1. The plurality of np1 and np2 may be the same or different at each occurrence.]

The group represented by the formula (D-C) is preferably a group represented by the formulae (D-C1) to (D-C4), more preferably a group represented by the formulae (D-C1) to (D-C3), further preferably a group represented by the formula (D-C1) or (D-C2).

[Chemical Formula 31]

(D-C1)

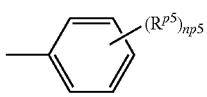

(D-C2)

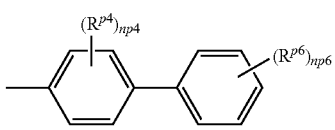

(D-C3)

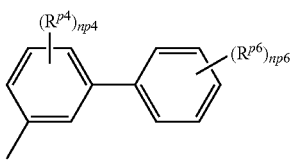

(D-C4)

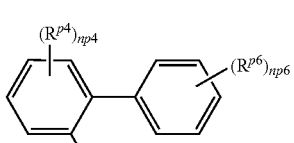

[wherein, $R^{p4}$, $R^{p5}$ and $R^{p6}$ each independently represent an alkyl group, a cycloalkyl group, an alkoxy group, a cycloalkoxy group or a halogen atom. When a plurality of $R^{p4}$, $R^{p5}$ and $R^{p6}$ are present, they may be the same or different at each occurrence.

np4 represents an integer of 0 to 4, np5 represents an integer of 0 to 5, and np6 represents an integer of 0 to 5.]

np1 is preferably 0 or 1, more preferably 1. np2 is preferably 0 or 1, more preferably 0. np3 is preferably 0. np4 is preferably an integer of 0 to 2. np5 is preferably an integer of 1 to 3. np6 is preferably an integer of 0 to 2.

$R^{p1}$, $R^{p2}$, $R^{p3}$, $R^{p4}$, $R^{p5}$ and $R^{p6}$ represent preferably an alkyl group or a cycloalkyl group, more preferably a methyl group, an ethyl group, an isopropyl group, a tert-butyl group, a hexyl group, a 2-ethylhexyl group, a cyclohexyl group, a methoxy group, a 2-ethylhexyloxy group, a tert-octyl group or a cyclohexyloxy group, further preferably a methyl group, an ethyl group, an isopropyl group, a tert-butyl group, a hexyl group, a 2-ethylhexyl group or a tert-octyl group.

The group represented by the formula (D-A) includes, for example, groups represented by the formulae (D-A-1) to (D-A-12).

[Chemical Formula 32]

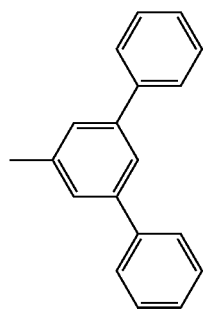
(D-A-1)

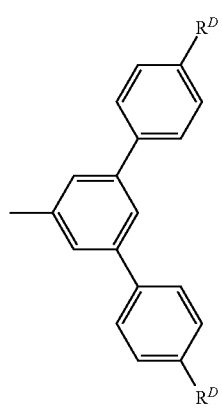
(D-A-2)

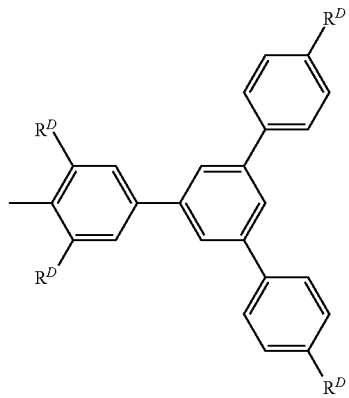
(D-A-3)

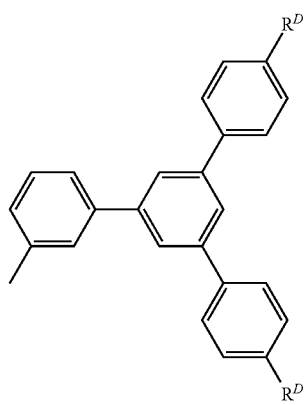
(D-A-4)

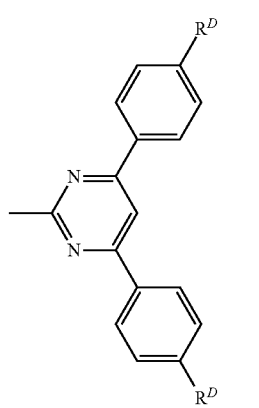
(D-A-5)

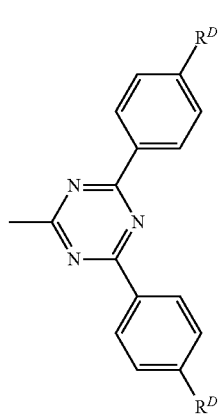
(D-A-6)

(D-A-7) 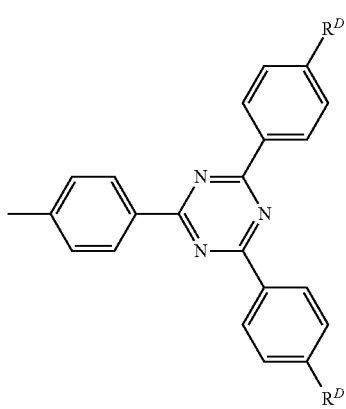

[Chemical Formula 33]

(D-A-8) 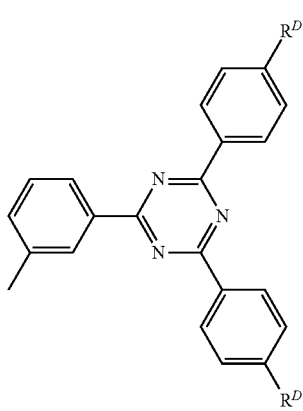

(D-A-9) 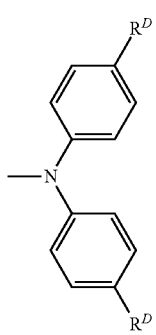

(D-A-10) 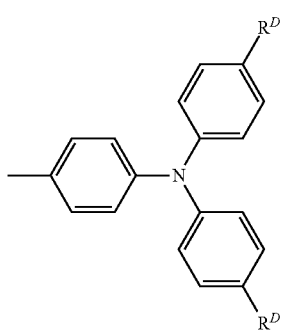

(D-A-11) 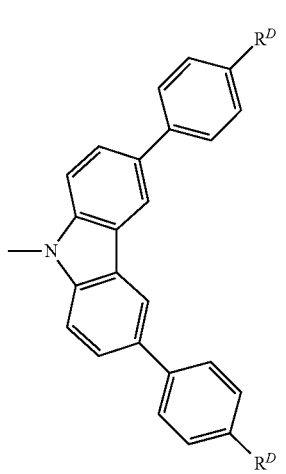

(D-A-12) 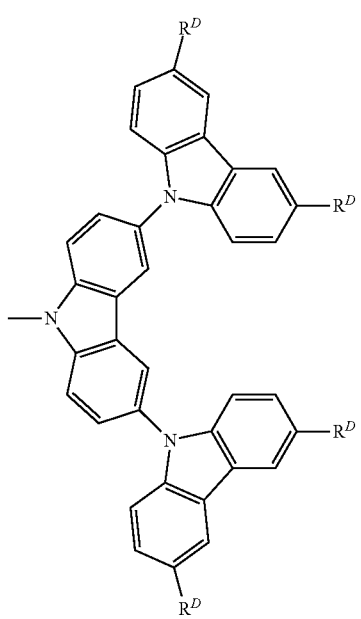

[wherein, $R^D$ represents a methyl group, an ethyl group, an isopropyl group, a tert-butyl group, a hexyl group, a 2-ethylhexyl group, a tert-octyl group, a cyclohexyl group, a methoxy group, a 2-ethylhexyloxy group or a cyclohexyloxy group. When a plurality of $R^D$ are present, they may be the same or different.]

The group represented by the formula (D-B) includes, for example, groups represented by the formulae (D-B-1) to (D-B-4).

[Chemical Formula 34]
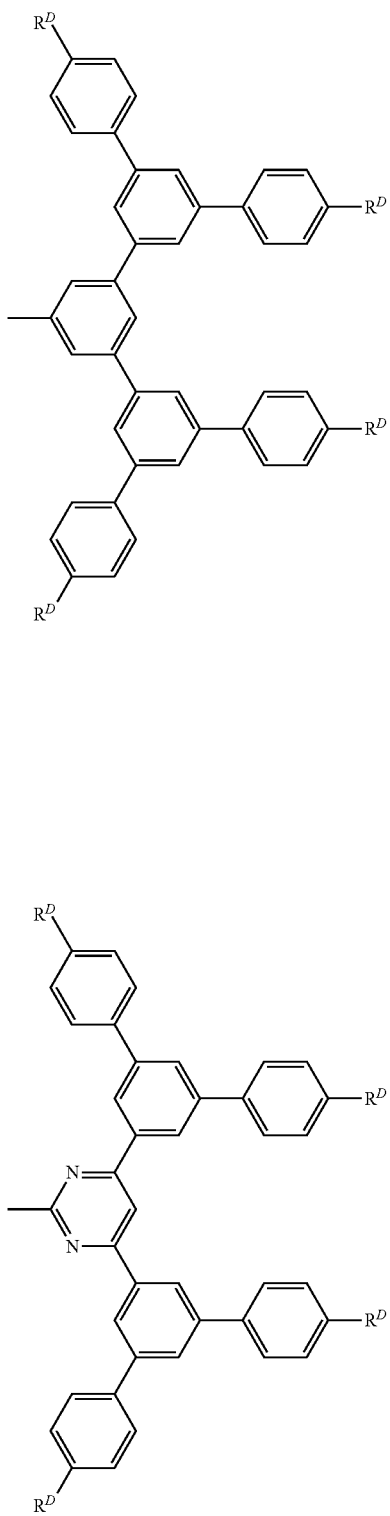
(D-B-1)
(D-B-2)
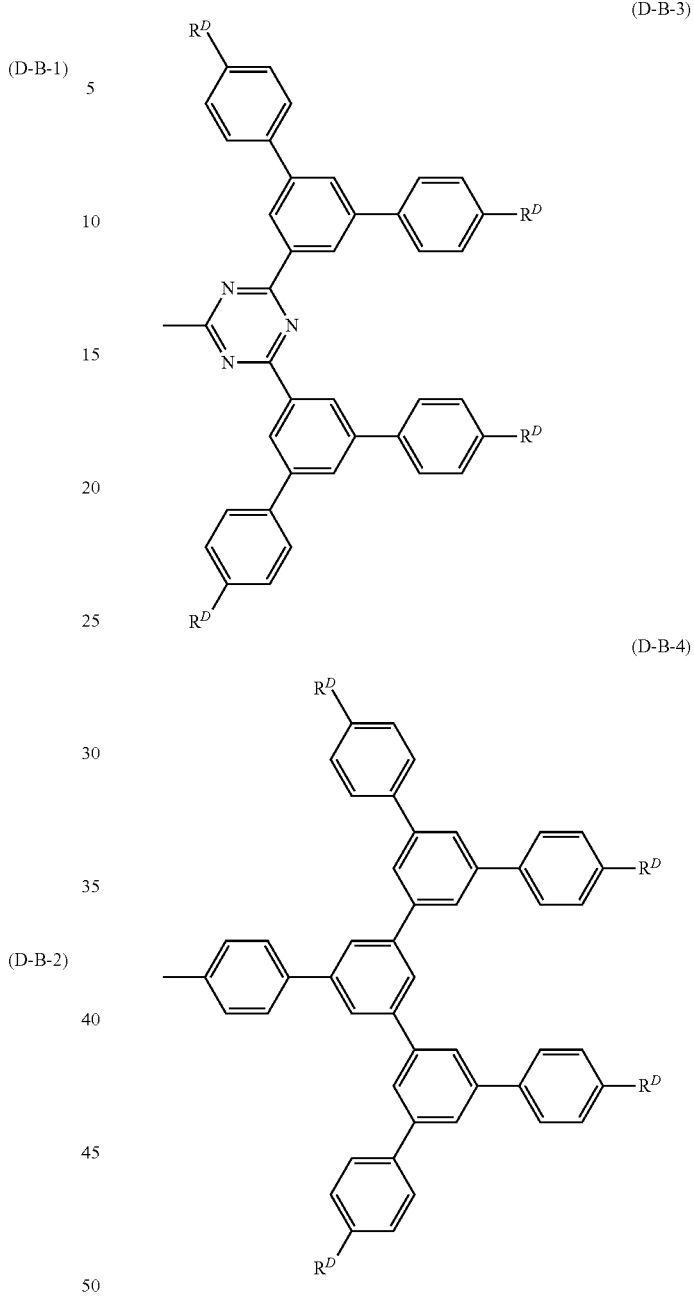
(D-B-3)
(D-B-4)
[wherein, $R^D$ represents the same meaning as described above.]
The group represented by the formula (D-C) includes, for example, groups represented by the formulae (D-C-1) to (D-C-13).
[Chemical Formula 35]
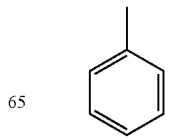
(D-C-1)

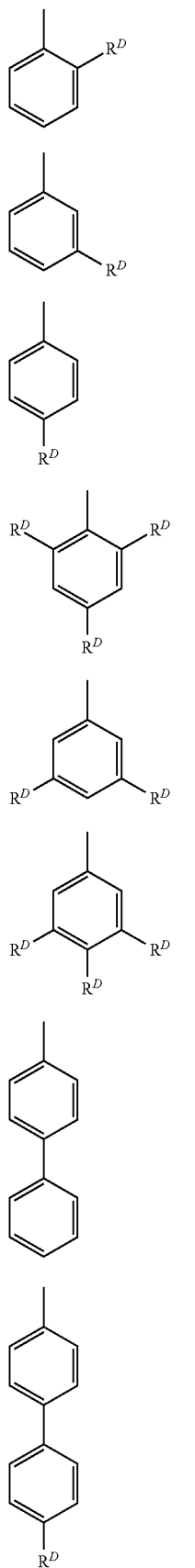
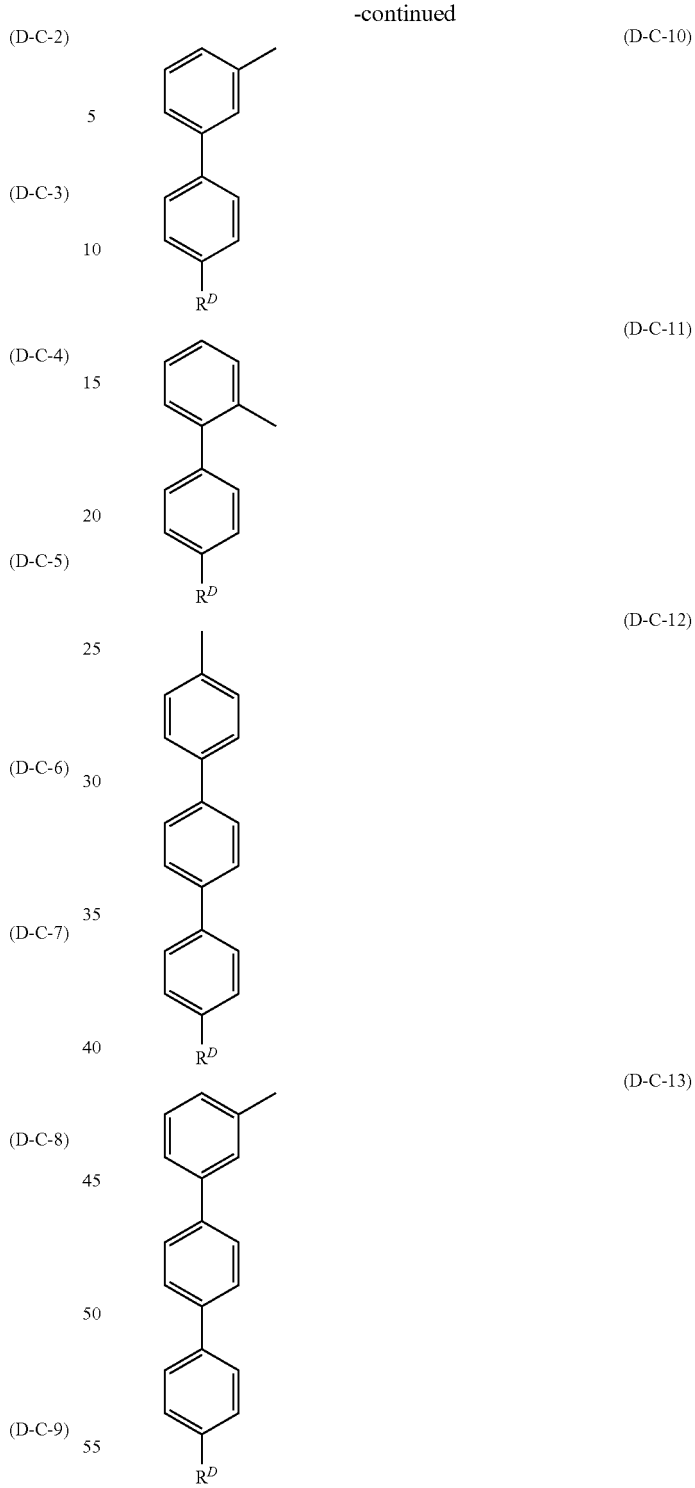

[wherein, $R^D$ represents the same meaning as described above.]

$R^D$ is preferably a methyl group, an ethyl group, an isopropyl group, a tert-butyl group, a hexyl group, a 2-ethylhexyl group or a tert-octyl group.

It is preferable that the at least one ring selected from the group consisting of the ring $R^1$ and the ring $R^2$ has a substituent, because the light emitting device of the present invention is more excellent in external quantum efficiency.

The substituent which the at least one ring selected from the group consisting of the ring $R^1$ and the ring $R^2$ has is further preferably an alkyl group or a group represented by the formulae (D-A) to (D-C), particularly preferably a group represented by the formulae (D-A) to (D-C). The group represented by the formulae (D-A) to (D-C) is preferably a group represented by the formulae (D-A1), (D-A3) to (D-A5), (D-B1), (D-B2), (D-B4) or (D-C1) to (D-C3), more preferably a group represented by the formulae (D-A1), (D-A3) to (D-A5), (D-B1), (D-C1) or (D-C2).

[Anionic Bidentate Ligand]

The anionic bidentate ligand represented by $A^1$-$G^1$-$A^2$ includes, for example, ligands represented by the following formulae.

[Chemical Formula 36]

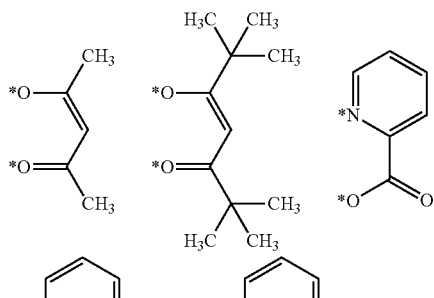

[Chemical Formula 37]

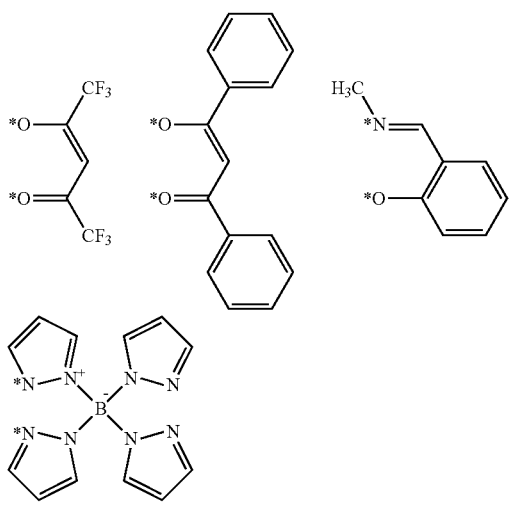

[wherein, * represents a site binding to an iridium atom.]

The iridium complex represented by the formula (A) is preferably an iridium complex represented by the formula (A-A) or an iridium complex represented by the formula (A-B), because the light emitting device of the present invention is more excellent in external quantum efficiency.

[Iridium Complex Represented by the Formula (A-A)]

When the ring $R^{1A}$ is a diazole ring, preferable is an imidazole ring in which $E^{11A}$ is a nitrogen atom or an imidazole ring in which $E^{12A}$ is a nitrogen atom, more preferable is an imidazole ring in which $E^{11A}$ is a nitrogen atom.

When the ring $R^{1A}$ is a triazole ring, preferable is a triazole ring in which $E^{11A}$ and $E^{12A}$ represent a nitrogen atom or a triazole ring in which $E^{11A}$ and $E^{13A}$ represent a nitrogen atom, more preferable is a triazole ring in which $E^{11A}$ and $E^{12A}$ represent a nitrogen atom.

The examples and the preferable range of the aryl group, the monovalent heterocyclic group and the substituted amino group represented by $R^{11A}$, $R^{12A}$, $R^{13A}$, $R^{21A}$, $R^{22A}$, $R^{23A}$ and $R^{24A}$ are the same as the examples and the preferable range of the aryl group, the monovalent heterocyclic group and the substituted amino group as the substituent which the ring $R^1$ and the ring $R^2$ optionally have, respectively.

The examples and the preferable range of the substituent which $R^{11A}$, $R^{12A}$, $R^{13A}$, $R^{21A}$, $R^{22A}$, $R^{23A}$ and $R^{24A}$ optionally have are the same as the examples and the preferable range of the substituent which the substituent which the ring $R^1$ and the ring $R^2$ optionally have further optionally has.

When $E^{11A}$ is a nitrogen atom and $R^{1A}$ is present, $R^{11A}$ is preferably an alkyl group, a cycloalkyl group, an aryl group or a monovalent heterocyclic group, more preferably an alkyl group, a cycloalkyl group or a group represented by the formulae (D-A) to (D-C), and these groups each optionally have a substituent. When $R^{11A}$ is a group represented by the formula (D-A) or (D-B) and $m^{DA1}$ is 0, it is preferable that $G^{DA}$ bonding to $E^{11A}$ is an aromatic hydrocarbon group or a heterocyclic group.

When $E^{11A}$ is a carbon atom, $R^{11A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, and these groups each optionally have a substituent.

When $E^{12A}$ is a nitrogen atom and $R^{12A}$ is present, $R^{12A}$ is preferably an alkyl group, a cycloalkyl group, an aryl group or a monovalent heterocyclic group, more preferably an alkyl group, a cycloalkyl group or a group represented by the formulae (D-A) to (D-C), and these groups each optionally have a substituent. When $R^{12A}$ is a group represented by the formula (D-A) or (D-B) and $m^{DA1}$ is 0, it is preferable that $G^{DA}$ bonding to $E^{12A}$ is an aromatic hydrocarbon group or a heterocyclic group.

When $E^{12A}$ is a carbon atom, $R^{12A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, and these groups each optionally have a substituent.

When $E^{13A}$ is a nitrogen atom and $R^{13A}$ is present, $R^{13A}$ is preferably an alkyl group, a cycloalkyl group, an aryl group or a monovalent heterocyclic group, more preferably an alkyl group, a cycloalkyl group or a group represented by the formulae (D-A) to (D-C), and these groups each optionally have a substituent. When $R^{13A}$ is a group represented by the formulae (D-A) or (D-B) and $m^{DA1}$ is 0, it is preferable that $G^{DA}$ bonding to $E^{13A}$ is an aromatic hydrocarbon group or a heterocyclic group.

When $E^{13A}$ is a carbon atom, $R^{13A}$ is preferably a hydrogen atom, an alkyl group, a cycloalkyl group, an aryl group, a monovalent heterocyclic group or a substituted amino group, more preferably a hydrogen atom, an alkyl group, a cycloalkyl group or an aryl group, further preferably a hydrogen atom, an alkyl group or a cycloalkyl group, and these groups each optionally have a substituent.

It is preferable that the at least one ring selected from the group consisting of the ring $R^{1A}$ and the ring $R^{2A}$ has a substituent, because the light emitting device of the present invention is more excellent in external quantum efficiency.

When the ring $R^{1A}$ has a group represented by the formulae (D-A) to (D-C), it is preferable that $R^{11A}$ or $R^{12A}$ is a group represented by the formulae (D-A) to (D-C), it is more preferable that $R^{11A}$ is a group represented by the formulae (D-A) to (D-C).

When the ring $R^{2A}$ is a pyridine ring, preferable is a pyridine ring in which $E^{21A}$ is a nitrogen atom, a pyridine ring in which $E^{22A}$ is a nitrogen atom or a pyridine ring in which $E^{23A}$ is a nitrogen atom, more preferable is a pyridine ring in which $E^{22A}$ is a nitrogen atom.

When the ring $R^{2A}$ is a pyrimidine ring, preferable is a pyrimidine ring in which $E^{21A}$ and $E^{23A}$ represent a nitrogen atom or a pyrimidine ring in which $E^{22A}$ and $E^{24A}$ represent a nitrogen atom, more preferable is a pyrimidine ring in which $E^{22A}$ and $E^{24A}$ represent a nitrogen atom.

The ring $R^{2A}$ is preferably a benzene ring.

$R^{21A}$, $R^{22A}$, $R^{23A}$ and $R^{24A}$ represent preferably a hydrogen atom, an alkyl group, a cycloalkyl group, an alkoxy group, a cycloalkoxy group, a halogen atom, an aryl group, a monovalent heterocyclic group or a substituted amino group, more preferably a hydrogen atom, an alkyl group, a cycloalkyl group or a group represented by the formulae (D-A) to (D-C), further preferably a hydrogen atom or a group represented by the formulae (D-A) to (D-C), and these groups each optionally have a substituent.

When the ring $R^{2A}$ has a group represented by the formulae (D-A) to (D-C), it is preferable that $R^{22A}$ or $R^{23A}$ is a group represented by the formulae (D-A) to (D-C), it is more preferable that $R^{22A}$ is a group represented by the formulae (D-A) to (D-C).

The iridium complex represented by the formula (A-A) is preferably an iridium complex represented by the formula (A-A1), an iridium complex represented by the formula (A-A2), an iridium complex represented by the formula (A-A3) or an iridium complex represented by the formula (A-A4), more preferably an iridium complex represented by the formula (A-A1) or an iridium complex represented by the formula (A-A3), because the light emitting device of the present invention is further excellent in external quantum efficiency.

[Chemical Formula 38]

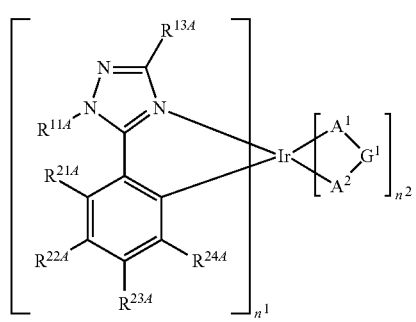
(A-A1)

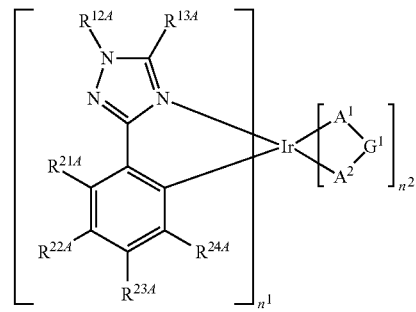
(A-A2)

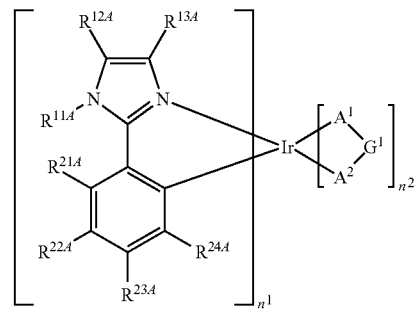
(A-A3)

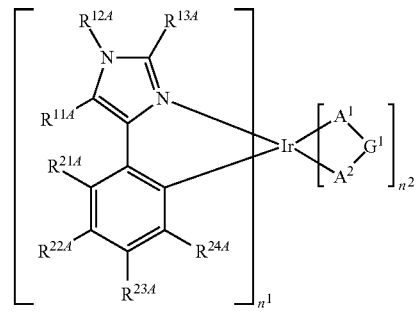
(A-A4)

[wherein, $n^1$, $n^2$, $R^{11A}$, $R^{12A}$, $R^{13A}$, $R^{21A}$, $R^{22A}$, $R^{23A}$, $R^{24A}$ and $A^1$-$G^1$-$A^2$ represent the same meaning as described above.]

[Iridium Complex Represented by the Formula (A-B)]

When the ring $R^{1B}$ is a pyrimidine ring, preferable is a pyrimidine ring in which $E^{11B}$ is a nitrogen atom.

The examples and the preferable range of the aryl group, the monovalent heterocyclic group and the substituted amino group represented by $R^{11B}$, $R^{12B}$, $R^{13B}$, $R^{14B}$, $R^{21B}$, $R^{22B}$, $R^{23B}$ and $R^{24B}$ are the same as the examples and the preferable range of the aryl group, the monovalent heterocyclic group and the substituted amino group as the substituent which the ring $R^1$ and the ring $R^2$ optionally have, respectively.

The examples and the preferable range of the substituent which $R^{11B}$, $R^{12B}$, $R^{13B}$, $R^{14B}$, $R^{21B}$, $R^{22B}$, $R^{23B}$ and $R^{24B}$ optionally have are the same as the examples and the preferable range of the substituent which the substituent which the ring $R^1$ and the ring $R^2$ optionally have further optionally has.

$R^{11B}$, $R^{12B}$, $R^{13B}$ and $R^{14B}$ represent preferably a hydrogen atom, an alkyl group, a cycloalkyl group, an aryl group, a monovalent heterocyclic group or a substituted amino group, more preferably a hydrogen atom, an alkyl group, a cycloalkyl group or a group represented by the formulae (D-A) to (D-C), further preferably a hydrogen atom or a group represented by the formulae (D-A) to (D-C), and these groups each optionally have a substituent.

It is preferable that the at least one ring selected from the group consisting of the ring $R^{1B}$ and the ring $R^{2B}$ has a substituent, because the light emitting device of the present invention is more excellent in external quantum efficiency.

When the ring $R^{1B}$ has a group represented by the formulae (D-A) to (D-C), it is preferable that $R^{11B}$, $R^{12B}$ or $R^{13B}$ is a group represented by the formulae (D-A) to (D-C), it is more preferable that $R^{12B}$ or $R^{13B}$ is a group represented by the formulae (D-A) to (D-C), it is further preferable that $R^{13B}$ is a group represented by the formulae (D-A) to (D-C).

When the ring $R^{2B}$ is a pyridine ring, preferable is a pyridine ring in which $E^{21B}$ is a nitrogen atom, a pyridine ring in which $E^{22B}$ is a nitrogen atom or a pyridine ring in which $E^{23B}$ is a nitrogen atom, more preferable is a pyridine ring in which $E^{22B}$ is a nitrogen atom.

When the ring $R^{2B}$ is a pyrimidine ring, preferable is a pyrimidine ring in which $E^{21B}$ and $E^{23B}$ represent a nitrogen atom or a pyrimidine ring in which $E^{22B}$ and $E^{24B}$ represent a nitrogen atom, more preferable is a pyrimidine ring in which $E^{22B}$ and $E^{24}$ represent a nitrogen atom.

The ring $R^{2B}$ is preferably a benzene ring.

$R^{21B}$, $R^{22B}$, $R^{23B}$ and $R^{24B}$ represent preferably a hydrogen atom, an alkyl group, a cycloalkyl group, an aryl group, a monovalent heterocyclic group or a substituted amino group, more preferably a hydrogen atom, an alkyl group, a cycloalkyl group or a group represented by the formulae (D-A) to (D-C), further preferably a hydrogen atom or a group represented by the formulae (D-A) to (D-C), and these groups each optionally have a substituent.

When the ring $R^{2B}$ has a group represented by the formulae (D-A) to (D-C), it is preferable that $R^{22B}$ or $R^{23B}$ is a group represented by the formulae (D-A) to (D-C), it is more preferable that $R^{22B}$ is a group represented by the formulae (D-A) to (D-C).

The iridium complex represented by the formula (A-B) is preferably an iridium complex represented by the formula (A-B1), an iridium complex represented by the formula (A-B2), an iridium complex represented by the formula (A-B3), an iridium complex represented by the formula (A-B4) or an iridium complex represented by the formula (A-B5), more preferably an iridium complex represented by the formula (A-B1), an iridium complex represented by the formula (A-B2) or an iridium complex represented by the formula (A-B3).

[Chemical Formula 39]

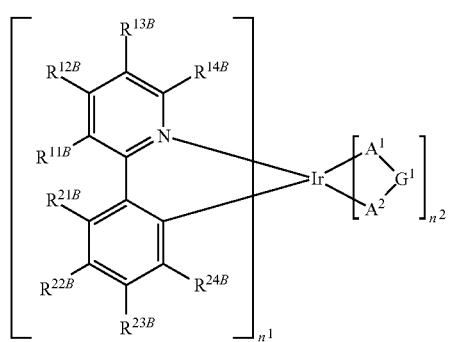
(A-B1)

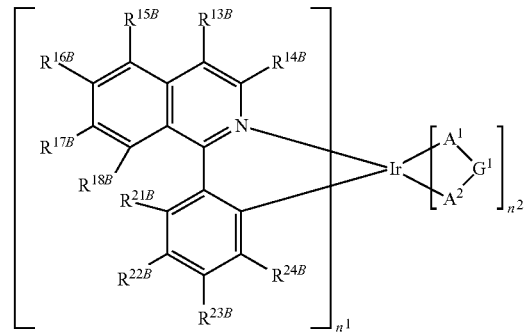
(A-B2)

[Chemical Formula 40]

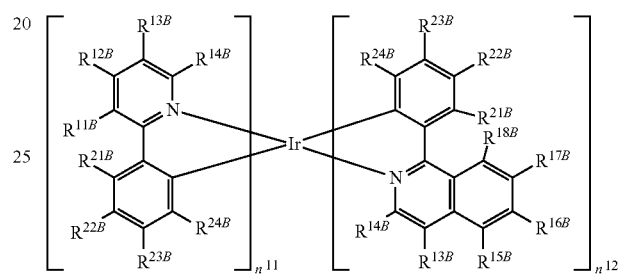
(A-B3)

[Chemical Formula 41]

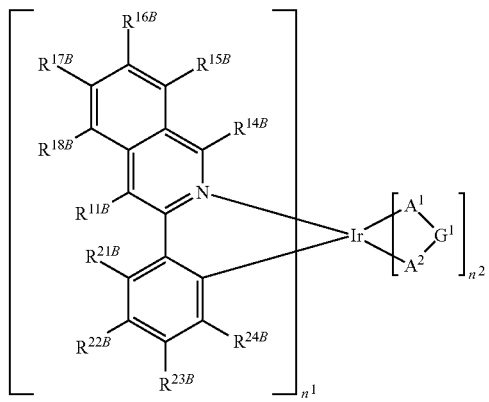
(A-B4)

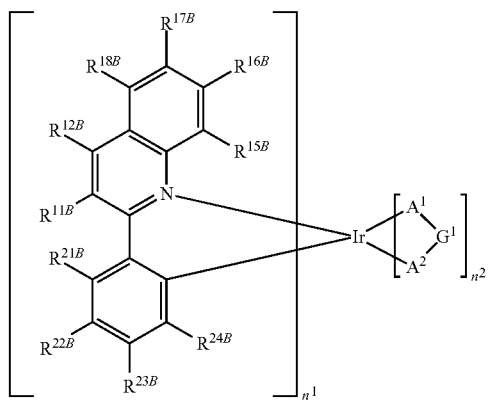
(A-B5)

[wherein, $n^1$, $n^2$, $A^1$-$G^1$-$A^1$, $R^{11B}$, $R^{12B}$, $R^{13B}$, $R^{14B}$, $R^{21B}$, $R^{22B}$, $R^{23B}$, and $R^{24B}$ represent the same meaning as described above.

$n^{11}$ and $n^{12}$ each independently represent an integer of 1 or more, and $n^{11}+n^{12}$ is 3.

$R^{15B}$, $R^{16B}$, $R^{17B}$ and $R^{18B}$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and these groups each optionally have a substituent. When a plurality of $R^{15B}$, $R^{16B}$, $R^{17B}$ and $R^{18B}$ are present, they may be the same or different at each occurrence. $R^{15B}$ and $R^{16B}$, $R^{16B}$ and $R^{17B}$, and $R^{17B}$ and $R^{18B}$ each may be combined together to form a ring together with the atoms to which they are attached.]

$R^{15B}$, $R^{16B}$, $R^{17B}$ and $R^{18B}$ represent preferably a hydrogen atom, an alkyl group, a cycloalkyl group, an alkoxy group, a cycloalkoxy group, an aryl group, a monovalent heterocyclic group or a substituted amino group, more preferably a hydrogen atom, an alkyl group, a cycloalkyl group or an aryl group, further preferably a hydrogen atom or an alkyl group, particularly preferably a hydrogen atom, and these groups each optionally have a substituent.

The iridium complex (A) includes, for example, iridium complexes represented by the formulae (A-A-1) to (A-A-20) and (A-B-1) to (A-B-26).

[Chemical Formula 42]

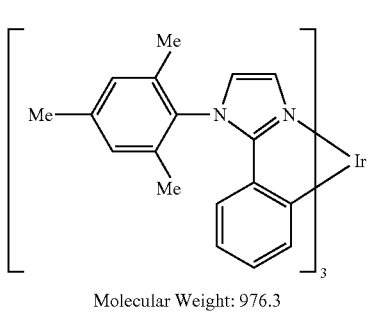

Iridium complex(A-A-1)

Molecular Weight: 976.3

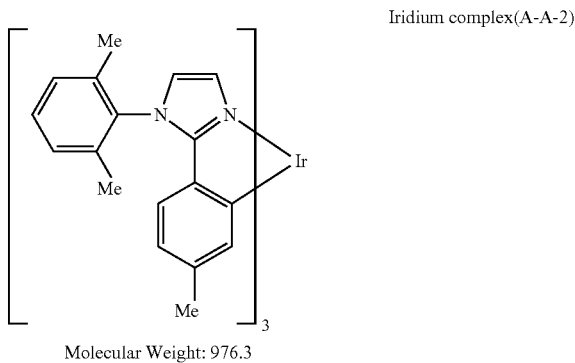

Iridium complex(A-A-2)

Molecular Weight: 976.3

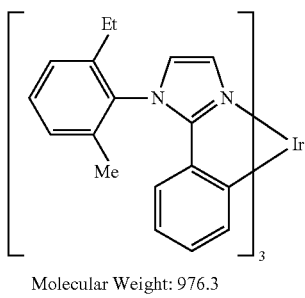

Iridium complex(A-A-3)

Molecular Weight: 976.3

[Chemical Formula 43]

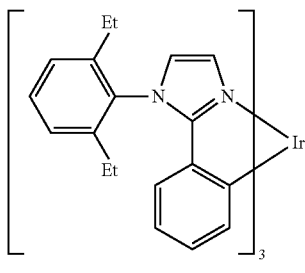

Iridium complex(A-A-4)

Molecular Weight: 1018.3

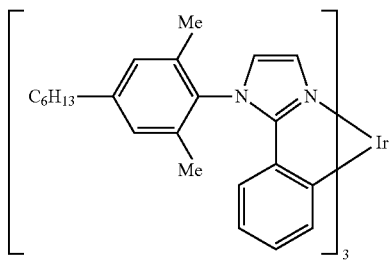

Iridium complex(A-A-5)

Molecular Weight: 1186.7

Iridium complex(A-A-6)
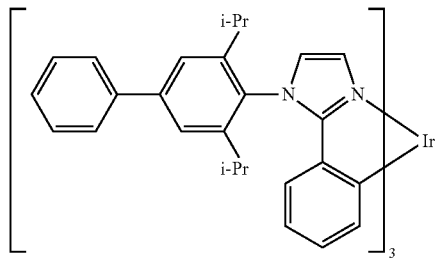
Molecular Weight: 1330.8
[Chemical Formula 44]
Iridium complex(A-A-7)
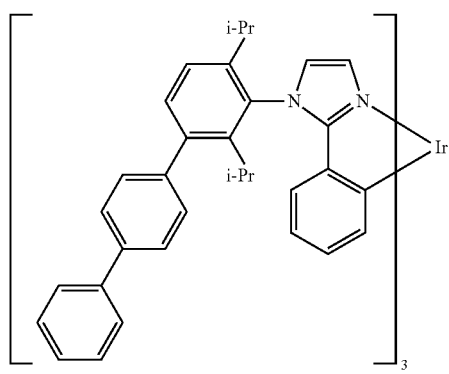
Molecular Weight: 1559.1
Iridium complex(A-A-8)
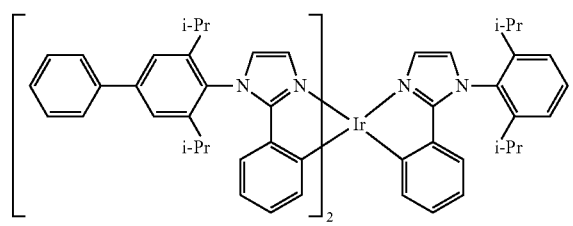
Molecular Weight: 1254.7
[Chemical Formula 45]
Iridium complex(A-A-9)
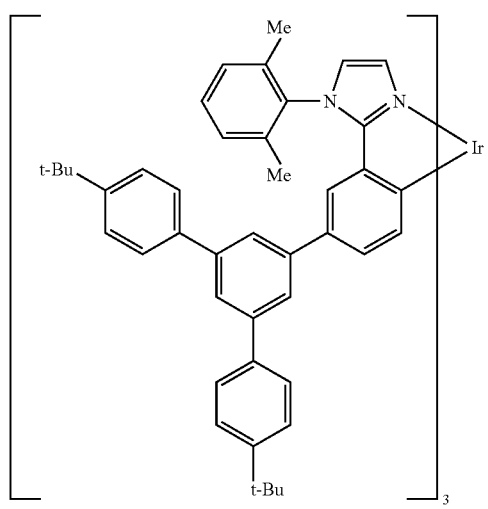
Molecular Weight: 1955.7
Iridium complex(A-A-10)
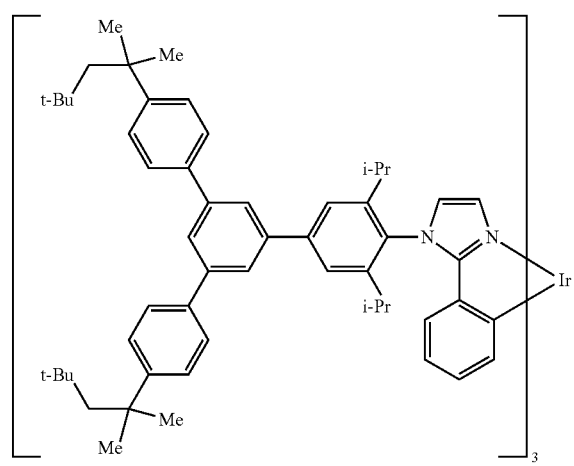
Molecular Weight: 2460.7

[Chemical Formula 46]
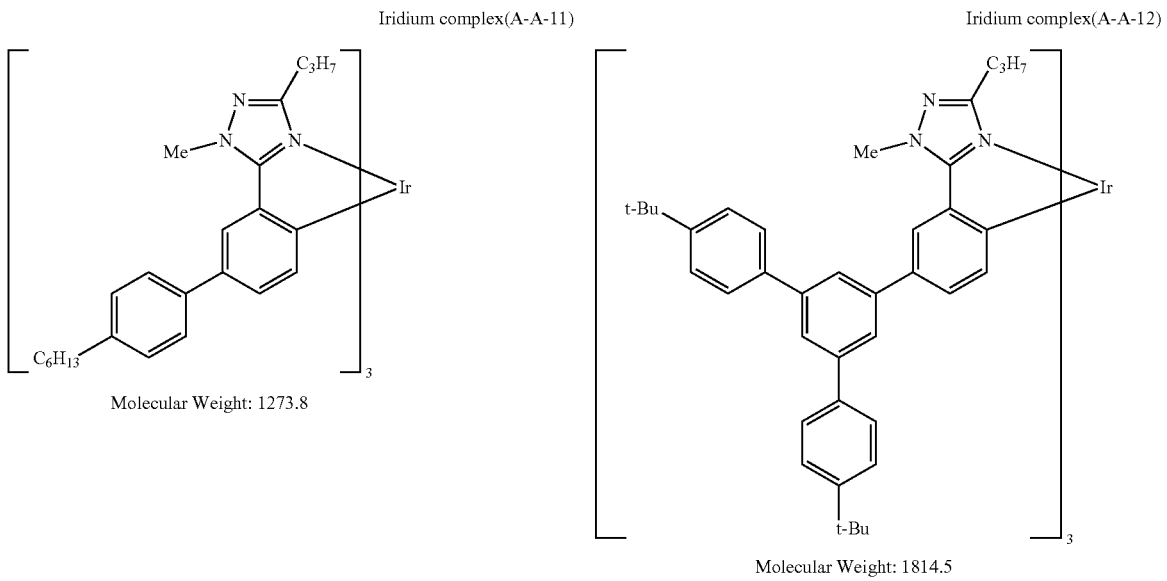
Iridium complex(A-A-11)
Molecular Weight: 1273.8
Iridium complex(A-A-12)
Molecular Weight: 1814.5
[Chemical Formula 47]
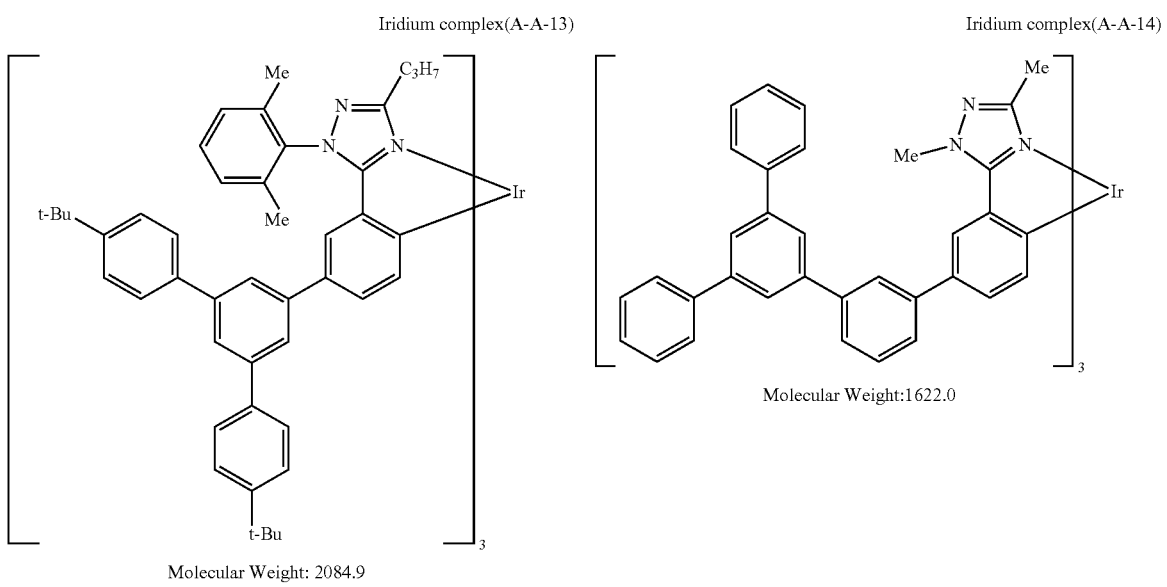
Iridium complex(A-A-13)
Molecular Weight: 2084.9
Iridium complex(A-A-14)
Molecular Weight: 1622.0

[Chemical Formula 48]
Iridium complex(A-A-15)
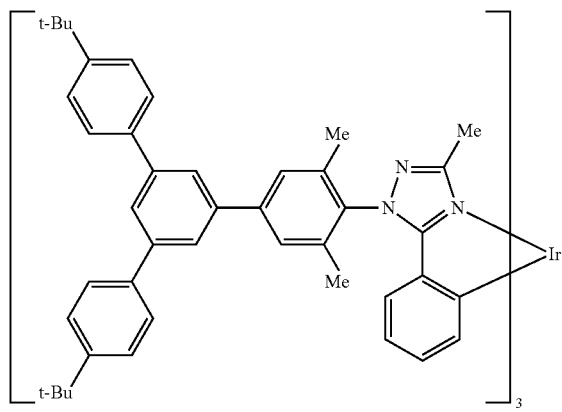
Molecular Weight: 2000.8
Iridium complex(A-A-16)
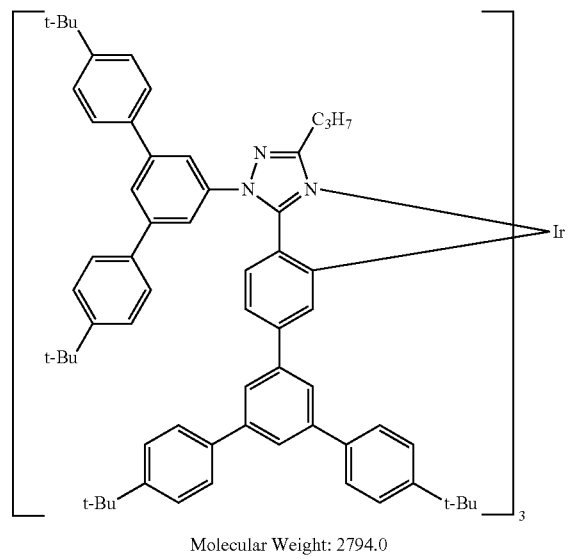
Molecular Weight: 2794.0
[Chemical Formula 49]
Iridium complex(A-A-17)
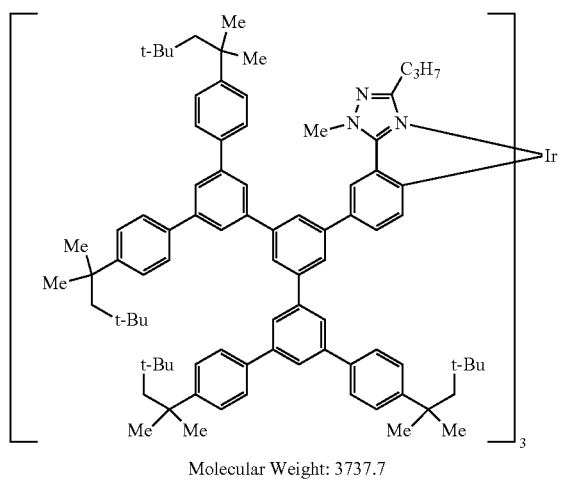
Molecular Weight: 3737.7
Iridium complex(A-A-18)
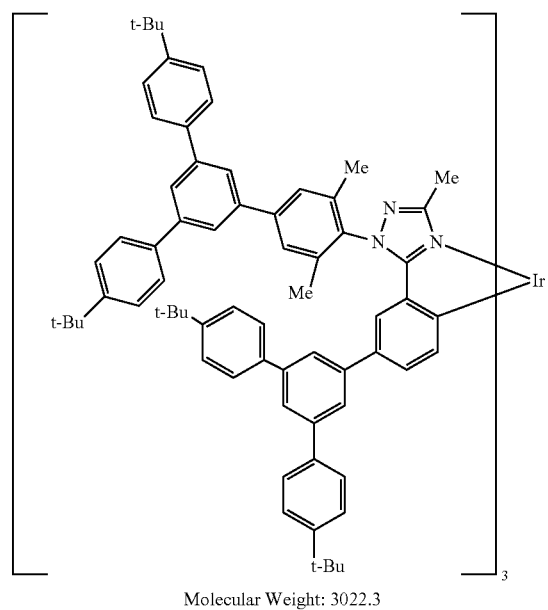
Molecular Weight: 3022.3

[Chemical Formula 50]
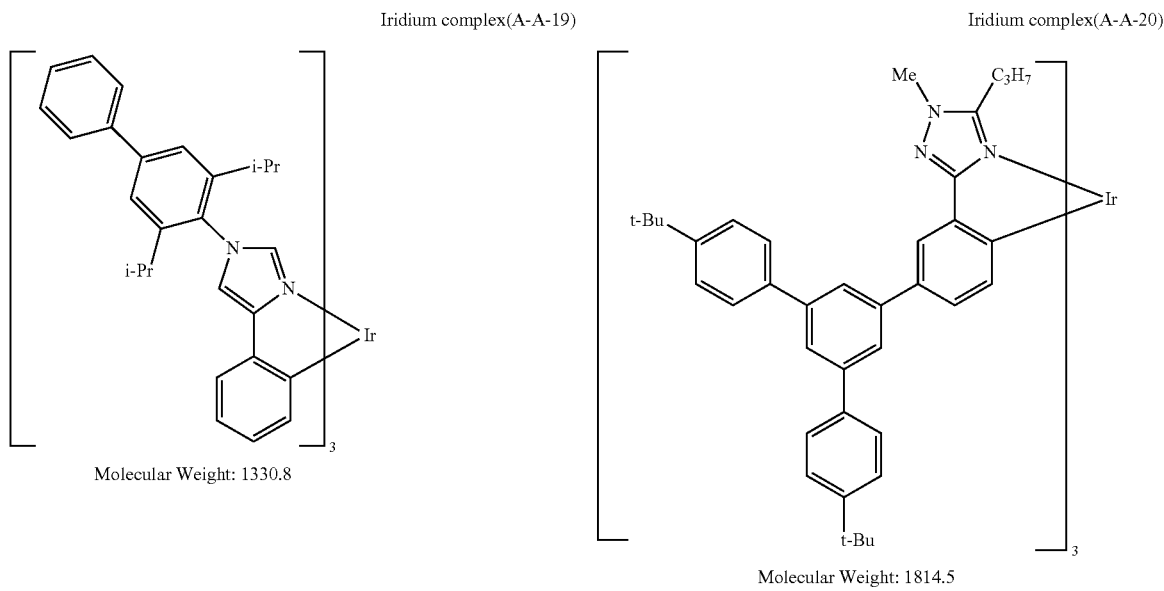
Iridium complex(A-A-19) Molecular Weight: 1330.8
Iridium complex(A-A-20) Molecular Weight: 1814.5
[Chemical Formula 51]
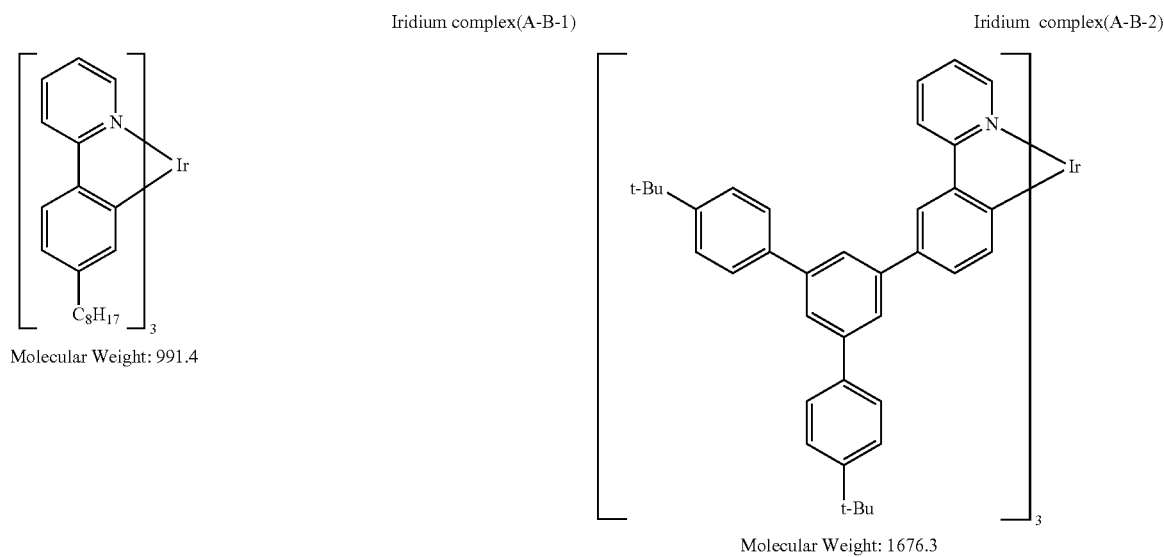
Iridium complex(A-B-1) Molecular Weight: 991.4
Iridium complex(A-B-2) Molecular Weight: 1676.3

-continued
Iridium complex(A-B-3)
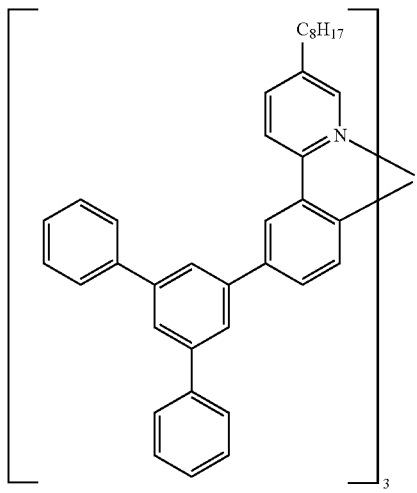
Molecular Weight: 1676.3
[Chemical Formula 52]
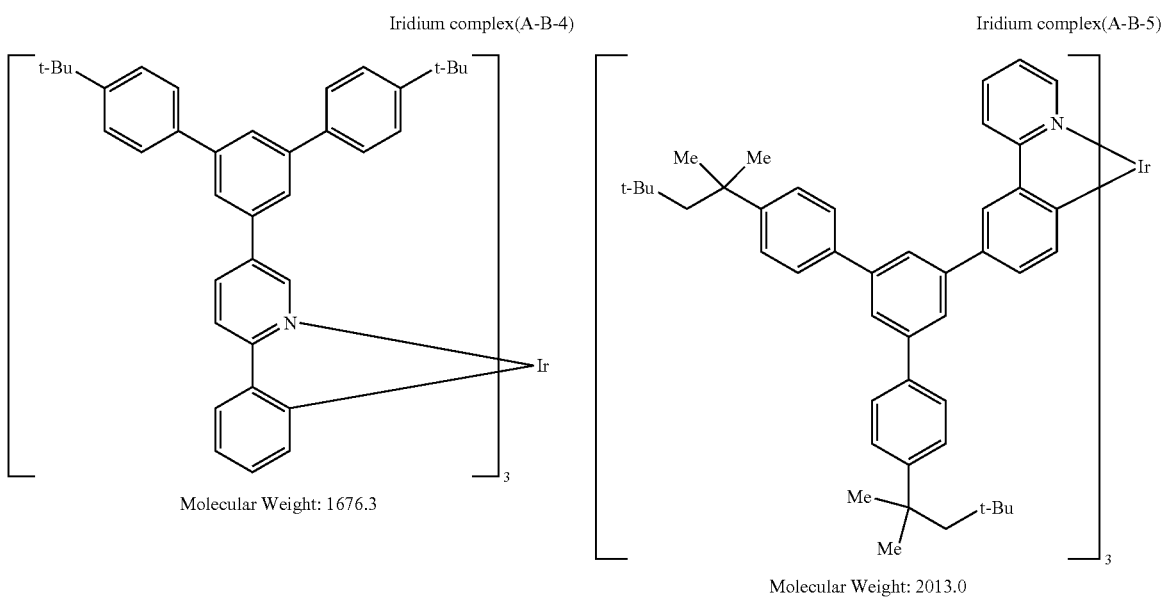
Iridium complex(A-B-4)  Iridium complex(A-B-5)
Molecular Weight: 1676.3  Molecular Weight: 2013.0
Iridium complex(A-B-6)
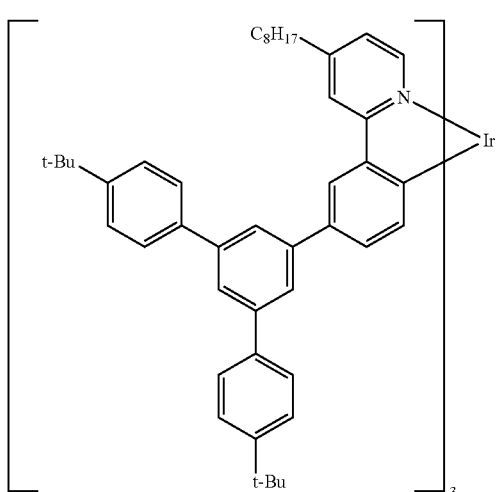
Molecular Weight: 2013.0

-continued
[Chemical Formula 53]
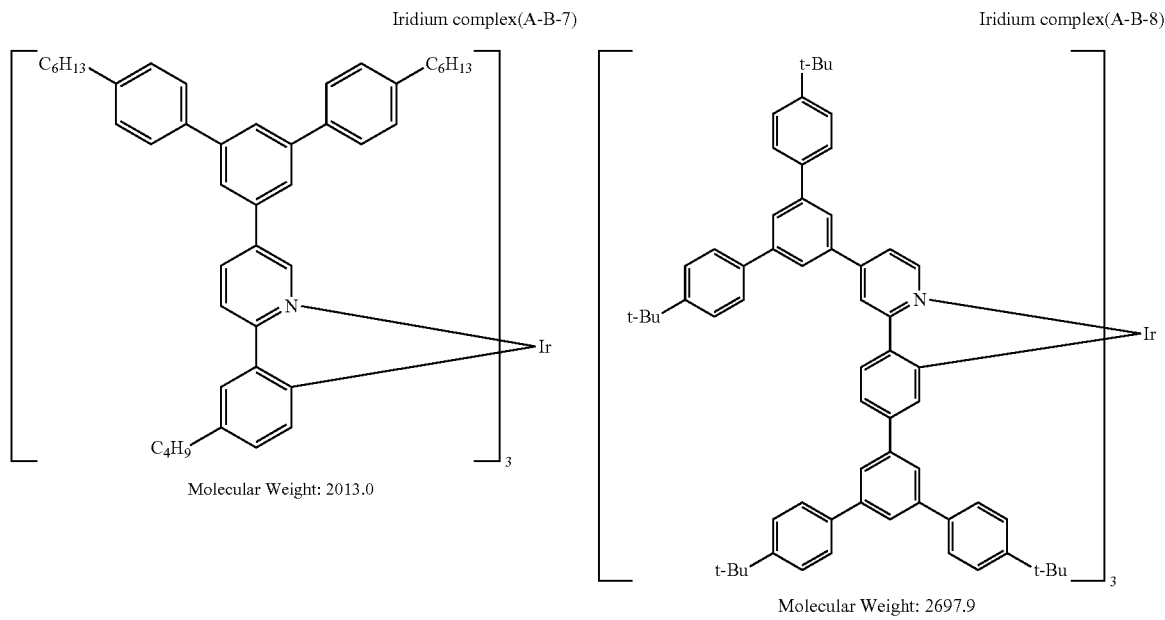
Iridium complex(A-B-7) Molecular Weight: 2013.0
Iridium complex(A-B-8) Molecular Weight: 2697.9
[Chemical Formula 54]
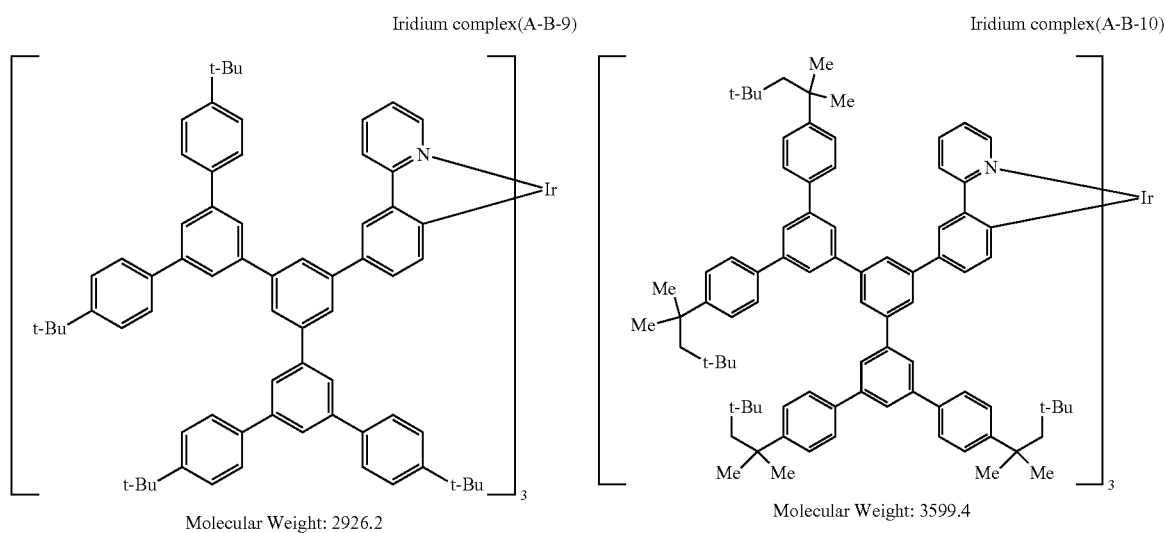
Iridium complex(A-B-9) Molecular Weight: 2926.2
Iridium complex(A-B-10) Molecular Weight: 3599.4
[Chemical Formula 55]
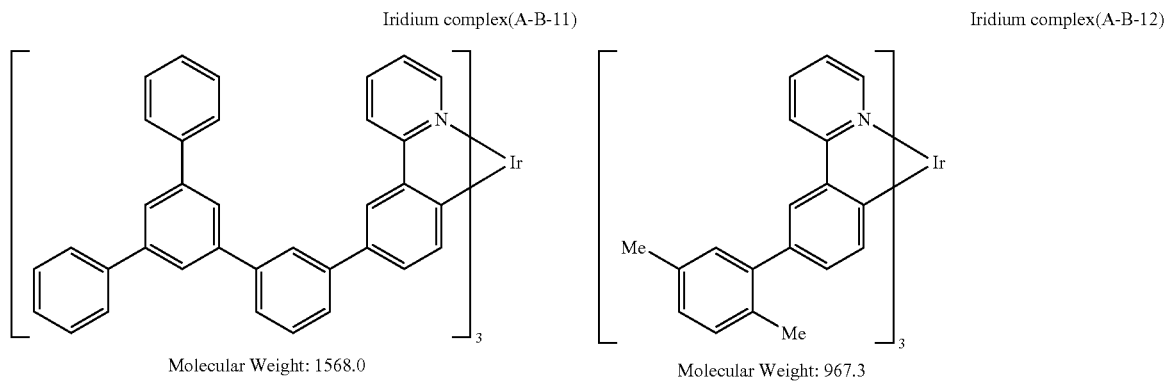
Iridium complex(A-B-11) Molecular Weight: 1568.0
Iridium complex(A-B-12) Molecular Weight: 967.3

Iridium complex(A-B-13)
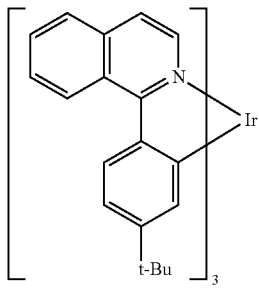
Molecular Weight: 973.3
[Chemical Formula 56]
Iridium complex(A-B-14)
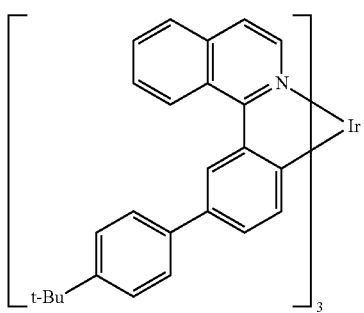
Molecular Weight: 1201.6
Iridium complex(A-B-15)
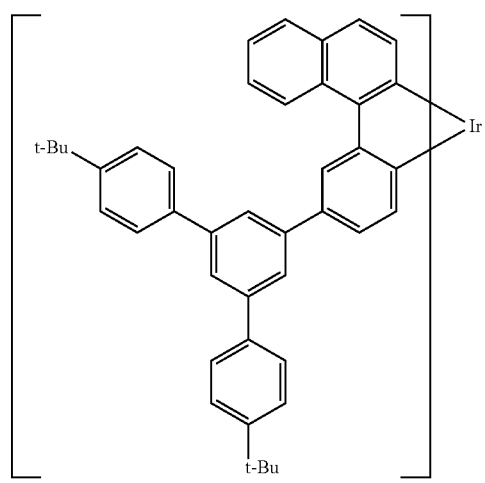
Molecular Weight: 1826.5
Iridium complex(A-B-16)
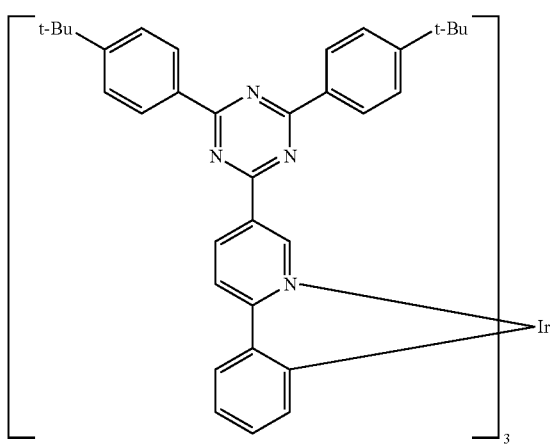
Molecular Weight: 1685.2

[Chemical Formula 57]
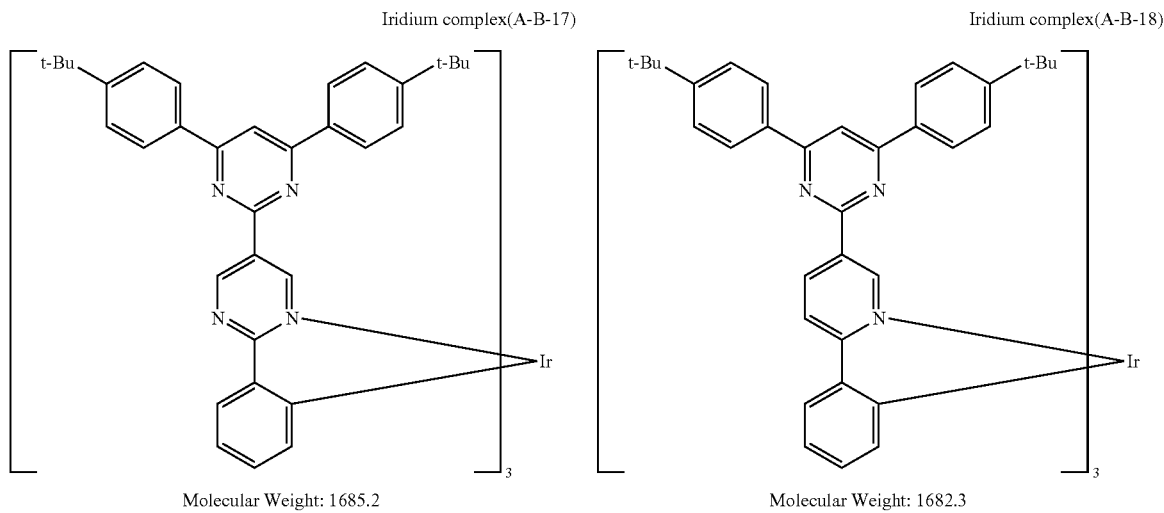
Iridium complex(A-B-17)
Molecular Weight: 1685.2
Iridium complex(A-B-18)
Molecular Weight: 1682.3
[Chemical Formula 58]
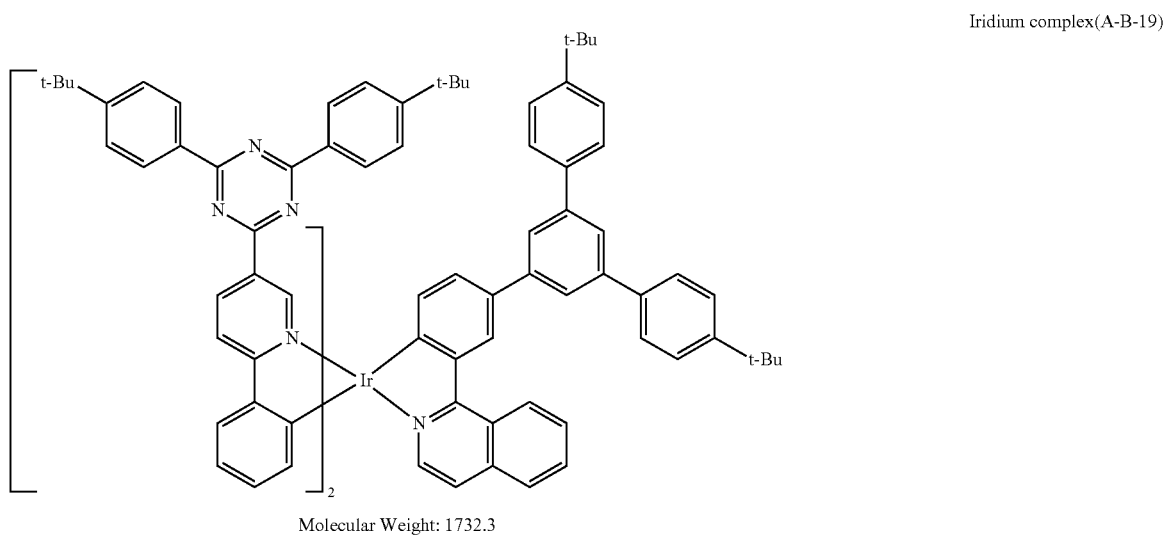
Iridium complex(A-B-19)
Molecular Weight: 1732.3

Iridium complex(A-B-20)
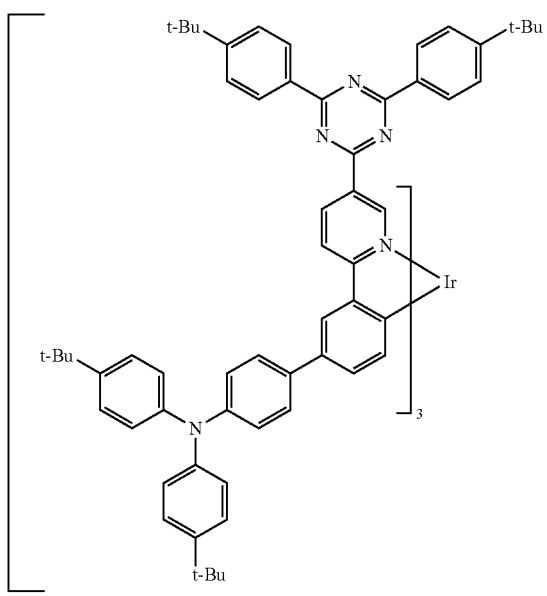
Molecular Weight: 2751.8
[Chemical Formula 59]
Iridium complex(A-B-21)
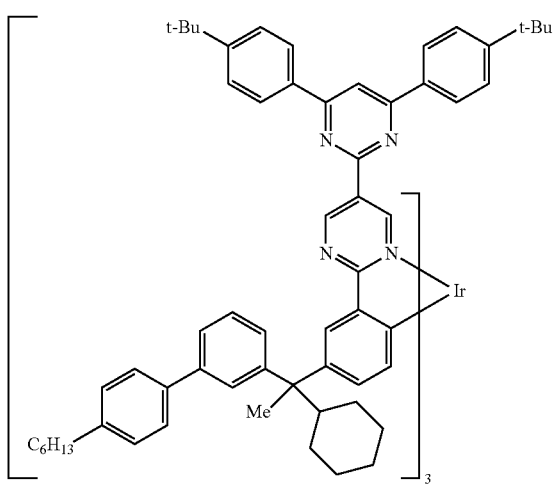
Molecular Weight: 2724.9
Iridium complex(A-B-22)
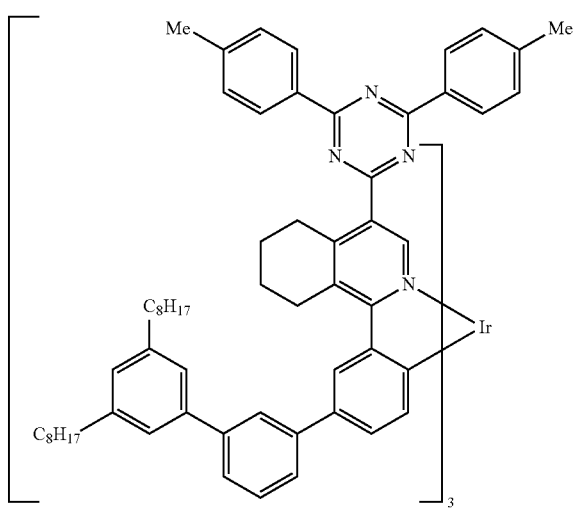
Molecular Weight: 2724.9

[Chemical Formula 60]

Iridium complex(A-B-23)

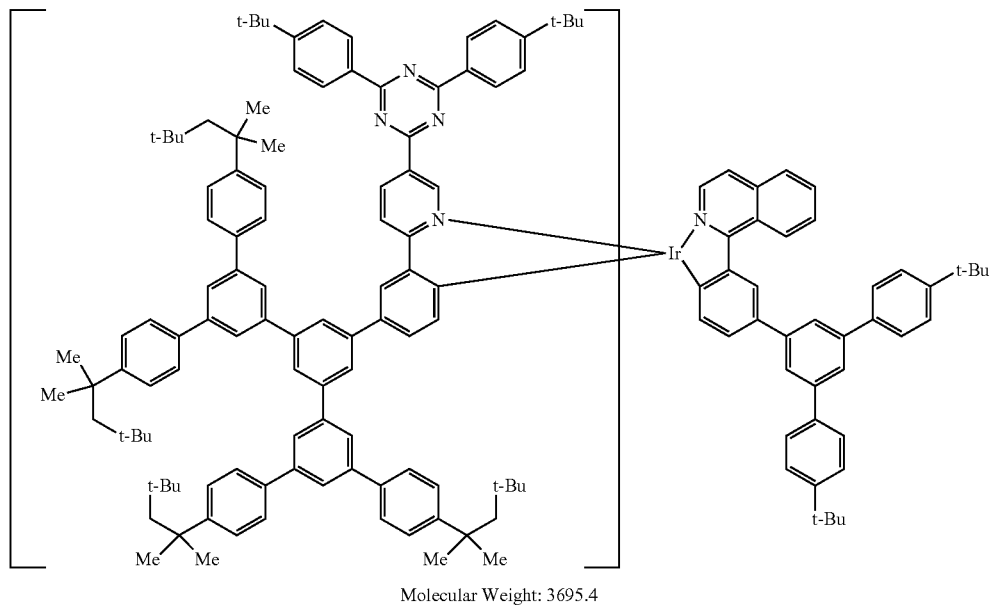

Molecular Weight: 3695.4

[Chemical Formula 61]

Iridium complex(A-B-24)

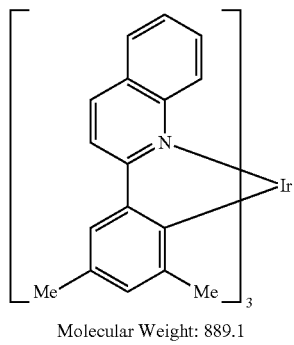

Molecular Weight: 889.1

Iridium complex(A-B-25)

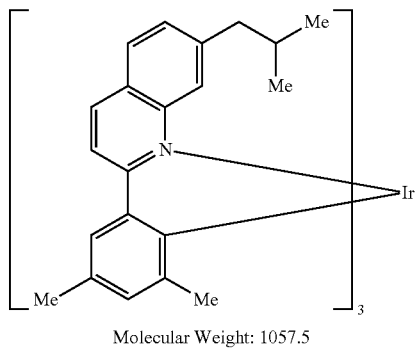

Molecular Weight: 1057.5

Iridium complex(A-B-26)

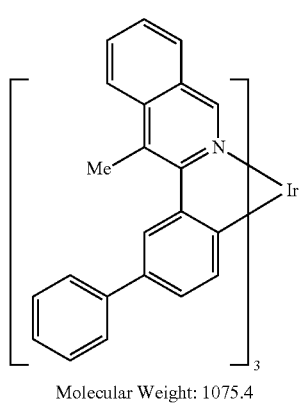

Molecular Weight: 1075.4

[Heterocyclic Compound (B)]

Next, the heterocyclic compound (B) will be illustrated.

The heterocyclic compound (B) is a heterocyclic compound constituted of typical elements. The heterocyclic compound (B) is preferably a heterocyclic compound constituted of a hydrogen atom, a carbon atom, and at least one atom selected from group XIII elements, group XIV elements, group XV elements, group XVI elements and group XVII elements, more preferably a heterocyclic compound constituted of a hydrogen atom, a carbon atom, and at least one atom selected from the group consisting of a boron atom, a silicon atom, a nitrogen atom, a phosphorus atom, an oxygen atom, a sulfur atom, a selenium atom and a halogen atom, further preferably a heterocyclic compound constituted of a hydrogen atom, a carbon atom, and at least one atom selected from the group consisting of a nitrogen atom, an oxygen atom and a sulfur atom, particularly preferably a heterocyclic compound constituted of a hydrogen atom, a carbon atom, and a nitrogen atom.

The substituent which the heterocyclic ring optionally has is preferably a halogen atom, an alkyl group, a cycloalkyl group, an alkoxy group, a cycloalkoxy group, an aryloxy group, an aryl group, a monovalent heterocyclic group or a substituted amino group, more preferably an alkyl group, a cycloalkyl group, an alkoxy group, an aryl group, a monovalent heterocyclic group or a substituted amino group, further preferably an alkyl group, a cycloalkyl group, an aryl group, a monovalent heterocyclic group or a substituted amino group, particularly preferably a group represented by the formulae (D-A) to (D-C), and these groups each optionally further have a substituent.

It is preferable that the heterocyclic compound (B) has at least one function selected from the group consisting of hole injectability, hole transportability, electron injectability and electron transportability.

It is preferable that the lowest excited triplet state ($T_1$) of the heterocyclic compound (B) is at energy level equivalent to or higher than the $T_1$ energy of the iridium complex (A), because a light emitting device excellent in external quantum efficiency is obtained.

The heterocyclic compound (B) is preferably a low molecular weight compound having an aromatic heterocyclic ring optionally having a substituent (namely, aromatic heterocyclic compound).

The preferable range of the atom constituting the aromatic heterocyclic ring is the same as the preferable range of the atom constituting the heterocyclic ring described above.

The preferable range of the substituent which the aromatic heterocyclic ring optionally has is the same as the preferable range of the substituent which the heterocyclic ring optionally has described above.

The heterocyclic ring in the heterocyclic compound (B) includes, for example, a pyrrole ring, a furan ring, a thiophene ring, an oxadiazole ring, a thiadiazole ring, a thiazole ring, an oxazole ring, a pyridine ring, a diazabenzene ring, a triazine ring, a quinoline ring, an isoquinoline ring, a quinazoline ring, a quinoxaline ring, a phenanthroline ring, a dibenzofuran ring, a dibenzothiophene ring, a dibenzosilole ring, a dibenzophosphole ring, a carbazole ring, an azacarbazole ring, a diazacarbazole ring, a phenoxazine ring and a phenothiazine ring, preferably a pyridine ring, a diazabenzene ring, a triazine ring, a quinoline ring, an isoquinoline ring, a quinazoline ring, a quinoxaline ring, a phenanthroline ring, a dibenzofuran ring, a dibenzothiophene ring, a carbazole ring, an azacarbazole ring or a diazacarbazole ring, more preferably a pyridine ring, a pyrimidine ring, a triazine ring, a quinoline ring, an isoquinoline ring, a quinazoline ring, a dibenzofuran ring, a dibenzothiophene ring or a carbazole ring, further preferably a pyridine ring, a pyrimidine ring, a triazine ring, a dibenzofuran ring, a dibenzothiophene ring or a carbazole ring, particularly preferably a triazine ring or a carbazole ring, and these groups each optionally have a substituent.

[Heterocyclic Compound Represented by the Formula (B)]

The heterocyclic compound (B) is more preferably a heterocyclic compound represented by the formula (B).

$n^{B1}$ is usually an integer of 1 to 10, and it is preferably an integer of 2 to 6, more preferably an integer of 2 to 4, further preferably 3 or 4, particularly preferably 3, because the light emitting device of the present invention is more excellent in external quantum efficiency.

The examples and the preferable range of the heterocyclic ring portion excluding $n^{B1}$ substituents in $Ar^{B1}$ are the same as the examples and the preferable range of the heterocyclic ring in the heterocyclic compound (B) described above.

$Ar^{B1}$ is preferably an aromatic heterocyclic group, and this aromatic heterocyclic group optionally has a substituent.

The substituent other than $Ar^{B2}$ which the heterocyclic group represented by $Ar^{B1}$ optionally has is preferably a halogen atom, an alkyl group, a cycloalkyl group, an alkoxy group, a cycloalkoxy group or an aryloxy group, more preferably an alkyl group, a cycloalkyl group, an alkoxy group or a cycloalkoxy group, further preferably an alkyl group or a cycloalkyl group, and these groups each optionally further have a substituent.

$Ar^{B2}$ is preferably a group represented by the formula (D-A), (D-B), (D-C2) or (D-C3), more preferably a group represented by the formula (D-A), (D-B) or (D-C2), further preferably a group represented by the formula (D-A) or (D-B), particularly preferably a group represented by the formula (D-A1), (D-A4), (D-A6), (D-A7), (D-B1) or (D-B2), especially preferably a group represented by the formula (D-A6), (D-A7), (D-B1) or (D-B2).

The heterocyclic compound represented by the formula (B) is preferably a heterocyclic compound represented by the formulae (B-1) to (B-11), more preferably a heterocyclic compound represented by the formulae (B-1) to (B-4) or the formulae (B-8) to (B-11), further preferably a heterocyclic compound represented by the formula (B-4), (B-10) or (B-11).

[Chemical Formula 62]

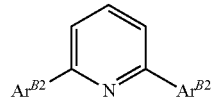

(B-1)

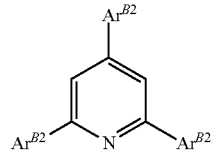

(B-2)

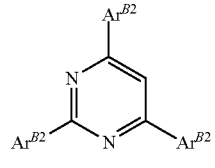

(B-3)

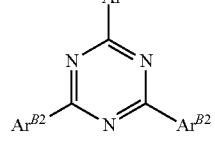

(B-4)

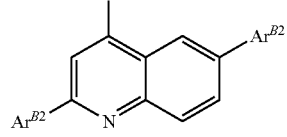

(B-5)

-continued

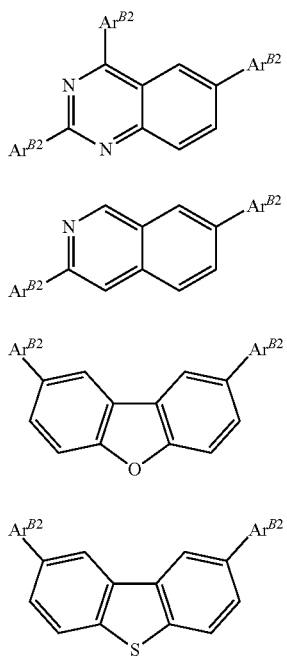

(B-6)
(B-7)
(B-8)
(B-9)

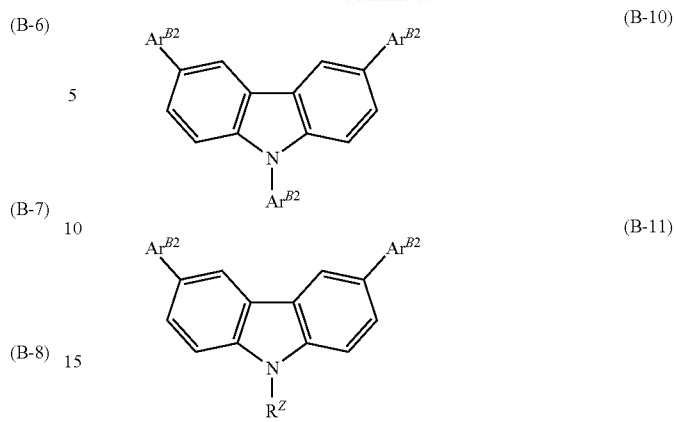

(B-10)
(B-11)

[wherein,
Ar$^{B2}$ represents the same meaning as described above.
R$^Z$ represents an alkyl group, a cycloalkyl group, an aryl group or a monovalent heterocyclic group, and these groups each optionally have a substituent.]

R$^Z$ is preferably an alkyl group or a cycloalkyl group, and these groups each optionally have a substituent.

The preferable range of the substituent which R$^Z$ optionally has is the same as the preferable range of the substituent which the heterocyclic ring optionally has described above.

The heterocyclic compound (B) includes, for example, compounds represented by the following formulae.

[Chemical Formula 63]

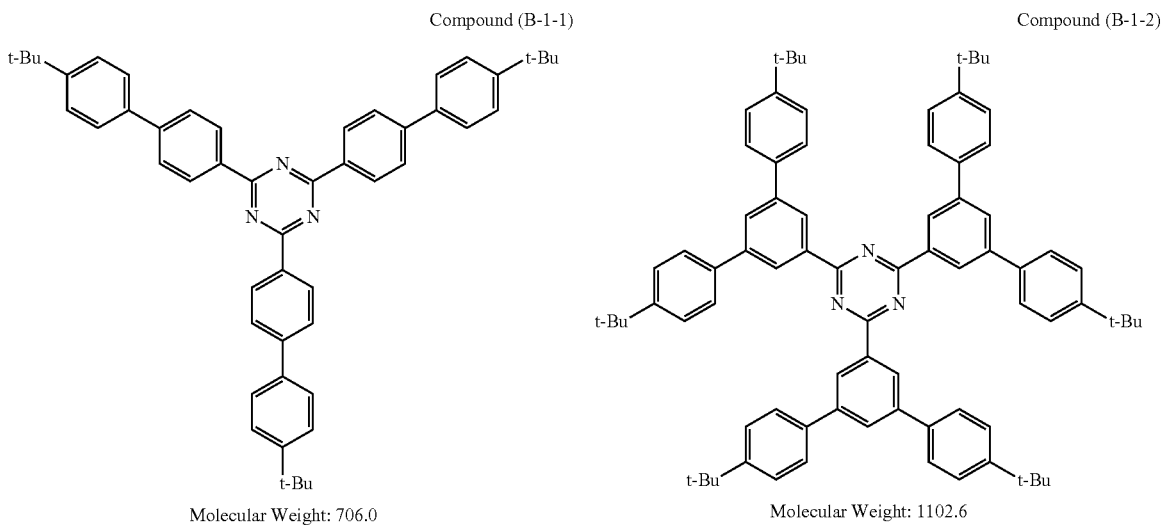

Compound (B-1-1)
Molecular Weight: 706.0

Compound (B-1-2)
Molecular Weight: 1102.6

[Chemical Formula 64]
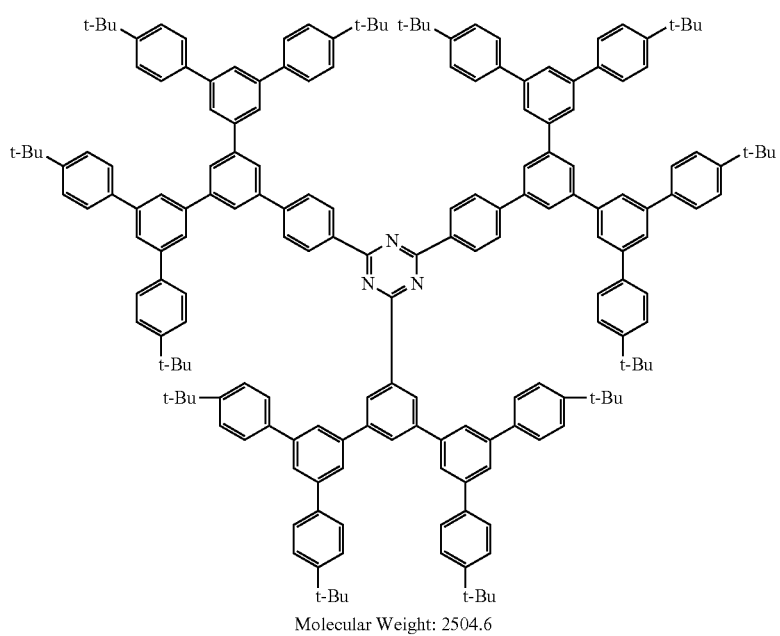
Molecular Weight: 2504.6
Compound (B-1-3)
[Chemical Formula 65]
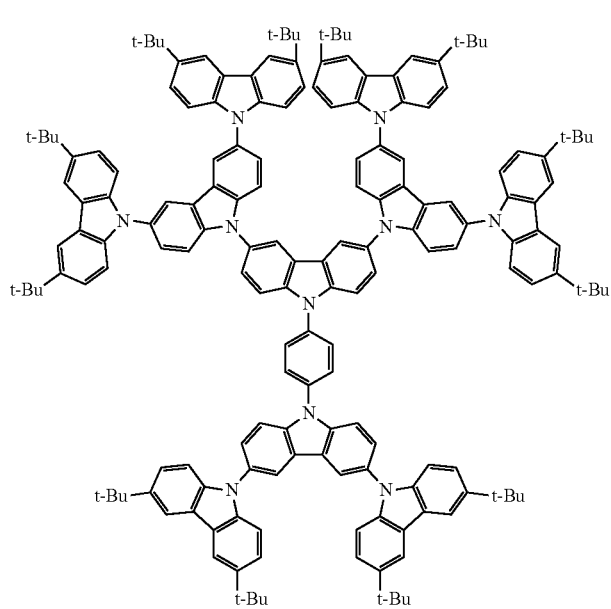
Molecular Weight: 2403.4
Compound (B-1-4)

[Chemical Formula 66]
Compound (B-1-5)
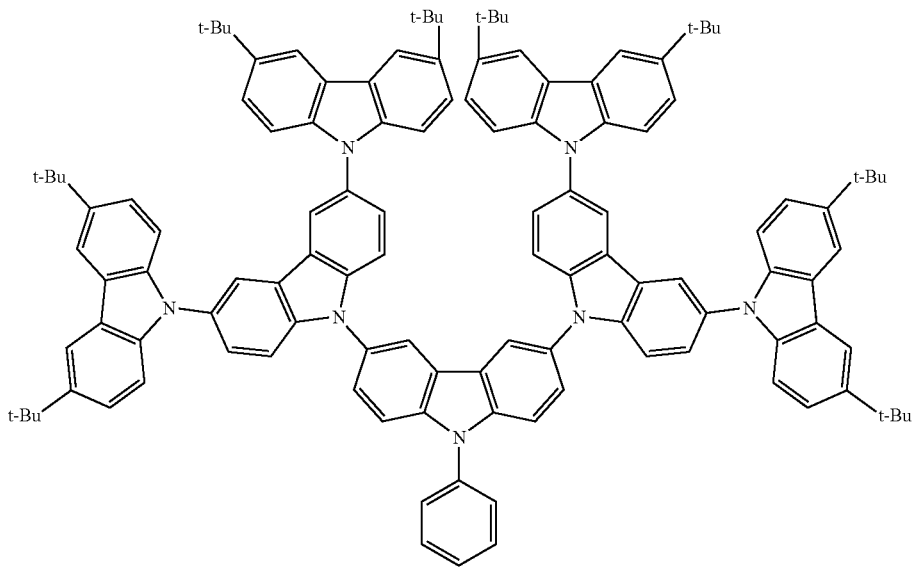
Molecular Weight: 1683.3
[Chemical Formula 67]
Compound (B-1-6)
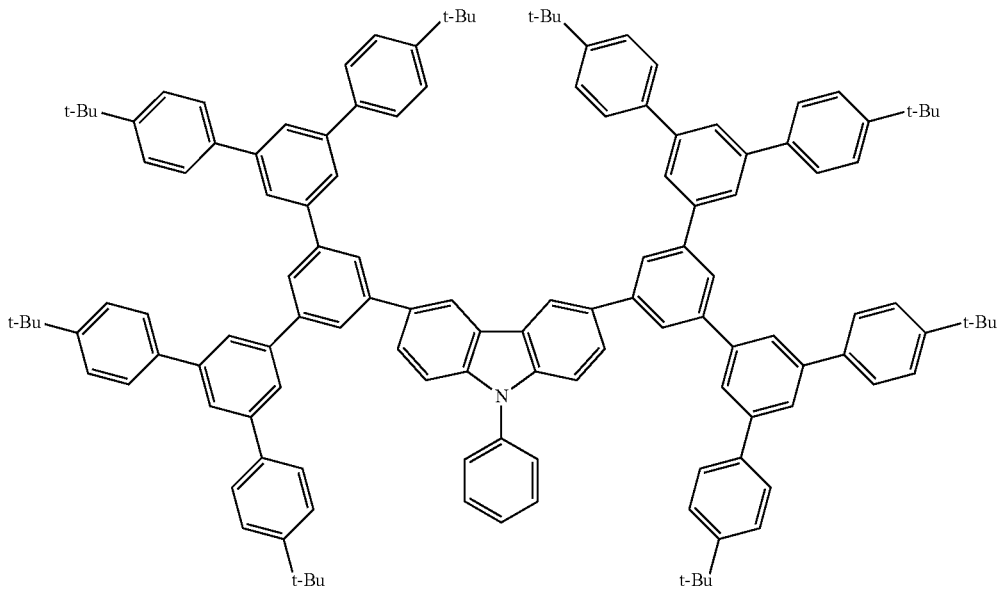
Molecular Weight: 1757.6

-continued

[Chemical Formula 68]

Compound (B-1-7)

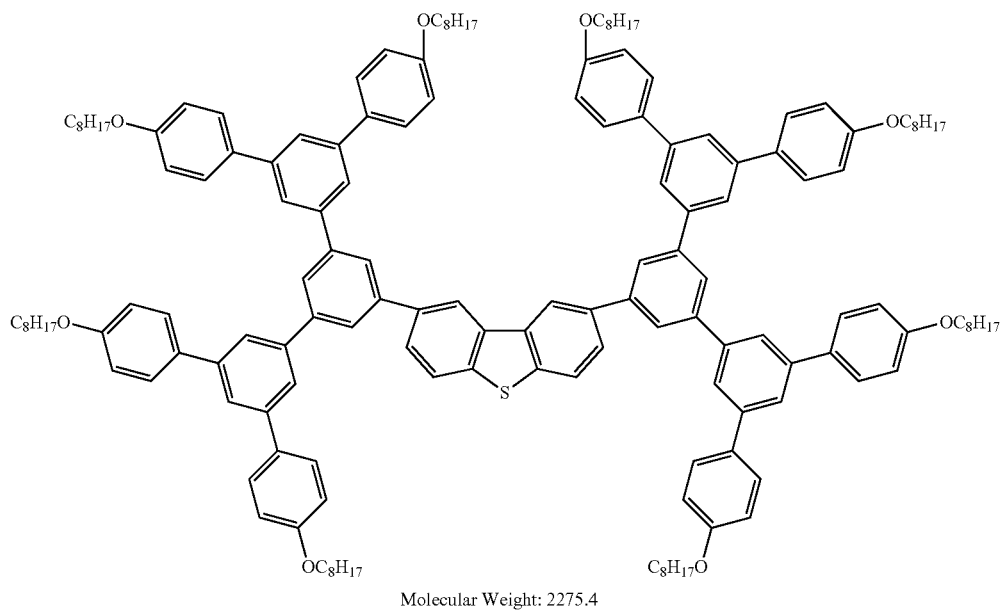

Molecular Weight: 2275.4

[Chemical Formula 69]

Compound (B-1-8)

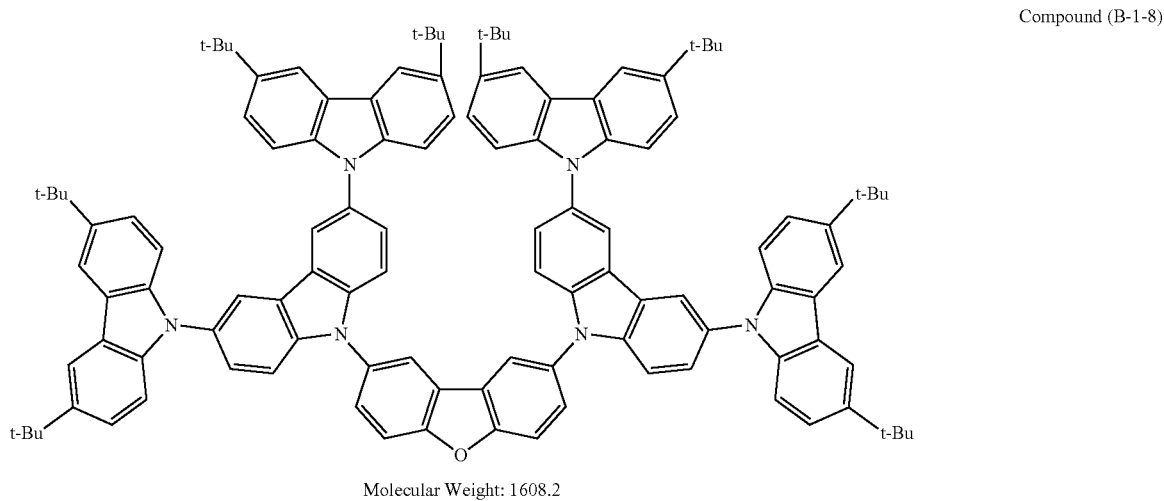 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1ccc2oc3ccc(-n4c5ccc(-n6c7ccc(C(C)(C)C)cc7c7cc(C(C)(C)C)ccc76)cc5c5cc(-n6c7ccc(C(C)(C)C)cc7c7cc(C(C)(C)C)ccc76)ccc54)cc3c2c1]

Molecular Weight: 1608.2

[Composition Ratio of Light Emitting Layer, and the Like]

The light emitting layer is a layer comprising the iridium complex (A) and the heterocyclic compound (B). That is, the light emitting layer comprises a composition comprising the iridium complex (A) and the heterocyclic compound (B).

In the light emitting layer, the iridium complex (A) may be contained singly or two or more kinds of the iridium complexes (A) may be contained. In the light emitting layer, the heterocyclic compound (B) may be contained singly or two or more kinds of the heterocyclic compounds (B) may be contained.

In the light emitting layer, the content of the iridium complex (A) is usually 0.01 to 90 parts by weight when the sum of the iridium complex (A) and the heterocyclic compound (B) is 100 parts by weight, and it is preferably 1 to 60 parts by weight, more preferably 10 to 40 parts by weight, because the light emitting device of the present invention is more excellent in external quantum efficiency.

The molecular weight (MA) of the iridium complex (A) is preferably 900 to 4000, more preferably 1200 to 4000, further preferably 1600 to 4000, particularly preferably 1600 to 3000, because the light emitting device of the present invention is more excellent in external quantum efficiency.

The molecular weight (MB) of the heterocyclic compound (B) is preferably 700 to 3000, more preferably 1500 to 3000, further preferably 2000 to 3000, because the light emitting device of the present invention is more excellent in external quantum efficiency.

The sum (MA+MB) of the molecular weight (MA) of the iridium complex (A) and the molecular weight (MB) of the heterocyclic compound (B) is preferably 3400 or more, more preferably 4000 or more, because the light emitting device of the present invention is more excellent in external quantum efficiency.

The sum (MA+MB) of the molecular weight (MA) of the iridium complex (A) and the molecular weight (MB) of the heterocyclic compound (B) is preferably 7000 or less, more preferably 6000 or less, because the light emitting device of the present invention is more excellent in external quantum efficiency.

When the sum (MA+MB) of the molecular weight (MA) of the iridium complex (A) and the molecular weight (MB) of the heterocyclic compound (B) is over 10000, solubility of the iridium complex (A) and the heterocyclic compound (B) in a solvent is problematic in fabricating the light emitting device of the present invention by a solution application process.

When the sum (MA+MB) of the molecular weight (MA) of the iridium complex (A) and the molecular weight (MB) of the heterocyclic compound (B) is less than 2700, external quantum efficiency of a light emitting device lowers.

The sum (MA+MB) of the molecular weight (MA) of the iridium complex (A) and the molecular weight (MB) of the heterocyclic compound (B) preferably satisfies the above-described formula (M1-2), more preferably satisfies the above-described formula (M1-3), further preferably satisfies the formula (M1-4), because the light emitting device of the present invention is more excellent in external quantum efficiency.

$$4000 \leq MA+MB \leq 5400 \quad (M1\text{-}4)$$

The ratio (MA/MB) of the molecular weight (MA) of the iridium complex (A) to the molecular weight (MB) of the heterocyclic compound (B) is preferably 0.65 or more, because the light emitting device of the present invention is more excellent in external quantum efficiency. When the ratio (MA/MB) of the molecular weight (MA) of the iridium complex (A) to the molecular weight (MB) of the heterocyclic compound (B) is less than 0.35, external quantum efficiency of a light emitting device lowers.

The ratio (MA/MB) of the molecular weight (MA) of the iridium complex (A) to the molecular weight (MB) of the heterocyclic compound (B) is preferably 2.00 or less, more preferably 1.30 or less, because the light emitting device of the present invention is more excellent in external quantum efficiency. When the ratio (MA/MB) of the molecular weight (MA) of the iridium complex (A) to the molecular weight (MB) of the heterocyclic compound (B) is over 3.00, external quantum efficiency of a light emitting device lowers.

The ratio (MA/MB) of the molecular weight (MA) of the iridium complex (A) to the molecular weight (MB) of the heterocyclic compound (B) preferably satisfies the above-described formula (M2-2), more preferably satisfies the above-described formula (M2-3), because the light emitting device of the present invention is more excellent in external quantum efficiency.

The molecular weight (MA) of the iridium complex (A) and the molecular weight (MB) of the heterocyclic compound (B) preferably satisfy the formula (M1-1) and the formula (M2-2), more preferably satisfy the formula (M1-2) and the formula (M2-2), further preferably satisfy the formula (M1-3) and the formula (M2-3), particularly preferably satisfy the formula (M1-4) and the formula (M2-3).

The light emitting layer may further comprise at least one material selected from the group consisting of a hole transporting material, a hole injection material, an electron transporting material, an electron injection material, a light emitting material (different from the iridium complex (A) and the heterocyclic compound (B)) and an antioxidant. In the light emitting layer, a hole transporting material, a hole injection material, an electron transporting material and an electron injection material are different from the heterocyclic compound (B).

[Hole Transporting Material]

The hole transporting material is classified into low molecular weight compounds and polymer compounds, and is preferably polymer compounds. The hole transporting material optionally has a crosslinkable group.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene, trinitrofluorenone, preferably fullerene.

In the light emitting layer, the compounding amount of the hole transporting material is usually 1 to 400 parts by weight, preferably 5 to 150 parts by weight when the total content of the iridium complex (A) and the heterocyclic compound (B) is 100 parts by weight.

The hole transporting material may be used singly or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof.

The polymer compound includes, for example, polyphenylene, polyfluorene and derivatives thereof. These polymer compounds may be doped with a metal.

In the light emitting layer, the compounding amount of the electron transporting material is usually 1 to 400 parts by weight, preferably 5 to 150 parts by weight when the total content of the iridium complex (A) and the heterocyclic compound (B) is 100 parts by weight.

The electron transporting material may be used singly or two or more electron transporting materials may be used in combination.

[Hole Injection Material and Electron Injection Material]

The hole injection material and the electron injection material are each classified into low molecular weight compounds and polymer compounds. The hole injection material and the electron injection material optionally have a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the side chain or main chain.

In the light emitting layer, the compounding amounts of the hole injection material and the electron injection material are each usually 1 to 400 parts by weight, preferably 5 to 150 parts by weight when the total content of the iridium complex (A) and the heterocyclic compound (B) is 100 parts by weight.

The hole injection material and the electron injection material may each be used singly or two or more of them may be used in combination.

[Ion Dope]

When the hole injection material or the electron injection material comprises an electrically conductive polymer, the electric conductivity of the electrically conductive polymer is preferably $1\times10^{-5}$ S/cm to $1\times10^{3}$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly or two or more ions to be doped may be used.

[Light Emitting Material]

The light emitting material (different from the iridium complex (A) and the heterocyclic compound (B)) is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof.

The polymer compound includes, for example, polymer compounds comprising a phenylene group, a naphthalenediyl group, an anthracenediyl group, a fluorenediyl group, a phenanthrenediyl group, dihydrophenanthrenediyl group, a group represented by the formula (X) described below, a carbazolediyl group, a phenoxazinediyl group, a phenothiazinediyl group, a pyrenediyl group and the like.

A triplet light emitting complex includes, for example, metal complexes listed below.

[Chemical Formula 70]

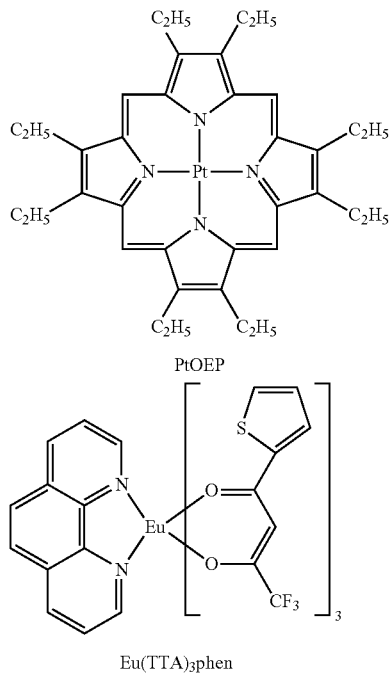

PtOEP

Eu(TTA)₃phen

In the light emitting layer, the compounding amount of the light emitting material is usually 0.001 to 10 parts by weight when the total content of the iridium complex (A) and the heterocyclic compound (B) is 100 parts by weight.

The light emitting material may be used singly or two or more of them may be used in combination.

[Antioxidant]

The antioxidant may advantageously be one which is soluble in the same solvent as for the iridium complex (A) and the heterocyclic compound (B) and does not disturb light emission and charge transportation, and the examples thereof include phenol antioxidants and phosphorus-based antioxidants.

In the light emitting layer, the compounding amount of the antioxidant is usually 0.001 to 10 parts by weight when the content of a metal complex is 100 parts by weight.

The antioxidant may be used singly or two or more antioxidants may be used in combination.

[Ink of Light Emitting Layer]

The composition of the light emitting layer comprising the iridium complex (A), the heterocyclic compound (B) and a solvent (hereinafter, referred to also as "ink of light emitting layer") can be suitably used in application methods such as a spin coating method, a casting method, a micro gravure coating method, a gravure coating method, a bar coating method, a roll coating method, a wire bar coating method, a dip coating method, a spray coating method, a screen printing method, a flexo printing method, an offset printing method, an inkjet printing method, a capillary coating method and a nozzle coating method.

The viscosity of the ink of the light emitting layer may be adjusted depending on the kind of the printing method, and when a solution goes through a discharge apparatus such as in an inkjet printing method, the viscosity is preferably in the range of 1 to 20 mPa·s at 25° C. because clogging in discharging and curved aviation are less likely to occur.

As the solvent contained in the ink of the light emitting layer, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as THF, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; poly-hydric alcohols such as ethylene glycol, glycerin and 1,2-hexanediol and derivatives thereof; alcohol solvents such as isopropylalcohol and cyclohexanol; sulfoxide solvents such as dimethyl sulfoxide; and amide solvents such as N-methyl-2-pyrrolidone and N,N-dimethylformamide. These solvents may be used singly or two or more of them may be used in combination.

In the ink of the light emitting layer, the compounding amount of the solvent is usually 1000 to 100000 parts by weight, preferably 2000 to 20000 parts by weight when the content of the metal complex is 100 parts by weight.

<Hole Transporting Layer>

The hole transporting layer is a layer comprising a crosslinked body of a crosslinkable material.

83

[Crosslinkable Material]

The crosslinkable material may be a low molecular weight compound or a polymer compound, and is preferably a low molecular weight compound having at least one crosslinkable group selected from Group A of crosslinkable group (hereinafter, referred to also as "low molecular weight compound of hole transporting layer") or a polymer compound comprising a crosslinkable constitutional unit having at least one crosslinkable group selected from Group A of crosslinkable group (hereinafter, referred to also as "polymer compound of hole transporting layer") because the light emitting device of the present invention is more excellent in external quantum efficiency, and the polymer compound comprising a crosslinkable constitutional unit having at least one crosslinkable group selected from Group A of crosslinkable group is better.

The crosslinkable group selected from Group A of crosslinkable group is preferably a crosslinkable group represented by the formula (XL-1), (XL-3), (XL-9), (XL-16) or (XL-17), more preferably a crosslinkable group represented by the formula (XL-1), (XL-16) or (XL-17), further preferably a crosslinkable group represented by the formula (XL-1) or (XL-17), because the light emitting device of the present invention is more excellent in external quantum efficiency.

[Polymer Compound of Hole Transporting Layer]

The constitutional unit having at least one crosslinkable group selected from Group A of crosslinkable group contained in the polymer compound of hole transporting layer is preferably a constitutional unit represented by the formula (2) or a constitutional unit represented by the formula (2') described later, and may also be a constitutional unit represented by the following formulae.

[Chemical Formula 71]

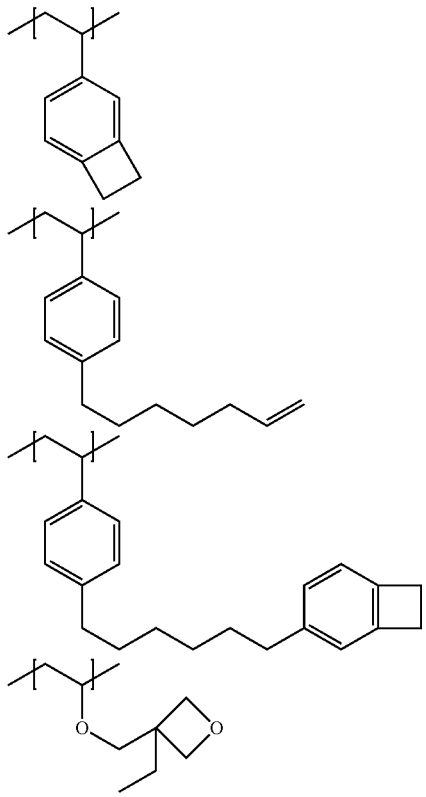

-continued

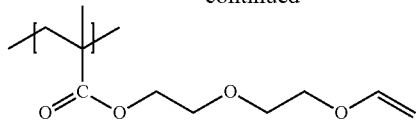

The constitutional unit having at least one crosslinkable group selected from Group A of crosslinkable group contained in the polymer compound of hole transporting layer is preferably a constitutional unit represented by the formula (2) or a constitutional unit represented by the formula (2').

[Constitutional Unit Represented by the Formula (2)]

nA is preferably an integer of 0 to 3, more preferably an integer of 0 to 2, because the light emitting device of the present invention is more excellent in external quantum efficiency.

n is preferably 2, because the light emitting device of the present invention is more excellent in external quantum efficiency.

$Ar^3$ is preferably an aromatic hydrocarbon group optionally having a substituent, because the light emitting device of the present invention is more excellent in external quantum efficiency.

The number of carbon atoms of the aromatic hydrocarbon group represented by $Ar^3$ is usually 6 to 60, preferably 6 to 30, more preferably 6 to 18, not including the number of carbon atoms of a substituent.

The arylene group portion obtained by removing n substituents of the aromatic hydrocarbon group represented by $Ar^3$ is preferably a group represented by the formula (A-1) to the formula (A-20), more preferably a group represented by the formula (A-1), the formula (A-2), the formula (A-6) to the formula (A-10), the formula (A-19) or the formula (A-20), further preferably a group represented by the formula (A-1), the formula (A-2), the formula (A-7), the formula (A-9) or the formula (A-19), and these groups each optionally have a substituent.

The number of carbon atoms of the heterocyclic group represented by $Ar^3$ is usually 2 to 60, preferably 3 to 30, more preferably 4 to 18, not including the number of carbon atoms of a substituent.

The divalent heterocyclic group portion obtained by removing n substituents of the heterocyclic group represented by $Ar^3$ is preferably a group represented by the formula (AA-1) to the formula (AA-34).

The aromatic hydrocarbon group and the heterocyclic group represented by $Ar^3$ each optionally have a substituent, and the substituent includes, for example, an alkyl group, a cycloalkyl group, an alkoxy group, a cycloalkoxy group, an aryl group, an aryloxy group, a halogen atom, a monovalent heterocyclic group and a cyano group.

The number of carbon atoms of the alkylene group represented by $L^4$ is usually 1 to 20, preferably 1 to 15, more preferably 1 to 10, not including the number of carbon atoms of a substituent. The number of carbon atoms of the cycloalkylene group represented by $L^4$ is usually 3 to 20, not including the number of carbon atoms of a substituent.

The alkylene group and the cycloalkylene group optionally have a substituent, and examples thereof include a methylene group, an ethylene group, a propylene group, a butylene group, a hexylene group, a cyclohexylene group and an octylene group.

The alkylene group and the cycloalkylene group represented by $L^4$ each optionally have a substituent. The substituent which the alkylene group and the cycloalkylene group optionally have includes, for example, an alkyl group, a cycloalkyl group, an alkoxy group, a cycloalkoxy group, a halogen atom and a cyano group.

The arylene group represented by $L^4$ optionally has a substituent. The arylene group is preferably a phenylene group or a fluorenediyl group, more preferably a m-phenylene group, a p-phenylene group, a fluorene-2,7-diyl group or a fluorene-9,9-diyl group. The substituent which the arylene group optionally has includes, for example, an alkyl group, a cycloalkyl group, an alkoxy group, a cycloalkoxy group, an aryl group, an aryloxy group, a monovalent heterocyclic group, a halogen atom, a cyano group and a crosslinkable group selected from Group A of crosslinkable group.

$L^4$ is preferably an arylene group or an alkylene group, more preferably a phenylene group, a fluorenediyl group or an alkylene group, and these groups each optionally have a substituent, because synthesis of the polymer compound of the hole transporting layer is easy.

The crosslinkable group represented by X is preferably a crosslinkable group represented by the formula (XL-1), (XL-3), (XL-7) to (XL-10), (XL-16) or (XL-17), more preferably a crosslinkable group represented by the formula (XL-1), (XL-3), (XL-9), (XL-16) or (XL-17), further preferably a crosslinkable group represented by the formula (XL-1), (XL-16) or (XL-17), particularly preferably a crosslinkable group represented by the formula (XL-1) or (XL-17), because the polymer compound of the hole transporting layer is excellent in cross-linkability.

The amount of the constitutional unit represented by the formula (2) is preferably 0.5 to 90 mol %, more preferably 3 to 75 mol %, further preferably 5 to 60 mol %, with respect to the total amount of constitutional units contained in the polymer compound of the hole transporting layer, because the polymer compound of the hole transporting layer is excellent in stability and cross-linkability.

One kind of the constitutional unit represented by the formula (2) may be contained singly or two or more kinds of the constitutional units may be contained in the polymer compound of the hole transporting layer.

[Constitutional Unit Represented by the Formula (2')]

mA is preferably 0 to 1, more preferably 0, because the light emitting device of the present invention is more excellent in external quantum efficiency.

m is preferably 2, because the light emitting device of the present invention is more excellent in external quantum efficiency.

c is preferably 0, because synthesis of the polymer compound of the hole transporting layer is easy and the light emitting device of the present invention is more excellent in external quantum efficiency.

$Ar^5$ is preferably an aromatic hydrocarbon group optionally having a substituent, because the light emitting device of the present invention is more excellent in external quantum efficiency.

The definition and examples of the arylene group portion obtained by removing m substituents of the aromatic hydrocarbon group represented by $Ar^5$ are the same as the definition and examples of the arylene group represented by $Ar^{X2}$ in the formula (X) described below.

The definition and examples of the divalent heterocyclic group portion obtained by removing m substituents of the heterocyclic group represented by $Ar^5$ are the same as the definition and examples of the divalent heterocyclic group portion represented by $Ar^{X2}$ in the formula (X) described below.

The definition and examples of the divalent group obtained by removing m substituents of the group in which at least one aromatic hydrocarbon ring and at least one heterocyclic ring are bonded directly to each other represented by $Ar^5$ are the same as the definition and examples of the divalent group in which at least one arylene group and at least one divalent heterocyclic group are bonded directly to each other represented by $Ar^{X2}$ in the formula (X) described below.

$Ar^4$ and $Ar^6$ represent preferably an arylene group optionally having a substituent, because the light emitting device of the present invention is more excellent in external quantum efficiency.

The definition and examples of the arylene group represented by $Ar^4$ and $Ar^6$ are the same as the definition and examples of the arylene group represented by $Ar^{X1}$ and $Ar^{X3}$ in the formula (X) described below.

The definition and examples of the divalent heterocyclic group represented by $Ar^4$ and $Ar^6$ are the same as the definition and examples of the divalent heterocyclic group represented by $Ar^{X1}$ and $Ar^{X3}$ in the formula (X) described below.

The groups represented by $Ar^4$, $Ar^5$ and $Ar^6$ each optionally have a substituent, and the substituent includes an alkyl group, a cycloalkyl group, an alkoxy group, a cycloalkoxy group, an aryl group, an aryloxy group, a halogen atom, a monovalent heterocyclic group and a cyano group.

The definitions and examples of the alkylene group, the cycloalkylene group, the arylene group and the divalent heterocyclic group represented by $K^4$ are the same as the definitions and examples of the alkylene group, the cycloalkylene group, the arylene group and the divalent heterocyclic group represented by $L^4$, respectively.

$K^4$ is preferably a phenylene group or a methylene group, because synthesis of a polymer compound of a hole transporting layer is easy.

The definition and examples of the crosslinkable group represented by X' are the same as the definition and examples of the crosslinkable group represented by X described above.

The amount of the constitutional unit represented by the formula (2') is preferably 0.5 to 50 mol %, more preferably 3 to 30 mol %, further preferably 3 to 20 mol %, with respect to the total amount of constitutional units contained in a polymer compound of a hole transporting layer, because the polymer compound of the hole transporting layer is excellent in stability and cross-linkability.

One kind of the constitutional unit represented by the formula (2') may be contained singly or two or more kinds of the constitutional units may be contained in the polymer compound of the hole transporting layer.

[Preferable Embodiment of Constitutional Unit Represented by the Formula (2) or (2')]

The constitutional unit represented by the formula (2) includes, for example, constitutional units represented by the formula (2-1) to the formula (2-30), and the constitutional unit represented by the formula (2') includes, for example, constitutional units represented by the formula (2'-1) to the formula (2'-9). Of them, preferable are constitutional units represented by the formula (2-1) to the formula (2-30), more preferable are constitutional units represented by the formula (2-1) to the formula (2-15), the formula (2-19), the formula (2-20), the formula (2-23), the formula (2-25) or the formula (2-30), further preferable are constitutional units represented by the formula (2-1) to the formula (2-9) or the formula (2-30), because the polymer compound of the hole transporting layer is excellent in cross-linkability.

[Chemical Formula 72]
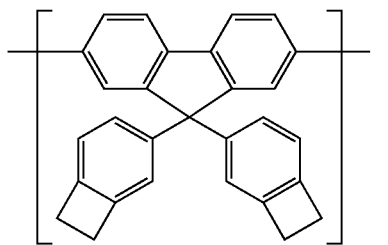 (2-1)
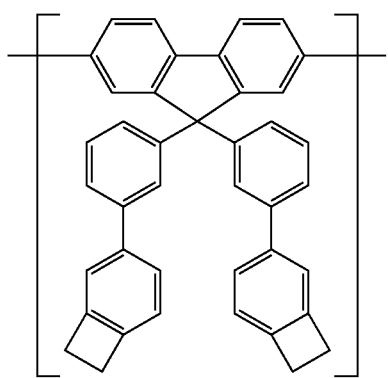 (2-2)
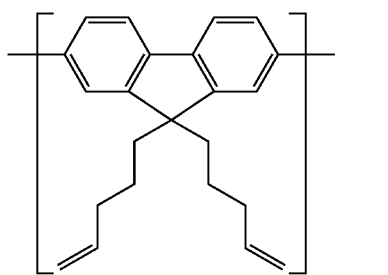 (2-3)
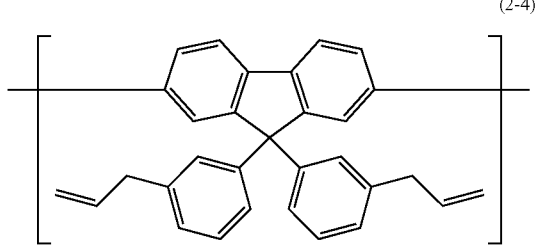 (2-4)
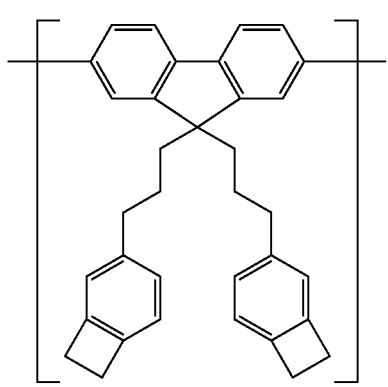 (2-5)
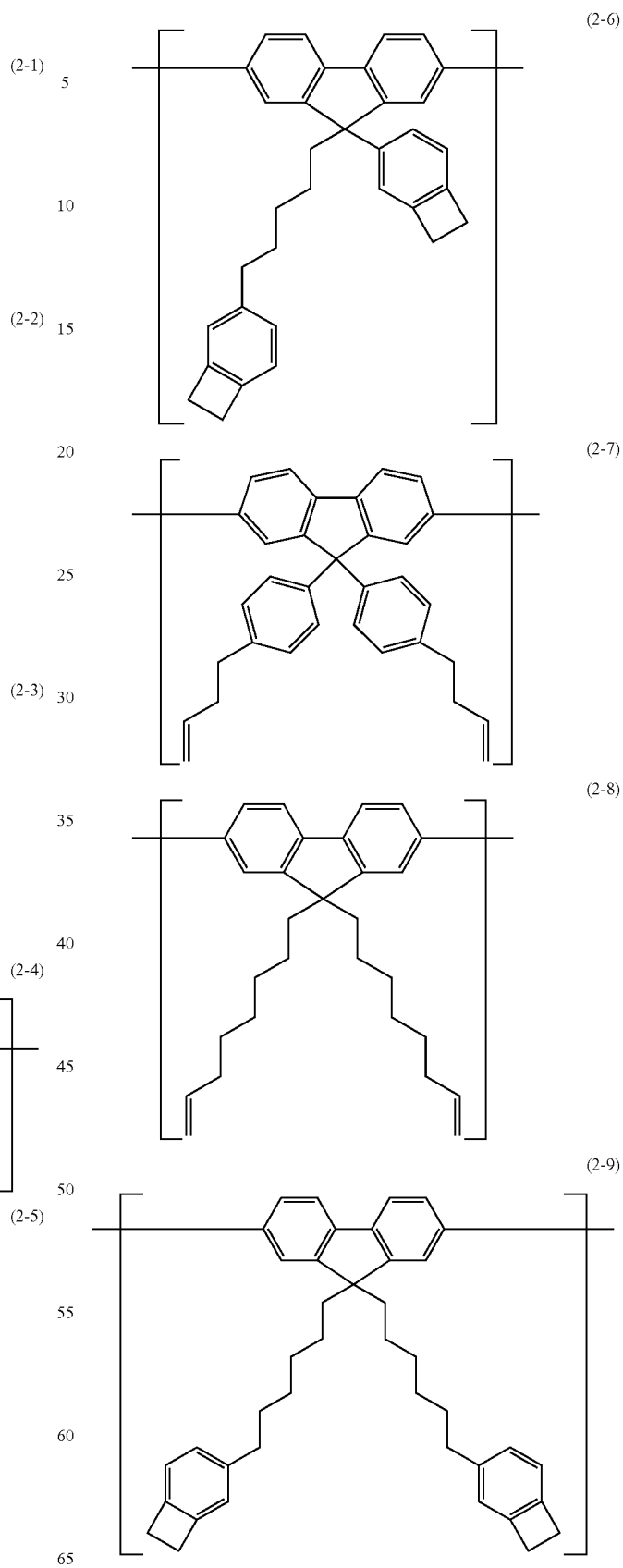

(2-10)
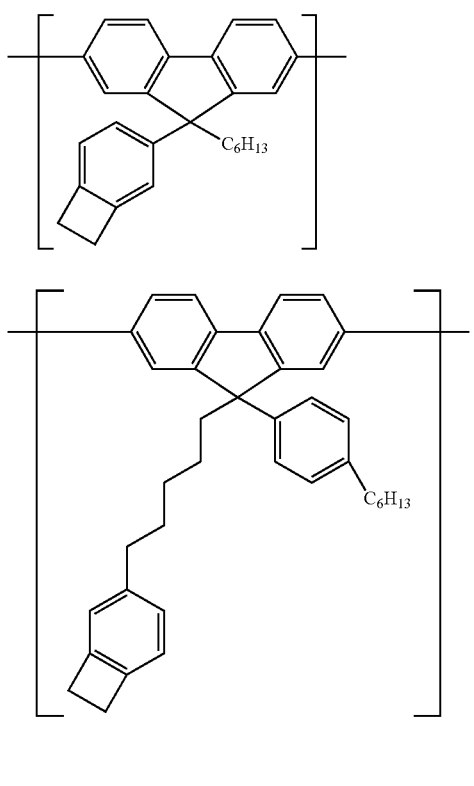
(2-11)
(2-12)
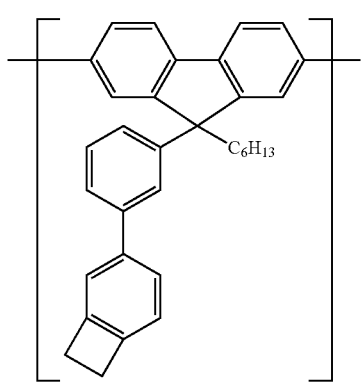
(2-13)
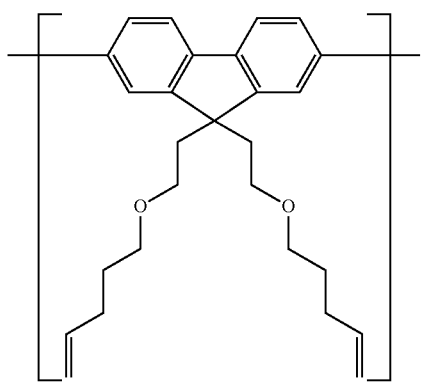
(2-14)
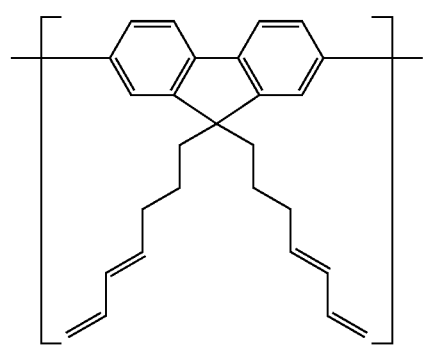
(2-15)
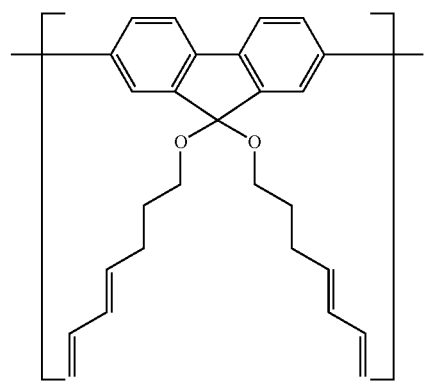
[Chemical Formula 73]
(2-16)
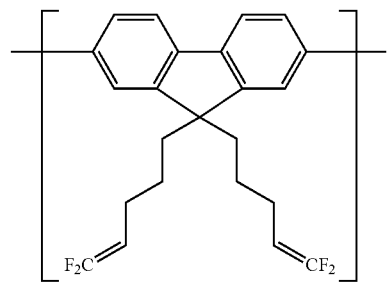
(2-17)
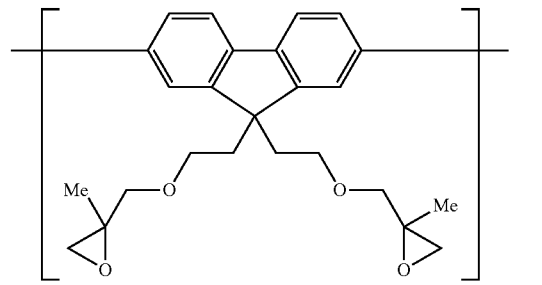

-continued
(2-18)
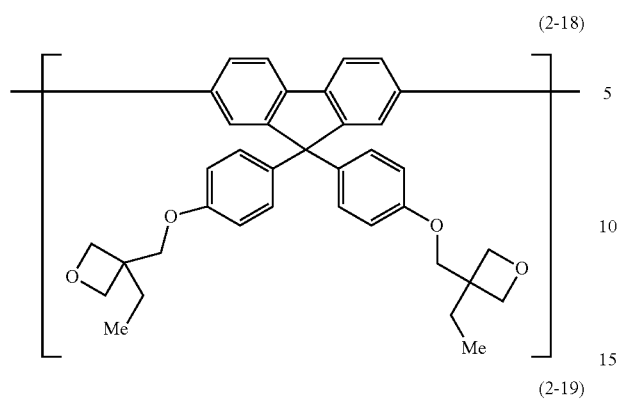
(2-19)
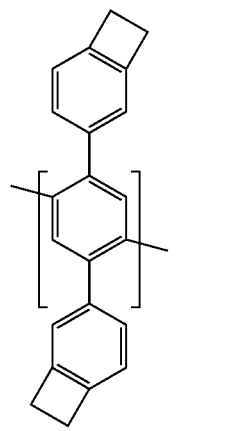
(2-20)
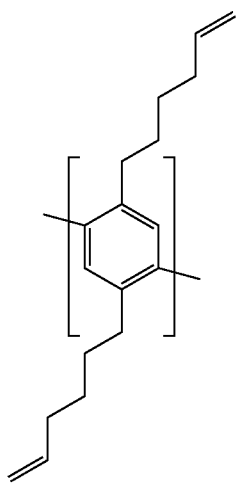
(2-21)
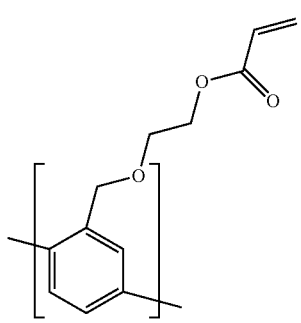
(2-22)
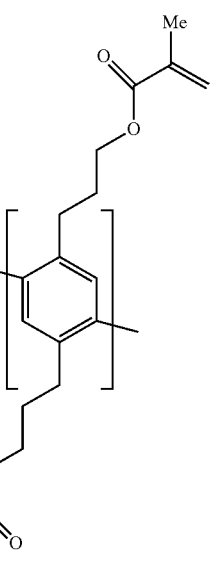
(2-23)
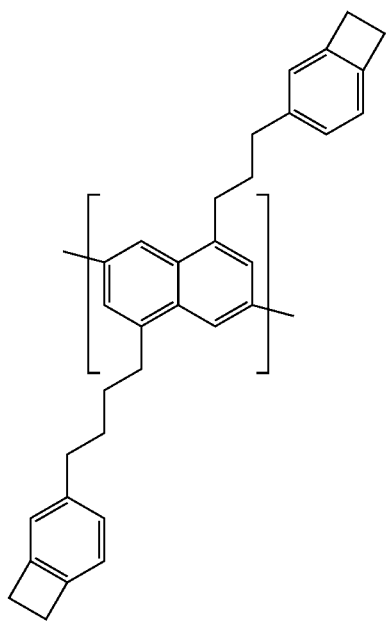

(2-24)
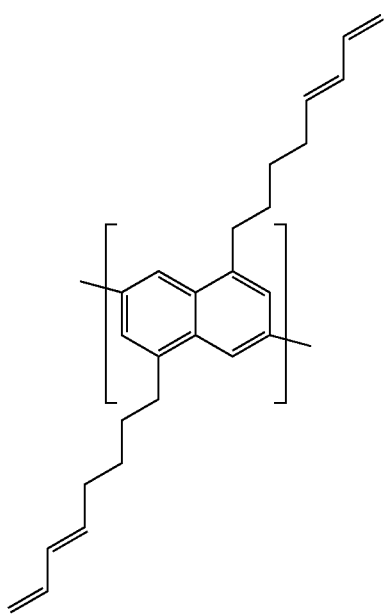
(2-25)
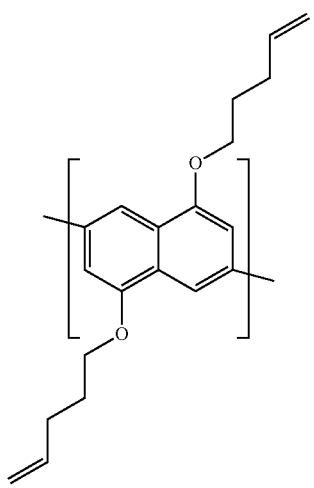
(2-26)
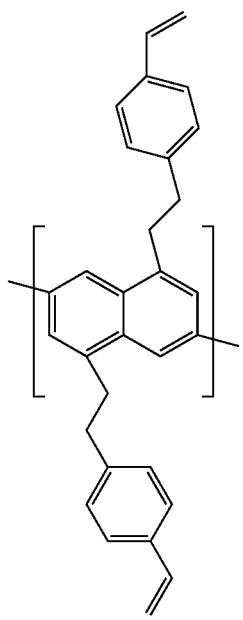
(2-27)
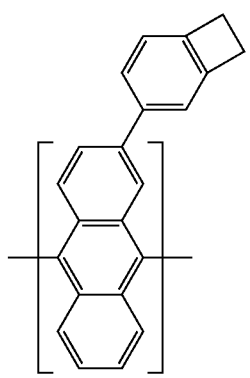
(2-28)
(2-29)
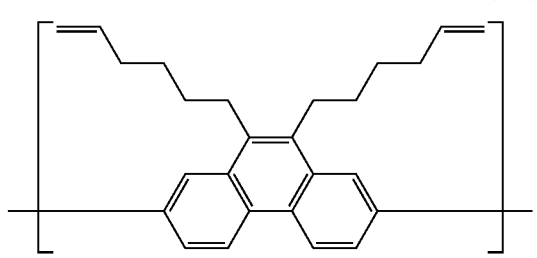

(2-30)
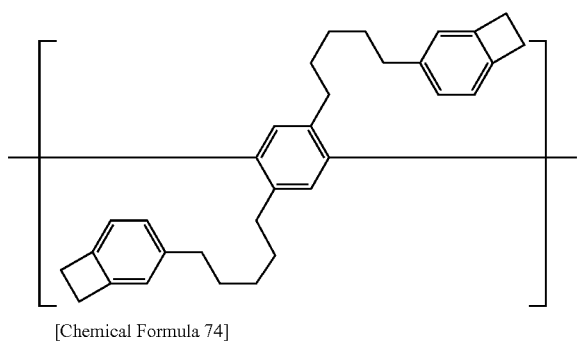
[Chemical Formula 74]
(2'-1)
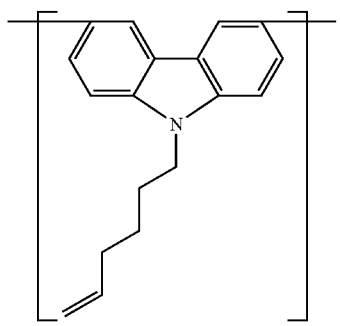
(2'-2)
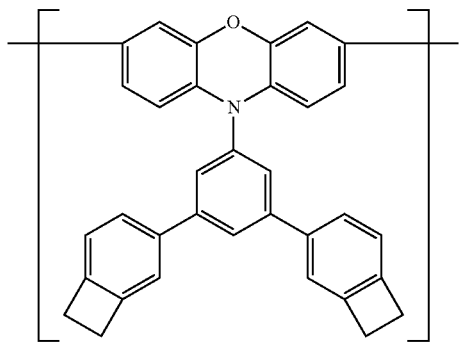
(2'-3)
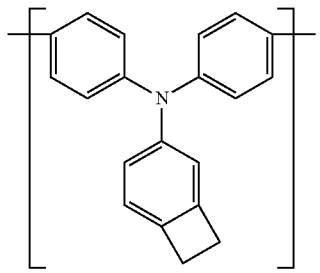
(2'-4)
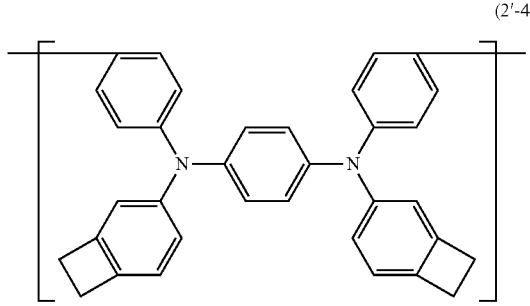
(2'-5)
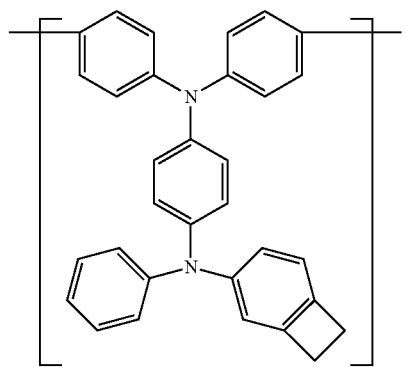
(2'-6)
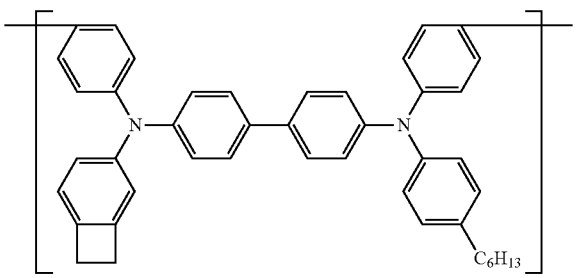
(2'-7)
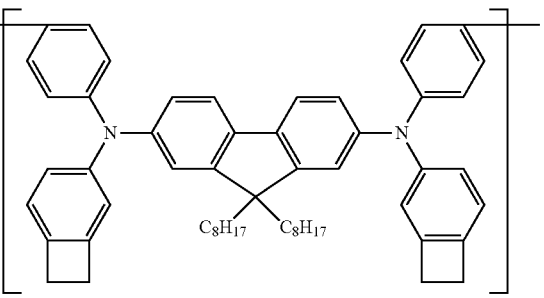
(2'-8)
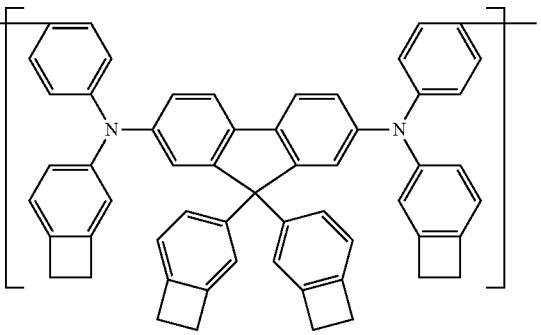

(2'-9)

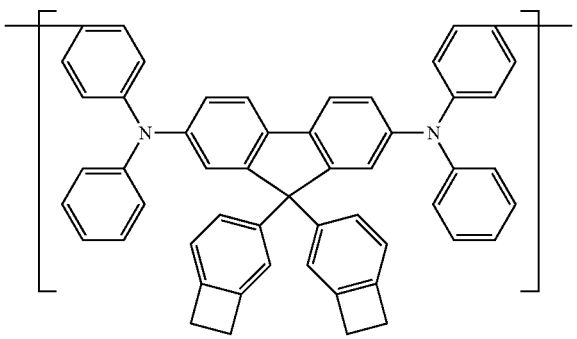

[Other Constitutional Unit]

It is preferable that the polymer compound of the hole transporting layer further comprises a constitutional unit represented by the formula (X), because hole transportability thereof is excellent.

[Chemical Formula 75]

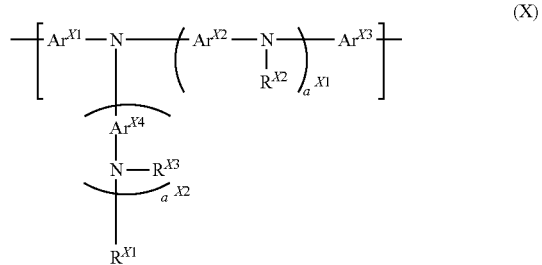

(X)

[wherein, $a^{X1}$ and $a^{X2}$ each independently represent an integer of 0 or more.

$Ar^{X1}$ and $Ar^{X3}$ each independently represent an arylene group or a divalent heterocyclic ring group, and these groups each optionally have a substituent.

$Ar^{X2}$ and $Ar^{X4}$ each independently represent an arylene group, a divalent heterocyclic ring group or a divalent group in which at least one arylene group and at least one divalent heterocyclic ring group are bonded directly to each other, and these groups each optionally have a substituent. When a plurality of $Ar^{X2}$ and $Ar^{X4}$ are present, they may be the same or different at each occurrence.

$R^{X1}$, $R^{X2}$ and $R^{X3}$ each independently represent a hydrogen atom, an alkyl group, a cycloalkyl group, an aryl group or a monovalent heterocyclic group, and these groups each option ally have a substituent. When a plurality of $R^{X2}$ and $R^{X3}$ are present, they may be the same or different at each occurrence.]

$a^{X1}$ is preferably an integer of 2 or less, more preferably 1, because the external quantum efficiency of the light emitting device of the present invention is more excellent.

$a^{X2}$ is preferably an integer of 2 or less, more preferably 0, because the external quantum efficiency of the light emitting device of the present invention is more excellent.

$R^{X1}$, $R^{X2}$ and $R^{X3}$ are preferably an alkyl group, a cycloalkyl group, an aryl group or a monovalent heterocyclic group, more preferably an aryl group, and these groups each optionally have a substituent.

The arylene group represented by $Ar^{X1}$ and $Ar^{X3}$ is more preferably a group represented by the formula (A-1) or the formula (A-9), further preferably a group represented by the formula (A-1), and these groups each optionally have a substituent.

The divalent heterocyclic group represented by $Ar^{X1}$ and $Ar^{X3}$ is more preferably a group represented by the formula (AA-1), the formula (AA-2) or the formula (AA-7) to the formula (AA-26), and these groups each optionally have a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formula (A-9) to the formula (A-11) or the formula (A-19), and these groups each optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes, for example, groups represented by the following formulae, and they each optionally have a substituent.

[Chemical Formula 76]

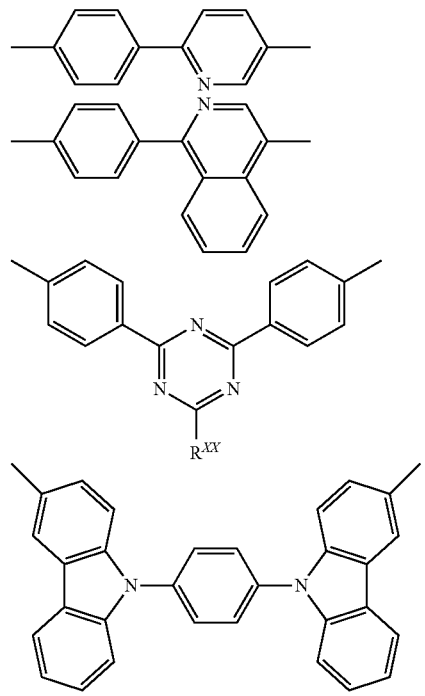

[wherein, $R^{XX}$ represents a hydrogen atom, an alkyl group, a cycloalkyl group, an aryl group or a monovalent heterocyclic group, and these groups each optionally have a substituent.]

$R^{XX}$ is preferably an alkyl group, a cycloalkyl group or an aryl group, and these groups each optionally have a substituent.

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, and these groups each optionally further have a substituent.

The constitutional unit represented by the formula (X) is preferably a constitutional unit represented by the formula (X-1) to (X-7), more preferably a constitutional unit represented by the formula (X-3) to (X-7), further preferably a constitutional unit represented by the formula (X-3) to (X-6).

[Chemical Formula 77]

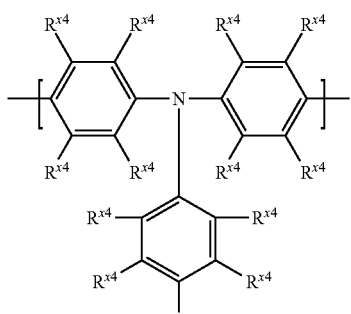
(X-1)

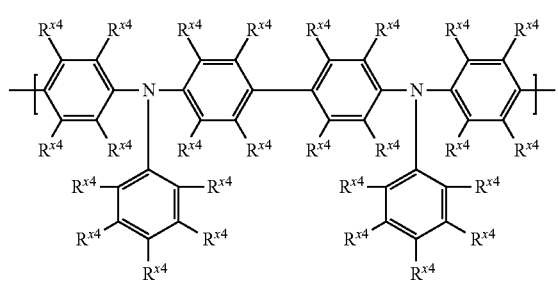
(X-2)

[Chemical Formula 78]

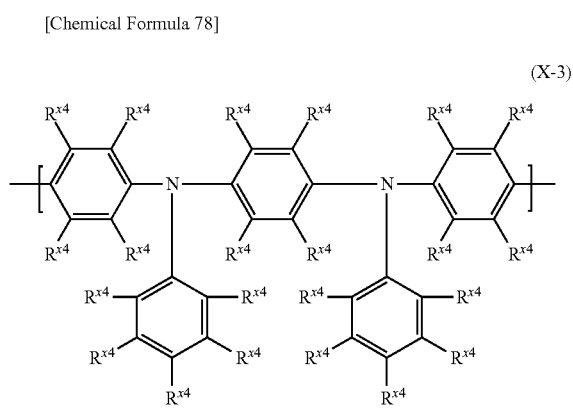
(X-3)

[Chemical Formula 79]

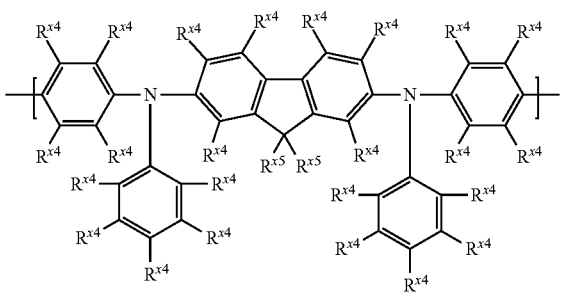
(X-4)

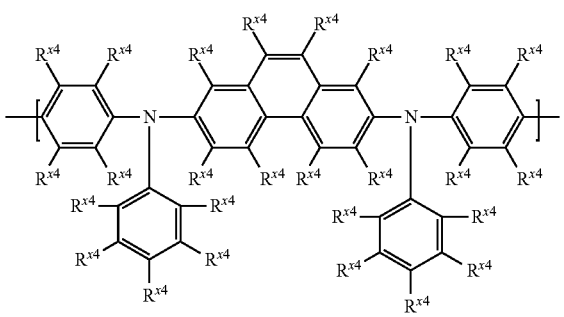
(X-5)

[Chemical Formula 80]

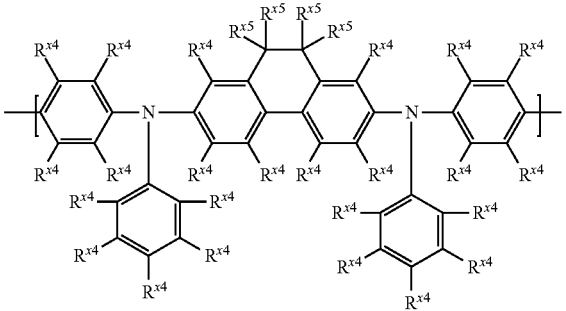
(X-6)

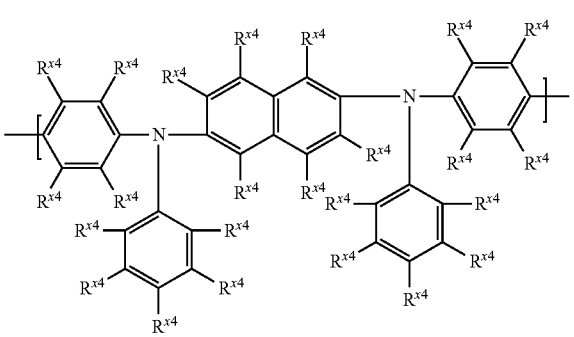
(X-7)

[wherein, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, and these groups each optionally have a substituent. The plurality of $R^{X4}$ may be the same or different. The plurality of $R^{X5}$ may be the same or different, and adjacent groups $R^{X5}$ may be combined together to form a ring together with the carbon atoms to which they are attached.]

The content of the constitutional unit represented by the formula (X) is preferably 0.1 to 90 mol %, more preferably 1 to 70 mol %, further preferably 10 to 50 mol % with respect to the total content of constitutional units contained in the polymer compound of the hole transporting layer, because hole transportability thereof is excellent.

The constitutional unit represented by the formula (X) includes, for example, constitutional units represented by the formulae (X1-1) to (X1-19), preferably constitutional units represented by the formulae (X1-6) to (X1-14).

[Chemical Formula 81]

(X1-1)

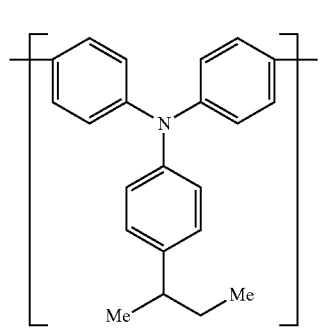

(X1-2)

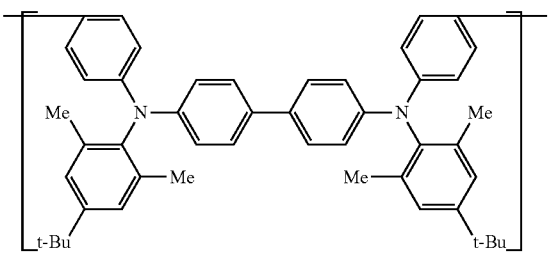

(X1-3)

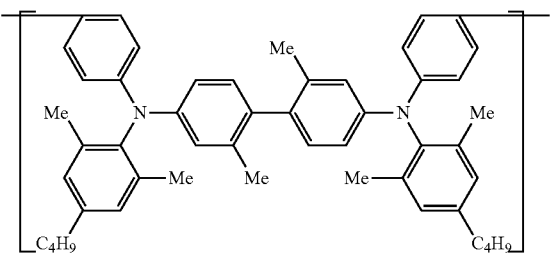

[Chemical Formula 82]

(X1-4)

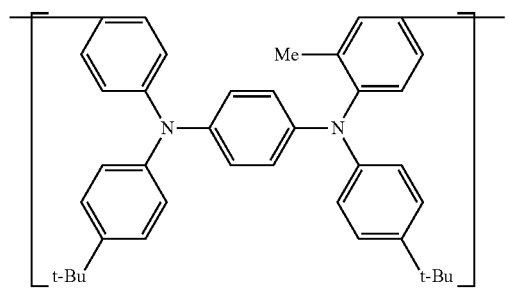

(X1-5)

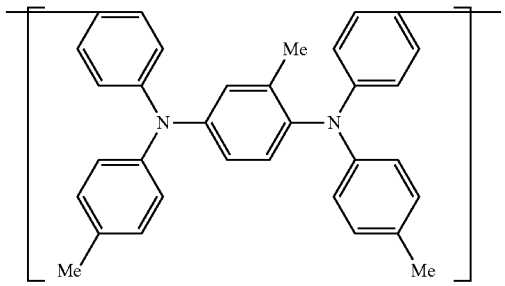

(X1-6)

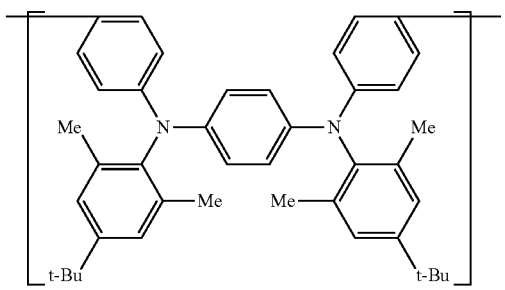

[Chemical Formula 83]

(X1-7)

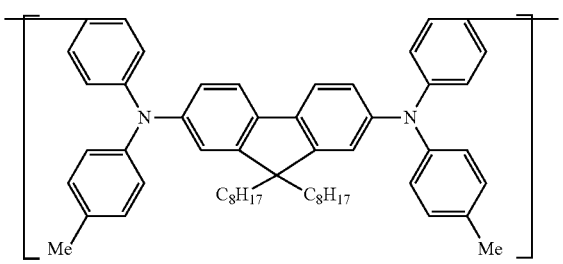

(X1-8)

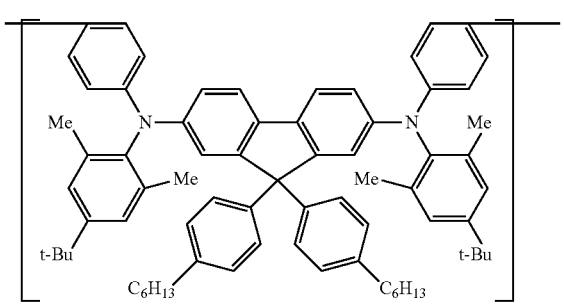

[Chemical Formula 84]

(X1-9)

[Chemical Formula 85]
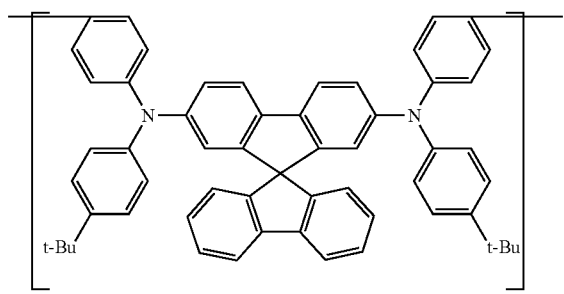
(X1-10)
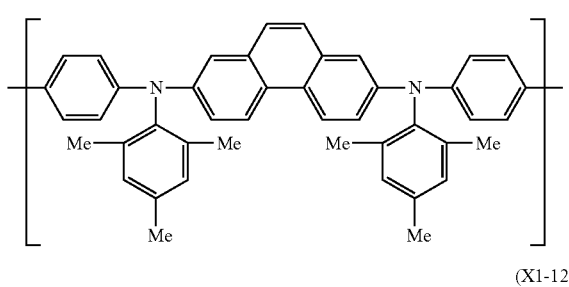
(X1-11)
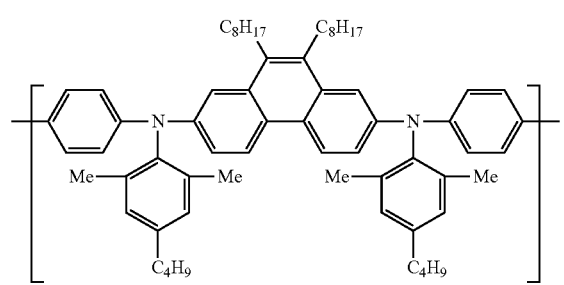
(X1-12)
[Chemical Formula 86]
(X1-13)
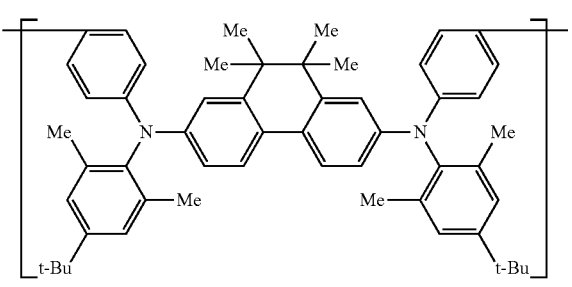
(X1-14)
[Chemical Formula 87]
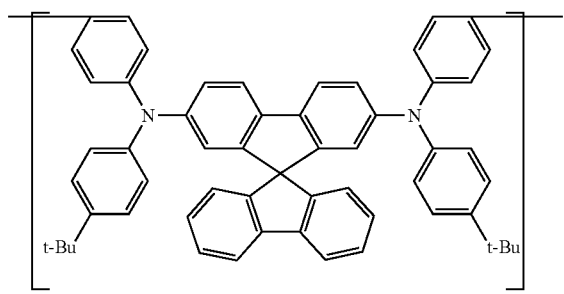
(X1-15)
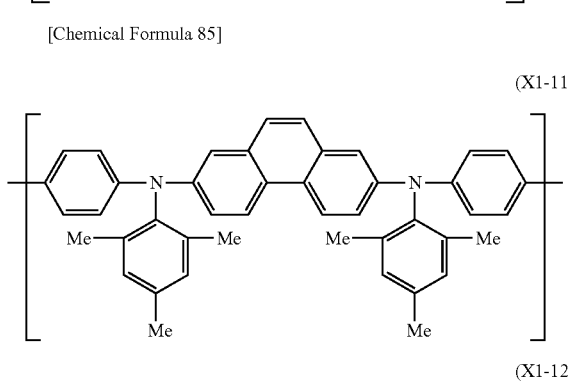
(X1-16)
[Chemical Formula 88]
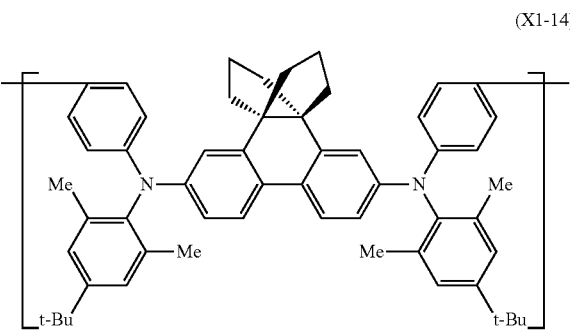
(X1-17)

(X1-18)

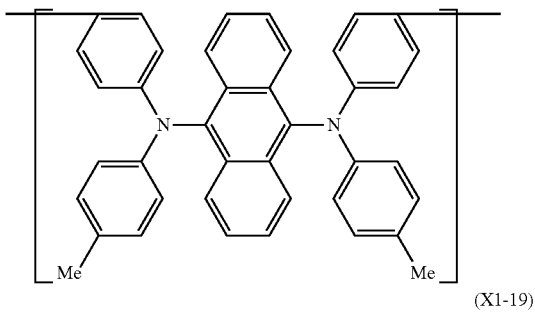

(X1-19)

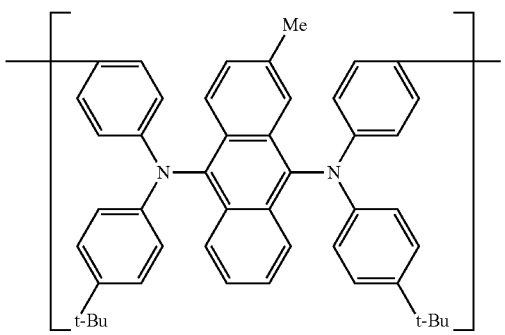

The constitutional unit represented by the formula (X) may be contained only singly or two or more units thereof may be contained in the polymer compound of the hole transporting layer.

It is preferable that the polymer compound of the hole transporting layer further comprises a constitutional unit represented by the formula (Y), because the external quantum efficiency of the light emitting device of the present invention is more excellent.

It is preferable that the polymer compound of the hole transporting layer further comprises a constitutional unit represented by the formula (X) and a constitutional unit represented by the formula (Y), because the external quantum efficiency of the light emitting device of the present invention is more excellent.

[Chemical Formula 89]

 (Y)

[wherein, $Ar^{Y1}$ represents an arylene group, a divalent heterocyclic ring group or a divalent group in which at least one arylene group and at least one divalent heterocyclic ring group are bonded directly to each other, and these groups each optionally have a substituent.]

The arylene group represented by $Ar^{Y1}$ is more preferably a group represented by the formula (A-1), the formula (A-6), the formula (A-7), the formula (A-9) to the formula (A-11), the formula (A-13) or the formula (A-19), further preferably a group represented by the formula (A-1), the formula (A-7), the formula (A-9) or the formula (A-19), and these groups each optionally have a substituent.

The divalent heterocyclic group represented by $Ar^{Y1}$ is more preferably a group represented by the formula (AA-4), the formula (AA-10), the formula (AA-13), the formula (AA-15), the formula (AA-18) or the formula (AA-20), further preferably a group represented by the formula (AA-4), the formula (AA-10), the formula (AA-18) or the formula (AA-20), and these groups each optionally have a substituent.

The more preferable range and the further preferable range of the arylene group and the divalent heterocyclic group in the divalent group in which at least one arylene group and at least one divalent heterocyclic group are bonded directly to each other represented by $Ar^{Y1}$ are the same as the more preferable range and the further preferable range of the arylene group and the divalent heterocyclic group represented by $Ar^{Y1}$ described above, respectively.

The divalent group in which at least one arylene group and at least one divalent heterocyclic group are bonded directly to each other represented by $Ar^{Y1}$ includes the same groups as the divalent group in which at least one arylene group and at least one divalent heterocyclic group are bonded directly to each other represented by $Ar^{X2}$ and $Ar^{X4}$ in the formula (X).

The substituent which the group represented by $Ar^{Y1}$ optionally has is preferably an alkyl group, a cycloalkyl group or an aryl group, and these groups each optionally further have a substituent.

The constitutional unit represented by the formula (Y) includes, for example, constitutional units represented by the formulae (Y-1) to (Y-7), and from the standpoint of the external quantum efficiency of the light emitting device of the present invention preferable is a constitutional unit represented by the formula (Y-1) or (Y-2), from the standpoint of electron transportability of the polymer compound of the hole transporting layer preferable is a constitutional unit represented by the formula (Y-3) or (Y-4), and from the standpoint of hole transportability of the polymer compound of the hole transporting layer preferable are constitutional units represented by the formulae (Y-5) to (Y-7).

[Chemical Formula 90]

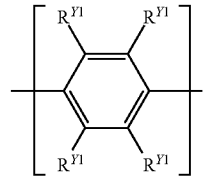 (Y-1)

[wherein, $R^{Y1}$ represents a hydrogen atom, an alkyl group, a cycloalkyl group, an alkoxyl group, a cycloalkoxy group, an aryl group or a monovalent heterocyclic group, and these groups each optionally have a substituent. The plurality of $R^{Y1}$ may be the same or different, and adjacent groups $R^{Y1}$ may be combined together to form a ring together with the carbon atoms to which they are attached.]

$R^{Y1}$ is preferably a hydrogen atom, an alkyl group, a cycloalkyl group or an aryl group, and these groups each optionally have a substituent.

The constitutional unit represented by the formula (Y-1) is preferably a constitutional unit represented by the formula (Y-1').

[Chemical Formula 91]

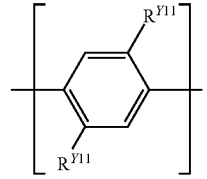 (Y-1')

[wherein, $R^{Y11}$ represents an alkyl group, a cycloalkyl group, an alkoxy group, a cycloalkoxy group, an aryl group or a monovalent heterocyclic group, and these groups each optionally have a substituent. The plurality of $R^{Y1}$ may be the same or different.]

$R^{Y11}$ is preferably an alkyl group, a cycloalkyl group or an aryl group, more preferably an alkyl group or a cycloalkyl group, and these groups each optionally have a substituent.

[Chemical Formula 92]

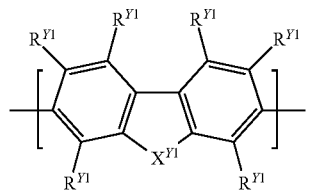

(Y-2)

[wherein, $R^{Y1}$ represents the same meaning as described above.

$X^{Y1}$ represents a group represented by —C($R^{Y2}$)$_2$—, —C($R^{Y2}$)=C($R^{Y2}$)— or —C($R^{Y2}$)$_2$—C($R^{Y2}$)$_2$—. $R^{Y2}$ represents a hydrogen atom, an alkyl group, a cycloalkyl group, an alkoxyl group, a cycloalkoxy group, an aryl group or a monovalent heterocyclic group, and these groups each optionally have a substituent. The plurality of $R^{Y2}$ may be the same or different, and groups $R^{Y2}$ may be combined together to form a ring together with the carbon atoms to which they are attached.]

$R^{Y2}$ is preferably an alkyl group, a cycloalkyl group, an aryl group or a monovalent heterocyclic group, more preferably an alkyl group a cycloalkyl group or an aryl group, and these groups each optionally have a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, and these groups each optionally have a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formula (Y-A1) to (Y-A5), more preferably a group represented by the formula (Y-A4), and these groups each optionally have a substituent.

[Chemical Formula 93]

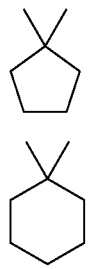

(Y-A1)

(Y-A2)

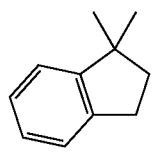

(Y-A3)

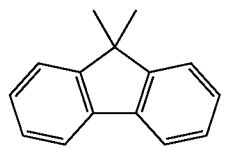

(Y-A4)

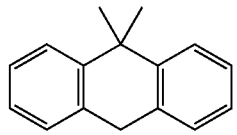

(Y-A5)

Regarding the combination of two $R^{Y2}$s in the group represented by —C($R^{Y2}$)=C($R^{Y2}$)— in $X^{Y1}$, it is preferable that the both are an alkyl group or cycloalkyl group, or one is an alkyl group or a cycloalkyl group and the other is an aryl group, and these groups each optionally have a substituent.

Four $R^{Y2}$s in the group represented by —C($R^{Y2}$)$_2$—C($R^{Y2}$)$_2$— in $X^{Y1}$ are preferably an alkyl group or a cycloalkyl group optionally having a substituent. The plurality of $R^{Y2}$ may be combined together to form a ring together with the atoms to which they are attached, and when the groups $R^{Y2}$ form a ring, the group represented by —C($R^{Y2}$)$_2$—C($R^{Y2}$)$_2$— is preferably a group represented by the formula (Y-B1) to (Y-B5), more preferably a group represented by the formula (Y-B3), and these groups each optionally have a substituent.

[Chemical Formula 94]

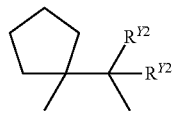

(Y-B1)

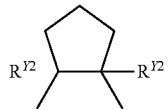

(Y-B2)

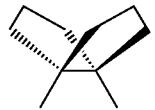

(Y-B3)

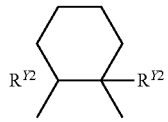

(Y-B4)

-continued

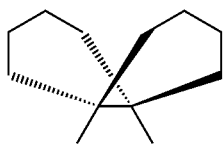
(Y-B5)

[wherein, $R^{Y2}$ represents the same meaning as described above.]

It is preferable that the constitutional unit represented by the formula (Y-2) is a constitutional unit represented by the formula (Y-2').

[Chemical Formula 95]

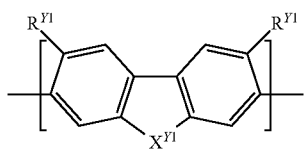
(Y-2')

[wherein, $R^{Y1}$ and $X^{Y1}$ represent the same meaning as described above.]

[Chemical Formula 96]

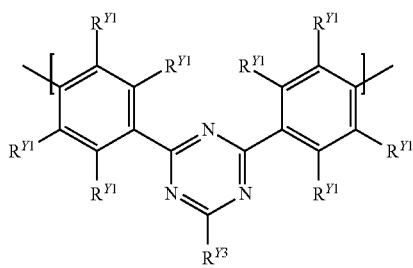
(Y-3)

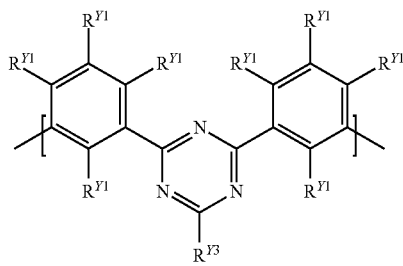
(Y-4)

[wherein, $R^{Y1}$ represents the same meaning as described above.

$R^{Y3}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y3}$ is preferably an alkyl group, a cycloalkyl group, an alkoxy group, a cycloalkoxy group, an aryl group or a monovalent heterocyclic group, more preferably an aryl group, and these groups each optionally have a substituent.

[Chemical Formula 97]

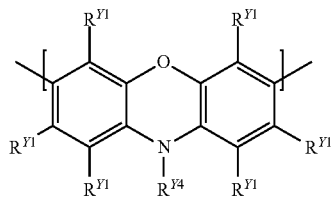
(Y-5)

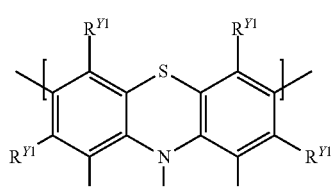
(Y-6)

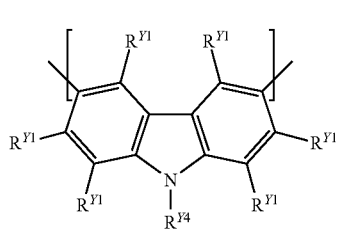
(Y-7)

[wherein, $R^{Y1}$ represents the same meaning as described above.

$R^{Y4}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, and these groups each optionally have a substituent.

The constitutional unit represented by the formula (Y) includes, for example, constitutional units represented by the formulae (Y-11) to (Y-55).

[Chemical Formula 98]

(Y-11)

(Y-12)

(Y-13)
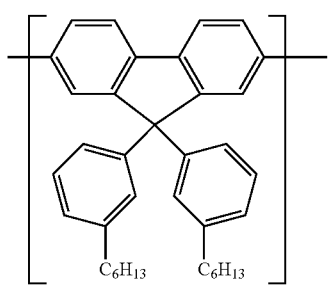
[Chemical Formula 99]
(Y-14)
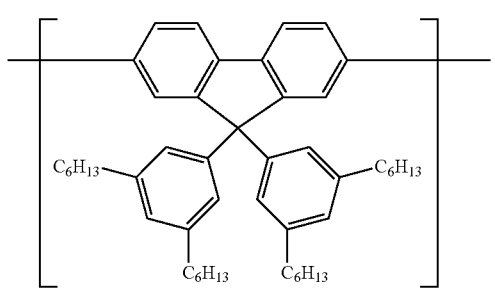
(Y-15)
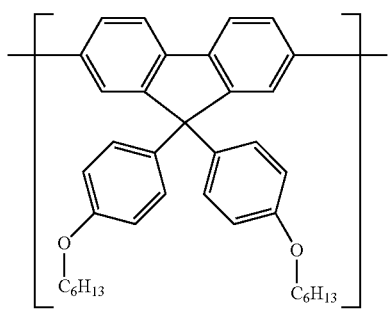
(Y-16)
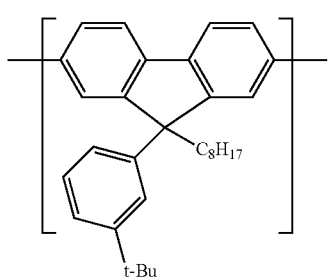
[Chemical Formula 100]
(Y-17)
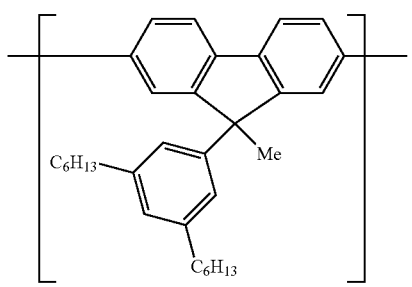
(Y-18)
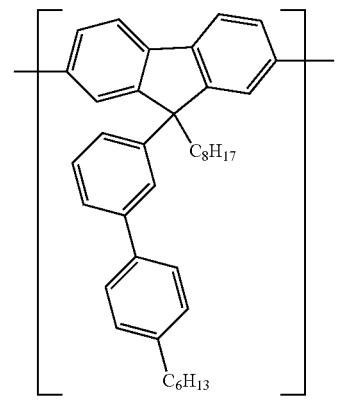
(Y-19)
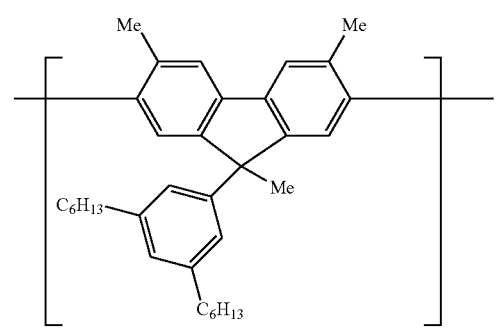
[Chemical Formula 101]
(Y-20)
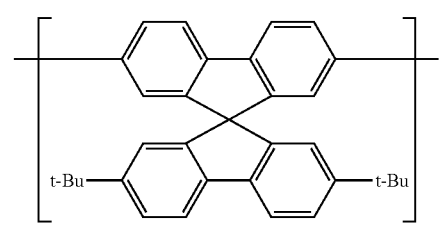
(Y-21)
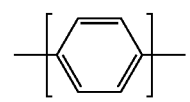
(Y-22)
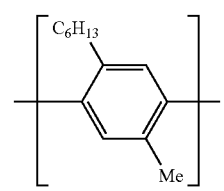
(Y-23)
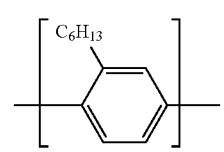

[Chemical Formula 102]
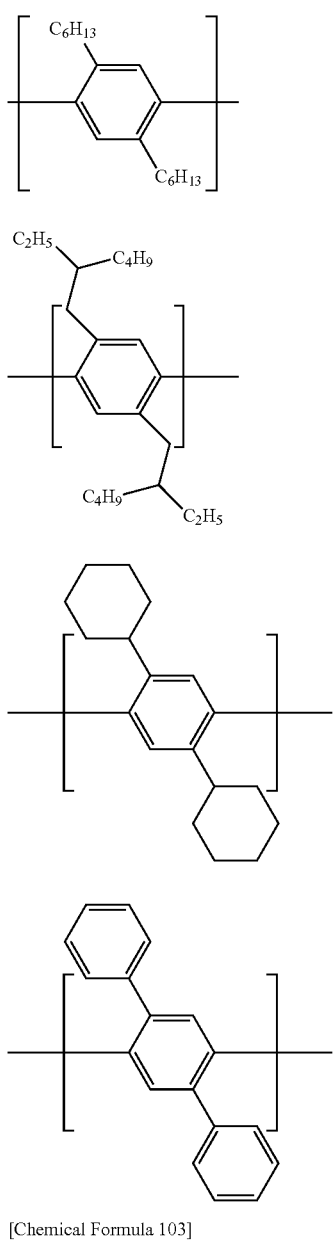
(Y-24)
(Y-25)
(Y-26)
(Y-27)
[Chemical Formula 103]
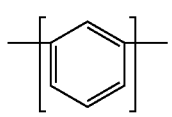
(Y-28)
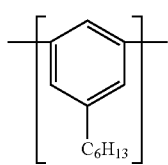
(Y-29)
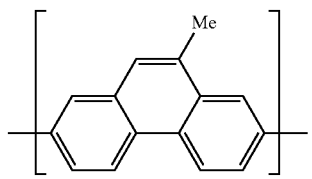
(Y-30)
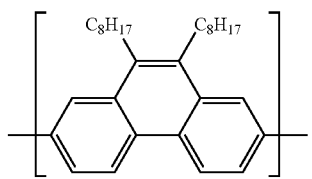
(Y-31)
[Chemical Formula 104]
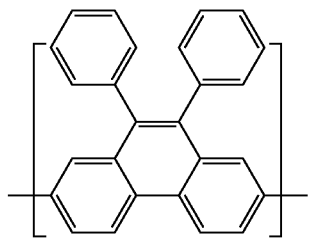
(Y-32)
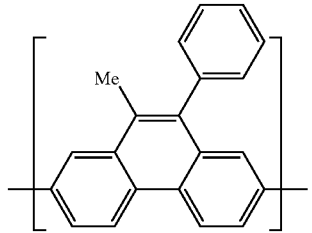
(Y-33)
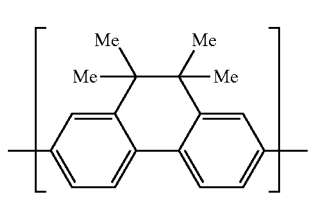
(Y-34)
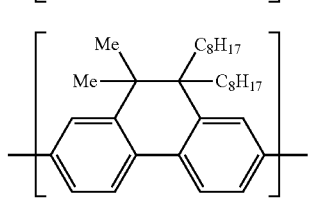
(Y-35)
[Chemical Formula 105]
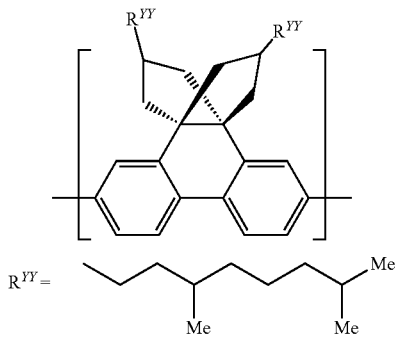
(Y-36)

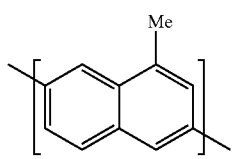 (Y-37)
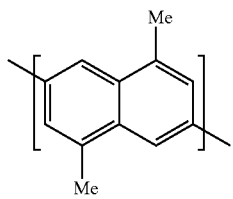 (Y-38)
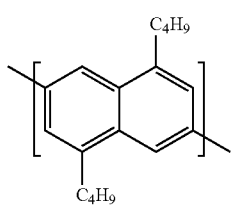 (Y-39)
[Chemical Formula 106]
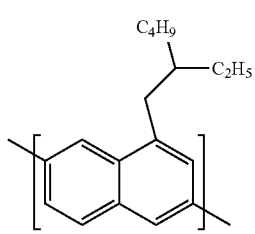 (Y-40)
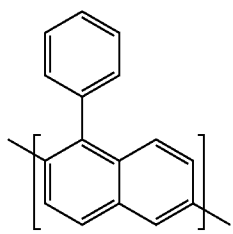 (Y-41)
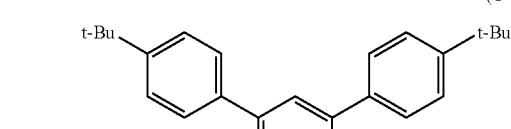 (Y-42)
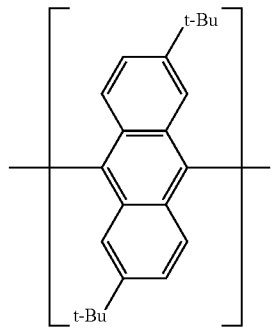 (Y-43)
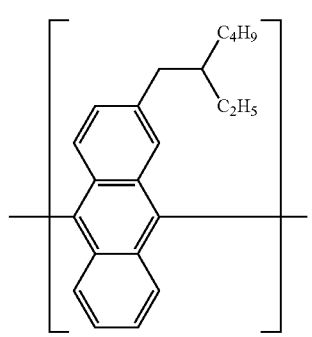 (Y-44)
[Chemical Formula 107]
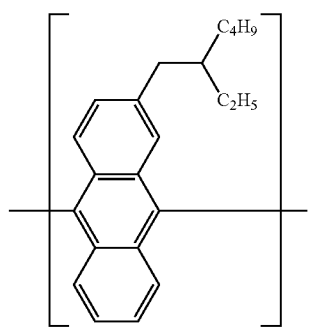 (Y-45)
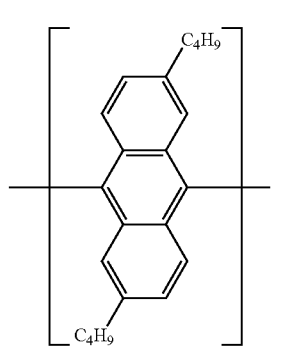 (Y-46)
$R^{YY} =$ 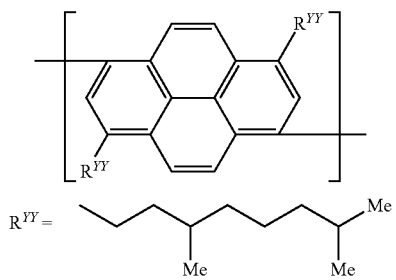
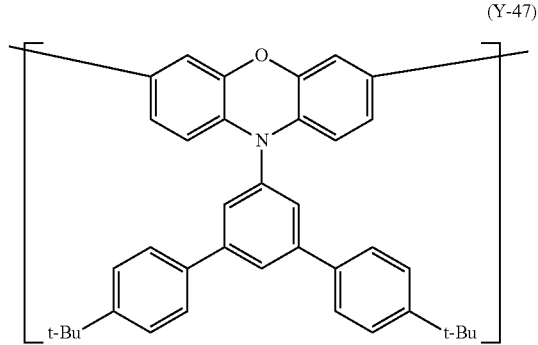 (Y-47)

[Chemical Formula 108]

(Y-48)
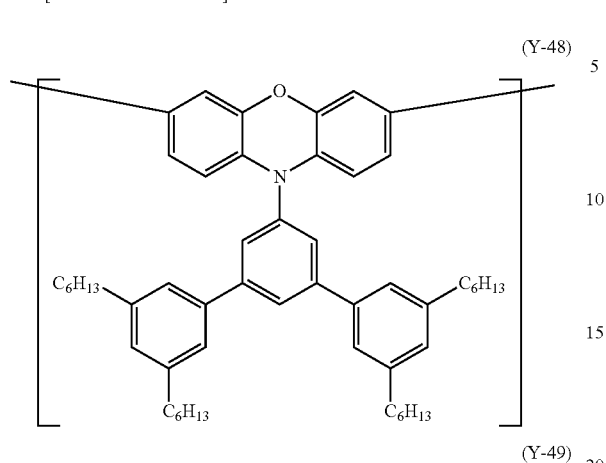

(Y-49)
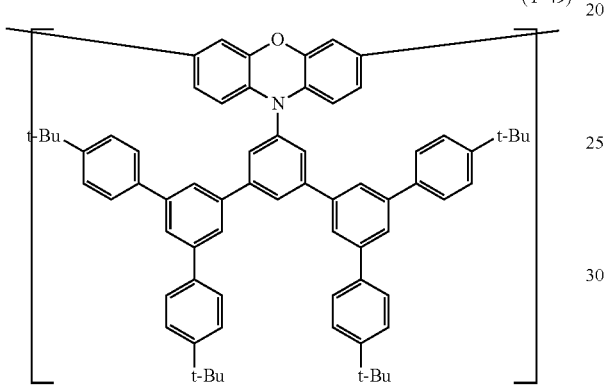

[Chemical Formula 109]

(Y-50)
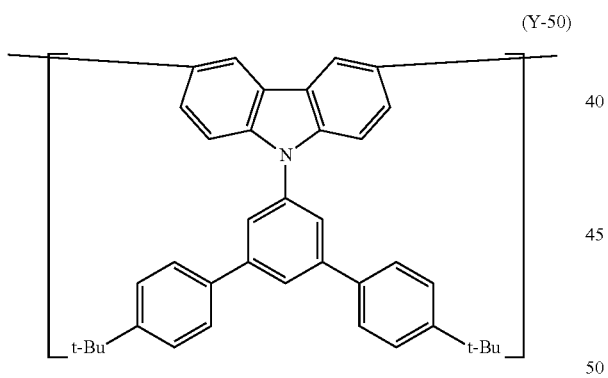

(Y-51)
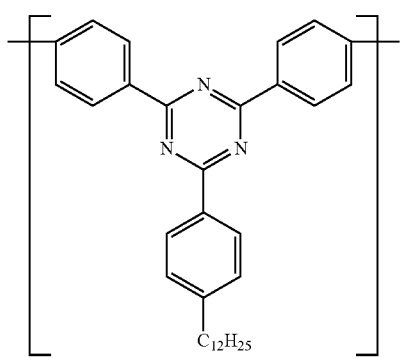

(Y-52)
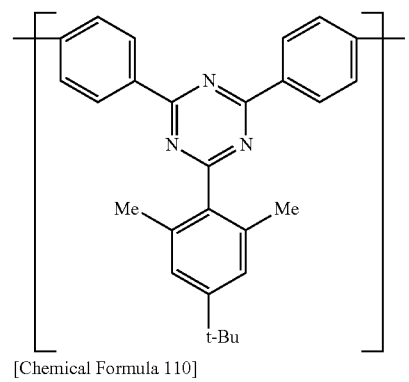

[Chemical Formula 110]

(Y-53)
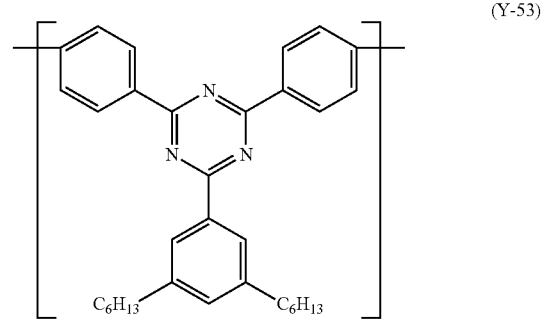

(Y-54)
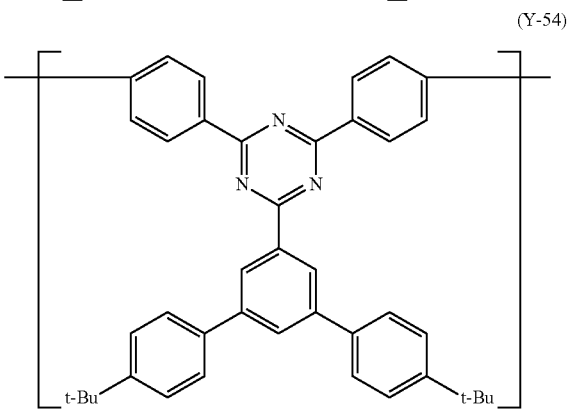

(Y-55)
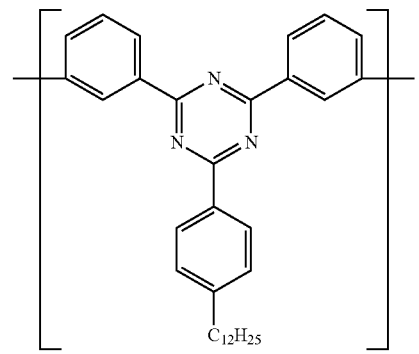

The content of the constitutional unit represented by the formula (Y) in which $Ar^{Y1}$ is an arylene group is preferably 0.5 to 80 mol %, more preferably 30 to 60 mol % with respect to the total content of constitutional units contained in the polymer compound of the hole transporting layer, because the external quantum efficiency of the light emitting device of the present invention is more excellent.

The content of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 40 mol %, more preferably 3 to 30 mol % with respect to the total content of constitutional units contained in the polymer compound of the hole transporting layer, because the charge transportability of the polymer compound of the hole transporting layer invention is excellent.

The constitutional unit represented by the formula (Y) may be contained only singly or two or more units thereof may be contained in the polymer compound of the hole transporting layer.

The polymer compound of the hole transporting layer includes, for example, polymer compounds P-1 to P-8 shown in Table 1. "Other constitutional unit" denotes a constitutional unit other than constitutional units represented by the formula (2), the formula (2'), the formula (X) and the formula (Y).

TABLE 1

| | constitutional unit and mole fraction thereof | | | | |
|---|---|---|---|---|---|
| polymer compound | formula (2) p' | formula (2') q' | formula (X) r' | formula (Y) s' | other t' |
| P-1 | 0.1 to 99.9 | 0.1 to 99.9 | 0 | 0 | 0 to 30 |
| P-2 | 0.1 to 99.9 | 0 | 0.1 to 99.9 | 0 | 0 to 30 |
| P-3 | 0.1 to 99.9 | 0 | 0 | 0.1 to 99.9 | 0 to 30 |
| P-4 | 0 | 0.1 to 99.9 | 0.1 to 99.9 | 0 | 0 to 30 |
| P-5 | 0 | 0.1 to 99.9 | 0 | 0.1 to 99.9 | 0 to 30 |
| P-6 | 0.1 to 99.8 | 0.1 to 99.8 | 0.1 to 99.8 | 0 | 0 to 30 |
| P-7 | 0.1 to 99.8 | 0.1 to 99.8 | 0 | 0.1 to 99.8 | 0 to 30 |
| P-8 | 0.1 to 99.7 | 0.1 to 99.7 | 0.1 to 99.7 | 0.1 to 99.7 | 0 to 30 |

[in the table, p', q', r', s' and t' represent the mole fraction of each constitutional unit. p'+q'+r'+s'+t'=100 and, 70≤p'+q'+r'+s'≤100.]

The examples and preferable ranges of constitutional units represented by the formula (2), the formula (2'), the formula (X) and the formula (Y) in the polymer compounds P-1 to P-8 are as described above.

The polystyrene-equivalent number average molecular weight of the polymer compound of the hole transporting layer is preferably $5\times10^3$ to $1\times10^6$, more preferably $1\times10^4$ to $5\times10^5$, more preferably $1.5\times10^4$ to $1\times10^5$.

<Production Method of Polymer Compound of the Hole Transporting Layer>

The polymer compound of the hole transporting layer can be produced by using known polymerization methods described in Chem. Rev., vol. 109, pp. 897-1091 (2009) and the like, and the known polymerization methods include, for example, methods for causing polymerization by a coupling reaction using a transition metal catalyst such as the Suzuki reaction, the Yamamoto reaction, the Buchwald reaction, the Stille reaction, the Negishi reaction and the Kumada reaction.

In the above-described polymerization methods, the monomer charging method includes a method in which the total amount of monomers is charged in a lump into the reaction system, a method in which a part of monomers is charged and reacted, then, the remaining monomers are charged in a lump, continuously or in divided doses, a method in which monomers are charged continuously or in divided doses, and the like.

The transition metal catalyst includes a palladium catalyst and a nickel catalyst.

The post treatment of the polymerization reaction is conducted by using known methods, for example, a method in which water-soluble impurities are removed by liquid-separation, a method in which the reaction solution after the polymerization reaction is added to a lower alcohol such as methanol and the like, the deposited precipitate is filtrated, then, dried, and other methods, singly or in combination. When the purity of the polymer host is low, purification can be carried out by usual methods such as, for example, crystallization, reprecipitation, continuous extraction using a Soxhlet extractor, column chromatography and the like.

[Low Molecular Weight Compound of Hole Transporting Layer]

The low molecular weight compound of the hole transporting layer is preferably a low molecular weight compound represented by the formula (3).

[Chemical Formula 111]

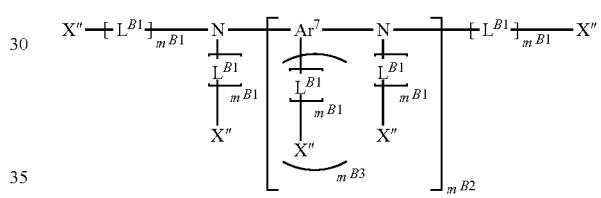

(3)

[wherein, $m^{B1}$ and $m^{32}$ each independently represent an integer of 0 or more. The plurality of $m^{B1}$ may be the same or different.

$n^{B1}$ represents an integer of 0 or more. When a plurality of $n^{B1}$ are present, they may be the same or different.

$Ar^7$ represents an aromatic hydrocarbon group, a heterocyclic group, or a group in which at least one aromatic hydrocarbon ring and at least one heterocyclic ring are bonded directly to each other, and these groups each optionally have a substituent. When a plurality of $Ar^5$ are present, they may be the same or different.

$L^{B1}$ represents an alkylene group, a cycloalkylene group, an arylene group, a divalent heterocyclic group, a group represented by —NR'"—, an oxygen atom or a sulfur atom, and these groups each optionally have a substituent. R'" represents a hydrogen atom, an alkyl group, a cycloalkyl group, an aryl group or a monovalent heterocyclic group, and these groups each optionally have a substituent. When a plurality of $L^{B1}$ are present, they may be the same or different.

X" represents a crosslinkable group selected from Group A of crosslinkable group, a hydrogen atom, an alkyl group, a cycloalkyl group, an aryl group or a monovalent heterocyclic group, and these groups each optionally have a substituent. The plurality of X" may be the same or different. At least one of the plurality of X" is a crosslinkable group selected from Group A of crosslinkable group.]

$m^{B1}$ is usually an integer of 0 to 10, preferably an integer of 0 to 5, more preferably an integer of 0 to 2, further preferably 0 or 1, particularly preferably 0, because synthesis of the low molecular weight compound of the hole transporting layer becomes easy.

$m^{B2}$ is usually an integer of 0 to 10, and it is preferably an integer of 1 to 5, more preferably an integer of 1 to 3, further preferably 1 or 2, particularly preferably 1, because synthesis of the low molecular weight compound of the hole transporting layer is easy and the external quantum efficiency of the light emitting device of the present invention is more excellent.

$m^{B3}$ is usually an integer of 0 to 5, preferably an integer of 0 to 4, more preferably an integer of 0 to 2, further preferably 0, because synthesis of the low molecular weight compound of the hole transporting layer becomes easy.

The definition and examples of the arylene group portion obtained by removing $m^{B3}$ substituents of the aromatic hydrocarbon group represented by $Ar^7$ are the same as the definition and examples of the arylene group represented by $Ar^{X2}$ in the formula (X) described above.

The definition and examples of the divalent heterocyclic group portion obtained by removing $m^{B3}$ substituents of the heterocyclic group represented by $Ar^7$ are the same as the definition and examples of the divalent heterocyclic group portion represented by $Ar^{X2}$ in the formula (X) described above.

The definition and examples of the divalent group obtained by removing $m^{B3}$ substituents of the group in which at least one aromatic hydrocarbon ring and at least one heterocyclic ring are bonded directly to each other represented by $Ar^7$ are the same as the definition and examples of the divalent group in which at least one arylene group and at least one divalent heterocyclic group are bonded directly to each other represented by $Ar^{X2}$ in the formula (X) described above.

$Ar^7$ is preferably an aromatic hydrocarbon group because the external quantum efficiency of the light emitting device of the present invention is excellent, and this aromatic hydrocarbon group optionally has a substituent.

The definitions and examples of the alkylene group, the cycloalkylene group, the arylene group and the divalent heterocyclic group represented by $L^{B1}$ are the same as the definitions and examples of the alkylene group, the cycloalkylene group, the arylene group and the divalent heterocyclic group represented by $L^A$, respectively.

$L^{B1}$ is preferably an alkylene group, an arylene group or an oxygen atom, more preferably an alkylene group or an arylene group, further preferably a phenylene group, a fluorenediyl group or an alkylene group, particularly preferably a phenylene group or an alkylene group, and these groups each optionally have a substituent, because synthesis of the low molecular weight compound of the hole transporting layer becomes easy.

X″ is preferably a crosslinkable group represented by any one of the formulae (XL-1) to (XL-17), an aryl group or a monovalent heterocyclic group, more preferably a crosslinkable group represented by the formula (XL-1), (XL-3), (XL-7) to (XL-10), (XL-16) or (XL-17) or an aryl group, further preferably a crosslinkable group represented by the formula (XL-1), (XL-16) or (XL-17), a phenyl group, a naphthyl group or a fluorenyl group, particularly preferably a crosslinkable group represented by the formula (XL-16) or (XL-17), a phenyl group or a naphthyl group, and these groups each optionally have a substituent.

The low molecular weight compound of the hole transporting layer includes, for example, low molecular weight compounds represented by the formulae (3-1) to (3-16), and is preferably a low molecular weight compound represented by the formulae (3-1) to (3-10), more preferably a low molecular weight compound represented by the formulae (3-5) to (3-9).

[Chemical Formula 112]

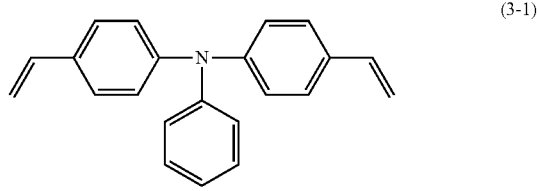

(3-1)

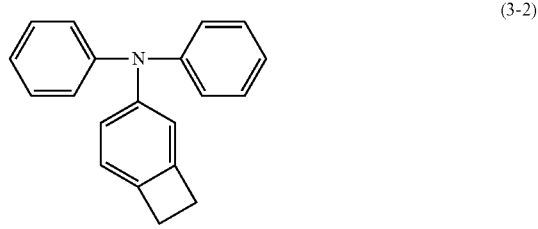

(3-2)

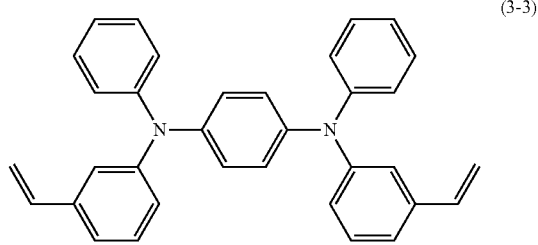

(3-3)

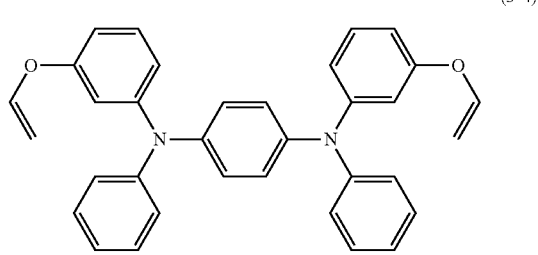

(3-4)

[Chemical Formula 113]

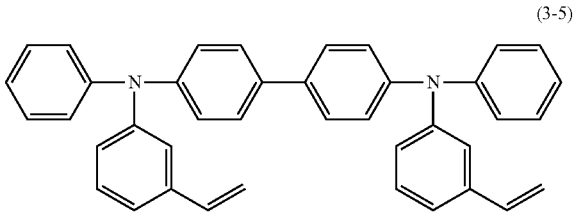

(3-5)

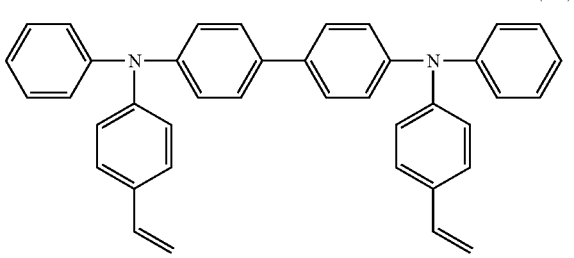

(3-6)

(3-7)
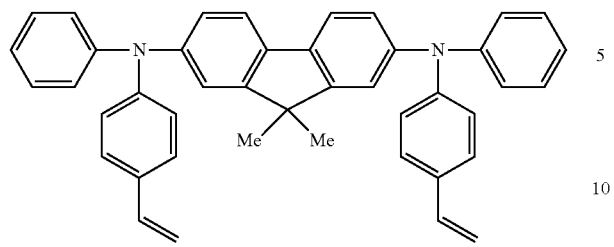
[Chemical Formula 114]
(3-8)
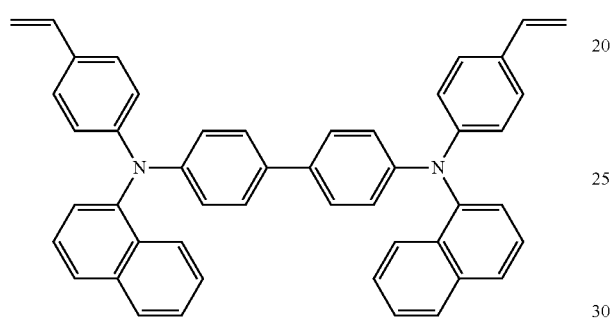
(3-9)
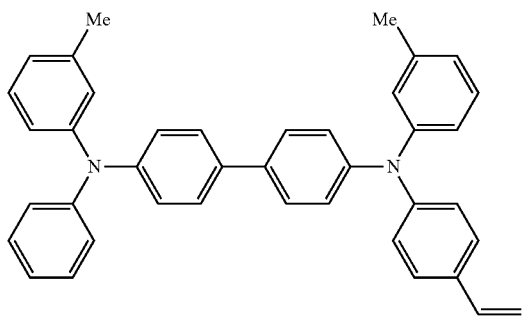
(3-10)
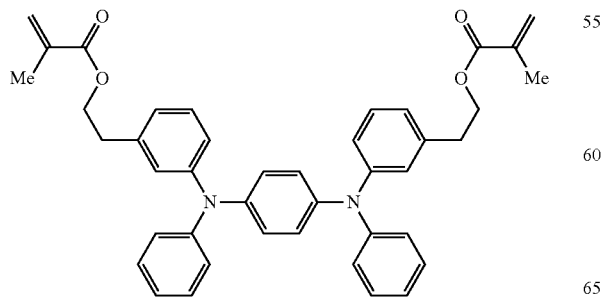
[Chemical Formula 115]
(3-11)
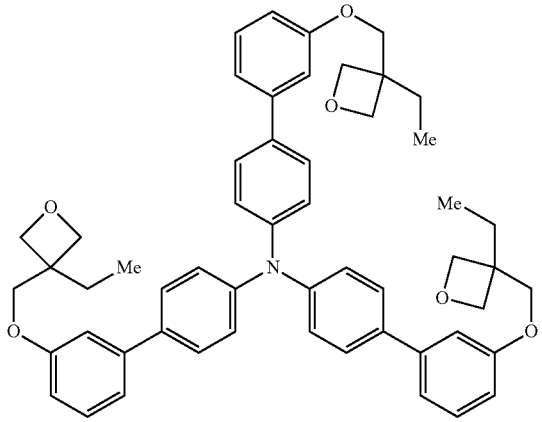
(3-12)
(3-13)
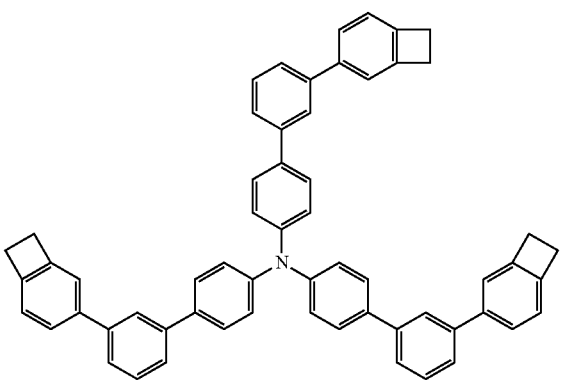

-continued
[Chemical Formula 116]

(3-14)
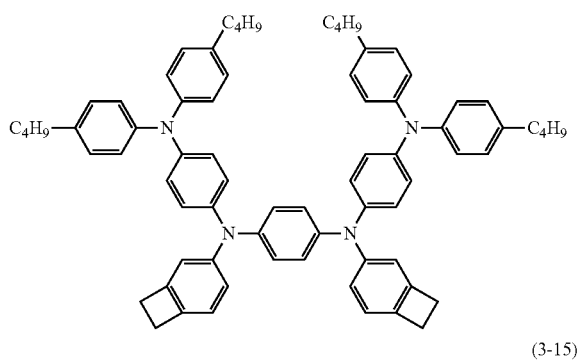

(3-15)
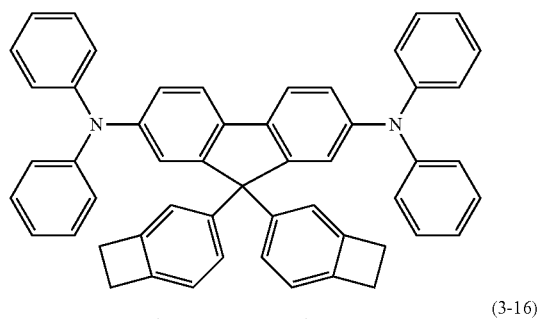

(3-16)
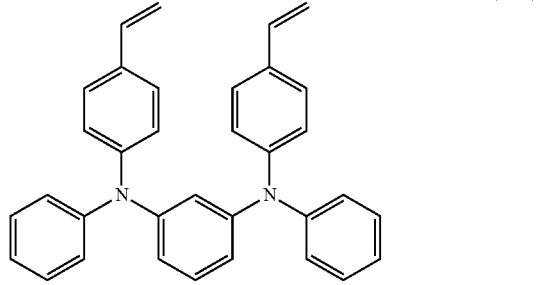

The low molecular weight compound of the hole transporting layer is available from Aldrich, Luminescence Technology Corp., American Dye Source, and the like.

Further, the low molecular weight compound can be synthesized according to methods disclosed, for example, in International Publication WO 1997/033193, International Publication WO 2005/035221 and International Publication WO 2005/049548, in addition to the above-described means.

[Composition Ratio of Hole Transporting Layer, and the Like]

The hole transporting layer may be a layer comprising a crosslinked body of a crosslinkable material, and at least one material selected from the group consisting of a hole transporting material (different from a crosslinked body of a crosslinkable material), a hole injection material, an electron transporting material, an electron injection material, a light emitting material and an antioxidant.

The examples and the preferable range of the hole transporting material, the electron transporting material, the hole injection material, the electron injection material and the light emitting material contained in the hole transporting layer are the same as the examples and the preferable range of the hole transporting material, the electron transporting material, the hole injection material, the electron injection material and the light emitting material contained in the light emitting layer. Each compounding amount of the hole transporting material, the electron transporting material, the hole injection material, the electron injection material and the light emitting material in the hole transporting layer is usually 1 to 400 parts by weight, preferably 5 to 150 parts by weight when the amount of the crosslinked body of a crosslinkable material is 100 parts by weight.

The examples and the preferable range of the antioxidant contained in the hole transporting layer are the same as the examples and the preferable range of the antioxidant contained in the light emitting layer. The compounding amount of the antioxidant in the hole transporting layer is usually 0.001 to 10 parts by weight when the amount of the crosslinked body of a crosslinkable material is 100 parts by weight.

[Ink of Hole Transporting Layer]

A composition of a hole transporting layer comprising a crosslinkable material and a solvent (hereinafter, referred to also as "ink of hole transporting layer") can be suitably used for application methods such as a spin coat method and an inkjet printing method, like the ink of the light emitting layer.

The preferable range of the viscosity of the ink of the hole transporting layer is the same as the preferable range of the viscosity of the ink of the light emitting layer.

The examples and the preferable range of the solvent contained in the ink of the hole transporting layer are the same as the examples and the preferable range of the solvent contained in the ink of the light emitting layer.

In the ink of the hole transporting layer, the compounding amount of a solvent is usually 1000 to 100000 parts by weight, preferably 2000 to 20000 parts by weight when the amount of the crosslinkable material is 100 parts by weight.

<Layer Constitution of Light Emitting Device>

The light emitting device of the present invention comprises an anode, a cathode, a light emitting layer disposed between the anode and the cathode, and a hole transporting layer disposed between the anode and the cathode. The light emitting device of the present invention may comprise layers other than the anode, the cathode, the light emitting layer and the hole transporting layer.

In the light emitting device of the present invention, it is preferable that the light emitting layer and the hole transporting layer are adjacent to each other, because the light emitting device of the present invention is more excellent in external quantum efficiency.

It is preferable for the light emitting device of the present invention to further comprise a hole injection layer between the anode and the hole transporting layer, because the light emitting device of the present invention is more excellent in external quantum efficiency. Further, it is preferable for the light emitting device of the present invention to further comprise at least one layer selected from the group consisting of an electron transporting layer and an electron injection layer, between the cathode and the light emitting layer, because the light emitting device of the present invention is more excellent in external quantum efficiency.

The preferable layer constitution of the light emitting device of the present invention includes, for example, the following layer constitutions.

(a) anode-hole transporting layer-light emitting layer-cathode (b) anode-hole transporting layer-light emitting layer-electron injection layer-cathode (c) anode-hole injection layer-hole transporting layer-light emitting layer-cathode (d) anode-hole injection layer-hole transporting layer-light emitting layer-electron injection layer-cathode (e) anode-hole injection layer-hole transporting layer-light emitting layer-electron injection layer-cathode (f) anode-hole transporting layer-light emitting layer-electron transporting layer-electron injection layer-cathode (g) anode-hole injection layer-hole transporting layer-light emitting layer-electron transporting layer-electron injection layer-cathode In the light emitting device of the present invention, an insulation layer may be further provided adjacent to an electrode, for improvement of close adhesion to the electrode and for improving charge injection from the electrode, and, a thin buffer layer may be inserted into the interface of a hole transporting layer, an electron transporting layer or a light emitting layer, for improvement of close adhesion of the interface and for prevention of mixing. The order and the number of layers to be laminated and the thickness of each layer may be adjusted in consideration of external quantum efficiency and device life.

Next, the constitution of the light emitting device of the present invention will be illustrated in detail.

[Substrate]

The substrate which the light emitting device of the present invention can have may advantageously be one which does not chemically change in forming an electrode and forming an organic layer, and for example, substrates composed of glass, plastic, polymer film, metal film, silicon and the like, and a substrate obtained by laminating them, are used.

In the light emitting device of the present invention, if necessary, two or more layers of an anode, a hole injection layer, an electron transporting layer, an electron injection layer and a cathode may be provided, respectively.

When a plurality of anodes, hole injection layers, electron transporting layers, electron injection layers and cathodes are present, they may be the same or different at each occurrence.

The thickness of an anode, a hole injection layer, a hole transporting layer, a light emitting layer, an electron transporting layer, an electron injection layer and a cathode is usually 1 nm to 1 µm, preferably 2 nm to 500 nm, further preferably 5 nm to 150 nm.

[Electron Transporting Layer]

The electron transporting layer is a layer comprising an electron transporting material. The electron transporting material includes, for example, electron transporting materials which the light emitting layer may comprise described above, and polymer compounds comprising at least one constitutional unit selected from the group consisting of a constitutional unit represented by the formula (ET-1) and a constitutional unit represented by the formula (ET-2) (hereinafter, referred to also as "polymer compound of electron transporting layer"), and preferable is the polymer compound of the electron transporting layer.

[Chemical Formula 117]

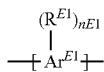

(ET-1)

[wherein, nE1 represents an integer of 1 or more.

$Ar^{E1}$ represents an aromatic hydrocarbon group or a heterocyclic group, and these groups each optionally have a substituent other than $R^{E1}$.

$R^{E1}$ represents a group represented by the formula (ES-1). When a plurality of $R^{E1}$ are present, they may be the same or different.]

$$—R^{E3}-\{(Q^{E1})_{nE3}-Y^{E1}(M^{E1})_{aE1}(Z^{E1})_{bE1}\}_{mE1} \quad \text{(ES-1)}$$

[wherein, nE3 represents an integer of 0 or more, aE1 represents an integer of 1 or more, bE1 represents an integer of 0 or more and mE1 represents an integer of 1 or more. When a plurality of nE3, aE1 and bE1 are present, they may be the same or different at each occurrence. When $R^{E3}$ is a single bond, mE1 is 1. Further, aE1 and bE1 are selected so that the charge of a group represented by the formula (ES-1) is 0.

$R^{E3}$ represents a single bond, a hydrocarbon group, a heterocyclic group or $—O—R^{E3'}$ ($R^{E3'}$ represents a hydrocarbon group or a heterocyclic group), and these groups each optionally have a substituent.

$Q^{E1}$ represents an alkylene group, a cycloalkylene group, an arylene group, an oxygen atom or a sulfur atom, and these groups optionally have a substituent. When a plurality of $Q^{E1}$ are present, they may be the same or different.

$Y^{E1}$ represents $—CO_2^-$, $—SO_3^-$, $—SO_2^-$ or $PO_3^{2-}$. When a plurality of $Y^{E1}$ are present, they may be the same or different.

$M^{E1}$ represents an alkali metal cation, an alkaline earth metal cation or an ammonium cation, and this ammonium cation optionally has a substituent. When a plurality of $M^{E1}$ are present, they may be the same or different.

$Z^{E1}$ represents $F^-$, $Cl^-$, $Br^-$, $I^-$, $OH^-$, $B(R^{E4})_4^-$, $R^{E4}SO_3^-$, $R^{E4}COO^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$. $R^{E4}$ represents an alkyl group, a cycloalkyl group or an aryl group, and these groups each optionally have a substituent. When a plurality of $Z^{E1}$ are present, they may be the same or different.]

nE1 is usually an integer of 1 to 4, preferably 1 or 2.

The aromatic hydrocarbon group or the heterocyclic group represented by $Ar^{E1}$ is preferably a group obtained by removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazolediyl group nE1 hydrogen atoms bonding directly to atoms constituting its ring, and optionally has a substituent other than $R^{E1}$.

The substituent other than $R^{E1}$ which $Ar^{E1}$ optionally has includes a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group, a cycloalkynyl group, a carboxyl group and a group represented by the formula (ES-3).

$$—O—(C_{n'}H_{2n'}O)_{nx}—C_{m'}H_{2m'+1} \quad \text{(ES-3)}$$

[wherein, n', m' and nx each independently represent an integer of 1 or more.]

nE3 is usually an integer of 0 to 10, preferably an integer of 0 to 8, more preferably an integer of 0 to 2.

aE1 is usually an integer of 1 to 10, preferably an integer of 1 to 5, more preferably 1 or 2.

bE1 is usually an integer of 0 to 10, preferably an integer of 0 to 4, more preferably 0 or 1.

mE1 is usually an integer of 1 to 5, preferably 1 or 2, more preferably 0 or 1.

When $R^{E3}$ is $-O-R^{E3'}$, the group represented by the formula (ES-1) is a group represented by the following formula.

$$-O-R^{E3'}-\{(Q^{E1})_{nE3}-Y^{E1}(M^{E1})_{aE1}(Z^{E1})_{bE1}\}_{mE1}$$

$R^{E3}$ is preferably a hydrocarbon group or a heterocyclic group, more preferably an aromatic hydrocarbon group or an aromatic heterocyclic group, further preferably an aromatic hydrocarbon group.

The substituent which $R^{E3}$ optionally has includes an alkyl group, a cycloalkyl group, an aryl group, a monovalent heterocyclic group and a group represented by the formula (ES-3), and is preferably a group represented by the formula (ES-3).

$Q^{E1}$ is preferably an alkylene group, an arylene group or an oxygen atom, more preferably an alkylene group or an oxygen atom.

$Y^{E1}$ is preferably $-CO_2^-$, $-SO_2^-$ or $PO_3^{2-}$, more preferably $-CO_2^-$.

The alkali metal cation represented by $M^{E1}$ includes, for example, $Li^+$, $Na^+$, $K^+$, $Rb^+$ and $Cs^+$, and is preferably $K^+$, $Rb^+$ or $Cs^+$, more preferably $Cs^+$.

The alkaline earth metal cation represented by $M^{E1}$ includes, for example, $Be^{2+}$, $Mg^{2+}$, $Ca^{2+}$, $Sr^{2+}$ and $Ba^{2+}$, and is preferably $Mg^{2+}$, $Ca^{2+}$, $Sr^{2+}$ or $Ba^{2+}$, more preferably $Ba^{2+}$.

$M^{E1}$ is preferably an alkali metal cation or an alkaline earth metal cation, more preferably an alkali metal cation.

$Z^{E1}$ is preferably $F^-$, $Cl^-$, $Br^-$, $I^-$, $OH^-$, $B(R^{E4})_4^-$, $R^{E4}SO_3^-$, $R^{E4}COO^-$ or $NO_3^-$, more preferably $F^-$, $Cl^-$, $Br^-$, $I^-$, $OH^-$, $R^{E4}SO_3^-$ or $R^{E4}COO^-$. $R^{E4}$ is preferably an alkyl group.

The group represented by the formula (ES-1) includes, for example, groups represented by the following formulae.

[Chemical Formula 118]

[Chemical Formula 119]

[wherein, $M^+$ represents $Li^+$, $Na^+$, $K^+$, $Cs^+$ or $N(CH_3)_4^+$. When a plurality of $M^+$ are present, they may be the same or different.]

[Chemical Formula 120]

$$-\{Ar^{E2}\}-\quad\text{(ET-2)}$$

with $(R^{E2})_{nE2}$ substituent

[wherein,
nE2 represents an integer of 1 or more.
$Ar^{E2}$ represents an aromatic hydrocarbon group or a heterocyclic group, and these groups each optionally have a substituent other than $R^{E2}$.
$R^{E2}$ represents a group represented by the formula (ES-2). When a plurality of $R^{E2}$ are present, they may be the same or different.]

$$-R^{E5}-\{(Q^{E2})_{nE4}-Y^{E2}(M^{E2})_{aE2}(Z^{E2})_{bE2}\}_{mE2} \quad\text{(ES-2)}$$

[wherein, nE4 represents an integer of 0 or more, aE2 represents an integer of 1 or more, bE2 represents an integer of 0 or more and mE2 represents an integer of 1 or more. When a plurality of nE4, aE2 and bE2 are present, they may be the same or different at each occurrence. When $R^{E5}$ is a single bond, mE2 is 1. Further, aE2 and bE2 are selected so that the charge of a group represented by the formula (ES-2) is 0.

$R^{E5}$ represents a single bond, a hydrocarbon group, a heterocyclic group or —O—$R^{E5'}$ ($R^{E5'}$ represents a hydrocarbon group or a heterocyclic group), and these groups each optionally have a substituent.

$Q^{E2}$ represents an alkylene group, a cycloalkylene group, an arylene group, an oxygen atom or a sulfur atom, and these groups each optionally have a substituent. When a plurality of $Q^{E2}$ are present, they may be the same or different.

$Y^{E2}$ represents —$C^+R^{E6}_2$, —$N^+R^{E6}_3$, —$P^+R^{E6}_3$, —$S^+R^{E6}_2$ or —$I^+R^{E6}_2$. $R^{E6}$ represents a hydrogen atom, an alkyl group, a cycloalkyl group or an aryl group, and these groups each optionally have a substituent. The plurality of $R^{E6}$ may be the same or different. When a plurality of $Y^{E2}$ are present, they may be the same or different.

$M^{E2}$ represents F⁻, Cl⁻, Br⁻, I⁻, OH⁻, $B(R^{E7})_4^-$, $R^{E7}SO_3^-$, $R^{E7}COO^-$, $BF_4^-$, $SbCl_6^-$ or $SbF_6^-$. $R^{E7}$ represents an alkyl group, a cycloalkyl group or an aryl group, and these groups each optionally have a substituent. When a plurality of $M^{E2}$ are present, they may be the same or different.

$Z^{E2}$ represents an alkali metal cation or an alkaline earth metal cation. When a plurality of $Z^{E2}$ are present, they may be the same or different.]

nE2 is usually an integer of 1 to 4, preferably 1 or 2.

The aromatic hydrocarbon group or heterocyclic group represented by $Ar^{E2}$ is preferably a group obtained by removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, 2,7-phenanthrenediyl group or a 2,7-carbazolediyl group nE2 hydrogen atoms bonding directly to atoms constituting its ring, and optionally has a substituent other than $R^{E2}$.

The substituent other than $R^{E2}$ which $Ar^{E2}$ optionally has is the same as the substituent other than $R^{E1}$ which $Ar^{E1}$ optionally has.

nE4 is usually an integer of 0 to 10, preferably an integer of 0 to 8, more preferably an integer of 0 to 2.

aE2 is usually an integer of 1 to 10, preferably an integer of 1 to 5, more preferably 1 or 2.

bE2 is usually an integer of 0 to 10, preferably an integer of 0 to 4, more preferably 0 or 1.

mE2 is usually an integer of 1 to 5, preferably 1 or 2, more preferably 0 or 1.

When $R^{E5}$ is —O—$R^{E5'}$, the group represented by the formula (ES-2) is a group represented by the following formula.

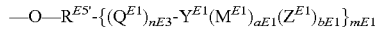

$R^{E5}$ is preferably a hydrocarbon group or a heterocyclic group, more preferably an aromatic hydrocarbon group or an aromatic heterocyclic ring, further preferably an aromatic hydrocarbon group.

The substituent which $R^{E5}$ optionally has includes an alkyl group, a cycloalkyl group, an aryl group, a monovalent heterocyclic group and a group represented by the formula (ES-3), and is preferably a group represented by the formula (ES-3).

$Q^{E2}$ is preferably an alkylene group, an arylene group or an oxygen atom, more preferably an alkylene group or an oxygen atom.

$Y^{E2}$ is preferably —$C^+R^{E6}_2$, —$N^+R^{E6}_3$, —$P^+R^{E6}_3$ or $S^+R^{E6}_2$, more preferably —$N^+R^{E6}_3$. $R^{E6}$ is preferably a hydrogen atom, an alkyl group or an aryl group, more preferably a hydrogen atom or an alkyl group.

$M^{E2}$ is preferably F⁻, Cl⁻, Br⁻, I⁻, $B(R^{E7})_4^-$, $R^{E7}SO_3^-$, $R^{E7}COO^-$, $BF_4^-$ or $SbF_6^-$, more preferably Br⁻, I⁻, $B(R^{E7})_4^-$, $R^{E7}COO^-$ or $SbF_6^-$. $R^{E7}$ is preferably an alkyl group.

The alkali metal cation represented by $Z^{E2}$ includes, for example, Li⁺, Na⁺, K⁺, Rb⁺ and Cs⁺, and is preferably Li⁺, Na⁺ or K⁺.

The alkaline earth metal cation represented by $Z^{E2}$ includes, for example, Be²⁺, Mg²⁺, C²⁺, Sr²⁻ and Ba²⁺, and is preferably Mg²⁺ or Ca²⁺.

$Z^{E2}$ is preferably an alkali metal cation.

The group represented by the formula (ES-2) includes, for example, groups represented by the following formulae.

[Chemical Formula 121]

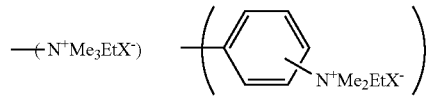

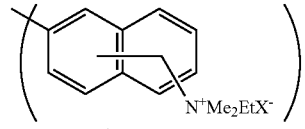

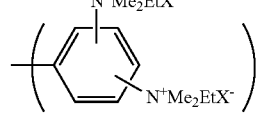

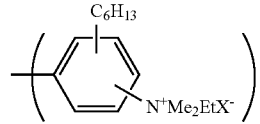

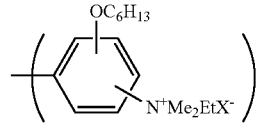

[Chemical Formula 122]

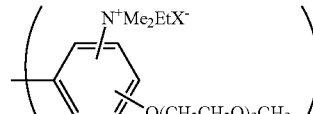

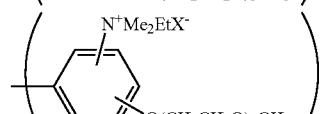

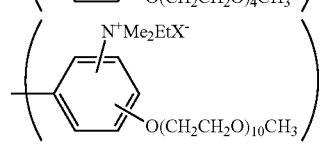

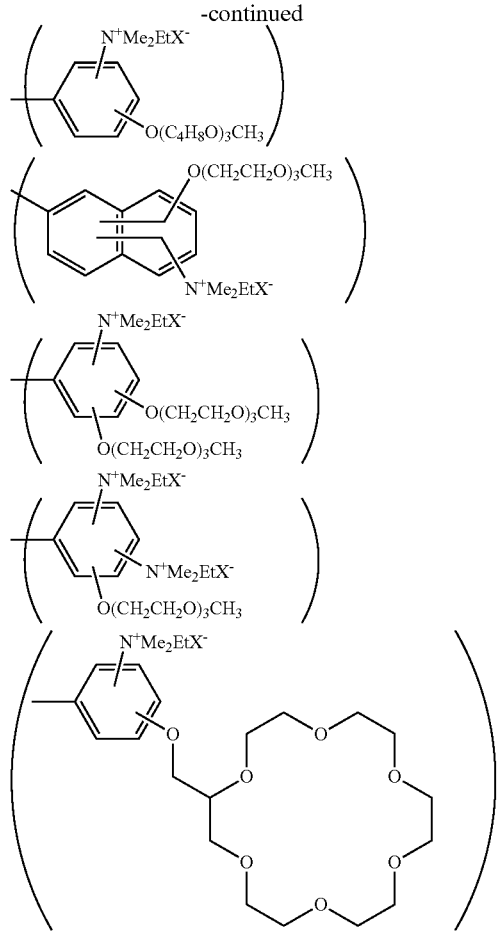

[wherein, X⁻ represents F⁻, Cl⁻, Br⁻, I⁻, B(C₆H₅)₄⁻, CH₃COO⁻ or CF₃SO₃⁻. When a plurality of X⁻ are present, they may be the same or different.]

The constitutional unit represented by the formula (ET-1) and the formula (ET-2) includes, for example, constitutional units represented by the formula (ET-31) to the formula (ET-38) described below.

[Chemical Formula 123]

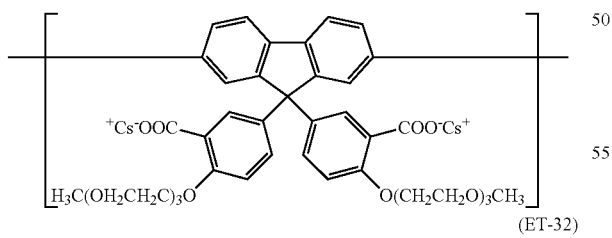

(ET-31)

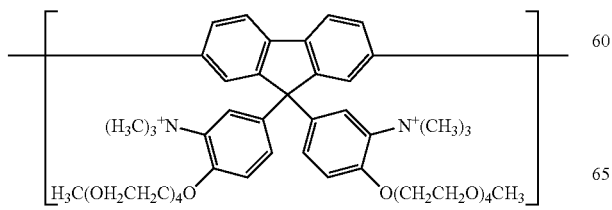

(ET-32)

[Chemical Formula 124]

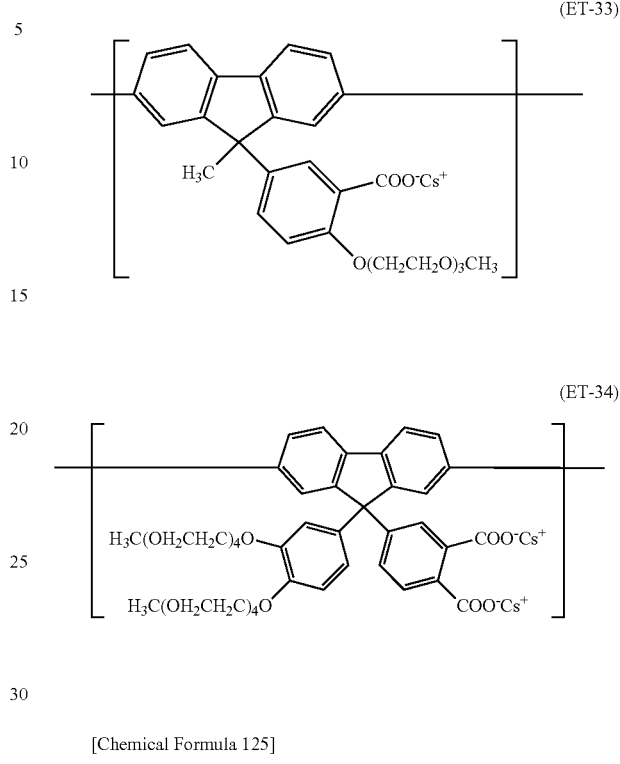

(ET-33)

(ET-34)

[Chemical Formula 125]

(ET-35)

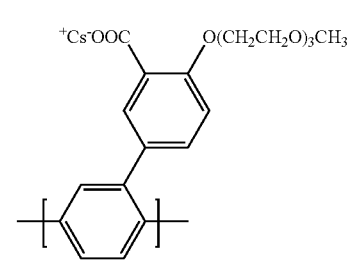

(ET-36)

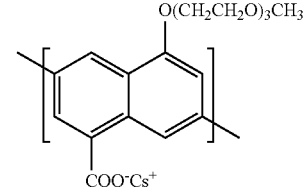

(ET-37)

-continued

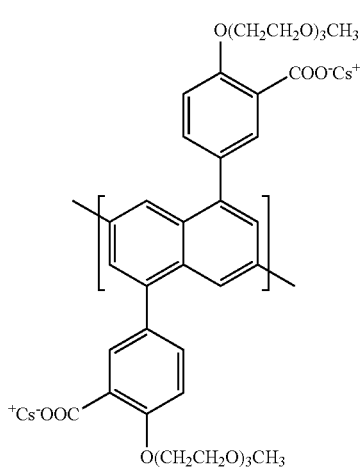

(ET-38)

The polymer compound of the electron transporting layer can be synthesized, for example, according to methods disclosed in JP-A No. 2009-239279, JP-A No. 2012-033845, JP-A No. 2012-216821, JP-A No. 2012-216822 and JP-A No. 2012-216815.

When a material used for formation of a hole injection layer described later, a material used for formation of a light emitting layer, a material used for formation of a hole transporting layer, a material used for formation of an electron transporting layer and a material used for formation of an electron injection layer described later are soluble in solvents used in forming a layer adjacent to a hole injection layer, a light emitting layer, a hole transporting layer, an electron transporting layer and an electron injection layer, respectively, in fabrication of a light emitting device, it is preferable to avoid dissolution of the material in the solvent. The method of avoiding dissolution of the material is preferably i) a method of using a material having a crosslinkable group, or ii) a method of making a difference in solubility between adjacent layers. In the above-described method i), a layer is formed using a material having a crosslinkable group, then, the crosslinkable group is crosslinked, thus, the layer can be insolubilized.

In laminating an electron transporting layer by utilizing a difference of solubility on a light emitting layer, the electron transporting layer can be laminated by using a solution having low solubility for the light emitting layer.

As the solvent used in laminating an electron transporting layer by utilizing a difference of solubility on a light emitting layer, water, alcohols, ethers, esters, nitrile compounds, nitro compounds, fluorinated alcohols, thiols, sulfides, sulfoxides, thioketones, amides, carboxylic acids and the like are preferable. Specific examples of the solvent include methanol, ethanol, 2-propanol, 1-butanol, tert-butyl alcohol, acetonitrile, 1,2-ethanediol, N,N-dimethylformamide, dimethyl sulfoxide, acetic acid, nitromethane, propylene carbonate, pyridine, carbon disulfide, and a mixed solvent of them. When a mixed solvent is used, it may be a mixed solvent composed of at least solvent selected from water, alcohols, ethers, esters, nitrile compounds, nitro compounds, fluorinated alcohols, thiols, sulfides, sulfoxides, thioketones, amides, carboxylic acids and the like, and at least one solvent selected from chlorine-based solvents, aromatic hydrocarbon solvents, aliphatic hydrocarbon solvents and ketone solvents.

[Hole Injection Layer and Electron Injection Layer]

The hole injection layer is a layer comprising a hole injection material. The hole injection material includes, for example, hole injection materials which the light emitting layer may comprise described above. The hole injection material may be contained singly or two or more kinds of the hole injection materials may be contained.

The electron injection layer is a layer comprising an electron injection material. The electron injection material includes, for example, electron injection materials which the light emitting layer may comprise described above. The electron injection material may be contained singly or two or more kinds of the electron injection materials may be contained.

[Electrode]

The material of an anode includes, for example, electrically conductive metal oxides and semitransparent metals, preferably, indium oxide, zinc oxide, tin oxide; electrically conductive compounds such as indium.tin.oxide (ITO), indium.zinc.oxide and the like; a composite of Ag and palladium and copper (APC); NESA, gold, platinum, silver and copper.

The material of a cathode includes, for example, metals such as lithium, sodium, potassium, rubidium, cesium, beryllium, magnesium, calcium, strontium, barium, aluminum, zinc, indium and the like; alloys composed of two or more of them; alloys composed of at least one of them and at least one of silver, copper, manganese, titanium, cobalt, nickel, tungsten and tin; and graphite and graphite intercalation compound. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

In the light emitting device of the present invention, at least one of an anode and a cathode is usually transparent or semitransparent, and it is preferable that an anode is transparent or semitransparent.

The method of forming an anode and a cathode includes, for example, a vacuum vapor deposition method, a sputtering method, an ion plating method, a plating method and a laminate method.

[Production Method of Light Emitting Device]

The method of forming each layer such as a light emitting layer, a hole transporting layer, an electron transporting layer, a hole injection layer, an electron injection layer and the like in the light emitting device of the present invention includes, for example, a vacuum vapor-deposition method from powder and a method by film formation from solution or melted state when a low molecular weight compound is used, and for example, a method by film formation from solution or melted state when a polymer compound is used.

The light emitting layer can be formed using the ink of the light emitting layer, the hole transporting layer can be formed using the ink of the hole transporting layer, and the electron transporting layer, the hole injection layer and the electron injection layer can be formed using the inks comprising the electron transporting material, the hole injection material and the electron injection material, respectively, described above, by an application method typified by a spin coat method and an inkjet printing method.

The light emitting device of the present invention can be produced by laminating respective layers sequentially on a substrate.

The light emitting device of the present invention can be produced, for example, by forming an anode on a substrate, and if necessary forming a hole injection layer on the anode, forming a hole transporting layer on the anode or the hole injection layer, forming a light emitting layer on the hole transporting layer, and if necessary forming an electron transporting layer and/or an electron injection layer on the light emitting layer, and forming a method on the light emitting layer, on the electron transporting layer or on the electron injection layer.

Further, the light emitting device of the present invention can be produced, for example, by forming a cathode on a substrate, and if necessary forming an electron injection layer and/or an electron transporting layer on the cathode, forming a light emitting layer on the cathode, the electron injection layer or the electron transporting layer, forming a hole transporting layer on the light emitting layer, and if necessary forming a hole injection layer on the hole transporting layer, and forming an anode on the electron transporting layer or on the hole injection layer.

[Use of Light Emitting Device]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming extremely thick a layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross orthogonally with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

Examples

The present invention will be illustrated further in detail by examples below, but the present invention is not limited to these examples.

In examples, the polystyrene-equivalent number-average molecular weight (Mn) and the polystyrene-equivalent weight-average molecular weight (Mw) of a polymer compound were determined by any of the following size exclusion chromatography (SEC) using tetrahydrofuran as a mobile phase. Measurement conditions of each SEC are as described below.

<Measurement Condition 1>

A polymer compound to be measured was dissolved in tetrahydrofuran at a concentration of about 0.05 wt %, and 10 μL of the solution was injected into SEC. A mobile phase was flowed at a flow rate of 2.0 mL/min. As the column, PLgel MIXED-B (manufactured by Polymer Laboratories Ltd.) was used. As the detector, an UV-VIS detector (manufactured by Shimadzu Corp., tradename: SPD-10Avp) was used.

<Measurement Condition 2>

A polymer compound to be measured was dissolved in tetrahydrofuran at a concentration of about 0.05 wt %, and 10 μL of the solution was injected into SEC. A mobile phase was flowed at a flow rate of 1.0 mL/min. As the column, PLgel MIXED-B (manufactured by Polymer Laboratories Ltd.) was used. As the detector, an UV-VIS detector (manufactured by Tosoh Corp., tradename: UV-8320GPC) was used.

<Measurement Condition 3>

A polymer compound to be measured was dissolved in tetrahydrofuran at a concentration of about 0.05 wt %, and 10 μL of the solution was injected into SEC. A mobile phase was flowed at a flow rate of 0.6 mL/min. As the column, each one column of TSKguardcolumn SuperAW-H, TSKgel Super AWM-H and TSKgel SuperAW3000 (all are manufactured by Tosoh Corp.) were connected serially and used. As the detector, an UV-VIS detector (manufactured by Tosoh Corp., tradename: UV-8320GPC) was used.

LC-MS was measured by the following method.

A measurement sample was dissolved in chloroform or tetrahydrofuran so as to give a concentration of about 2 mg/mL, and about 1 μL of the solution was injected into LC-MS (manufactured by Agilent Technologies, tradename: 1100LCMSD). As the mobile phase of LC-MS, acetonitrole and tetrahydrofuran were used while changing the ratio thereof, and flowed at a flow rate of 0.2 mL/min. As the column, L-column 2 ODS (3 μm) (manufactured by Chemicals Evaluation and Research Institute, Japan, internal diameter: 2.1 mm, length: 100 mm, particle size: 3 μm) was used.

TLC-MS was measured by the following method.

A measurement sample was dissolved in any solvent of toluene, tetrahydrofuran or chloroform at any concentration, and the solution was applied on a TLC plate for DART (manufactured by Techno Applications Co., tradename: YSK5-100), and TLC-MS was measured using TLC-MS (manufactured by JEOL Ltd., tradename: JMS-T100TD (The AccuTOF TLC)). The temperature of a helium gas in measurement was controlled in the range of 200 to 400° C.

NMR was measured by the following method.

Five to ten milligrams of a measurement sample was dissolved in about 0.5 mL of deuterated chloroform ($CDCl_3$), deuterated tetrahydrofuran, deuterated dimethyl sulfoxide, deuterated acetone, deuterated N,N-dimethylformamide, deuterated toluene, deuterated methanol, deuterated ethanol, deuterated 2-propanol or deuterated methylene chloride, and NMR was measured using an NMR apparatus (manufactured by Agilent Technologies, tradename: INOVA300 or MERCURY 400VX).

As the index of the purity of a compound, the value of high performance liquid chromatography (HPLC) area percentage was used. This value is a value at UV=254 nm by HPLC (manufactured by Shimadzu Corp., tradename: LC-20A), unless otherwise stated. In this operation, a compound to be measured was dissolved in tetrahydrofuran or chloroform so as to give a concentration of 0.01 to 0.2 wt %, and 1 to 10 μL of the solution was injected into HPLC, depending on the concentration. As the mobile phase of HPLC, acetonitrile and tetrahydrofuran were used while changing the ratio of acetonitrile/tetrahydrofuran from 100/0 to 0/100 (volume ratio), and flowed at a flow rate of 1.0 mL/min. As the column, Kaseisorb LC ODS 2000 (manufactured by Tokyo Chemical Industry Co., Ltd.) or an ODS column having the equivalent performance was used. As the detector, a photodiode array detector (manufactured by Shimadzu Corp., tradename: SPD-M20A) was used.

In examples, the molecular weight (MA) of the iridium complex (A) and the molecular weight (MB) of the low molecular weight compound (B) were calculated using values of Molecular Weight of ChemDraw Pro 13.0 (manufactured by HULINKS Inc.).

<Synthesis Example 1> Synthesis of Iridium Complex 1

An iridium complex 1 was synthesized according to a method disclosed in JP-A No. 2013-237789. The iridium complex 1 had a molecular weight (MA) of 991.4.

[Chemical Formula 126]

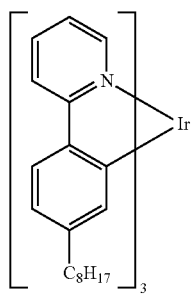

Iridium complex 1

Molecular Weight: 991.4

<Synthesis Example 2> Synthesis of Iridium Complex 2

An iridium complex 2 was synthesized according to a method disclosed in International Publication WO2009/131255. The iridium complex 2 had a molecular weight (MA) of 1676.3.

[Chemical Formula 127]

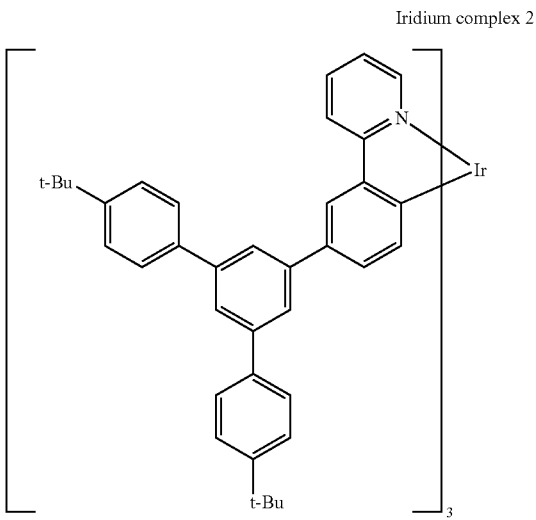

Iridium complex 2

Molecular Weight: 1676.3

<Synthesis Example 3> Synthesis of Iridium Complex 3

An iridium complex 3 was synthesized according to a method disclosed in JP-A No. 2014-224101. The iridium complex 3 had a molecular weight (MA) of 2013.0.

[Chemical Formula 128]

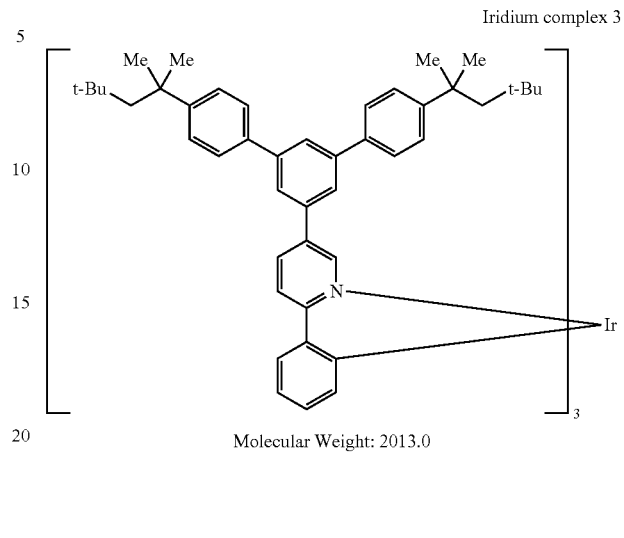

Iridium complex 3

Molecular Weight: 2013.0

<Synthesis Example 4> Synthesis of Iridium Complex 4

An iridium complex 4 was synthesized based on a method disclosed in JP-A No. 2014-224101 and International Publication WO2009/131255. The iridium complex 4 had a molecular weight (MA) of 1676.3.

[Chemical Formula 129]

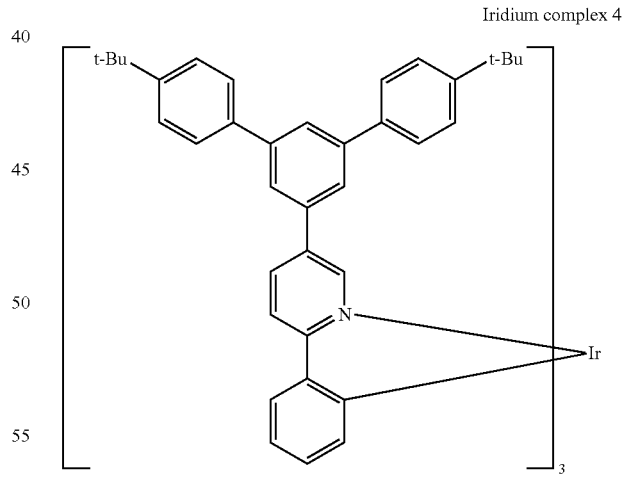

Iridium complex 4

Molecular Weight: 1676.3

<Synthesis Example 5> Synthesis of Iridium Complex 5

An iridium complex 5 was synthesized based on a method disclosed in JP-A No. 2014-224101. The iridium complex 5 had a molecular weight of 2013.0.

[Chemical Formula 130]

Iridium complex 5

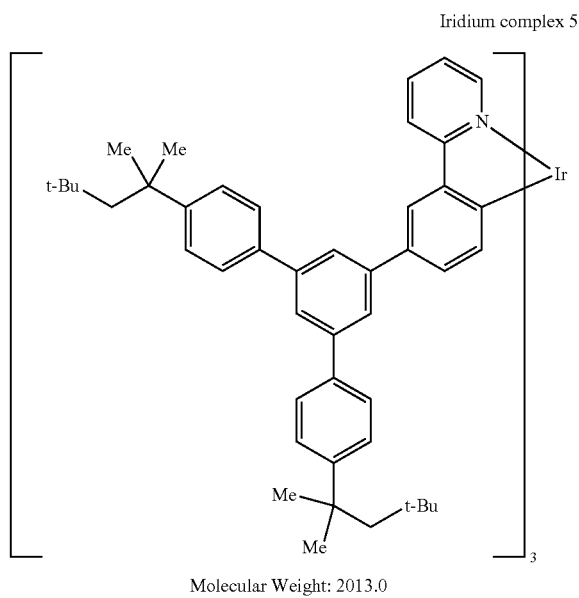

Molecular Weight: 2013.0

<Synthesis Example 6> Synthesis of Iridium Complex 6

An iridium complex 6 was synthesized based on a method disclosed in JP-A No. 2014-224101. The iridium complex 6 had a molecular weight (MA) of 2926.2.

[Chemical Formula 131]

Iridium complex 6

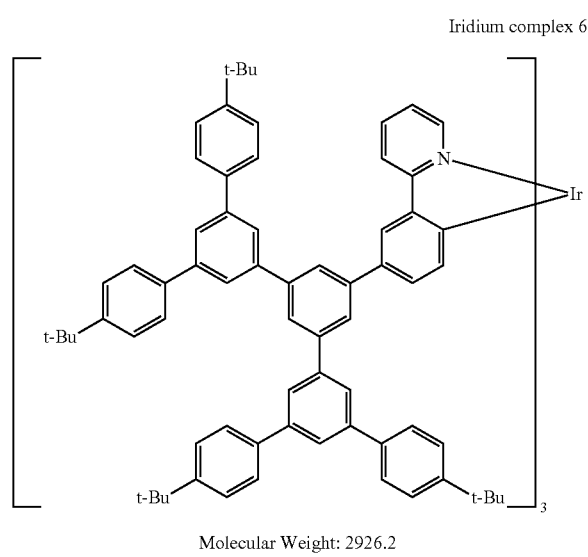

Molecular Weight: 2926.2

<Synthesis Example 7> Synthesis of Iridium Complex 7

An iridium complex 7 was synthesized according to a method disclosed in JP-A No. 2014-224101. The iridium complex 7 had a molecular weight (MA) of 3599.4.

[Chemical Formula 132]

Iridium complex 7

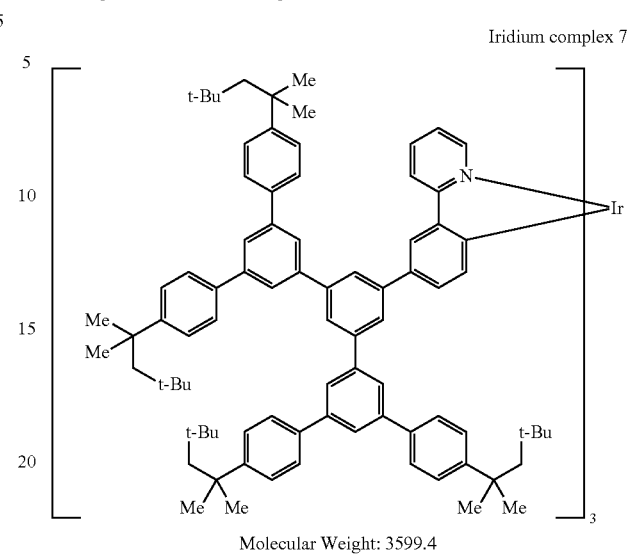

Molecular Weight: 3599.4

<Synthesis Example 8> Synthesis of Iridium Complex 8

An iridium complex 8 was synthesized based on a method disclosed in JP-A No. 2006-188673. The iridium complex 8 had a molecular weight (MA) of 1826.5.

[Chemical Formula 133]

Iridium complex 8

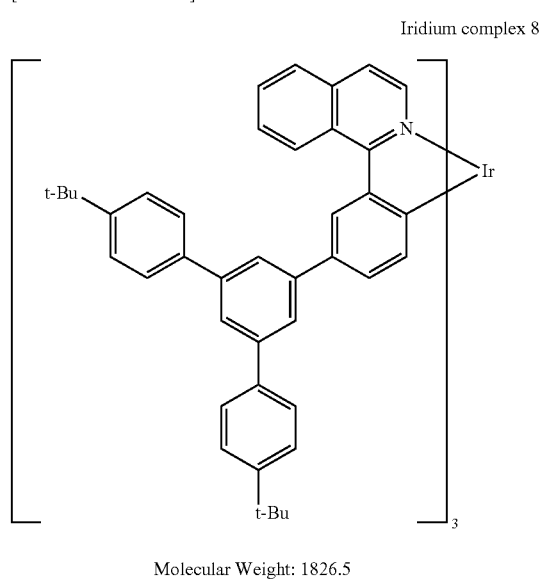

Molecular Weight: 1826.5

<Synthesis Example 9> Synthesis of Iridium Complex 9

An iridium complex 9 was synthesized based on a method disclosed in International Publication WO2002/44189. The iridium complex 9 had a molecular weight (MA) of 973.3.

[Chemical Formula 134]

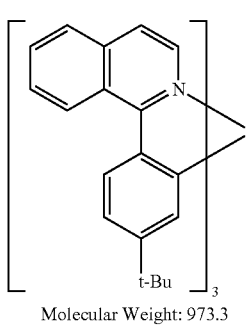

Iridium complex 9

Molecular Weight: 973.3

<Synthesis Example 10> Synthesis of Iridium Complex 10

An iridium complex 10 was synthesized according to a method disclosed in JP-A No. 2008-179617. The iridium complex 10 had a molecular weight (MA) of 1685.2.

[Chemical Formula 135]

Iridium complex 10

Molecular Weight: 1685.2

<Synthesis Example 11> Synthesis of Iridium Complex 11

(Synthesis of Iridium Complex 11-1)

[Chemical Formula 136]

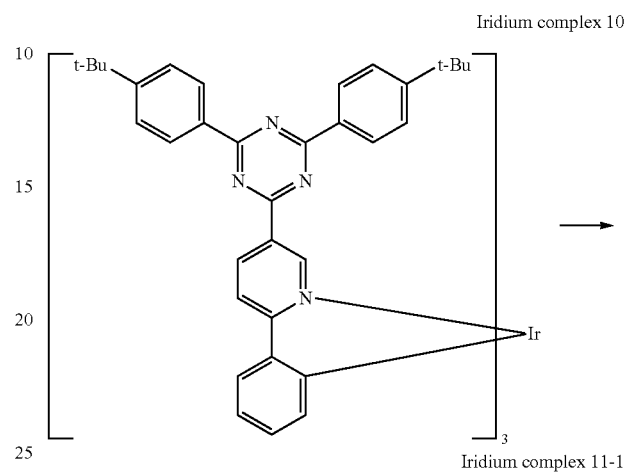

Iridium complex 10

Iridium complex 11-1

A nitrogen gas atmosphere was prepared in a light-shielded reaction vessel, then, the iridium complex 10 (38 g), N-bromosuccinimide (12.1 g) and chloroform (1800 mL) were added, and the mixture was stirred at room temperature for 24 hours. The resultant reaction mixture was allowed to pass through a filter paved with silica gel, to remove solid components. The resultant filtrate was concentrated under reduced pressure to distill off the solvent, obtaining a solid. The resultant solid was purified by silica gel column chromatography (mixed solvent of chloroform and hexane), to obtain a fraction containing a target. The resultant fraction was concentrated, purified by repeating crystallization (mixed solvent of dichloromethane and hexane) three times, and dried under reduced pressure at 50° C. overnight, to obtain an iridium complex 11-1 (22.1 g) in the form of a red solid. The HPLC area percentage value (detection wavelength: UV 254 nm) of the resultant iridium complex 11-1 was 99.4%.

LC/MS (APCI-posi): m/z=1920 [M+H]$^+$ $^1$H-NMR (300 MHz/CD$_2$Cl$_2$): δ (ppm=) 9.31 (d, 3H), 9.26 (dd, 3H), 8.38 (d, 12H), 8.22 (d, 3H), 7.96 (d, 3H), 7.43 (d, 12H), 7.00 (dd, 3H), 6.82 (d, 3H), 1.23 (s, 54H).

(Synthesis of Iridium Complex 11)

[Chemical Formula 137]

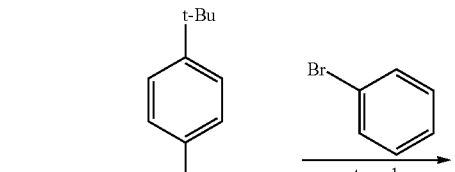

stage 1

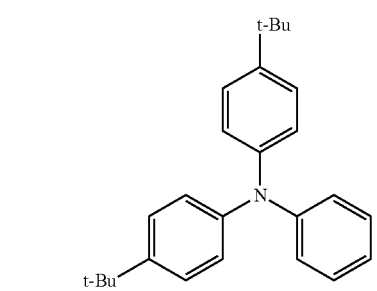

Compound 11-S1 stage 2

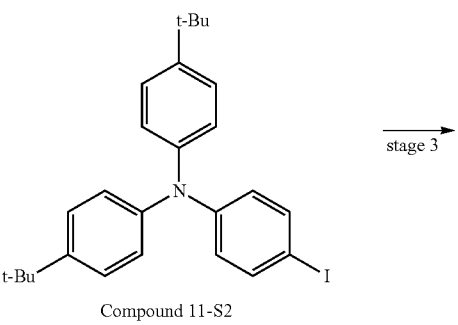

Compound 11-S2 stage 3

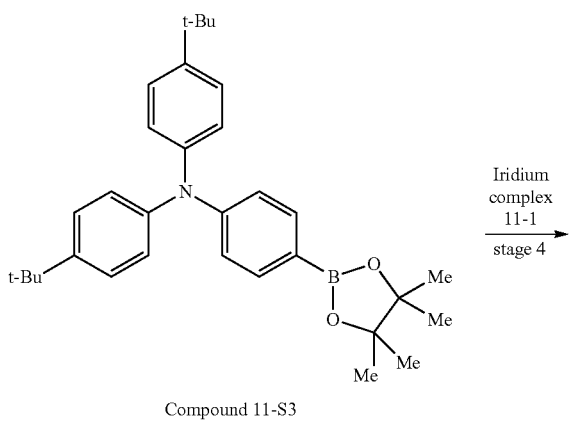

Compound 11-S3

Iridium complex 11-1
stage 4

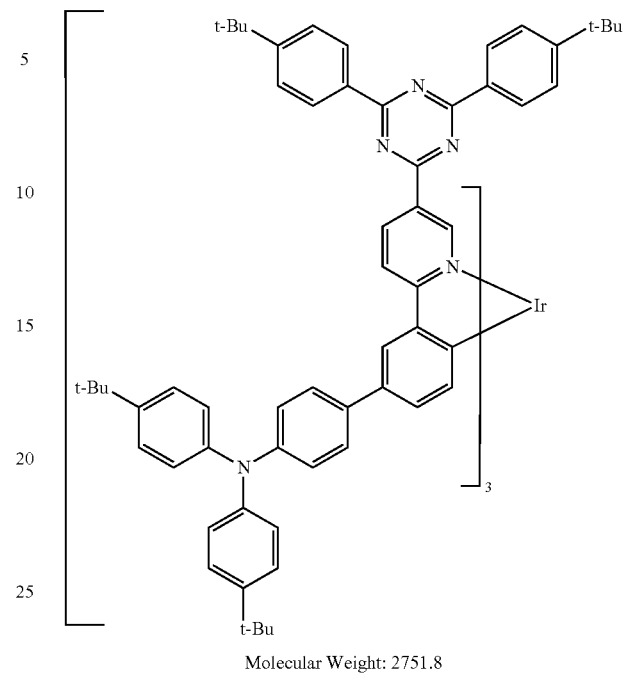

Iridium complex 11

Molecular Weight: 2751.8

<Stage 1>

An argon gas atmosphere was prepared in a reaction vessel, then, bis(4-tert-butylphenyl)amine (98.5 g), tris(dibenzylideneacetone)dipalladium(0) (3.21 g), tri-tert-butylphosphine tetrafluoroborate salt (4.06 g), sodium-tert-butoxide (67.3 g) and toluene (665 mL) were added, and the mixture was heated at 80° C. while stirring. Thereafter, into this was dropped bromobenzene (57.1 g) dissolved in toluene (55 ml), and the mixture was stirred at 85° C. for 4 hours. The resultant reaction mixture was diluted with toluene (680 ml), then, hot-filtrated to remove a solid. To the resultant filtrate were added activated white earth (35 g) and active alumina (35 g), and the mixture was stirred at 90° C. for 1.5 hours, then, hot-filtrated to remove a solid. The resultant filtrate was concentrated under reduced pressure to remove the solvent, obtaining a solid. The resultant solid was purified by repeating crystallization (mixed solvent of hexane and ethanol) twice, and dried under reduced pressure at 50° C. overnight, to obtain a compound 11-S1 (99 g) as a target in the form of a solid. The HPLC area percentage value (detection wavelength: UV 254 nm) of the resultant compound 11-S1 was 99.5% or more.

<Stage 2>

An argon gas atmosphere was prepared in a light-shielded reaction vessel, then, the compound 11-S1 (71.5 g), N-iodosuccinimide (49.5 g) and N,N-dimethylformamide (800 mL) were added, and the mixture was heated at 30° C. while stirring. Thereafter, into this was dropped trifluoroacetic acid (11.4 g), and the mixture was stirred at 50° C. for 4 hours. Thereafter, the light-shielded reaction vessel was cooled using an ice bath, and ion exchanged water (800 mL) and a 10% sodium chloride aqueous solution (200 mL) were dropped, to obtain a solid. The resultant solid was dissolved in toluene (1 L), then, washed twice using ion exchanged water (800 mL). The resultant organic layer was dried over anhydrous sodium sulfate, then, concentrated under reduced pressure to distill off the solvent, obtaining a solid. The resultant solid was dried under reduced pressure at 50° C. overnight, then, purified by conducting crystallization (mixed solvent of chloroform and methanol), and dried under reduced pressure at 50° C. overnight, to obtain a compound 11-S2 (84 g) as a target in the form of a solid. The HPLC area percentage value (detection wavelength: UV 254 nm) of the resultant compound 11-S2 was 99.4%.

<Stage 3>

A nitrogen gas atmosphere was prepared in a light-shielded reaction vessel, then, the compound 11-S2 (7.5 g) and tetrahydrofuran (80 mL) were added. Thereafter, into this was dropped isopropylmagnesium chloride dissolved in tetrahydrofuran (2 mol/L, 15 mL), and the mixture was stirred at room temperature for 1 hour. Thereafter, the light-shielded reaction vessel was cooled using an ice bath, and 2-isopropoxy-4,4,5,5-tetramethyl-1,3,2-dioxaborolane (6.4 mL) was added and the mixture was stirred for 5 minutes. Thereafter, the light-shielded reaction vessel was removed from the ice bath, and the mixture was stirred for 3 hours while heating up to room temperature. Thereafter, the light-shielded reaction vessel was cooled using an ice bath, and the reaction liquid was extracted using a mixed solvent of ethyl acetate (90 mL) and toluene (30 mL). The resultant organic layer was washed with 15 wt % saline (50 mL) twice. The resultant organic layer was dried over anhydrous sodium sulfate, then, concentrated under reduced pressure to distill off the solvent, obtaining a solid. The resultant solid was purified by repeating crystallization (mixed solvent of chloroform and methanol) twice, and dried under reduced pressure at 50° C. overnight, to obtain a compound 11-S3 (5.5 g) as a target in the form of a white solid. The HPLC area percentage value (detection wavelength: UV 254 nm) of the resultant compound 11-S3 was 99.5% or more.

TLC/MS (DART positive): m/z=484 [M+H]$^+$

<Stage 4>

A nitrogen gas atmosphere was prepared in a light-shielded reaction vessel, then, the iridium complex 11-1 (5.0 g), the compound 11-S3 (4.4 g), tetrakis(triphenylphosphine)palladium(0) (360 mg), a 20 wt % tetraethylammonium hydroxide aqueous solution (20 mL) and tetrahydrofuran (210 ml) were added, and the mixture was stirred under reflux with heating for 24 hours. Thereafter, the mixture was cooled down to room temperature, and toluene (400 mL) and ion exchanged water (400 mL) were added, and the reaction liquid was extracted. The resultant organic layer was washed with ion exchanged water twice and with 5 wt % saline once. The resultant organic layer was dried over anhydrous sodium sulfate, then, concentrated under reduced pressure to distill off the solvent, obtaining a solid. The resultant solid was purified by conducting crystallization (mixed solvent of toluene and isopropanol), and dried under reduced pressure at 50° C. overnight, to obtain an iridium complex 11 (3.9 g) as a target in the form of a red solid. The HPLC area percentage value (detection wavelength: UV 254 nm) of the resultant iridium complex 11 was 99.5% or more.

$^1$H-NMR (300 MHz/CD$_2$Cl$_2$): δ (ppm)=9.41 (d, 3H), 9.21 (dd, 3H), 8.39 (d, 12H), 8.26 (d, 3H), 7.96 (s, 3H), 7.45 to 7.38 (m, 18H), 7.27 (dd, 12H), 7.23 to 7.16 (m, 6H), 6.96 (d, 18H), 1.30 (s, 54H), 1.22 (s, 54H).

LC/MS (APCI positive): m/z=2751 [M+H]$^+$

The iridium complex 11 had a molecular weight (MA) of 2751.8.

<Synthesis Example 12> Synthesis of Iridium Complex 12

An iridium complex 12 was synthesized according to a method disclosed in JP-A No. 2014-224101. The iridium complex 12 had a molecular weight (MA) of 3695.4.

[Chemical Formula 138]

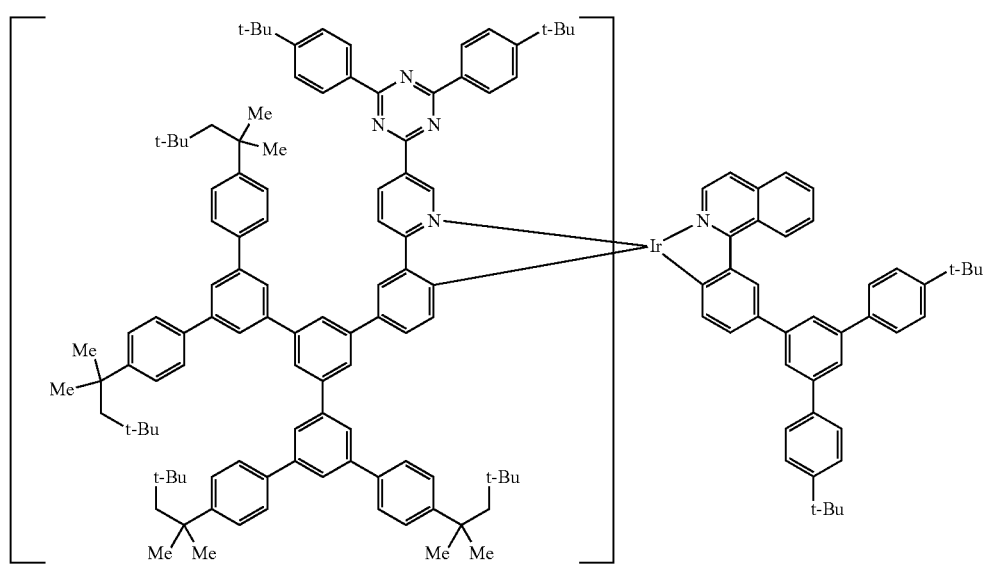

Iridium complex 12

Molecular Weight: 3695.4

<Synthesis Example 13> Synthesis of Iridium Complex 13

An iridium complex 13 was synthesized according to a method disclosed in JP-A No. 2013-147551. The iridium complex 13 had a molecular weight (MA) of 793.0.

[Chemical Formula 139]

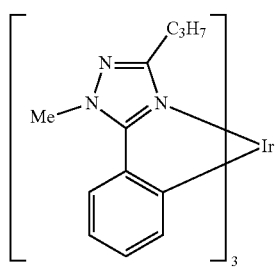

Iridium complex 13

Molecular Weight: 793.0

<Synthesis Example 14> Synthesis of Iridium Complex 14

An iridium complex 14 was synthesized according to a method disclosed in JP-A No. 2013-147551. The iridium complex 14 had a molecular weight (MA) of 1814.5.

[Chemical Formula 140]

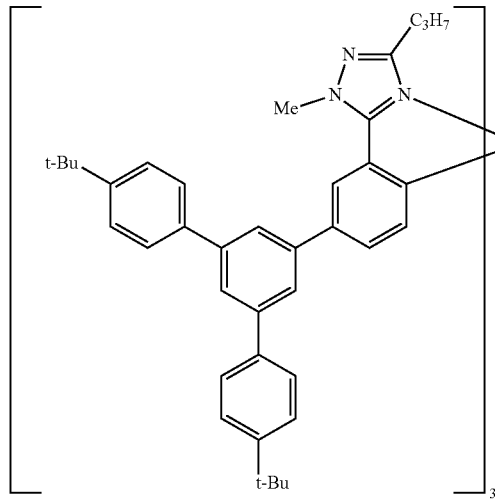

Iridium complex 14

Molecular Weight: 1814.5

<Synthesis Example 15> Synthesis of Iridium Complex 15

An iridium complex 15 was synthesized according to a method disclosed in JP-A No. 2014-224101. The iridium complex 15 had a molecular weight (MA) of 3737.7.

[Chemical Formula 141]

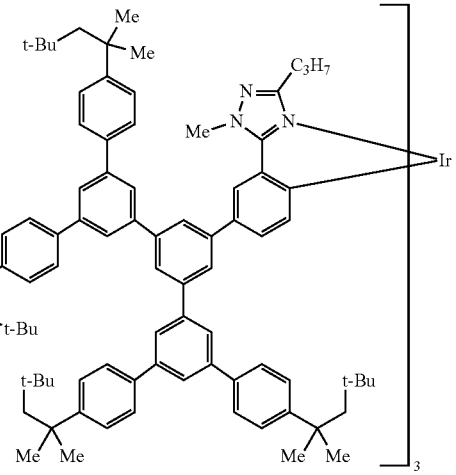

Iridium complex 15

Molecular Weight: 3737.7

<Synthesis Example 16> Synthesis of Iridium Complex 16

An iridium complex 16 was synthesized according to a method disclosed in International Publication WO2015/008851. The iridium complex 16 had a molecular weight (MA) of 2460.7.

[Chemical Formula 142]

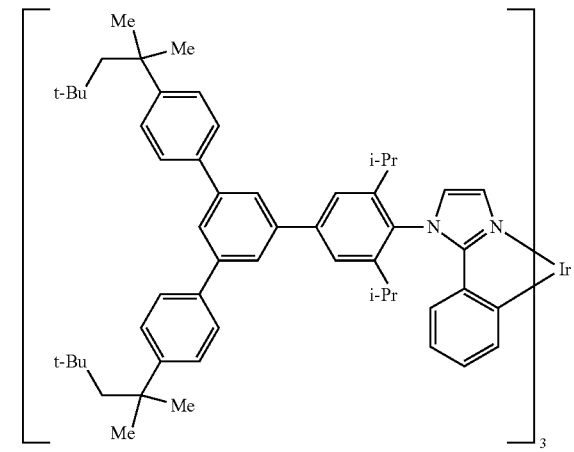

Iridium complex 16

Molecular Weight: 2460.7

<Synthesis Example 17> Synthesis of Iridium Complex 17

An iridium complex 17 was synthesized based on a method disclosed in International Publication WO2006/121811 and JP-A No. 2013-048190. The iridium complex 17 had a molecular weight (MA) of 1330.8.

[Chemical Formula 143]

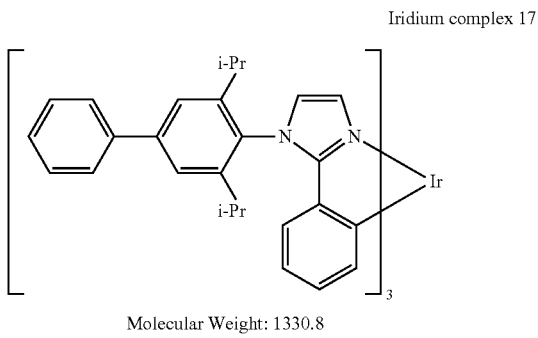

Iridium complex 17

Molecular Weight: 1330.8

<Synthesis Example 18> Synthesis of Iridium Complex 18

A iridium complex 18 was synthesized based on a method disclosed in International Publication WO2006/121811. The iridium complex 18 had a molecular weight (MA) of 1186.7.

[Chemical Formula 144]

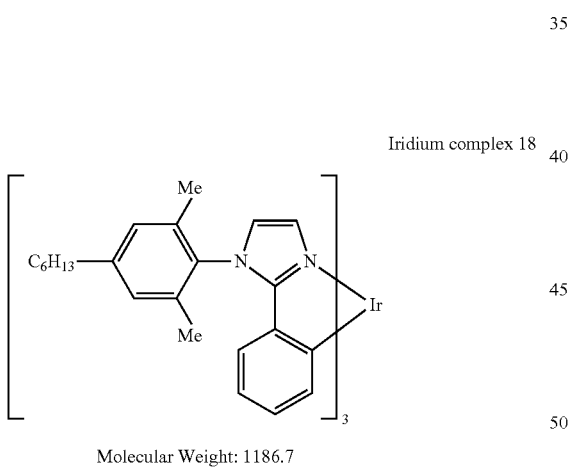

Iridium complex 18

Molecular Weight: 1186.7

<Synthesis Example H1> Synthesis of Compound H1

A compound H1 was purchased from Luminescense Technology. The compound H1 had a molecular weight (MB) of 484.6.

[Chemical Formula 145]

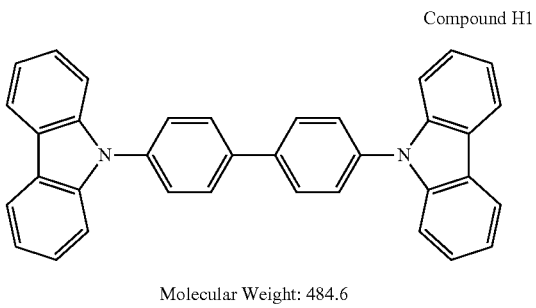

Compound H1

Molecular Weight: 484.6

<Synthesis Example H2> Synthesis of Compound H2

A compound H2 was synthesized according to a method disclosed in JP-A No. 2010-189630. The compound H2 had a molecular weight (MB) of 706.0.

[Chemical Formula 146]

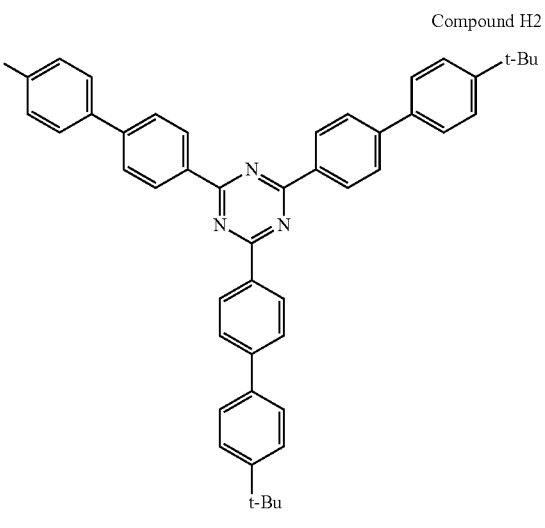

Compound H2

Molecular Weight: 706.0

<Synthesis Example H3> Synthesis of Compound H3

A compound H3 was purchased from Luminescense Technology. The compound H3 had a molecular weight (MB) of 975.3.

[Chemical Formula 147]
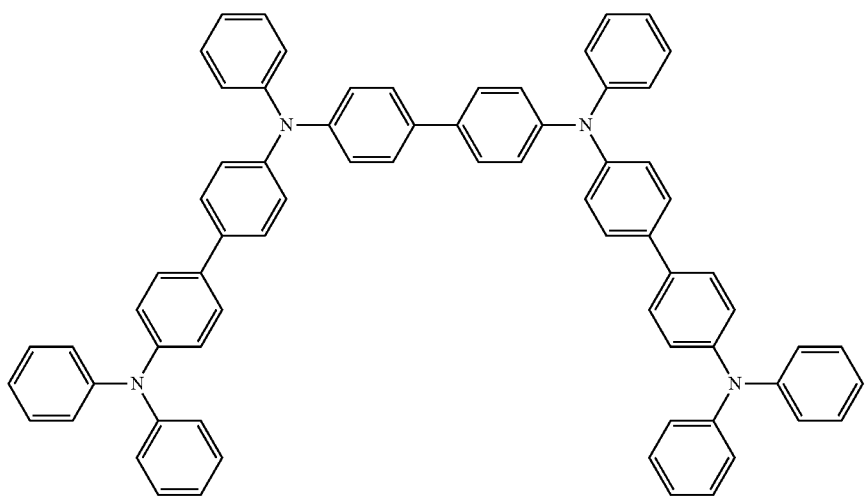
Compound H3
Molecular Weight: 975.3
<Synthesis Example H4> Synthesis of Compound H4
(Synthesis of Compound H4-2)
[Chemical Formula 148]
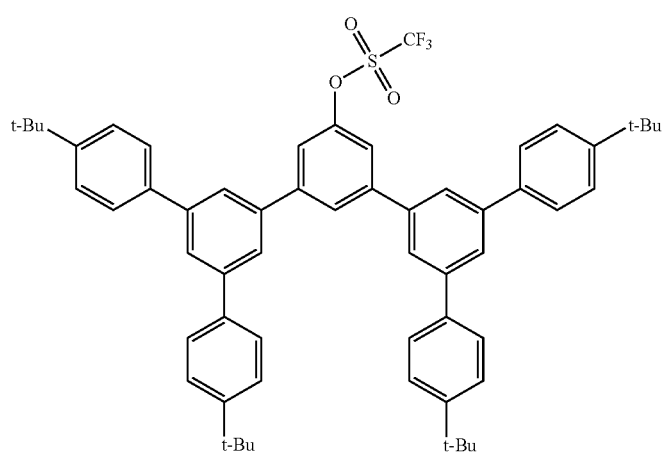
Compound H4-1
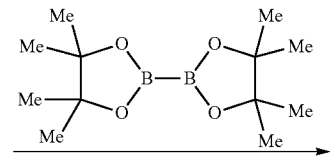

-continued

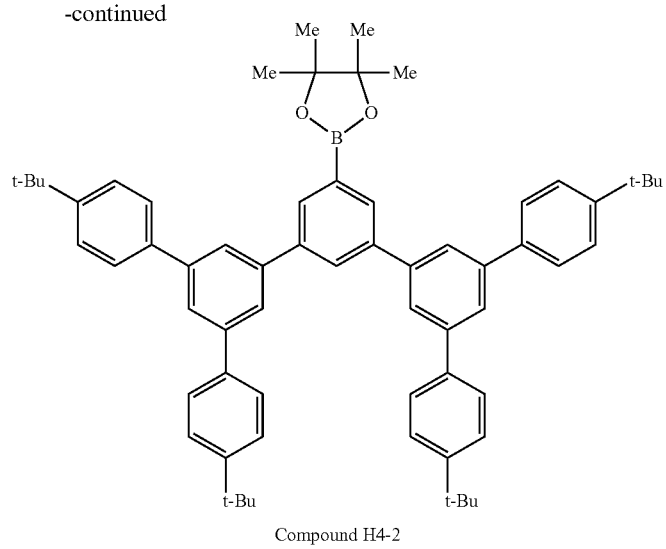

Compound H4-2

A nitrogen gas atmosphere was prepared in a reaction vessel, then, a compound H4-1 (336 g) synthesized according to a method described in JP-A No. 2010-31259, bis (pinacolato)diboron (113 g), palladium(II) acetate (1.88 g), tricyclohexylphosphine (4.68 g), potassium acetate (72.7 g) and 1,4-dioxane (1580 mL) were added, and the mixture was stirred under reflux with heating for 26 hours. After cooling down to room temperature, 1,4-dioxane (1000 mL) was added for dilution, and the liquid was filtrated, to remove a solid. The resultant filtrate was concentrated under reduced pressure, to obtain a solid. The resultant solid was purified by silica gel column chromatography (mixed solvent of n-hexane and dichloromethane), then, purified by further conducting crystallization (mixed solvent of dichloromethane and acetonitrile) twice. The resultant solid was dried under reduced pressure at 50° C. overnight, to obtain a compound H4-2 (276 g) as a target in the form of a white solid. The HPLC area percentage value (detection wavelength: UV 254 nm) of the resultant compound H4-2 was 99.3%.

TLC/MS (DART positive): m/z=886 [M+H]$^+$ $^1$H-NMR (300 MHz/CD$_2$Cl$_2$): δ (ppm)=8.14 (brs, 3H), 7.88 (d, 4H), 7.84-7.82 (m, 2H), 7.69 (d, 8H), 7.53 (d, 8H), 1.38 (brs, 48H).

(Synthesis of Compound H4)

[Chemical Formula 149]

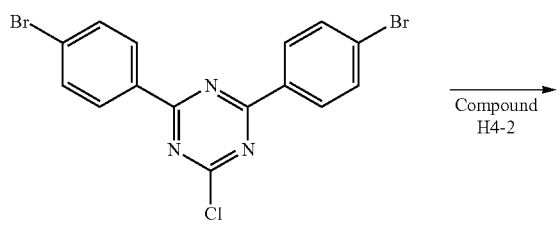

Compound H4-3

-continued

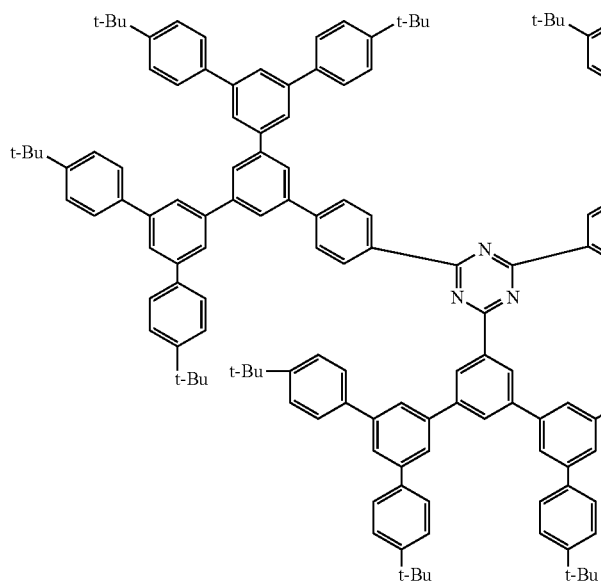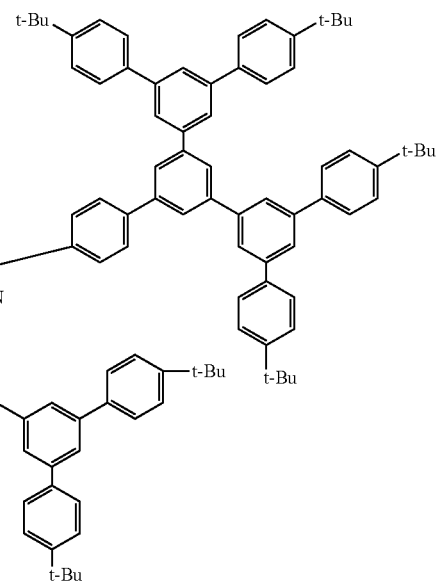

Compound H4

Molecular Weight: 2504.6

An argon gas atmosphere was prepared in a reaction vessel, then, a compound H4-3 (4.26 g) synthesized according to a method described in JP-A No. 2010-189630, the compound H4-2 (29.21 g), toluene (100 mL), PdCl$_2$ (PPh$_3$)$_2$ (35 mg) and a 20 wt % tetraethylammonium hydroxide aqueous solution (22 g) were added, and the mixture was stirred under reflux with heating for 3 hours. After cooling down to room temperature, toluene (600 mL) was added for dilution, and the liquid was washed with ion exchanged water (200 mL) twice, further washed with 15 wt % saline (200 mL), and separated. The resultant organic layer was dried by adding anhydrous sodium sulfate, and filtrated, to remove a solid. The resultant filtrate was allowed to pass through a silica gel column, and the resultant solution was concentrated under reduced pressure, to obtain a solid. The resultant solid was purified by using medium-pressure silica gel chromatography (mixed solvent of hexane and chloroform), then, purified by further conducting crystallization (mixed solvent of hexane and ethanol) three times. The resultant solid was dried under reduced pressure at 50° C. overnight, to obtain a compound H4 (10.9 g) as a target in the form of a white solid. The HPLC area percentage value (detection wavelength: UV 254 nm) of the resultant compound H4 was 99.5% or more.

$^1$H-NMR (300 MHz, CDCl$_3$): δ (ppm)=9.09 (s, 2H), 8.94 (d, 4H), 8.18 (s, 1H), 7.82 (m, 28H), 7.67 (m, 24H), 7.50 (d, 24H), 1.38 (s, 72H), 1.34 (s, 36H).

The compound H4 had a molecular weight (MB) of 2504.6.

<Synthesis Example H5> Synthesis of Compound H5

A compound H5 was purchased from Luminescense Technology. The compound H5 had a molecular weight (MB) of 2403.4.

[Chemical Formula 150]

Compound H5

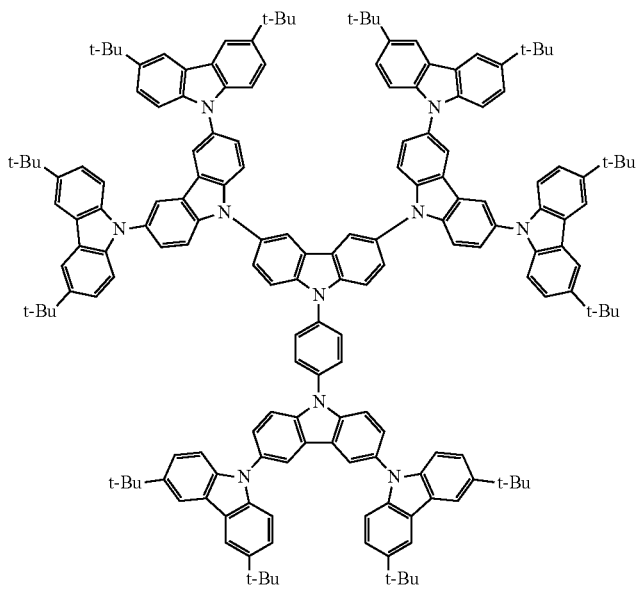

Molecular Weight: 2403.4

<Synthesis Example H6> Synthesis of Compound H6

The compound H6 was purchased from Luminescense Technology. The compound H6 had a molecular weight (MB) 609.8.

[Chemical Formula 151]

Compound H6

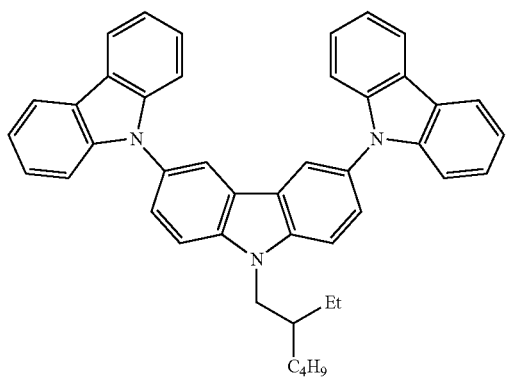

Molecular Weight: 609.8

<Synthesis Example M1 to M7> Synthesis of Compounds M1 to M7

A compound M1 was synthesized according to a method disclosed in JP-A No. 2010-189630.
A compound M2 was synthesized according to a method disclosed in International Publication WO2005/049546.
A compound M3 was synthesized according to a method disclosed in International Publication WO2013/146806.
A compound M4 was synthesized according to a method disclosed in JP-A No. 2008-106241.
A compound M5 was synthesized according to a method disclosed in International Publication WO2011/049241.
A compound M6 was synthesized according to a method disclosed in International Publication WO2002/045184.
A compound M7 was synthesized according to a method disclosed in JP-A No. 2010-215886.

[Chemical Formula 152]

Compound M1

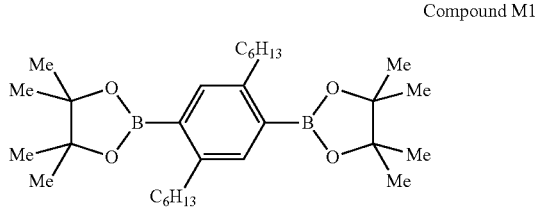

Compound M2

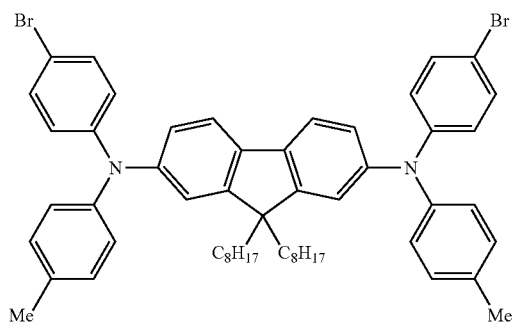

Compound M3

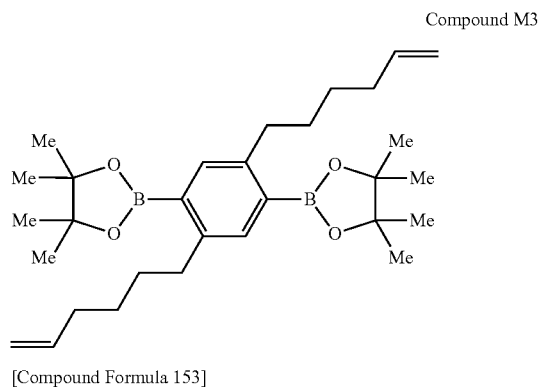

[Compound Formula 153]

Compound M4

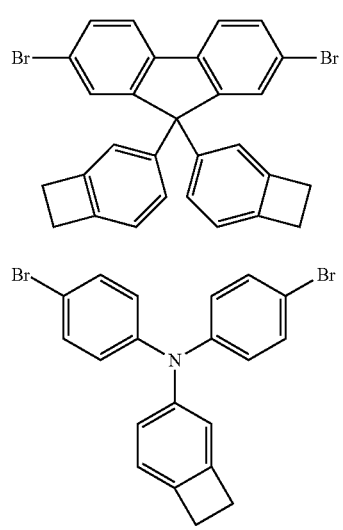

Compound M5

Compound M6

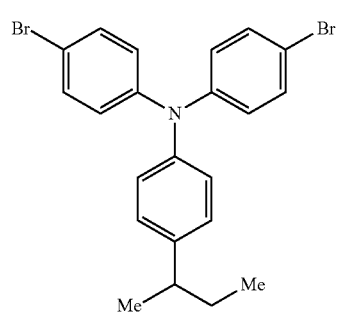

Compound M7

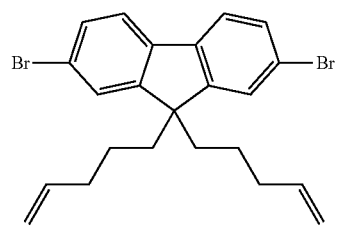

<Synthesis Example M8> Synthesis of Compound M8

<Synthesis Example M8-1> Synthesis of Compound Ma3

[Chemical Formula 154]

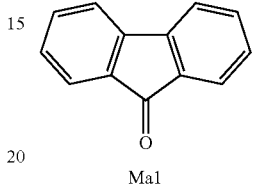

A gas in a flask equipped with a stirrer was purged with a nitrogen gas, then, a compound Ma2 (64.6 g) and tetrahydro furan (615 mL) were added, and the mixture was cooled down to −70° C. Into this, a n-butyllithium hexane solution (1.6 M, 218 mL) was dropped over a period of 1 hour, then, the mixture was stirred at −70° C. for 2 hours. To this, a compound Ma1 (42.1 g) was added in several batches, then, the mixture was stirred at −70° C. for 2 hours. Into this, methanol (40 mL) was dropped over a period of 1 hour, then, the mixture was heated up to room temperature. Thereafter, the solvent was distilled off by concentrating under reduced pressure, and toluene and water were added. Thereafter, an aqueous layer was separated and the resultant organic layer was further washed with water. The resultant organic layer was concentrated under reduced pressure, and the resultant residue was purified by using a silica gel column (a mixed solvent of hexane and ethyl acetate), thereby obtaining 71 g of a compound Ma3 as a colorless oil. The compound Ma3 had an HPLC area percentage value (UV: 254 nm) of 97.5%. This operation was repeated, thereby obtaining a necessary amount of the compound Ma3.

$^1$H-NMR (CDCl$_3$, 300 MHz): δ (ppm): 2.43 (1H, s), 3.07-3.13 (4H, m), 6.95 (1H, d), 7.07 (1H. s), 7.18-7.28 (3H, m), 7.28-7.40 (4H, m), 7.66 (2H, s).

<Synthesis Example M8-2> Synthesis of Compound Ma4

[Chemical Formula 155]

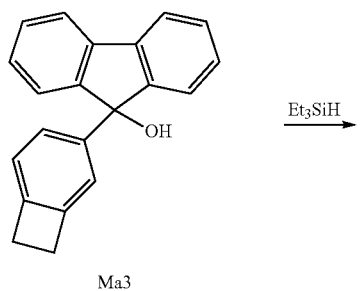

A gas in a flask equipped with a stirrer was purged with a nitrogen gas, then, the compound Ma3 (72.3 g), toluene (723 mL) and triethylsilane (118.0 g) were added, and the mixture was heated up to 70° C. Into this, methanesulfonic acid 97.7 g) was dropped over a period of 1.5 hours, then, the mixture was stirred at 70° C. for 0.5 hours. Thereafter, the mixture was cooled down to room temperature, and toluene (1 L) and water (1 L) were added, then, an aqueous layer was separated. The resultant organic layer was washed with water, a 5 wt % sodium hydrogen carbonate aqueous solution and water in this order. The resultant organic layer was concentrated under reduced pressure, and the resultant coarse product was crystallized from a mixed solvent of toluene and ethanol, thereby obtaining 51.8 g of a compound Ma4 as a white solid. The compound Ma4 had an HPLC area percentage value (UV: 254 nm) of 99.5% or more. This operation was repeated, thereby obtaining a necessary amount of the compound Ma4.

$^1$H-NMR (CDCl$_3$, 300 MHz): δ (ppm): 3.03-3.14 (4H, m), 4.99 (1H, s), 6.68 (1H, s), 6.92-7.01 (2H, m), 7.20-7.28 (2H, m), 7.29-7.38 (4H, m), 7.78 (2H, d).

<Synthesis Example M8-3> Synthesis of Compound Mb3

[Chemical Formula 156]

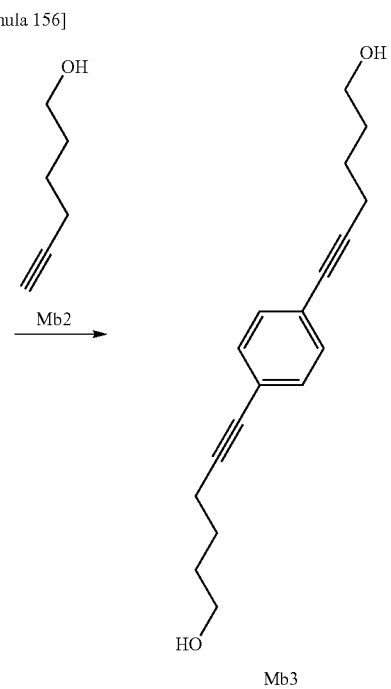

A gas in a flask equipped with a stirrer was purged with a nitrogen gas, then, a compound Mb1 (185.0 g), a compound M b2 (121.1 g), copper iodide (I) (CuI, 3.2 g), dichloromethane (185 mL) and triethylamine (2.59 L) were added, and the mixture was heated up to the reflux temperature. Thereafter, the mixture was stirred at the reflux temperature for 0.5 hours, and cooled down to room temperature. To this was added dichloromethane (1.85 L), then, the mixture was filtrated through a filter paved with celite. To the resultant filtrate was added a 10 wt % sodium hydrogen carbonate aqueous solution, then, an aqueous layer was separated. The resultant organic layer was washed with water twice, washed with a saturated sodium chloride aqueous solution, then, magnesium sulfate was added. The resultant mixture was filtrated, and the resultant filtrate was concentrated under reduced pressure. The resultant residue was purified by using a silica gel column (a mixed solvent of chloroform and ethyl acetate), there by obtaining a coarse product. The resultant coarse product was dissolved in ethanol (1.4 L), then, activated carbon (5 g) was added, and the mixture was filtrated. The resultant filtrate was concentrated under reduced pressure, and the resultant residue was crystallized from hexane, thereby obtaining 99.0 g of a compound Mb3 as a white solid. The compound Mb3 had an HPLC area percentage value (UV: 254 nm) of 99.5% or more. This operation was repeated, thereby obtaining a necessary amount of the compound Mb3.

$^1$H-NMR (DMSO-d$_6$, 300 MHz): δ (ppm): 1.52-1.55 (8H, m), 2.42 (4H, t), 3.38-3.44 (4H, m), 4.39-4.43 (2H, m), 7.31 (4H, s).

<Synthesis Example M8-4> Synthesis of Compound Mb4

[Chemical Formula 157]

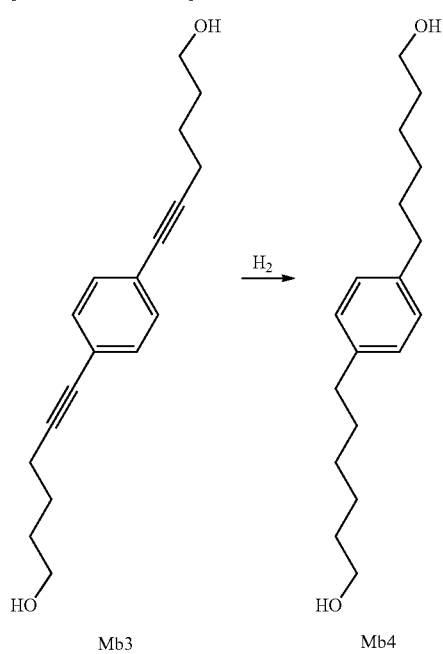

A gas in a flask equipped with a stirrer was purged with a nitrogen gas, then, the compound Mb3 (110.0 g), ethanol (1.65 L) and palladium/carbon (Pd weight: 10%) (11.0 g) were added, and the mixture was heated up to 30° C. Thereafter, a gas in the flask was purged with a hydrogen gas. Thereafter, the mixture was stirred at 30° C. for 3 hours while feeding a hydrogen gas into the flask. Thereafter, a gas in the flask was purged with a nitrogen gas. The resultant mixture was filtrated, and the resultant filtrate was concentrated under reduced pressure. The resultant residue was purified by using a silica gel column (a mixed solvent of chloroform and ethyl acetate), thereby obtaining a coarse product. The resultant coarse product was crystallized from hexane, thereby obtaining 93.4 g of a compound Mb4 as a white solid. The compound Mb4 had an HPLC area percentage value (UV: 254 nm) of 98.3%.

$^1$H-NMR (CDCl$_3$, 300 MHz): δ (ppm): 1.30-1.40 (8H, m), 1.55-1.65 (8H, m), 2.58 (4H, t), 3.64 (4H, t), 7.09 (4H, s).

$^{13}$C-NMR (CDCl$_3$, 75 MHz): δ (ppm): 25.53, 28.99, 31.39, 32.62, 35.37, 62.90, 128.18, 139.85.

<Synthesis Example M8-5> Synthesis of Compound Mb5

[Chemical Formula 158]

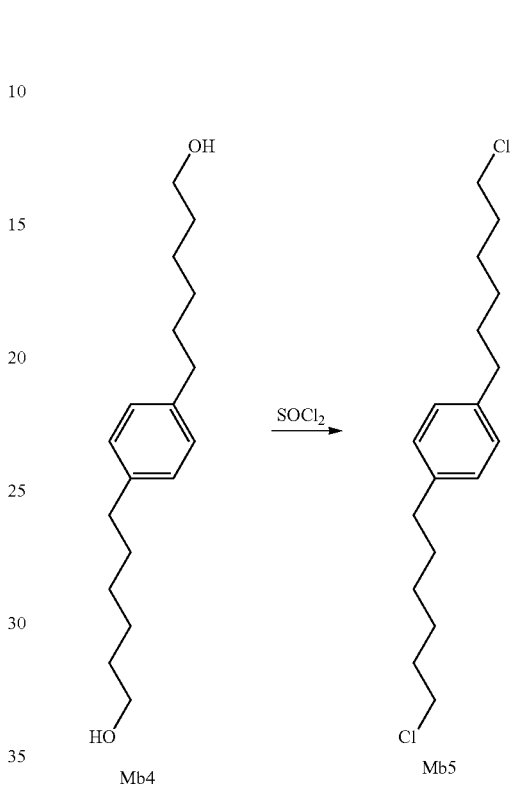

A gas in a flask equipped with a stirrer was purged with a nitrogen gas, then, the compound Mb4 (61.0 g), pyridine (0.9 g) and toluene (732 mL) were added, and the mixture was heated up to 60° C. Into this, thionyl chloride (91.4 g) was dropped over a period of 1.5 hours, then, the mixture was stirred at 60° C. for 5 hours. The resultant mixture was cooled down to room temperature, then, concentrated under reduced pressure. The resultant residue was purified by using a silica gel column (a mixed solvent of hexane and ethyl acetate), thereby obtaining 64.3 g of a compound Mb5 as a colorless oil. The resultant compound Mb5 had an HPLC area percentage value (UV: 254 nm) of 97.2%.

$^1$H-NMR (CDCl$_3$, 300 MHz): δ (ppm): 1.35-1.40 (4H, m), 1.41-1.50 (4H, m), 1.60-1.68 (4H, m), 1.75-1.82 (4H, m), 2.60 (4H, t), 3.55 (4H, t), 7.11 (4H, s).

Synthesis Example M8-6> Synthesis of Compound Mb6

[Chemical Formula 159]

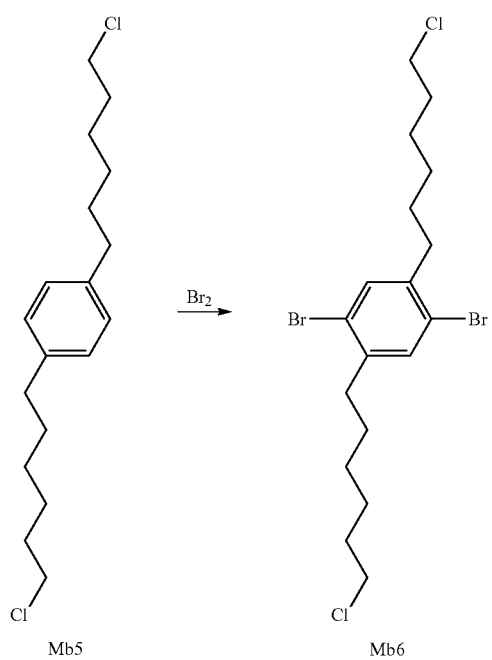

A gas in a flask equipped with a stirrer was purged with a nitrogen gas, then, the compound Mb5 (42.0 g), an iron powder (1.7 g), iodine (0.3 g) and dichloromethane (800 mL) were added. Thereafter, the whole flask was light-shielded, and cooled at 0 to 5° C. Into this, a mixed liquid of bromine (44.7 g) and dichloromethane (200 mL) was dropped over a period of 1 hour, then, the mixture was stirred at 0 to 5° C. overnight. The resultant mixed liquid was added to water (1.2 L) cooled at 0 to 5° C., then, an organic layer was separated. The resultant organic layer was washed with a 10 wt % sodium thiosulfate aqueous solution, and further, washed with a saturated sodium chloride aqueous solution and water in this order. To the resultant organic layer was added sodium sulfate, then, the mixture was filtrated, and the resultant filtrate was concentrated under reduced pressure. The resultant residue was purified by using a silica gel column (hexane), thereby obtaining a coarse product. The resultant coarse product was crystallized from hexane, thereby obtaining 47.0 g of a compound Mb6 as a white solid. The compound Mb6 had an HPLC area percentage value (UV: 254 nm) of 98.3%.

$^1$H-NMR (CDCl$_3$, 300 MHz): δ (ppm): 1.38-1.45 (4H, m), 1.47-1.55 (4H, m), 1.57-1.67 (4H, m), 1.77-1.84 (4H, m), 2.66 (4H, t), 3.55 (4H, t), 7.36 (2H, s).

Synthesis Example M8-7> Synthesis of Compound Mb7

[Chemical Formula 160]

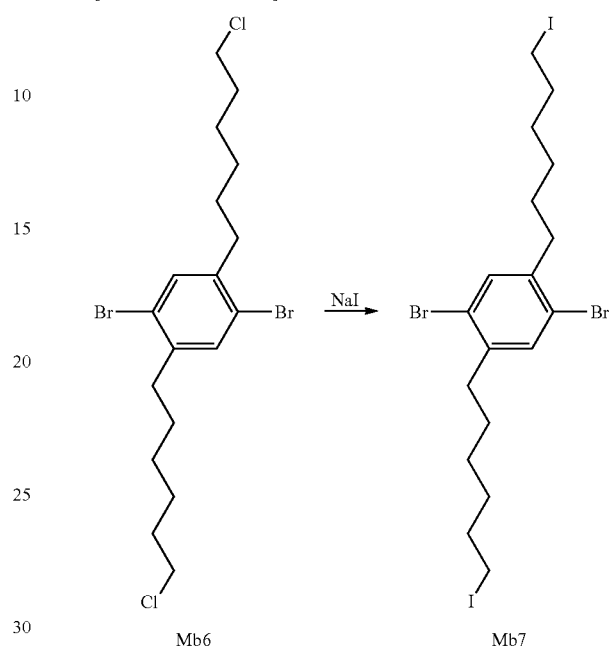

A gas in a flask equipped with a stirrer was purged with a nitrogen gas, then, sodium iodide (152.1 g) and acetone (600 mL) were added, and the mixture was stirred at room temperature for 0.5 hours. To this was added the compound Mb6 (40.0 g), then, the mixture was heated up to the reflux temperature, and stirred at the reflux temperature for 24 hours. Thereafter, the mixture was cooled down to room temperature, and the resultant mixed liquid was added to water (1.2 L). The deposited solid was separated by filtration, then, washed with water, thereby obtaining a coarse product. The resultant coarse product was crystallized from a mixed liquid of toluene and methanol, thereby obtaining 46.0 g of a compound Mb7 as a white solid. The resultant compound Mb7 had an HPLC area percentage value (UV: 254 nm) of 99.4%. This operation was repeated, thereby obtaining a necessary amount of the compound Mb7.

$^1$H-NMR (CDCl$_3$, 300 MHz): δ (ppm): 1.35-1.50 (8H, m), 1.57-1.65 (4H, m), 1.80-1.89 (4H, m), 2.65 (4H, t), 3.20 (4H, t), 7.36 (2H, s).

<Synthesis Example M8-8> Synthesis of Compound Mb8

[Chemical Formula 161]

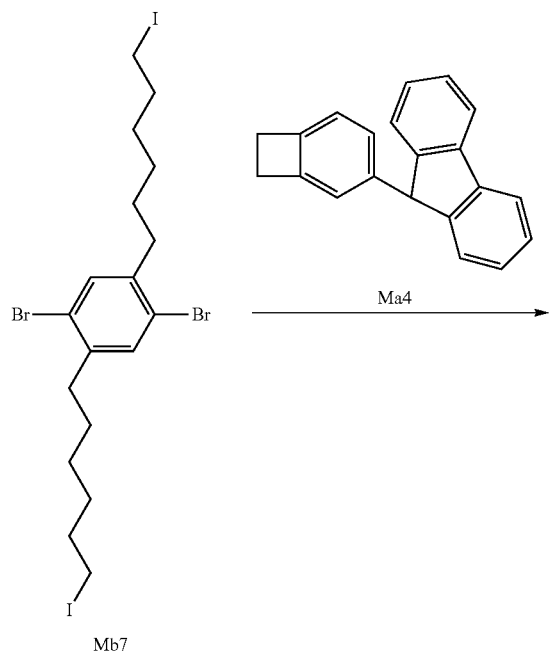

A gas in a flask equipped with a stirrer was purged with a nitrogen gas, then, sodium hydride (60 wt %, dispersed in liquid paraffin) (9.4 g), tetrahydrofuran (110 mL) and the compound Mb7 (63.2 g) were added. To this, a compound Ma4 (55.0 g) was added in several batches, then, the mixture was stirred for 12 hours. To this were added toluene (440 mL) and water (220 mL), then, an aqueous layer was separated. The resultant organic layer was washed with water, then, magnesium sulfate was added. The resultant mixed liquid was filtrated, and the resultant filtrate was concentrated under reduced pressure, thereby obtaining a coarse product. The resultant coarse product was purified by using a silica gel column a mixed solvent of hexane and toluene). Thereafter, the product was crystallized from heptane, thereby obtaining 84.1 g of a compound Mb8 as a white solid. The resultant compound Mb8 had an HPLC area percentage value (UV: 254 nm) of 99.5% or more.

$^1$H-NMR (CDCl$_3$, 300 MHz): δ (ppm): 0.70-0.76 (4H, m), 1.10-1.21 (8H, m), 1.32-1.44 (4H, m), 2.39-2.58 (8H, m), 3.00-3.12 (8H, m), 6.82-6.94 (4H, m), 7.00-7.05 (2H, m), 7.17-7.28 (10H, m), 7.30-7.38 (4H, m), 7.71-7.77 (4H, m).

<Synthesis Example M8-9> Synthesis of Compound M8

[Chemical Formula 162]

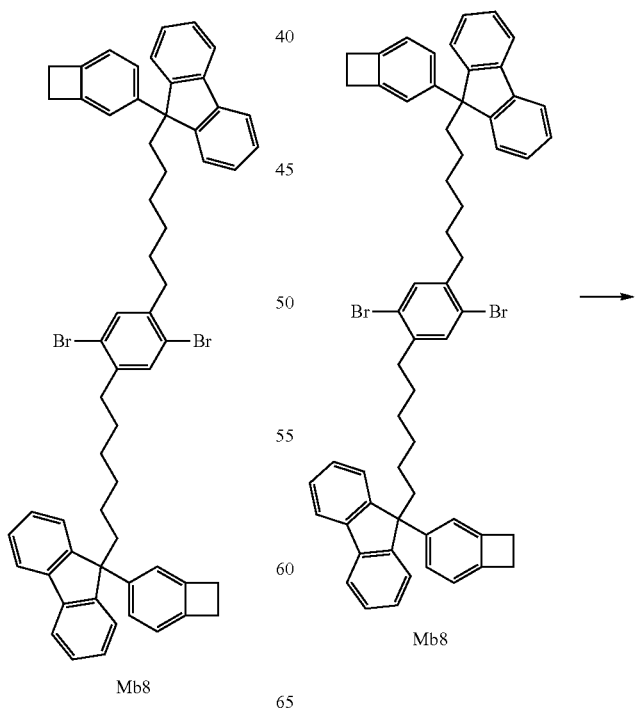

-continued

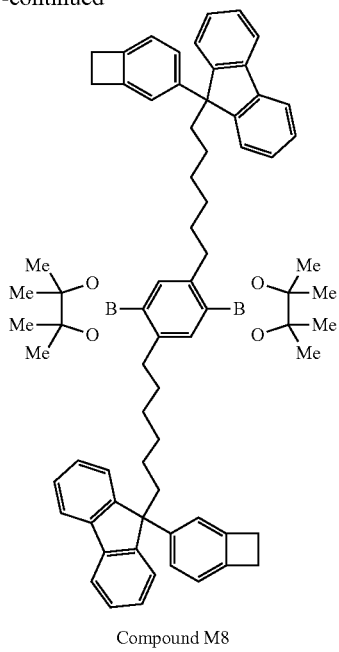

Compound M8

A gas in a flask equipped with a stirrer was purged with a nitrogen gas, then, the compound Mb8 (84.0 g), [1,1'-bis(diphenylphosphino)ferrocene]palladium(II) dichloride dichloromethane adduct (PdCl$_2$(dppf).CH$_2$Cl$_2$, 2.2 g), bispinacolatodiboron (68.3 g), potassium acetate (52.8 g) and cyclopentyl methyl ether (840 mL) were added, and the mixture was heated up to the reflux temperature, then, stirred at the reflux temperature for 5 hours. Thereafter, the mixture was cooled down to room temperature, and toluene (500 mL) and water (300 mL) were added, then, an aqueous layer was separated. The resultant organic layer was washed with water, then, activated carbon (18.5 g) was added. The resultant mixed liquid was filtrated, and the resultant filtrate was concentrated under reduced pressure, thereby obtaining a coarse product. The resultant coarse product was purified by using a silica gel column (a mixed solvent of hexane and toluene). Thereafter, an operation of crystallization from a mixed liquid of toluene and acetonitrile was repeated, thereby obtaining 45.8 g of a compound M8 as a white solid. The resultant compound M8 had an HPLC area percentage value (UV: 254 nm) of 99.4%.

$^1$H-NMR (CDCl$_3$, 300 MHz): δ (ppm): 0.70-0.76 (4H, m), 1.24-1.40 (36H, m), 2.39-2.48 (4H, m), 2.66-2.75 (4H, m), 3.00-3.10 (8H, m), 6.76-6.90 (4H, m), 7.00-7.05 (2H, m), 7.19-7.30 (8H, m), 7.30-7.36 (4H, m), 7.43 (2H, s), 7.72 (4H, d).

<Synthesis Example P1> Synthesis of Polymer Compound HTL-1

A polymer compound HTL-1 was synthesized according to a method disclosed in International Publication WO2013/146806 using the compound M1, the compound M2 and the compound M4

The polymer compound HTL-1 had an Mn of $5.5 \times 10^4$ and an Mw of $1.4 \times 10^5$.

The polymer compound HTL-1 is a copolymer constituted of a constitutional unit derived from the compound M1, a constitutional unit derived from the compound M2 and a constitutional unit derived from the compound M4 at a molar ratio of 50:42.5:7.5, according to the theoretical values calculated from the amounts of the charging raw materials.

<Synthesis Example P2> Synthesis of Polymer Compound HTL-2

(Step 1) An inert gas atmosphere was prepared in a reaction vessel, then, the compound M1 (0.493 g), the compound M3 (0.0620 g), the compound M8 (0.130 g), the compound M2 (1.15 g), dichlorobis(tris(2-methoxyphenyl)phosphine)palladium (2.2 mg) and toluene (34 mL) were added, and the mixture was heated at 105° C.

(Step 2) Into the reaction liquid was dropped a 20 wt % tetraethylammonium hydroxide aqueous solution (8.3 mL), and the mixture was refluxed for 6 hours.

(Step 3) After the reaction, to this were added phenylboronic acid (61.0 mg) and dichlorobis(tris-o-methoxyphenylphosphine)palladium (1.1 mg), and the mixture was refluxed for 14.5 hours.

(Step 4) Thereafter, to this was added a sodium diethyldithiacarbamate aqueous solution, and the mixture was stirred at 80° C. for 2 hours. After cooling, the resultant reaction liquid was washed with water twice, with a 3 wt % acetic acid aqueous solution twice and with water twice, and the resultant solution was dropped into methanol, to generate precipitation. The resultant precipitate was dissolved in toluene, and purified by passing through an alumina column and a silica gel column in this order. The resultant solution was dropped into methanol, the mixture was stirred, then, the resultant precipitate was isolated by filtration, and dried, to obtain 1.05 g of a polymer compound HTL-2.

The polymer compound HTL-2 had a polystyrene-equivalent number-average molecular weight of $2.4 \times 10^4$ and a polystyrene-equivalent weight-average molecular weight of $1.8 \times 10^5$.

The polymer compound HTL-2 is a copolymer constituted of a constitutional unit derived from the compound M1, a constitutional unit derived from the compound M3, a constitutional unit derived from the compound M8 and a constitutional unit derived from the compound M2 at a molar ratio of 40:5:5:50, according to the theoretical values calculated from the amounts of the charging raw materials.

<Synthesis Example P3> Synthesis of Polymer Compound HTL-3

The polymer compound HTL-3 was synthesized according to a method disclosed in International Publication WO2013/146806, using the compound M1, the compound M2 and the compound M5.

The polymer compound HTL-3 had an Mn of $1.9 \times 10^4$ and an Mw of $9.9 \times 10^4$.

The polymer compound HTL-3 is a copolymer constituted of a constitutional unit derived from the compound M1, a constitutional unit derived from the compound M2 and a constitutional unit derived from the compound M5 at a molar ratio of 50:42.5:7.5, according to the theoretical values calculated from the amounts of the charging raw materials.

<Synthesis Example P4> Synthesis of Polymer Compound HTL-4

The polymer compound HTL-4 was synthesized according to a method disclosed in JP-A No. 2014-1327, using the compound M1, the compound M4, the compound M7 and the compound M6.

The polymer compound HTL-4 had an Mn of $5.2 \times 10^4$ and an Mw of $2.5 \times 10^5$.

The polymer compound HTL-4 is a copolymer constituted of a constitutional unit derived from the compound M1, a constitutional unit derived from the compound M4, a constitutional unit derived from the compound M7 and a constitutional unit derived from the compound M6 at a molar ratio of 50:5:5:40, according to the theoretical values calculated from the amounts of the charging raw materials.

<Synthesis Example P5> Synthesis of Polymer Compound ET1

(Synthesis of Polymer Compound ET1a)

A polymer compound ET1a was synthesized according to a method disclosed in JP-A No. 2012-33845, using a compound ET1-1 synthesized according to a method disclosed in JP-A No. 2012-33845 and a compound ET1-2 synthesized according to a method disclosed in JP-A No. 2012-33845.

[Chemical Formula 163]

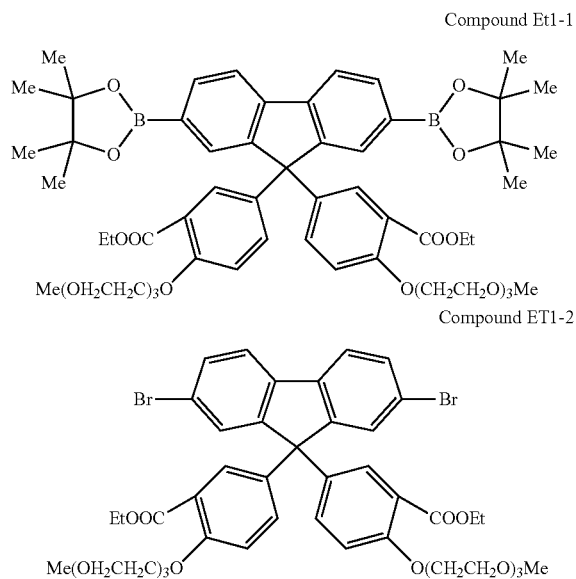

The polymer compound ET1a had a Mn of $5.2 \times 10^4$.

The polymer compound ET1a is a copolymer constituted of a constitutional unit derived from a compound ET1-1 and a constitutional unit derived from a compound ET1-2 at a molar ratio of 50:50, according to theoretical values calculated from the amounts of charged raw materials.

(Synthesis of Polymer Compound ET1)

An inert gas atmosphere was prepared in a reaction vessel, then, a polymer compound ET1a (200 mg), tetrahydrofuran (20 ml) and ethanol (20 ml) were added, and the mixture was heated at 55° C. Thereafter, to this was added cesium hydroxide (200 mg) dissolved in water (2 ml), and the mixture was stirred at 55° C. for 6 hours. Thereafter, the mixture was cooled down to room temperature, then, concentrated under reduced pressure, to obtain a solid. The resultant solid was washed with water, then, dried under reduced pressure, to obtain a polymer compound ET1 (150 mg, pale yellow solid). It was confirmed that a signal derived from an ethyl group of an ethyl ester portion of a polymer compound ET1a disappeared completely, by the NMR spectrum of the resultant polymer compound ET1.

[Chemical Formula 164]

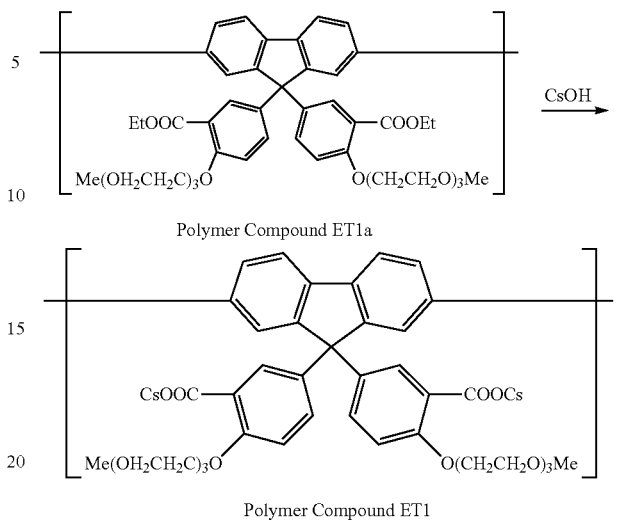

<Comparative Example CD1> Fabrication and Evaluation of Light Emitting Device CD1

(Formation of Anode and Hole Injection Layer)

To a glass substrate was attached an ITO film with a thickness of 45 nm by a sputtering method, to form an anode. A film was formed with a thickness of 35 nm by spin-coating a polythiophene-sulfonic acid type hole injection agent AQ-1200 (manufactured by Plextronics) on the anode, and heated on a hot plate at 170° C. under an air atmosphere for 15 minutes, to form a hole injection layer.

(Formation of Hole Transporting Layer)

Into xylene was dissolved the polymer compound HTL-1 at a concentration of 0.7 wt %. Using the resultant xylene solution, a film was formed with a thickness of 20 nm on the hole injection layer by a spin coat method, and heated on a hot plate at 180° C. under a nitrogen gas atmosphere for 60 minutes, to form a hole transporting layer.

(Formation of Light Emitting Layer)

Into chlorobenzene were dissolved the iridium complex 1 and the compound H1 (iridium complex 1/compound H1=30 wt %/70 wt %, MA+MB=1476, MA/MB=2.05) at a concentration of 2.5 wt %. Using the resultant chlorobenzene solution, a film was formed with a thickness of 80 nm on the hole transporting layer by a spin coat method, and heated at 130° C. under a nitrogen gas atmosphere for 10 minutes, to form a light emitting layer.

(Formation of Cathode)

The substrate carrying the light emitting layer formed thereon was placed in a vapor deposition machine and the pressure in the machine was reduced to $1.0 \times 10^{-4}$ Pa or less, then, as a cathode, sodium fluoride was vapor-deposited with a thickness of about 4 nm on the light emitting layer and aluminum was vapor-deposited with a thickness of about 80 nm on the sodium fluoride layer. After vapor deposition, sealing was performed using a glass substrate, to fabricate a light emitting device CD1.

(Evaluation of Light Emitting Device)

When voltage was applied to the light emitting device CD1, EL emission was observed. The external quantum efficiency at 1000 cd/m² was 0.11%, and the CIE chromaticity coordinate (x, y)=(0.28, 0.63).

<Comparative Example CD2> Fabrication and Evaluation of Light Emitting Device CD2

A light emitting device CD2 was fabricated in the same manner as in Comparative Example CD1 excepting that the iridium complex 2 and the compound H3 (iridium complex 2/compound H3=30 wt %/70 wt %, MA+MB=2652, MA/MB=1.72) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device CD2, EL emission was observed. The external quantum efficiency at 1000 cd/m$^2$ was 2.14%, and the CIE chromaticity coordinate (x, y)=(0.29, 0.64).

<Example D1> Fabrication and Evaluation of Light Emitting Device D1

A light emitting device D1 was fabricated in the same manner as in Comparative Example CD1 excepting that the iridium complex 3 and the compound H2 (iridium complex 3/compound H2=30 wt %/70 wt %, MA+MB=2719, MA/MB=2.85) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D1, EL emission was observed. The external quantum efficiency at 1000 cd/m$^2$ was 7.31%, and the CIE chromaticity coordinate (x, y)=(0.43, 0.56).

<Example D2> Fabrication and Evaluation of Light Emitting Device D2

A light emitting device D2 was fabricated in the same manner as in Comparative Example CD1 excepting that the iridium complex 1 and the compound H4 (iridium complex 1/compound H4=30 wt %/70 wt %, MA+MB=3496, MA/MB=0.40) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D2, EL emission was observed. The external quantum efficiency at 1000 cd/m$^2$ was 15.15%, and the CIE chromaticity coordinate (x, y)=(0.36, 0.59).

<Example D3> Fabrication and Evaluation of Light Emitting Device D3

A light emitting device D3 was fabricated in the same manner as in Comparative Example CD1 excepting that the iridium complex 2 and the compound H4 (iridium complex 2/compound H4=30 wt %/70 wt %, MA+MB=4181, MA/MB=0.67) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D3, EL emission was observed. The external quantum efficiency at 1000 cd/m$^2$ was 16.96%, and the CIE chromaticity coordinate (x, y)=(0.31, 0.63).

<Example D4> Fabrication and Evaluation of Light Emitting Device D4

A light emitting device D4 was fabricated in the same manner as in Comparative Example CD1 excepting that the iridium complex 4 and the compound H4 (iridium complex 4/compound H4=30 wt %/70 wt %, MA+MB=4181, MA/MB=0.67) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D4, EL emission was observed. The external quantum efficiency at 1000 cd/m$^2$ was 20.27%, and the CIE chromaticity coordinate (x, y)=(0.44, 0.55).

<Example D5> Fabrication and Evaluation of Light Emitting Device D5

A light emitting device D5 was fabricated in the same manner as in Comparative Example CD1 excepting that the iridium complex 3 and the compound H4 (iridium complex 3/compound H4=30 wt %/70 wt %, MA+MB=4518, MA/MB=0.80) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D5, EL emission was observed. The external quantum efficiency at 1000 cd/m$^2$ was 19.27%, and the CIE chromaticity coordinate (x, y)=(0.44, 0.55).

<Example D6> Fabrication and Evaluation of Light Emitting Device D6

A light emitting device D6 was fabricated in the same manner as in Comparative Example CD1 excepting that the iridium complex 5 and the compound H4 (iridium complex 5/compound H4=30 wt %/70 wt %, MA+MB=4518, MA/MB=0.80) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D6, EL emission was observed. The external quantum efficiency at 1000 cd/m$^2$ was 18.38%, and the CIE chromaticity coordinate (x, y)=(0.31, 0.63).

<Example D7> Fabrication and Evaluation of Light Emitting Device D7

A light emitting device D7 was fabricated in the same manner as in Comparative Example CD1 excepting that the iridium complex 6 and the compound H4 (iridium complex 6/compound H4=30 wt %/70 wt %, MA+MB=5431, MA/MB=1.17) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D7, EL emission was observed. The external quantum efficiency at 1000 cd/m$^2$ was 15.22%, and the CIE chromaticity coordinate (x, y)=(0.30, 0.64).

<Example D8> Fabrication and Evaluation of Light Emitting Device D8

A light emitting device D8 was fabricated in the same manner as in Comparative Example CD1 excepting that the iridium complex 7 and the compound H4 (iridium complex 6/compound H4=30 wt %/70 wt %, MA+MB=6104, MA/MB=1.44) were used instead of the iridium complex 1 and the compound H1 (iridium complex 1/compound H1=30 wt %/70 wt %, MA+MB=1476, MA/MB=2.05) in Comparative Example CD1.

When voltage was applied to the light emitting device D8, EL emission was observed. The external quantum efficiency at 1000 cd/m² was 12.47%, and the CIE chromaticity coordinate (x, y)=(0.30, 0.63).

<Example D9> Fabrication and Evaluation of Light Emitting Device D9

A light emitting device D9 was fabricated in the same manner as in Comparative Example CD1 excepting that (Formation of hole transporting layer) was changed to (Formation of hole transporting layer: -D9) described below and (Formation of light emitting layer) was changed to (Formation of light emitting layer: -D9) described below, in Comparative Example CD1.
(Formation of Hole Transporting Layer: -D9)
Into xylene was dissolved the polymer compound HTL-2 at a concentration of 0.7 wt %. Using the resultant xylene solution, a film was formed with a thickness of 20 nm on the hole injection layer by a spin coat method, and heated on a hot plate at 180° C. under a nitrogen gas atmosphere for 60 minutes, to form a hole transporting layer.
(Formation of Light Emitting Layer: -D9)
Into toluene were dissolved the iridium complex 2 and the compound H4 (iridium complex 2/compound H4=30 wt %/70 wt %, MA+MB=4181, MA/MB=0.67) at a concentration of 2.5 wt %. Using the resultant toluene solution, a film was formed with a thickness of 80 nm on the hole transporting layer by a spin coat method, and heated at 130° C. under a nitrogen gas atmosphere for 10 minutes, to form a light emitting layer.
(Evaluation of Light Emitting Device)
When voltage was applied to the light emitting device D9, EL emission was observed. The external quantum efficiency at 1000 cd/m² was 19.09%, and the CIE chromaticity coordinate (x, y)=(0.31, 0.63).

<Example D10> Fabrication and Evaluation of Light Emitting Device D10

A light emitting device D10 was fabricated in the same manner as in Example D3 excepting that the polymer compound HTL-3 was used instead of the polymer compound HTL-1 in Example D3.

When voltage was applied to the light emitting device D10, EL emission was observed. The external quantum efficiency at 1000 cd/m² was 18.63%, and the CIE chromaticity coordinate (x, y)=(0.31, 0.63).

<Example D11> Fabrication and Evaluation of Light Emitting Device D11

A light emitting device D11 was fabricated in the same manner as in Example D3 excepting that (Formation of hole transporting layer) was changed to (Formation of hole transporting layer: -D11) described below in Example D3.
(Formation of Hole Transporting Layer: -D11)
Into chlorobenzene was dissolved the low molecular weight compound HTL-M1 (manufactured by Luminescense Technology) at a concentration of 0.7 wt %. Using the resultant chlorobenzene solution, a film was formed with a thickness of 20 nm on the hole injection layer by a spin coat method, and heated on a hot plate at 180° C. under a nitrogen gas atmosphere for 60 minutes, to form a hole transporting layer.

[Chemical Formula 165]

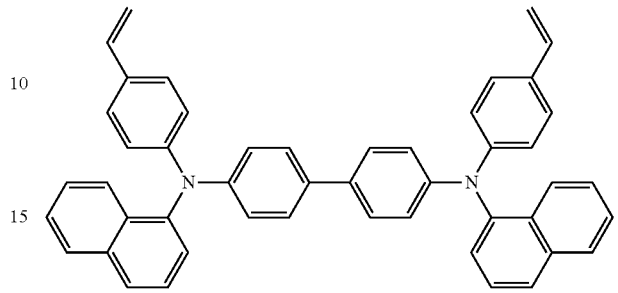

Low Molecular Weight Compound HTL-M1-3
When voltage was applied to the light emitting device D11, EL emission was observed. The external quantum efficiency at 1000 cd/m² was 13.09%, and the CIE chromaticity coordinate (x, y)=(0.32, 0.63).

<Comparative Example CD3> Fabrication and Evaluation of Light Emitting Device CD3

(Formation of Anode and Hole Injection Layer)
To a glass substrate was attached an ITO film with a thickness of 45 nm by a sputtering method, to form an anode. A film was formed with a thickness of 65 nm by spin-coating a polythiophene-sulfonic acid type hole injection agent AQ-1200 (manufactured by Plextronics) on the anode, and heated on a hot plate at 170° C. under an air atmosphere for 15 minutes, to form a hole injection layer.
(Formation of Hole Transporting Layer)
Into xylene was dissolved the polymer compound HTL-3 at a concentration of 0.7 wt %. Using the resultant xylene solution, a film was formed with a thickness of 20 nm on the hole injection layer by a spin coat method, and heated on a hot plate at 180° C. under a nitrogen gas atmosphere for 60 minutes, to form a hole transporting layer.
(Formation of Light Emitting Layer)
Into xylene were dissolved the iridium complex 8 and the compound H2 (iridium complex 8/compound H2=10 wt %/90 wt %, MA+MB=2532, MA/MB=2.59) at a concentration of 3 wt %. Using the resultant xylene solution, a film was formed with a thickness of 80 nm on the hole transporting layer by a spin coat method, and heated at 130° C. under a nitrogen gas atmosphere for 10 minutes, to form a light emitting layer.
(Formation of Cathode)
The substrate carrying the light emitting layer formed thereon was placed in a vapor deposition machine and the pressure in the machine was reduced to 1.0×10⁻⁴ Pa or less, then, as a cathode, sodium fluoride was vapor-deposited with a thickness of about 4 nm on the light emitting layer and aluminum was vapor-deposited with a thickness of about 80 nm on the sodium fluoride layer. After vapor deposition, sealing was performed using a glass substrate, to fabricate a light emitting device CD3.
(Evaluation of Light Emitting Device)
When voltage was applied to the light emitting device CD3, EL emission was observed. The external quantum efficiency at 400 cd/m² was 1.75%, and the CIE chromaticity coordinate (x, y)=(0.66, 0.34).

<Example D12> Fabrication and Evaluation of Light Emitting Device D12

A light emitting device D12 was fabricated in the same manner as in Comparative Example CD3 excepting that (Formation of light emitting layer) was changed to (Formation of light emitting layer: -D12) described below in Comparative Example CD3.
(Formation of Light Emitting Layer: -D12)
Into chlorobenzene were dissolved the iridium complex 9 and the compound H4 (iridium complex 9/compound H2=10 wt %/90 wt %, MA+MB=3478, MA/MB=0.39) at a concentration of 2.5 wt %. Using the resultant chlorobenzene solution, a film was formed with a thickness of 80 nm on the hole transporting layer by a spin coat method, and heated at 130° C. under a nitrogen gas atmosphere for 10 minutes, to form a light emitting layer.
(Evaluation of Light Emitting Device)
When voltage was applied to the light emitting device D12, EL emission was observed. The external quantum efficiency at 400 cd/m² was 11.10%, and the CIE chromaticity coordinate (x, y)=(0.68, 0.32).

<Example D13> Fabrication and Evaluation of Light Emitting Device D13

A light emitting device D13 was fabricated in the same manner as in Comparative Example CD3 excepting that the iridium complex 10 and the compound H4 (iridium complex 10/compound H4=10 wt %/90 wt %, MA+MB=4190, MA/MB=0.67) were used instead of the iridium complex 8 and the compound H2 (iridium complex 8/compound H2=10 wt %/90 wt %, MA+MB=2532, MA/MB=2.59) in Comparative Example CD3.
When voltage was applied to the light emitting device D13, EL emission was observed. The external quantum efficiency at 400 cd/m² was 14.64%, and the CIE chromaticity coordinate (x, y)=(0.61, 0.39).

<Example D14> Fabrication and Evaluation of Light Emitting Device D14

A light emitting device D14 was fabricated in the same manner as in Comparative Example CD3 excepting that the iridium complex 11 and the compound H4 (iridium complex 11/compound H4=10 wt %/90 wt %, MA+MB=5256, MA/MB=1.10) were used instead of the iridium complex 8 and the compound H2 (iridium complex 8/compound H2=10 wt %/90 wt %, MA+MB=2532, MA/MB=2.59) in Comparative Example CD3.

When voltage was applied to the light emitting device D14, EL emission was observed. The external quantum efficiency at 400 cd/m² was 13.36%, and the CIE chromaticity coordinate (x, y)=(0.65, 0.35).

<Example D15> Fabrication and Evaluation of Light Emitting Device D15

A light emitting device D15 was fabricated in the same manner as in Comparative Example CD3 excepting that the iridium complex 12 and the compound H4 (iridium complex 12/compound H4=10 wt %/90 wt %, MA+MB=6200, MA/MB=1.48) were used instead of the iridium complex 8 and the compound H2 (iridium complex 8/compound H2=10 wt %/90 wt %, MA+MB=2532, MA/MB=2.59) in Comparative Example CD3.
When voltage was applied to the light emitting device D15, EL emission was observed. The external quantum efficiency at 400 cd/m² was 11.00%, and the CIE chromaticity coordinate (x, y)=(0.63, 0.37).

<Comparative Example CD4> Fabrication and Evaluation of Light Emitting Device CD4

A light emitting device CD4 was fabricated in the same manner as in Comparative Example CD3 excepting that the iridium complex 11 and the compound H2 (iridium complex 11/compound H2=10 wt %/90 wt %, MA+MB=3458, MA/MB=3.90) were used instead of the iridium complex 8 and the compound H2 (iridium complex 8/compound H2=10 wt %/90 wt %, MA+MB=2532, MA/MB=2.59) in Comparative Example CD3.
When voltage was applied to the light emitting device CD4, EL emission was observed. The external quantum efficiency at 400 cd/m² was 0.83%, and the CIE chromaticity coordinate (x, y)=(0.62, 0.38).

<Comparative Example CD5> Fabrication and Evaluation of Light Emitting Device CD5

A light emitting device CD5 was fabricated in the same manner as in Comparative Example CD3 excepting that the iridium complex 12 and the compound H2 (iridium complex 12/compound H2=10 wt %/90 wt %, MA+MB=4401, MA/MB=5.23) were used instead of the iridium complex 8 and the compound H2 (iridium complex 8/compound H2=10 wt %/90 wt %, MA+MB=2532, MA/MB=2.59) in Comparative Example CD3.
When voltage was applied to the light emitting device CD5, EL emission was observed. The external quantum efficiency at 400 cd/m² was 0.89%, and the CIE chromaticity coordinate (x, y)=(0.61, 0.38).

TABLE 2

|  | hole transporting layer | light emitting layer | | | | external quantum efficiency (%) |
| --- | --- | --- | --- | --- | --- | --- |
|  |  | complex | compound | MA + MB | MA/MB |  |
| Comparative Example CD1 | HTL-1 | complex 1 | H1 | 1476 | 2.05 | 0.11 |
| Comparative Example CD2 | HTL-1 | complex 2 | H3 | 2652 | 1.72 | 2.14 |
| Example D1 | HTL-1 | complex 3 | H2 | 2719 | 2.85 | 7.31 |
| Example D2 | HTL-1 | complex 1 | H4 | 3496 | 0.40 | 15.15 |

TABLE 2-continued

|  | hole transporting layer | light emitting layer | | | | external quantum efficiency |
| --- | --- | --- | --- | --- | --- | --- |
|  |  | complex | compound | MA + MB | MA/MB | (%) |
| Example D3 | HTL-1 | complex 2 | H4 | 4181 | 0.67 | 16.96 |
| Example D4 | HTL-1 | complex 4 | H4 | 4181 | 0.67 | 20.27 |
| Example D5 | HTL-1 | complex 3 | H4 | 4518 | 0.80 | 19.27 |
| Example D6 | HTL-1 | complex 5 | H4 | 4518 | 0.80 | 18.38 |
| Example D7 | HTL-1 | complex 6 | H4 | 5431 | 1.17 | 15.22 |
| Example D8 | HTL-1 | complex 7 | H4 | 6104 | 1.44 | 12.47 |
| Example D9 | HTL-2 | complex 2 | H4 | 4181 | 0.67 | 19.09 |
| Example D10 | HTL-3 | complex 2 | H4 | 4181 | 0.67 | 18.63 |
| Example D11 | HTL-M1 | complex 2 | H4 | 4181 | 0.67 | 13.09 |
| Comparative Example CD3 | HTL-3 | complex 8 | H2 | 2532 | 2.59 | 1.75 |
| Example D12 | HTL-3 | complex 9 | H4 | 3478 | 0.39 | 11.10 |
| Example D13 | HTL-3 | complex 10 | H4 | 4190 | 0.67 | 14.64 |
| Example D14 | HTL-3 | complex 11 | H4 | 5256 | 1.10 | 13.36 |
| Example D15 | HTL-3 | complex 12 | H4 | 6200 | 1.48 | 11.00 |
| Comparative Example CD4 | HTL-3 | complex 11 | H2 | 3458 | 3.90 | 0.83 |
| Comparative Example CD5 | HTL-3 | complex 12 | H2 | 4401 | 5.23 | 0.89 |

<Comparative Example CD6> Fabrication and Evaluation of Light Emitting Device CD6

(Formation of Anode and Hole Injection Layer)

To a glass substrate was attached an ITO film with a thickness of 45 nm by a sputtering method, to form an anode. A film was formed with a thickness of 35 nm by spin-coating a polythiophene-sulfonic acid type hole injection agent AQ-1200 (manufactured by Plextronics) on the anode, and heated on a hot plate at 170° C. under an air atmosphere for 15 minutes, to form a hole injection layer.

(Formation of Hole Transporting Layer)

Into xylene was dissolved the polymer compound HTL-4 at a concentration of 0.7 wt %. Using the resultant xylene solution, a film was formed with a thickness of 20 nm on the hole injection layer by a spin coat method, and heated on a hot plate at 180° C. under a nitrogen gas atmosphere for 60 minutes, to form a hole transporting layer.

(Formation of Light Emitting Layer)

Into chlorobenzene were dissolved the iridium complex 13 and the compound H5 (iridium complex 13/compound H5=25 wt %/75 wt %, MA+MB=3196, MA/MB=0.33) at a concentration of 2 wt %. Using the resultant chlorobenzene solution, a film was formed with a thickness of 60 nm on the hole transporting layer by a spin coat method, and heated at 130° C. under a nitrogen gas atmosphere for 10 minutes, to form a light emitting layer.

(Formation of Electron Transporting Layer)

Into 2,2,3,3,4,4,5,5-octafluoro-1-pentanol was dissolved the polymer compound ET1 at a concentration of 0.25 wt %. Using the resultant 2,2,3,3,4,4,5,5-octafluoro-1-pentanol solution, a film was formed with a thickness of 10 nm on the light emitting layer by a spin coat method, and heated at 130° C. under a nitrogen gas atmosphere for 10 minutes, to form an electron transporting layer.

(Formation of Cathode)

The substrate carrying the electron transporting layer formed thereon was placed in a vapor deposition machine, and the pressure in the machine was reduced to $1.0 \times 10^4$ Pa or less, then, as a cathode, sodium fluoride was vapor-deposited with a thickness of about 4 nm on the electron transporting layer, then, aluminum was vapor-deposited with a thickness of about 80 nm on the sodium fluoride layer. After vapor deposition, sealing was performed using a glass substrate, to fabricate a light emitting device CD6.

(Evaluation of Light Emitting Device)

When voltage was applied to the light emitting device CD6, EL emission was observed. The external quantum efficiency at 200 cd/m$^2$ was 0.89%, and the CIE chromaticity coordinate (x, y)=(0.16, 0.22).

<Example D16> Fabrication and Evaluation of Light Emitting Device D16

A light emitting device D16 was fabricated in the same manner as in Comparative Example CD6 excepting that the iridium complex 14 and the compound H5 (iridium complex 14/compound H5=25 wt %/75 wt %, MA+MB=4218, MA/MB=0.76) were used instead of the iridium complex 13 and the compound H5 (iridium complex 13/compound H5=25 wt %/75 wt %, MA+MB=3196, MA/MB=0.33) in Comparative Example CD6.

When voltage was applied to the light emitting device D16, EL emission was observed. The external quantum efficiency at 200 cd/m$^2$ was 5.41%, and the CIE chromaticity coordinate (x, y)=(0.15, 0.30).

<Example D17> Fabrication and Evaluation of Light Emitting Device D17

A light emitting device D17 was fabricated in the same manner as in Comparative Example CD6 excepting that the iridium complex 15 and the compound H5 (iridium complex 15/compound H5=25 wt %/75 wt %, MA+MB=6141, MA/MB=1.56) were used instead of the iridium complex 13 and the compound H5 (iridium complex 13/compound H5=25 wt %/75 wt %, MA+MB=3196, MA/MB=0.33) in Comparative Example CD6.

When voltage was applied to the light emitting device D17, EL emission was observed. The external quantum efficiency at 200 cd/m$^2$ was 3.06%, and the CIE chromaticity coordinate (x, y)=(0.15, 0.29).

<Example D18> Fabrication and Evaluation of Light Emitting Device D18

A light emitting device D18 was fabricated in the same manner as in Comparative Example CD6 excepting that the iridium complex 16 and the compound H5 (iridium complex 16/compound H5=25 wt %/75 wt %, MA+MB=4864, MA/MB=1.02) were used instead of the iridium complex 13 and the compound H5 (iridium complex 13/compound H5=25 wt %/75 wt %, MA+MB=3196, MA/MB=0.33) in Comparative Example CD6.

When voltage was applied to the light emitting device D18, EL emission was observed. The external quantum efficiency at 50 cd/m$^2$ was 7.20%, and the CIE chromaticity coordinate (x, y)=(0.18, 0.39).

<Example D19> Fabrication and Evaluation of Light Emitting Device D19

A light emitting device D19 was fabricated in the same manner as in Comparative Example CD6 excepting that the iridium complex 17 and the compound H5 (iridium complex 17/compound H5=25 wt %/75 wt %, MA+MB=3734, MA/MB=0.55) were used instead of the iridium complex 13 and the compound H5 (iridium complex 13/compound H5=25 wt %/75 wt %, MA+MB=3196, MA/MB=0.33) in Comparative Example CD6.

When voltage was applied to the light emitting device D19, EL emission was observed. The external quantum efficiency at 50 cd/m$^2$ was 2.80%, and the CIE chromaticity coordinate (x, y)=(0.18, 0.39).

<Comparative Example CD7> Fabrication and Evaluation of Light Emitting Device CD7

A light emitting device CD7 was fabricated in the same manner as in Comparative Example CD6 excepting that the iridium complex 18 and the compound H6 (iridium complex 18/compound H6=25 wt %/75 wt %, MA+MB=1796, MA/MB=1.95) were used instead of the iridium complex 13 and the compound H5 (iridium complex 13/compound H5=25 wt %/75 wt %, MA+MB=3196, MA/MB=0.33) in Comparative Example CD6.

When voltage was applied to the light emitting device CD7, EL emission was observed. The external quantum efficiency at 50 cd/m$^2$ was 0.60%, and the CIE chromaticity coordinate (x, y)=(0.20, 0.40).

<Example D20> Fabrication and Evaluation of Light Emitting Device D20

(Formation of Anode and Hole Injection Layer)

To a glass substrate was attached an ITO film with a thickness of 45 nm by a sputtering method, to form an anode. A film was formed with a thickness of 65 nm by spin-coating a polythiophene-sulfonic acid type hole injection agent AQ-1200 (manufactured by Plextronics) on the anode, and heated on a hot plate at 170° C. under an air atmosphere for 15 minutes, to form a hole injection layer.

(Formation of Hole Transporting Layer)

Into xylene was dissolved the polymer compound HTL-3 at a concentration of 0.7 wt %. Using the resultant xylene solution, a film was formed with a thickness of 20 nm on the hole injection layer by a spin coat method, and heated on a hot plate at 180° C. under a nitrogen gas atmosphere for 60 minutes, to form a hole transporting layer.

(Formation of Light Emitting Layer)

Into chlorobenzene were dissolved the iridium complex 16 and the compound H5 (iridium complex 16/compound H5=25 wt %/75 wt %, MA+MB=4864, MA/MB=1.02) at a concentration of 2 wt %. Using the resultant chlorobenzene solution, a film was formed with a thickness of 80 nm on the hole transporting layer by a spin coat method, and heated at 130° C. under a nitrogen gas atmosphere for 10 minutes, to form a light emitting layer.

(Formation of Electron Transporting Layer)

Into 2,2,3,3,4,4,5,5-octafluoro-1-pentanol was dissolved the polymer compound ET1 at a concentration of 0.25 wt %. Using the resultant 2,2,3,3,4,4,5,5-octafluoro-1-pentanol solution, a film was formed with a thickness of 10 nm on the light emitting layer by a spin coat method, and heated at 130° C. under a nitrogen gas atmosphere for 10 minutes, to form an electron transporting layer.

(Formation of Cathode)

The substrate carrying the electron transporting layer formed thereon was placed in a vapor deposition machine, and the pressure in the machine was reduced to $1.0 \times 10^{-4}$ Pa or less, then, as a cathode, sodium fluoride was vapor-deposited with a thickness of about 4 nm on the electron transporting layer, then, aluminum was vapor-deposited with a thickness of about 80 nm on the sodium fluoride layer. After vapor deposition, sealing was performed using a glass substrate, to fabricate a light emitting device D20.

(Evaluation of Light Emitting Device)

When voltage was applied to the light emitting device D20, EL emission was observed. The external quantum efficiency at 200 cd/m$^2$ was 7.82%, and the CIE chromaticity coordinate (x, y)=(0.19, 0.44).

<Example D21> Fabrication and Evaluation of Light Emitting Device D21

A light emitting device D21 was fabricated in the same manner as in Example D20 excepting that the iridium complex 17 and the compound H5 (iridium complex 17/compound H5=25 wt %/75 wt %, MA+MB=3734, MA/MB=0.55) were used instead of the iridium complex 16 and the compound H5 (iridium complex 16/compound H5=25 wt %/75 wt %, MA+MB=4864, MA/MB=1.02), in Example D20.

When voltage was applied to the light emitting device D21, EL emission was observed. The external quantum efficiency at 200 cd/m$^2$ was 3.17%, and the CIE chromaticity coordinate (x, y)=(0.19, 0.44).

TABLE 3

| | hole transporting layer | light emitting layer | | | external quantum efficiency (%) |
|---|---|---|---|---|---|
| | | complex | compound | MA + MB | MA/MB | |
| Comparative Example CD6 | HTL-4 | complex 13 | H5 | 3196 | 0.33 | 0.89 |

TABLE 3-continued

| | hole transporting layer | light emitting layer | | | | external quantum efficiency (%) |
|---|---|---|---|---|---|---|
| | | complex | compound | MA + MB | MA/MB | |
| Example D16 | HTL-4 | complex 14 | H5 | 4218 | 0.76 | 5.41 |
| Example D17 | HTL-4 | complex 15 | H5 | 6141 | 1.56 | 3.06 |
| Example D18 | HTL-4 | complex 16 | H5 | 4864 | 1.02 | 7.20 |
| Example D19 | HTL-4 | complex 17 | H5 | 3734 | 0.55 | 2.80 |
| Comparative Example CD7 | HTL-4 | complex 18 | H6 | 1796 | 1.95 | 0.60 |
| Example D20 | HTL-3 | complex 16 | H5 | 4864 | 1.02 | 7.82 |
| Example D21 | HTL-3 | complex 17 | H5 | 3734 | 0.55 | 3.17 |

INDUSTRIAL APPLICABILITY

According to the present invention, a light emitting device excellent in external quantum efficiency can be provided. Further, according to the present invention, a composition which is useful for production of a light emitting device excellent in external quantum efficiency can be provided.

The invention claimed is:

1. A light emitting device comprising an anode, a cathode, a light emitting layer disposed between the anode and the cathode, and a hole transporting layer disposed between the anode and the light emitting layer, wherein the light emitting layer is a layer comprising at least one iridium complex (A) represented by formula (A) and at least one heterocyclic compound (B) represented by formula (B), the hole transporting layer is a layer comprising a crosslinked body of a crosslinkable material, and the molecular weight (MA) of the at least one iridium complex (A) and the molecular weight (MB) of the at least one heterocyclic compound (B) satisfy the formula (M1-2) and the formula (M2-1), wherein when more than one iridium complex (A) and/or more than one heterocyclic compound (B) is present, MA refers to the molecular weight of a single iridium complex (A) and MB refers to the molecular weight of a single heterocyclic compound (B):

$$3400 \leq MA+MB \leq 7000 \quad (M1\text{-}2)$$

$$0.35 \leq MA/MB \leq 3.00 \quad (M2\text{-}1),$$

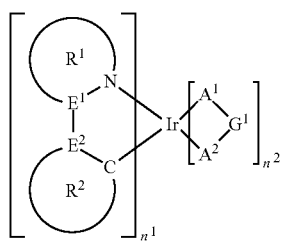

(A)

wherein $n^1$ represents an integer of 1 or more, $n^2$ represents an integer of 0 or more, and $n^1+n^2$ is 3, $E^1$ and $E^2$ each independently represent a carbon atom or a nitrogen atom, and at least one of $E^1$ and $E^2$ is a carbon atom, ring $R^1$ represents an unsubstituted or substituted aromatic heterocyclic ring, wherein the substituted aromatic heterocyclic ring is substituted with at least one atom or group selected from the group consisting of a halogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryloxy group, an unsubstituted or substituted aryl group, an unsubstituted or substituted pyridyl group, an unsubstituted or substituted pyrimidinyl group, and an unsubstituted or substituted triazinyl group wherein the substituted alkyl group, the substituted cycloalkyl group, the substituted alkoxy group, the substituted cycloalkoxy group, the substituted aryloxy group, the substituted aryl group, the substituted pyridyl group, the substituted pyrimidinyl group, and the substituted triazinyl group is substituted with at least one group selected from the group consisting of an unsubstituted alkyl group; a substituted alkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted aryl group; and a substituted aryl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group, and when the aromatic heterocyclic ring of the ring $R^1$ is substituted with a plurality of substituents, the substituents can be the same or different, and when a plurality of the rings $R^1$ are present, they can be the same or different, ring $R^2$ represents an unsubstituted or substituted aromatic hydrocarbon ring or an unsubstituted or substituted aromatic heterocyclic ring, wherein the substituted substituted aromatic hydrocarbon ring and substituted aromatic heterocyclic ring is substituted with at least one atom or group selected from the group consisting of a halogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryloxy group, an unsubstituted or substituted aryl group, an unsubstituted or substituted pyridyl group, an unsubstituted or substituted pyrimidinyl group, and an unsubstituted or substituted triazinyl group, wherein the substituted alkyl group, the substituted cycloalkyl group, the substituted alkoxy group, the substituted cycloalkoxy group, the substituted aryloxy group, the substituted aryl group, the substituted pyridyl group, the substituted pyrimidinyl group, and the substituted triazinyl group is substituted with at least one atom or group selected from the group consisting of an unsubstituted alkyl group; a substituted alkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, a unsubstituted cycloalkenyl group, an unsubstituted alkynyl group and an unsubstituted cycloalkynyl group; an unsubstituted aryl group; and a substituted aryl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an aryloxy group, an unsubstituted alkenyl group, an unsubstituted cycloalkenyl group, an unsubstituted alkynyl group and an unsubstituted cycloalkynyl group, and when the aromatic hydrocarbon ring or the aromatic heterocyclic ring of the ring $R^2$ is substituted with a plurality of substituents, each substituent can be the same or different, and when a plurality of the rings $R^2$ are present, they can be the same or different, and $A^1$-$G^1$-$A^2$ represents an anionic bidentate ligand, wherein $A^1$ and $A^2$ each independently represent a carbon atom, an oxygen atom or a nitrogen atom and these atoms can be an atom constituting a ring, $G^1$ represents a single bond or an atomic group constituting the bidentate ligand together with $A^1$ and $A^2$, and when a plurality of $A^1$-$G^1$-$A^2$ are present, they can be the same or different,

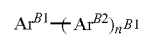

(B)

wherein $n^{B1}$ represents an integer of 1 or more, $Ar^{B1}$ represents a pyridine ring, a pyrimidine ring or a triazine ring and each of these rings is optionally substituted with a substituent, and $Ar^{B2}$ represents a group represented by the formula (D-A), (D-B) or (D-C), and when a plurality of $Ar^{B2}$ are present, they can be the same or different:

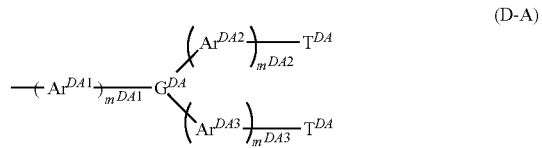

(D-A)

wherein $m^{DA1}$, $m^{DA2}$ and $m^{DA3}$ each independently represent an integer of 0 or more, $G^{DA}$ represents a nitrogen atom, an aromatic hydrocarbon group or a heterocyclic group and each of these groups is optionally substituted with a substituent, $Ar^{DA1}$, $Ar^{DA2}$ and $Ar^{DA3}$ each independently represent an arylene group or a divalent heterocyclic group and each of these groups is optionally substituted with a substituent, and when a plurality of $Ar^{DA1}$, $Ar^{DA2}$ and $Ar^{DA3}$ are present, they can be the same or different at each occurrence, and $T^{DA}$ represents an aryl group or a monovalent heterocyclic group and each of these groups is optionally substituted with a substituent, and a plurality of $T^{DA}$ can be the same or different:

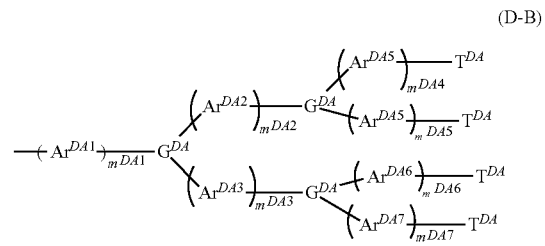

(D-B)

wherein $m^{DA1}$, $m^{DA2}$, $m^{DA3}$, $m^{DA4}$, $m^{DA5}$, $m^{DA6}$ and $m^{DA7}$ each independently represent an integer of 0 or more, $G^{DA1}$, $G^{DA2}$, and $G^{DA3}$ each independently represent a nitrogen atom, an aromatic hydrocarbon group or a heterocyclic group and each of these groups is optionally substituted with a substituent, provided that $m^{DA2}$ is an integer of 1 or more when $G^{DA1}$ and $G^{DA2}$ are each a nitrogen atom, and $m^{DA3}$ is an integer of 1 or more when $G^{DA1}$ and $G^{DA3}$ are each a nitrogen atom, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and each of these groups is optionally substituted with a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they can be the same or different at each occurrence, and $T^{DA}$ represents an aryl group or a monovalent heterocyclic group and each of these groups is optionally substituted with a substituent, and a plurality of $T^{DA}$ can be the same or different:

(D-C)

wherein $m^{DA1}$ represents an integer of 0 or more, $Ar^{DA1}$ represents an arylene group or a divalent heterocyclic group and each of these groups is optionally substituted with a substituent, and when a plurality of $Ar^{DA1}$ are present, they can be the same or different, and $T^{DA}$ represents an aryl group or a monovalent heterocyclic group and each of these groups is optionally substituted with a substituent.

2. The light emitting device according to claim 1, wherein the molecular weight (MA) and the molecular weight (MB) satisfy the formula (M2-2):

$$0.35 \leq MA/MB \leq 2.00 \quad \text{(M2-2)}.$$

3. The light emitting device according to claim 2, wherein the molecular weight (MA) and the molecular weight (MB) satisfy the formula (M1-3) and the formula (M2-3):

$$4000 \leq MA+MB \leq 6000 \quad \text{(M1-3)}$$

$$0.65 \leq MA/MB \leq 1.30 \quad \text{(M2-3)}.$$

4. The light emitting device according to claim 1, wherein the light emitting layer and the hole transporting layer are adjacent to each other.

5. The light emitting device according to claim 1, wherein the at least one iridium complex represented by formula (A) is an iridium complex represented by formula (A-A) or an iridium complex represented by formula (A-B):

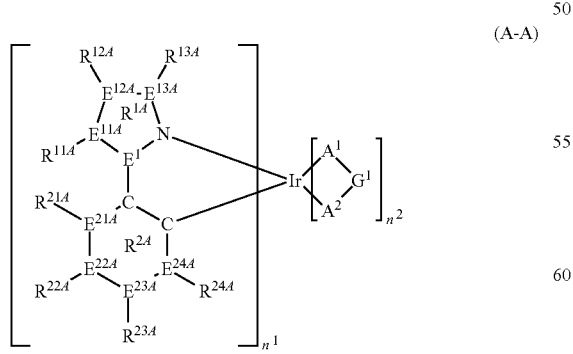

(A-A)

wherein $n^1$, $n^2$, and $A^1$-$G^1$-$A^2$ represent the same meaning as described above, two selected from among $E^1$, $E^{11A}$, $E^{12A}$ and $E^{13A}$ represent a nitrogen atom and the other two represent a carbon atom, or one selected from among $E^1$, $E^{11A}$, $E^{12A}$ and $E^{13A}$ represents a nitrogen atom and the other three represent a carbon atom, and when a plurality of $E^1$, $E^{11A}$, $E^{12A}$ and $E^{13A}$ are present, they can be the same or different at each occurrence, and $R^{11A}$ is either present or not present when $E^{11A}$ is a nitrogen atom, $R^{12A}$ is either present or not present when $E^{12A}$ is a nitrogen atom, and $R^{13A}$ is either present or not present when $E^{13A}$ is a nitrogen atom, $E^{21A}$, $E^{22A}$, $E^{23A}$ and $E^{24A}$ represent a carbon atom, or one selected from among $E^{21A}$, $E^{22A}$, $E^{23A}$ and $E^{24A}$ represents a nitrogen atom and the other three represent a carbon atom, or $E^{21A}$ and $E^{23A}$ represent a nitrogen atom and $E^{22A}$ and $E^{24A}$ represent a carbon atom, or $E^{22A}$ and $E^{24A}$ represent a nitrogen atom and $E^{21A}$ and $E^{23A}$ represent a carbon atom, and when a plurality of $E^{21A}$, $E^{22A}$, $E^{23A}$ and $E^{24A}$ are present, they can be the same or different at each occurrence, and $R^{21A}$ is not present when $E^{21A}$ is a nitrogen atom, $R^{22A}$ is not present when $E^{22A}$ is a nitrogen atom, $R^{23A}$ is not present when $E^{23A}$ is a nitrogen atom, and $R^{24A}$ is not present when $E^{24A}$ is a nitrogen atom, $R^{11A}$, $R^{12A}$, $R^{13A}$, $R^{21A}$, $R^{22A}$, $R^{23A}$ and $R^{24A}$ each independently represent a hydrogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryl group, an unsubstituted or substituted aryloxy group, an unsubstituted or substituted pyridyl group, an unsubstituted or substituted pyrimidinyl group, an unsubstituted or substituted triazinyl group, or a halogen atom, and the substituted alkyl group, the substituted cycloalkyl group, the substituted alkoxy group, the substituted cycloalkoxy group, the substituted aryloxy group, the substituted aryl group, the substituted pyridyl group, the substituted pyrimidinyl group, and the substituted triazinyl group is substituted with at least one group selected from the group consisting of an unsubstituted alkyl group; a substituted alkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and a unsubstituted cycloalkynyl group; an unsubstituted aryl group; and a substituted aryl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group, and when a plurality of $R^{11A}$, $R^{12A}$, $R^{13A}$, $R^{21A}$, $R^{22A}$, $R^{23A}$ and $R^{24A}$ are present, they can be the same or different at each occurrence, ring $R^{1A}$ represents a triazole ring or a diazole ring, and ring $R^{2A}$ represents a benzene ring, a pyridine ring or a pyrimidine ring:

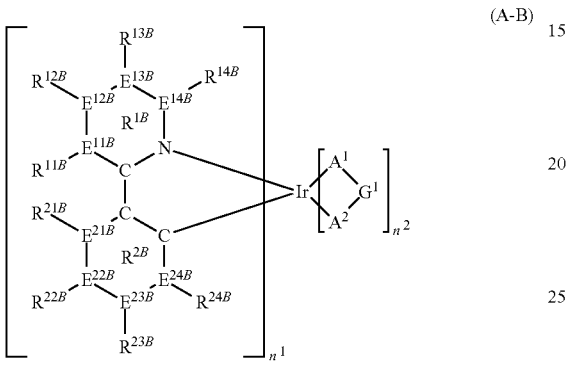

(A-B)

wherein $n^1$, $n^2$ and $A^1$-$G^1$-$A^2$ represent the same meaning as described above, $E^{11B}$, $E^{12B}$, $E^{13B}$ and $E^{14B}$ represent a carbon atom, or either $E^{11B}$ or $E^{13B}$ represents a nitrogen atom and $E^{12B}$, $E^{14B}$ and the other of $E^{11B}$ or $E^{13B}$ represent a carbon atom, and when a plurality of $E^{11B}$ and $E^{13B}$ are present, they can be the same or different at each occurrence, and $R^{11B}$ is not present when $E^{11B}$ is a nitrogen atom, and $R^{13B}$ is not present when $E^{13B}$ is a nitrogen atom, $E^{21B}$, $E^{22B}$, $E^{23B}$ and $E^{24B}$ represent a carbon atom, or one selected from among $E^{21B}$, $E^{22B}$, $E^{23B}$ and $E^{24B}$ represents a nitrogen atom and the other three represent a carbon atom, or $E^{21B}$ and $E^{23B}$ represent a nitrogen atom and $E^{22B}$ and $E^{24B}$ represent a carbon atom, or $E^{22B}$ and $E^{24B}$ represent a nitrogen atom and $E^{21B}$ and $E^{23B}$ represent a carbon atom, and when a plurality of $E^{21B}$, $E^{22B}$, $E^{23B}$ and $E^{24B}$ are present, they can be the same or different at each occurrence, and $R^{21B}$ is not present when $E^{21B}$ is a nitrogen atom, $R^{22B}$ is not present when $E^{22B}$ is a nitrogen atom, $R^{23B}$ is not present when $E^{23B}$ is a nitrogen atom, and $R^{24B}$ is not present when $E^{24B}$ is a nitrogen atom, $R^{11B}$, $R^{12B}$, $R^{13B}$, $R^{14B}$, $R^{21B}$, $R^{22B}$, $R^{23B}$ and $R^{24B}$ each independently represent a hydrogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryl group, an unsubstituted or substituted aryloxy group, an unsubstituted or substituted pyridyl group, an unsubstituted or substituted pyrimidinyl group, an unsubstituted or substituted triazinyl group, or a halogen atom, and the substituted alkyl group, the substituted cycloalkyl group, the substituted alkoxy group, the substituted cycloalkoxy group, the substituted aryl group, the substituted aryloxy group, the substituted pyridyl group, the substituted pyrimidinyl group, and the substituted triazinyl group is substituted with at least one group selected from the group consisting of an unsubstituted alkyl group; a substituted alkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group selected from the group consisting of a halogen atom, a cyano group, an unsubstituted alkyl group, a unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted aryl group; and a substituted aryl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group, and when a plurality of $R^{11B}$, $R^{12B}$, $R^{13B}$, $R^{14B}$, $R^{21B}$, $R^{22B}$, $R^{23B}$ and $R^{24B}$ are present, they can be the same or different at each occurrence, ring $R^{1B}$ represents a pyridine ring or a pyrimidine ring and ring $R^{2B}$ represents a benzene ring, a pyridine ring or a pyrimidine ring.

6. The light emitting device according to claim 1, wherein the crosslinkable material is a low molecular weight compound having at least one crosslinkable group selected from Group A of crosslinkable group or a polymer compound comprising a crosslinkable constitutional unit having at least one crosslinkable group selected from Group A of crosslinkable group, wherein Group A is a crosslinkable group selected from the group consisting of:

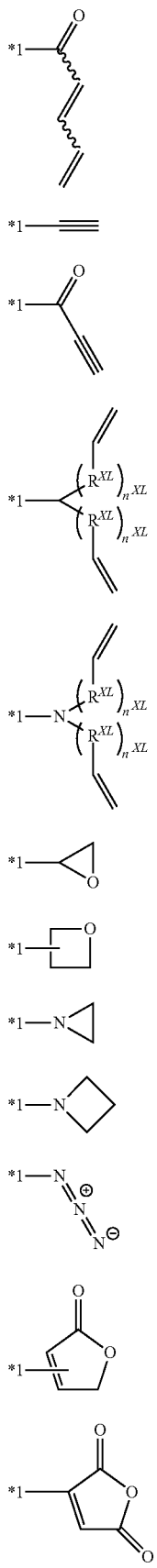

(XL-4)
(XL-5)
(XL-6)
(XL-7)
(XL-8)
(XL-9)
(XL-10)
(XL-11)
(XL-12)
(XL-13)
(XL-14)
(XL-15)

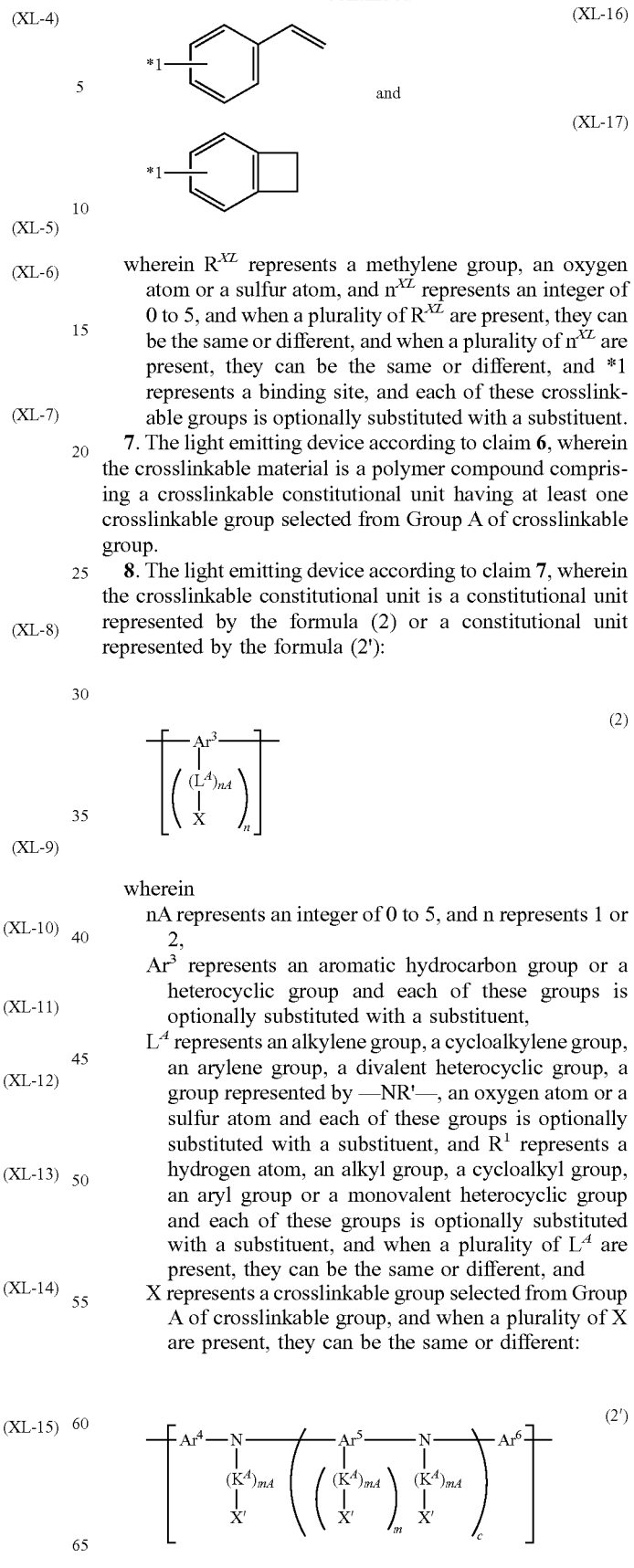

(XL-16)
and
(XL-17)

wherein $R^{XL}$ represents a methylene group, an oxygen atom or a sulfur atom, and $n^{XL}$ represents an integer of 0 to 5, and when a plurality of $R^{XL}$ are present, they can be the same or different, and when a plurality of $n^{XL}$ are present, they can be the same or different, and *1 represents a binding site, and each of these crosslinkable groups is optionally substituted with a substituent.

7. The light emitting device according to claim 6, wherein the crosslinkable material is a polymer compound comprising a crosslinkable constitutional unit having at least one crosslinkable group selected from Group A of crosslinkable group.

8. The light emitting device according to claim 7, wherein the crosslinkable constitutional unit is a constitutional unit represented by the formula (2) or a constitutional unit represented by the formula (2'):

$$\left[ \begin{array}{c} Ar^3 \\ | \\ \left( (L^A)_{nA} \right) \\ | \\ X \end{array} \right]_n \tag{2}$$

wherein nA represents an integer of 0 to 5, and n represents 1 or 2, $Ar^3$ represents an aromatic hydrocarbon group or a heterocyclic group and each of these groups is optionally substituted with a substituent, $L^A$ represents an alkylene group, a cycloalkylene group, an arylene group, a divalent heterocyclic group, a group represented by —NR'—, an oxygen atom or a sulfur atom and each of these groups is optionally substituted with a substituent, and $R^1$ represents a hydrogen atom, an alkyl group, a cycloalkyl group, an aryl group or a monovalent heterocyclic group and each of these groups is optionally substituted with a substituent, and when a plurality of $L^A$ are present, they can be the same or different, and X represents a crosslinkable group selected from Group A of crosslinkable group, and when a plurality of X are present, they can be the same or different:

$$\left[ Ar^4 - N - \left( Ar^5 - N \right)_m - Ar^6 \right]_c \tag{2'}$$
$$\begin{array}{ccc} | & | & | \\ (K^A)_{mA} & (K^A)_{mA} & (K^A)_{mA} \\ | & | & | \\ X' & X' & X' \end{array}$$

wherein, mA represents an integer of 0 to 5, m represents an integer of 1 to 4, and c represents an integer of 0 or 1, and when a plurality of mA are present, they can be the same or different, $Ar^5$ represents an aromatic hydrocarbon group, a heterocyclic group or a group in which at least one aromatic hydrocarbon ring and at least one heterocyclic ring are bonded directly to each other, and each of these groups is optionally substituted with a substituent, $Ar^4$ and $Ar^6$ each independently represent an arylene group or a divalent heterocyclic group and each of these groups is optionally substituted with a substituent, one selected from among $Ar^4$, $Ar^5$ and $Ar^6$ can be bonded directly or via an oxygen atom or a sulfur atom to one selected from the other two bonding to the nitrogen atom to which the one selected from among $Ar^4$, $Ar^5$, and $Ar^6$ is attached, thereby forming a ring, $K^A$ represents an alkylene group, a cycloalkylene group, an arylene group, a divalent heterocyclic group, a group represented by —NR'—, an oxygen atom or a sulfur atom and each of these groups is optionally substituted with a substituent, and R' represents a hydrogen atom, an alkyl group, a cycloalkyl group, an aryl group or a monovalent heterocyclic group and each of these groups is optionally substituted with a substituent, and when a plurality of $K^A$ are present, they can be the same or different, and X' represents a crosslinkable group selected from Group A of crosslinkable group, a hydrogen atom, an alkyl group, a cycloalkyl group, an aryl group or a monovalent heterocyclic group and each of these groups is optionally substituted with a substituent, and at least one X' is a crosslinkable group selected from Group A of crosslinkable group.

9. A composition comprising at least one iridium complex (A) and at least one heterocyclic compound (B), wherein the at least one iridium complex (A) is an iridium complex represented by formula (A), the at least one heterocyclic compound (B) is a heterocyclic compound represented by formula (B), and the molecular weight (MA) of the at least one iridium complex (A) and the molecular weight (MB) of the at least one heterocyclic compound (B) satisfy formula (M1-2) and formula (M2-1), wherein when more than one iridium complex (A) and/or more than one heterocyclic compound (B) is present, MA refers to the molecular weight of a single iridium complex (A) and MB refers to the molecular weight of a single heterocyclic compound (B):

$$3400 \leq MA+MB \leq 7000 \quad (M1\text{-}2)$$

$$0.35 \leq MA/MB \leq 3.00 \quad (M2\text{-}1):$$

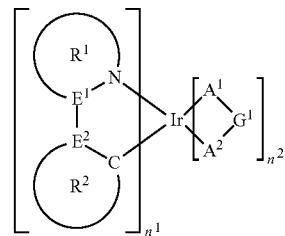

(A)

wherein $n^1$ represents an integer of 1 or more, $n^2$ represents an integer of 0 or more, and $n^1+n^2$ is 3, $E^1$ and $E^2$ each independently represent a carbon atom or a nitrogen atom, and at least one of $E^1$ and $E^2$ is a carbon atom, ring $R^1$ represents an unsubstituted or substituted aromatic heterocyclic ring, and the substituted aromatic heterocyclic ring is substituted with at least one atom or group selected from the group consisting of a halogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryloxy group, an unsubstituted or substituted aryl group, an unsubstituted or substituted pyridyl group, an unsubstituted or substituted pyrimidinyl group, and an unsubstituted or substituted triazinyl group, and the substituted alkyl group, the substituted cycloalkyl group, the substituted alkoxy group, the substituted cycloalkoxy group, the substituted aryloxy group, the substituted aryl group, the substituted pyridyl group, the substituted pyrmidinyl group, and the substituted triazinyl group is substituted with at least one group selected from the group consisting of an unsubstituted alkyl group; a substituted alkyl group substituted with at least one group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group independently selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted aryl group; and a substituted aryl group substituted with at least one group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group and when the aromatic heterocyclic ring of ring $R^1$ is substituted with a plurality of substituents, they can be the same or different, and when a plurality of the rings $R^1$ are present, they can be the same or different, ring $R^2$ represents an unsubstituted or substituted aromatic hydrocarbon ring or an unsubstituted or substituted aromatic heterocyclic ring, and the substituted aromatic hydrocarbon ring and substituted aromatic heterocyclic ring is substituted with at least one atom or group selected from the group consisting of a halogen atom, an unsubstituted or substituted alkyl group, an unsubstituted or substituted cycloalkyl group, an unsubstituted or substituted alkoxy group, an unsubstituted or substituted cycloalkoxy group, an unsubstituted or substituted aryloxy group, an unsubstituted or substituted aryl group, an unsubstituted or substituted pyridyl group, an unsubstituted or substituted pyrimidinyl group, and an unsubstituted or substituted triazinyl group, and the substituted alkyl group, the substituted cycloalkyl group, the substituted alkoxy group, the substituted cycloalkoxy group, the substituted aryloxy group, the substituted aryl group, the substituted pyridyl group, the substituted pyrimidinyl group, and the substituted triazinyl group is substituted with at least one group selected from the group consisting of an unsubstituted alkyl group; a substituted alkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted cycloalkyl group; a substituted cycloalkyl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group; an unsubstituted aryl group; and a substituted aryl group substituted with at least one atom or group selected from the group consisting of a halogen atom, a cyano group, an unsubstituted alkyl group, an unsubstituted cycloalkyl group, an unsubstituted aryl group, an unsubstituted alkoxy group, an unsubstituted cycloalkoxy group, an unsubstituted aryloxy group, an unsubstituted alkenyl group, an unsubstituted cycloalkenyl group, an unsubstituted alkynyl group and an unsubstituted cycloalkynyl group, and when the aromatic hydrocarbon ring or the aromatic heterocyclic ring of ring $R^2$ is substituted with a plurality of substituents, they can be the same or different, and when a plurality of the rings $R^2$ are present, they can be the same or different, and $A^1$-$G^1$-$A^2$ represents an anionic bidentate ligand, $A^1$ and $A^2$ each independently represent a carbon atom, an oxygen atom or a nitrogen atom and these atoms can be an atom constituting a ring, $G^1$ represents a single bond or an atomic group constituting the bidentate ligand together with $A^1$ and $A^2$, and when a plurality of $A^1$-$G^1$-$A^2$ are present, they can be the same or different,

wherein
$n^{B1}$ represents an integer of 1 or more,
$Ar^{B1}$ represents a pyridine ring, a pyrimidine ring or a triazine ring and each of these rings is optionally substituted with a substituent, and
$Ar^{B2}$ represents a group represented by the formula (D-A), (D-B) or (D-C), and when a plurality of $Ar^{B2}$ are present, they can be the same or different:

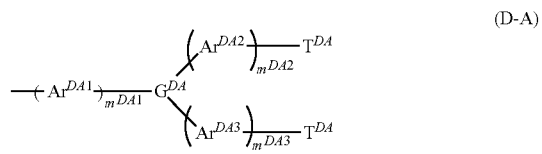

wherein
$m^{DA1}$, $m^{DA2}$ and $m^{DA3}$ each independently represent an integer of 0 or more,
$G^{DA}$ represents a nitrogen atom, an aromatic hydrocarbon group or a heterocyclic group and each of these groups is optionally substituted with a substituent,
$Ar^{DA1}$, $Ar^{DA2}$ and $Ar^{DA3}$ each independently represent an arylene group or a divalent heterocyclic group and each of these groups is optionally substituted with a substituent, and when a plurality of $Ar^{DA1}$, $Ar^{DA2}$ and $Ar^{DA3}$ are present, they can be the same or different at each occurrence, and
$T^{DA}$ represents an aryl group or a monovalent heterocyclic group and each of these groups is optionally substituted with a substituent, and a plurality of $T^{DA}$ can be the same or different:

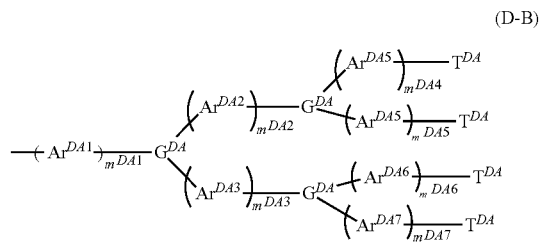

wherein
$m^{DA1}$, $m^{DA2}$, $m^{DA3}$, $m^{DA4}$, $m^{DA5}$, $m^{DA6}$ and $m^{DA7}$ each independently represent an integer of 0 or more,
$G^{DA1}$, $G^{DA2}$ and $G^{DA3}$ each independently represent a nitrogen atom, an aromatic hydrocarbon group or a heterocyclic group and each of these groups is optionally substituted with a substituent, provided that $m^{DA2}$ is an integer of 1 or more when $G^{DA1}$ and $G^{DA2}$ are each a nitrogen atom, and $m^{DA3}$ is an integer of 1 or more when $G^{DA1}$ and $G^{DA3}$ are each a nitrogen atom,
$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and each of these groups is optionally substituted with a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they can be the same or different at each occurrence, and $T^{DA}$ represents an aryl group or a monovalent heterocyclic group and each of these groups is optionally substituted with a substituent, and a plurality of $T^{DA}$ can be the same or different:

(D-C)

wherein
$m^{DA1}$ represents an integer of 0 or more,
$Ar^{DA1}$ represents an arylene group or a divalent heterocyclic group and each of these groups is optionally substituted with a substituent, and when a plurality of $Ar^{DA1}$ are present, they can be the same or different, and
$T^{DA}$ represents an aryl group or a monovalent heterocyclic group and each of these groups is optionally substituted with a substituent.

10. The composition according to claim 9, wherein the molecular weight (MA) and the molecular weight (MB) satisfy the formula (M1-3) and the formula (M2-3):

$$4000 \leq MA+MB \leq 6000 \quad (M1-3)$$

$$0.65 \leq MA/MB \leq 1.30 \quad (M2-3).$$

11. The light emitting device according to claim 1, wherein $Ar^{B1}$ in the formula (B) is a triazine ring.

12. The composition according to claim 9, wherein $Ar^{B1}$ in the formula (B) is triazine ring.

* * * * *